(12) United States Patent
Cuevas-Cordobés et al.

(10) Patent No.: US 9,981,942 B2
(45) Date of Patent: May 29, 2018

(54) PIPERIDINE DERIVATIVES HAVING MULTIMODAL ACTIVITY AGAINST PAIN

(71) Applicant: LABORATORIOS DEL DR. ESTEVE S.A., Barcelona (ES)

(72) Inventors: Félix Cuevas-Cordobés, Valdemoro (ES); Carmen Almansa-Rosales, Barcelona (ES); Monica Garcia Lopez, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days. days.

(21) Appl. No.: 15/106,363

(22) PCT Filed: Dec. 19, 2014

(86) PCT No.: PCT/EP2014/078717
§ 371 (c)(1),
(2) Date: Jun. 20, 2016

(87) PCT Pub. No.: WO2015/091939
PCT Pub. Date: Jun. 25, 2015

(65) Prior Publication Data
US 2017/0001978 A1    Jan. 5, 2017

(30) Foreign Application Priority Data
Dec. 20, 2013    (EP) .................... 13384004

(51) Int. Cl.
| C07D 401/06 | (2006.01) |
| C07D 401/14 | (2006.01) |
| C07D 413/06 | (2006.01) |
| C07D 405/14 | (2006.01) |
| C07D 413/14 | (2006.01) |
| C07D 417/14 | (2006.01) |
| C07D 487/04 | (2006.01) |

(52) U.S. Cl.
CPC ......... *C07D 401/06* (2013.01); *C07D 401/14* (2013.01); *C07D 405/14* (2013.01); *C07D 413/06* (2013.01); *C07D 413/14* (2013.01); *C07D 417/14* (2013.01); *C07D 487/04* (2013.01)

(58) Field of Classification Search
CPC .. C07D 401/06; C07D 401/14; C07D 413/06; C07D 405/14; C07D 413/14; C07D 417/14
See application file for complete search history.

(56) References Cited

U.S. PATENT DOCUMENTS

| 6,727,264 B1 | 4/2004 | Marzabadi |
| 7,645,755 B2 | 1/2010 | Illig |
| 2004/0186135 A1 | 9/2004 | Dolle |
| 2017/0001979 A1 | 1/2017 | Cuevas-Cordobés et al. |

FOREIGN PATENT DOCUMENTS

| DE | 21 09 155 | 9/1972 |
| EP | 1736472 | 12/2016 |
| GB | 950813 | 2/1964 |
| WO | WO 2009/029253 | 3/2009 |

OTHER PUBLICATIONS

International Search Report for PCT/EP2014/078717 dated Feb. 17, 2015.
European Search Report for European Application No. 13384004.1, dated May 14, 2014.

*Primary Examiner* — Theodore R. West
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to piperidene compounds having this pharmacological activity, to processes of preparation of such compounds, to pharmaceutical compositions comprising them, and to their use in therapy, in particular for the treatment of pain.

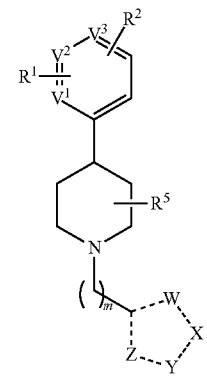

24 Claims, No Drawings

PIPERIDINE DERIVATIVES HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid) and more particularly to piperidine compounds having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies.* Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding as a ligand to two different receptors relevant for the treatment of pain. This was mainly achieved by providing the compound according to the invention that bind both to the μ-opiod receptor and to the σ₁ receptor.

SUMMARY OF THE INVENTION

In this invention a family of structurally distinct piperidine derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the σ₁ receptor and the μ-opioid receptor for use in the treatment of pain.

As this invention is aimed at providing a compound or a chemically related series of compounds which act as dual ligands of the σ₁ receptor and the μ-opioid receptor it is a very preferred embodiment if the compound has a binding expressed as $K_i$ which is <100 nm for both receptors, the μ-opioid receptor and the σ₁ receptor.

The invention is directed in a main aspect to a compound of general formula (I),

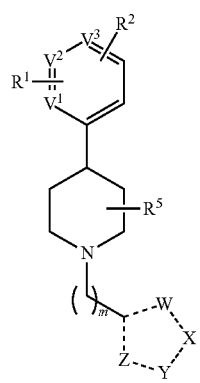

wherein $R^1$, $R^2$, $R^5$, $V^1$, $V^2$, $V^3$, W, X, Y, Z and m are as defined below in the detailed description.

DETAILED DESCRIPTION OF THE INVENTION

The invention is directed to a family of structurally distinct piperidine derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the σ₁ receptor and the μ-opioid receptor for use in the treatment of pain.

As this invention is aimed at providing a compound or a chemically related series of compounds which act as dual ligands of the σ₁ receptor and the μ-opioid receptor it is a very preferred embodiment if the compound has a binding expressed as $K_i$ which is <100 nm for both receptors, the μ-opioid receptor and the σ₁ receptor.

The applicant has surprisingly found that the problem on which the present invention is based can be solved by using a multimodal balanced analgesic approach combining two different synergistic activities in a single drug (i.e., dual ligands which are bifunctional and bind to MOR and to σ₁ receptor), thereby enhancing the opioid analgesia through the σ₁ activation without increasing the undesirable side effects. This supports the therapeutic value of a dual MOR/σ₁ receptor compound whereby the σ₁ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opiod receptor and to the σ₁ receptor shows a highly valuable therapeutic potential by achieving an outstanding analgesia (enhanced in respect to the potency of the opioid component alone) with a reduced side-effect profile (safety margin increased compared to that of the opioid component alone) versus existing opiod therapies.

Advantageously, the dual compounds according to the present invention would in addition show one or more the following functionalities: σ₁ receptor antagonism and MOR agonism. It has to be noted, though, that both functionalities "antagonism" and "agonism" are also sub-divided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while σ₁ receptor antagonists show outstanding effects in preclinical neuropathic pain models. Thus, the σ₁ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In a particular aspect, the present invention is directed to compounds of general formula (I):

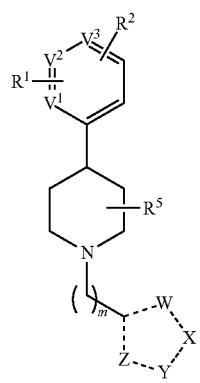 (I)

wherein m is 1 or 2;

one of $V^1$, $V^2$ and $V^3$ is selected from nitrogen or carbon while the other two are carbon;

$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;

$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;

or $R^1$ and $R^2$ are bonded to neighbouring atoms in the ring and together with these atoms form a saturated or unsaturated, substituted or unsubstituted ring, fused to the ring

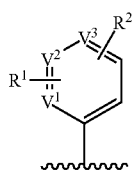

of the corestructure of formula I, which may be condensed with a further unsubstituted or substituted ring system;

$R^5$ is hydrogen, halogen, hydroxy, substituted or unsubstituted O-alkyl, substituted or unsubstituted alkyl;

$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

and wherein W, X, Y and Z are selected from carbon, nitrogen, or oxygen while W—X—Y—Z are forming together with the bridging C-atom, that is connected to the core scaffold, a 5-membered heterocyclic ring, which is either substituted on one of W, X, Y or Z by

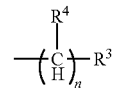

or in which this said 5-membered heterocyclic ring—being otherwise unsubstituted—is fused at W and X to a further ringsystem;

wherein n is 0 or 1;

$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;

$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof, In another embodiment the compound according to the invention—especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment the compound according to the invention—especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment the compound according to the invention—especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio.

In one embodiment one or more of the following provisos apply:

with the proviso that if $V^1$, $V^2$ and $V^3$ are carbon and one of W, X, Y or Z is

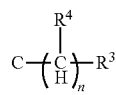

with n being 0, than $R^1$ may not be —NHC(O)-alkyl in meta position;

and/or with the proviso that if $V^1$, $V^2$ and $V^3$ are carbon and either W or Y is

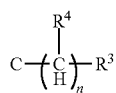

with n being 0, than $R^1$ may not be —NHC(O)-alkyl in meta position;
and/or
with the proviso that if $V^1$ is nitrogen while $V^2$ and $V^3$ are carbon and either X or Y is

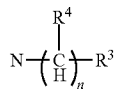

with n=0 and $R^3$ being alkyl, than $R^1$ may not be —$NR^6R^7$ in meta position;
and/or
with the proviso that if $V^1$ is nitrogen while $V^2$ and $V^3$ are carbon and either X or Y is

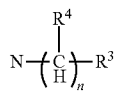

with n=0 and $R^3$ being alkyl, than $R^2$ may not be —$CH_3$ in meta position;
and/or
with the proviso that if $V^1$ is nitrogen while $V^2$ and $V^3$ are carbon and either X or Y is

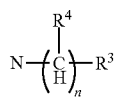

with n=0 and $R^3$ being alkyl, than $R^1$ and $R^2$ may not be —$NR^6R^7$ in meta position;
with the proviso that if $V^1$ is nitrogen while $V^2$ and $V^3$ are carbon and either X or Y is

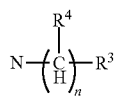

with n=0 and $R^3$ being alkyl, than neither $R^1$ nor $R^2$ may be —$NR^6R^7$ in meta position and $R^2$ may not be —$CH_3$ in meta position;
and/or
with the proviso that if $V^1$ is nitrogen while $V^2$ and $V^3$ are carbon and either X or Y is

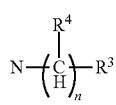

with n=0 and $R^3$ being alkyl, than $R^1$ may not be —$NR^6R^2$ in meta-position and $R^2$ may not be —$CH_3$ in meta position;

and/or
with the proviso that if $V^1$ is nitrogen while $V^2$ and $V^3$ are carbon and either W or Z is

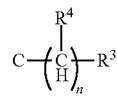

with n=0 and $R^3$ being alkyl, than $R^2$ may not be —$NR^6R^7$ in meta position
and/or
with the proviso that if n is 0, $R^3$ may not be alkyl;
and/or
with the proviso that if n is 0, $R^3$ may not be methyl;
and/or
with the proviso that the compound may not be 2-Pyridinamine, N-(5-ethyl-1,3,4-thiadiazol-2-yl)-6-[1-[(1-methyl-1H-pyrazol-4-yl)methyl]-4-piperidinyl]-;
and/or
with the proviso that the compound may not be 2-Pyridinamine, 6-[1-[(1-ethyl-1H-pyrazol-4-yl)methyl]-4-piperidinyl]-N-(5-methyl-3-isoxazolyl)-;
and/or
with the proviso that the compound may not be 3-Pyridinecarboxamide, 2-amino-N-[(3-methoxyphenyl)methyl]-6-[1-[(1-methyl-1H-pyrazol-4-yl)methyl]-4-piperidinyl]-;
and/or
with the proviso that the compound may not be 4-Pyridinol, 2-methyl-6-[1-[(1-methyl-1H-pyrazol-4-yl)methyl]-4-piperidinyl]-;
and/or
with the proviso that the compound may not be 2-Pyridinamine, N,N-dimethyl-6-[1-[(1-methyl-1H-pyrazol-4-yl)methyl]-4-piperidinyl]-;
and/or
with the proviso that the compound may not be Methanone, [2-amino-6-[1-[[3-(1,1-dimethylethyl)-1H-pyrazol-4-yl]methyl]-4-piperidinyl]-3-pyridinyl]-1-pyrrolidinyl-;
and/or
with the proviso that the compound may not be Propanamide, 2-methyl-N-[3-[1-[[3-[4-(trifluoromethyl)phenyl]-1H-pyrazol-4-yl]methyl]-4-piperidinyl]phenyl]-
and/or
with the proviso that the compound may not be Propanamide, N-[3-[1-[[3-(4-methoxyphenyl)-1H-pyrazol-4-yl]methyl]-4-piperidinyl]phenyl]-2-methyl;
and/or
with the proviso that the compound may not be Propanamide, 2-methyl-N-[3-[1-[(2-phenyl-1H-imidazol-5-yl)methyl]-4-piperidinyl]phenyl];
and/or
with the proviso that the compound may not be Propanamide, 2-methyl-N-[3-[1-[[3-(2-thienyl)-1H-pyrazol-4-yl]methyl]-4-piperidinyl]phenyl].

When different radicals $R^1$ to $R^8$ are present simultaneously in the different Formulas of the present invention they may be identical or different. In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—CH₃. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{1-6}$-alkenyl like ethylene, propylene, butylene, pentylene, or hexylene; or is $C_{1-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH₃ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by F, Cl, Br, I, $NH_2$, SH or OH, —C(O)OH, or —$OC_{1-4}$alkyl being unsubstituted or substituted by one or more of OH or halogen (F, Cl, I, Br). More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkoxy is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted by one or more of halogen (F, Cl, I, Br), —OH, —$NH_2$, —SH, —C(O)OH, or —$OC_{1-4}$alkyl being unsubstituted or substituted by one or more of OH or halogen (F, Cl, I, Br).

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkylaryl is understood as meaning an aryl group (see above) being connected to another atom through a $C_{1-6}$-alkyl (see above) which may be branched or linear and is unsubstituted or substituted once or several times. Thus, in the context of this invention alkylaryl is understood as meaning an aryl group (see above) being connected to another atom through a $C_{1-6}$-alkyl (see above). The alkyl may be branched or linear and is unsubstituted, while the aryl may be unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning a heterocyclyl group being connected to another atom through a $C_{1-6}$-alkyl (see above) which may be branched or linear and is unsubstituted or substituted once or several times. Thus, in the context of this invention alkylheterocyclyl is understood as meaning a heterocyclyl group being connected to another atom through a $C_{1-6}$-alkyl (see above). The alkyl may be branched or linear and is unsubstituted, while the heterocyclyl may be unsubstituted or substituted once or several times. Preferably alkylheterocyclyl is understood as meaning a heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning a cycloalkyl group being connected to another atom through a $C_{1-6}$-alkyl (see above) which may be branched or linear and is unsubstituted or substituted once or several times. Thus, in the context of this invention alkylcycloalkyl is understood as meaning a cycloalkyl group being connected to another atom through a $C_{1-6}$-alkyl (see above). The alkyl may be branched or linear and is unsubstituted, while the cycloalkyl may be unsubstituted or substituted once or several times. Preferably alkylcycloalkyl is understood as meaning a cycloalkyl group (see above) being connected to another atom through 1 to 4 (—$CH_2$—) groups. Most preferably alkylcycloalkyl is —$CH_2$— cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times. Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, indene, 2,3-dihydroindene (indane), tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, indene, 2,3-dihydroindene, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl.

Most preferably in connection with aryl, cycloalkyl and heterocyclyl, substituted is understood in the context of this invention that any aryl, cycloalkyl or heterocyclyl, which is substituted is substituted by one or more of halogen (F, Cl, I, Br), —OH, —$NH_2$, —SH, =O, —C(O)OH, —$OC_{1-4}$ alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br).

Most preferably in connection with aryl (including alkyl-aryl), substituted is understood in the context of this invention that any aryl which is substituted is substituted by one or more of halogen (F, Cl, I, Br), —OH, —$NH_2$, —SH— C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br).

Most preferably in connection with cycloalkyl (including alkyl-cycloalkyl) or heterocyclyl (including alkyl-heterocyclyl), substituted is understood in the context of this invention that any cycloalkyl and heterocyclyl (also in an alkyl-cycloalkyl or alkylheterocyclyl) which is substituted is substituted by one or more of halogen (F, Cl, I, Br), —OH, —NH$_2$, —SH, =O, —C(O)OH, —OC$_{1-4}$alkyl being unsubstituted or substituted by one or more of OH or halogen (F, Cl, I, Br), —CN, or —C$_{1-4}$alkyl being unsubstituted or substituted by one or more of OH or halogen (F, Cl, I, Br).

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—).

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well-known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts. This applies also to its solvates or prodrugs.

In a preferred embodiment of the compound according to the invention according to Compound according to general formula I,

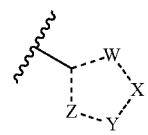

while being either substituted on one of W, X, Y or Z by

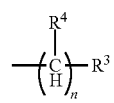

or being fused at W and X to a further ring system to the 5-membered heterocyclic ring formed by W—X—Y—Z while being otherwise unsubstituted—is selected from

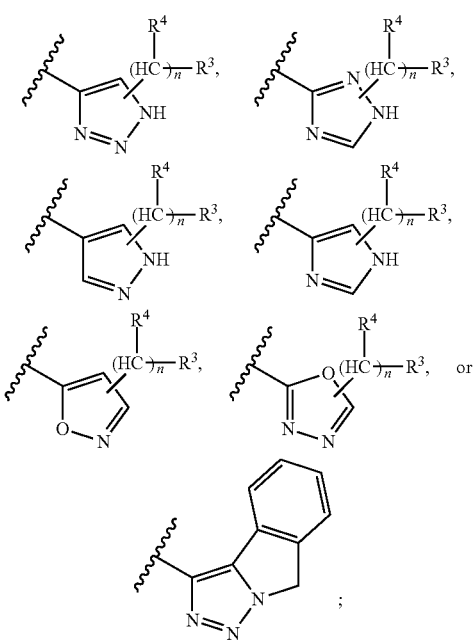

preferably is selected from

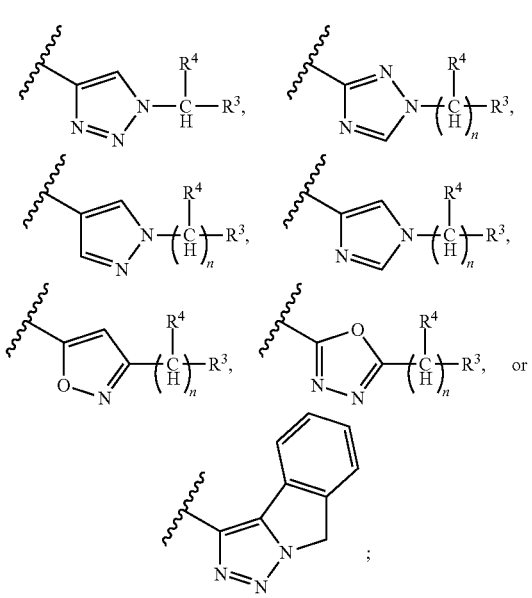

more preferably is selected from

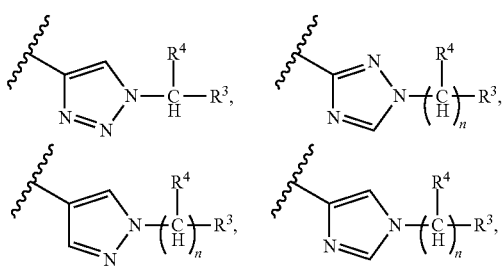

-continued

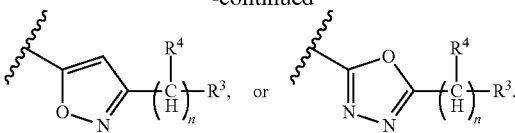

In another preferred embodiment of the compound according to the invention according to general Formula I the compound is a compound according to Formula II, (II)

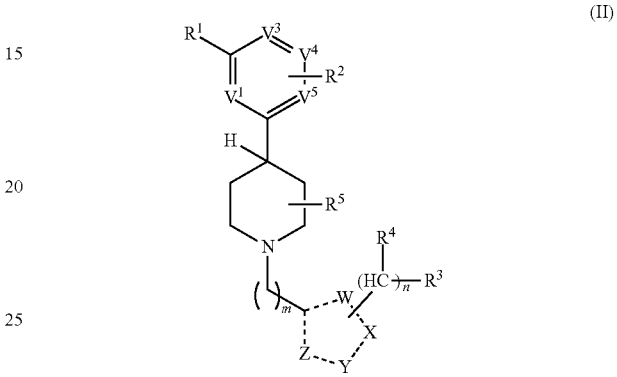

wherein
one of $V^1$, $V^3$, $V^4$ and $V^5$ is selected from nitrogen or carbon while the other three are carbon, preferably one of $V^1$ and $V^3$ is selected from nitrogen or carbon while the other—as well as $V^4$ and $V^5$—are carbon;

$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;

$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;

or $R^1$ and $R^2$ are bonded to neighbouring atoms in the ring and together with these atoms form a saturated or unsaturated, substituted or unsubstituted ring, fused to the ring

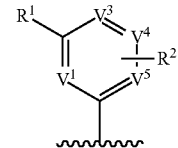

of the corestructure of formula II, which may be condensed with a further unsubstituted or substituted ring system;

$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl; and $R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

$R^5$ is hydrogen, halogen, hydroxy, substituted or unsubstituted O-alkyl, substituted or unsubstituted alkyl;

$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

and wherein W, X, Y and Z are selected from carbon, nitrogen, or oxygen while W—X—Y—Z are forming together with the bridging C-atom, that is connected to the core scaffold, a 5-membered heterocyclic ring, or wherein

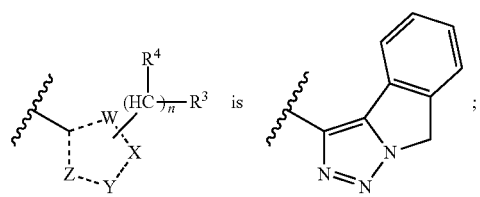

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

For the sake clarity

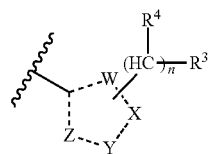

is thus either substituted on one—and just one—of W, X, Y or Z or the C-Atom connected to the core-structure by

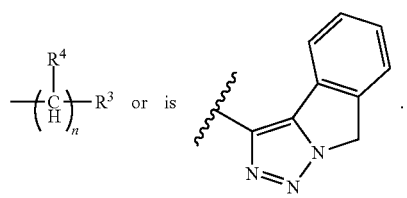

In one embodiment one or more of the following provisos apply:

with the proviso that if $V^1$, $V^3$, $V^4$ and $V^5$ are carbon and either W or Y is

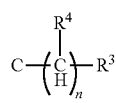

with n being 0, than $R^1$ may not be —NHC(O)-alkyl; and/or with the proviso that if $V^1$ is nitrogen while $V^3$, $V^4$ and $V^5$ are carbon and either X or Y is

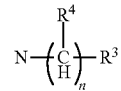

with n=0 and $R^3$ being alkyl, than $R^1$ may not be —$NR^6R^7$.

In a preferred embodiment of the compound according to the invention according to general Formula II

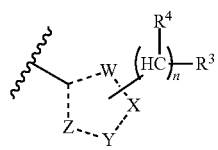

is selected from

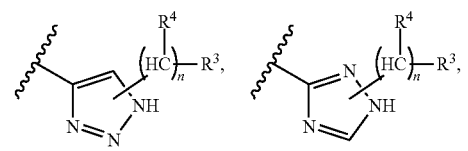

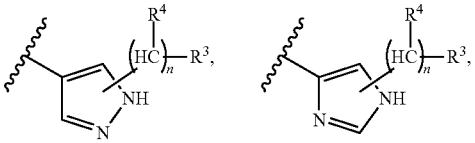

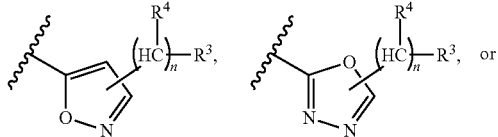

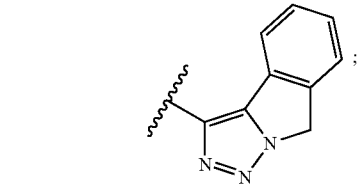

;

preferably is selected from

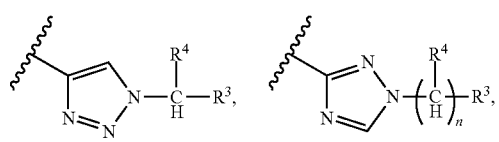

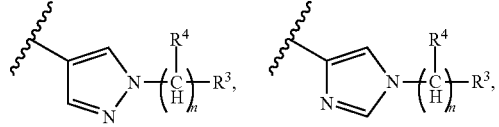

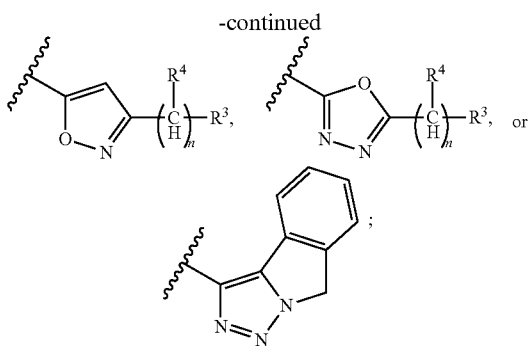

more preferably is selected from

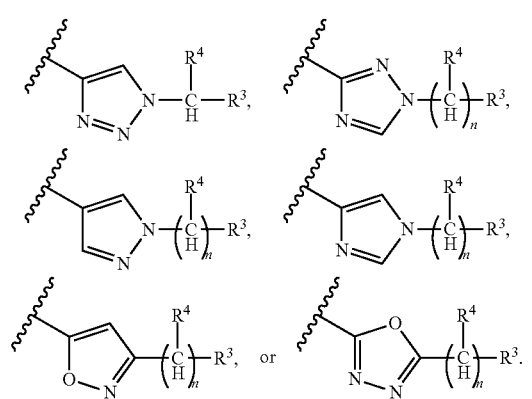

In another preferred embodiment of the compound according to the invention according to Formula I or II the compound according to formula I or II is selected from:

N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-((1R,2R)-2-hydroxycyclopentyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
4-(1-((1-phenyl-1H-1,2,3-triazol-4-yl)methyl)piperidin-4-yl)-1H-benzo[d]imidazole,
3-(1-((1-phenyl-1H-1,2,3-triazol-4-yl)methyl)piperidin-4-yl)-4-(trifluoromethyl)phenol,
4-(1-((1-phenyl-1H-1,2,3-triazol-4-yl)methyl)piperidin-4-yl)-1H-benzo[d]imidazol-2(3H)-one,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide,
N-methyl-3-(1-((1-phenyl-1H-1,2,3-triazol-4-yl)methyl)piperidin-4-yl)benzenesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
N-(3-(1-((1-phenyl-1H-1,2,3-triazol-4-yl)methyl)piperidin-4-yl)-4-(trifluoromethyl)phenyl)methanesulfonamide,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
N-(3-(1-((1-isopropyl-1H-1,2,3-triazol-4-yl)methyl)piperidin-4-yl)phenyl)methanesulfonamide,
3-(1-((1-isobutyl-1H-1,2,3-triazol-4-yl)methyl)piperidin-4-yl)phenol,
6-(1-((1-phenyl-1H-1,2,3-triazol-4-yl)methyl)piperidin-4-yl)-1H-indazole,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-N-(3-(1-((1-phenyl-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)indolin-2-one,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea,
N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
N,N-diethyl-2-(4-((4-(3-hydroxyphenyl)piperidin-1-yl)methyl)-1H-1,2,3-triazol-1-yl)acetamide,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine,
N-(3-(1-((1-(2,3-dihydro-1H-inden-1-yl)-1H-1,2,3-triazol-4-yl)methyl)piperidin-4-yl)phenyl)methanesulfonamide, N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
3-(1-((1-benzyl-1H-1,2,3-triazol-4-yl)methyl)piperidin-4-yl)-N-isopropylbenzamide,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
N-(3-(1-((1-(4,4-difluorocyclohexyl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propionamide,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
N-(6-(1-((1-phenyl-1H-1,2,3-triazol-4-yl)methyl)piperidin-4-yl)benzo[d]thiazol-2-yl)acetamide,
3-(1-((1-(1-(pyridin-2-yl)ethyl)-1H-1,2,3-triazol-4-yl)methyl)piperidin-4-yl)phenol,
N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
4-(3-(1H-tetrazol-5-yl)phenyl)-1-((1-phenyl-1H-1,2,3-triazol-4-yl)methyl)piperidine,
N-(3-(1-((1-(1-(pyridin-2-yl)ethyl)-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(5-(1-((1-benzyl-1H-1,2,3-triazol-4-yl)methyl)piperidin-4-yl)-2-fluorophenyl)methanesulfonamide,
N-(3-(1-((1-((1S,2S)-2-hydroxy-2,3-dihydro-1H-inden-1-yl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-((1S,2R)-1-hydroxy-2,3-dihydro-1H-inden-2-yl)-1H-1,2,3-triazol-4-yl)methyl)piperidin-4-yl)phenyl)methanesulfonamide,
N-(3-(1-((1-(pyridin-2-ylmethyl)-1H-1,2,3-triazol-4-yl)methyl)piperidin-4-yl)phenyl)methanesulfonamide,
N-(3-(1-((1-(pyridin-3-ylmethyl)-1H-1,2,3-triazol-4-yl)methyl)piperidin-4-yl)phenyl)methanesulfonamide,
N-(3-(1-((1-((1R,2R)-1-hydroxy-2,3-dihydro-1H-inden-2-yl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-2-methoxyphenyl)methanesulfonamide,
N-(3-(1-((1-(pyridin-2-ylmethyl)-1H-1,2,3-triazol-4-yl)methyl)piperidin-4-yl)phenyl)propionamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-((1S,2S)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-(2-hydroxy-2-methylpropoxy)phenyl)-1H-1,2,3-triazol-4-yl)methyl)piperidin-4-yl)phenol,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
3-(1-((1-(4-(2-hydroxyethoxy)phenyl)-1H-1,2,3-triazol-4-yl)methyl)piperidin-4-yl)phenol,
N-(3-((3R,4S)-3-hydroxy-1-((1-phenyl-1H-1,2,3-triazol-4-yl)methyl)piperidin-4-yl)phenyl)methanesulfonamide, 1-ethyl-3-(3-(1-((1-(pyridin-2-ylmethyl)-1H-1,2,3-triazol-4-yl)methyl)piperidin-4-yl)phenyl)urea,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-(1-((1-((6-(trifluoromethyl)pyridin-2-yl)methyl)-1H-1,2,3-triazol-4-yl)methyl)piperidin-4-yl)phenyl)propane-2-sulfonamide,
N-(3-(1-((1-((6-methylpyridin-2-yl)methyl)-1H-1,2,3-triazol-4-yl)methyl)piperidin-4-yl)phenyl)propane-2-sulfonamide,
N-(3-(1-((8H-[1,2,3]triazolo[5,1-a]isoindol-3-yl)methyl)piperidin-4-yl)phenyl)methanesulfonamide,
3-(1-((8H-[1,2,3]triazolo[5,1-a]isoindol-3-yl)methyl)piperidin-4-yl)phenol,
N-(3-(1-((1-((3-(trifluoromethyl)pyridin-2-yl)methyl)-1H-1,2,3-triazol-4-yl)methyl)piperidin-4-yl)phenyl)propane-2-sulfonamide,
N-(3-(1-((1-((5-(trifluoromethyl)pyridin-2-yl)methyl)-1H-1,2,3-triazol-4-yl)methyl)piperidin-4-yl)phenyl)propane-2-sulfonamide,
N-(3-((3R,4S)-1-((1-benzyl-1H-1,2,3-triazol-4-yl)methyl)-3-hydroxypiperidin-4-yl)phenyl)propane-2-sulfonamide,
N-(3-(1-((1-((6-(trifluoromethyl)pyridin-3-yl)methyl)-1H-1,2,3-triazol-4-yl)methyl)piperidin-4-yl)phenyl)propane-2-sulfonamide,
N-(3-((3R,4S)-3-hydroxy-1-((1-(pyridin-2-ylmethyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide,
N-(3-(1-((1-((4-azidopyridin-2-yl)methyl)-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)methanesulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol,
3-(1-((1-((3-fluoropyridin-2-yl)methyl)-1H-1,2,3-triazol-4-yl)methyl)piperidin-4-yl)phenol,
N-(3-(1-((1-((5-fluoropyridin-2-yl)methyl)-1H-1,2,3-triazol-4-yl)methyl)piperidin-4-yl)phenyl)propane-2-sulfonamide,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
N-methyl-3-(1-((1-(pyridin-2-ylmethyl)-1H-1,2,3-triazol-4-yl)methyl)piperidin-4-yl)benzenesulfonamide,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(pyridin-2-ylmethyl)-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-((3-chloropyridin-2-yl)methyl)-1H-1,2,3-triazol-4-yl)methyl)piperidin-4-yl)phenol,
3-(1-((1-(pyridin-3-ylmethyl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol,
3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
(R)-3-(1-((1-(2-hydroxy-1-phenylethyl)-1H-1,2,3-triazol-4-yl)methyl)piperidin-4-yl)phenol,
(S)-3-(1-((1-(2-hydroxy-1-phenylethyl)-1H-1,2,3-triazol-4-yl)methyl)piperidin-4-yl)phenol,
3-(1-((1-((3-(trifluoromethyl)pyridin-2-yl)methyl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(3-fluoropyridin-2-yl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
2-((4-((4-(3-hydroxyphenyl)piperidin-1-yl)methyl)-1H-1,2,3-triazol-1-yl)methyl)pyridin-3-ol,
3-(1-((1-(4-(trifluoromethyl)pyridin-2-yl)-1H-1,2,3-triazol-4-yl)methyl)piperidin-4-yl)phenol,
3-(1-((1-((3-methoxypyridin-2-yl)methyl)-1H-1,2,3-triazol-4-yl)methyl)piperidin-4-yl)phenol,
6-((4-((4-(3-hydroxyphenyl)piperidin-1-yl)methyl)-1H-1,2,3-triazol-1-yl)methyl)pyridin-3-ol,
3-(1-((1-((4-(trifluoromethyl)pyridin-2-yl)methyl)-1H-1,2,3-triazol-4-yl)methyl)piperidin-4-yl)phenol,
3-(1-((1-(3-chloropyridin-2-yl)-1H-1,2,3-triazol-4-yl)methyl)piperidin-4-yl)phenol,
3-(1-(2-(1-phenyl-1H-1,2,3-triazol-4-yl)ethyl)piperidin-4-yl)phenol,
N-(3-(1-((1-phenyl-1H-pyrazol-4-yl)methyl)piperidin-4-yl)phenyl)methanesulfonamide,
3-(1-((1-phenyl-1H-pyrazol-4-yl)methyl)piperidin-4-yl)phenol,
N-(3-((3R,4S)-3-hydroxy-1-((1-phenyl-1H-pyrazol-4-yl)methyl)piperidin-4-yl)phenyl)methanesulfonamide,
N-(3-(1-((1-((1R,2R)-2-hydroxy-2,3-dihydro-1H-inden-1-yl)-1H-pyrazol-4-yl)methyl)piperidin-4-yl)phenyl)methanesulfonamide,
N-(3-(1-((1-(pyridin-2-ylmethyl)-1H-pyrazol-4-yl)methyl)piperidin-4-yl)phenyl)propane-2-sulfonamide,
N-(3-(1-((1-(pyridin-2-ylmethyl)-1H-pyrazol-4-yl)methyl)piperidin-4-yl)phenyl)methanesulfonamide,
N-(3-((3R,4S)-3-hydroxy-1-((1-(pyridin-2-yl)-1H-pyrazol-4-yl)methyl)piperidin-4-yl)phenyl)propane-2-sulfonamide, N-(3-(1-((1-((6-fluoropyridin-2-yl)methyl)-1H-pyrazol-4-yl)methyl)piperidin-4-yl)phenyl)propane-2-sulfonamide,
3-(1-((1-(pyridin-2-ylmethyl)-1H-pyrazol-4-yl)methyl)piperidin-4-yl)phenol,
3-(1-((1-((3-fluoropyridin-2-yl)methyl)-1H-pyrazol-4-yl)methyl)piperidin-4-yl)phenol,
3-(1-((1-((5-fluoropyridin-2-yl)methyl)-1H-pyrazol-4-yl)methyl)piperidin-4-yl)phenol,
N-(3-(1-((3-phenylisoxazol-5-yl)methyl)piperidin-4-yl)phenyl)methanesulfonamide,
N-(3-(1-((5-phenyl-1,3,4-oxadiazol-2-yl)methyl)piperidin-4-yl)phenyl)methanesulfonamide,
3-(1-((3-phenylisoxazol-5-yl)methyl)piperidin-4-yl)phenol,
3-(1-((3-benzylisoxazol-5-yl)methyl)piperidin-4-yl)phenol,
N-(3-(1-((3-benzylisoxazol-5-yl)methyl)piperidin-4-yl)phenyl)methanesulfonamide,
N-(4-fluoro-3-(1-((3-phenylisoxazol-5-yl)methyl)piperidin-4-yl)phenyl)methanesulfonamide,
N-(2-fluoro-5-(1-((3-phenylisoxazol-5-yl)methyl)piperidin-4-yl)phenyl)methanesulfonamide,
N-(3-(1-((3-(pyridin-2-yl)isoxazol-5-yl)methyl)piperidin-4-yl)phenyl)propane-2-sulfonamide,
N-(3-(1-((1-phenyl-1H-1,2,4-triazol-3-yl)methyl)piperidin-4-yl)phenyl)methanesulfonamide,
N-(3-(1-((1-benzyl-1H-imidazol-4-yl)methyl)piperidin-4-yl)phenyl)methanesulfonamide,
3-(1-((1-benzyl-1H-imidazol-4-yl)methyl)piperidin-4-yl)phenol,
N-(3-(1-((1-benzyl-1H-imidazol-5-yl)methyl)piperidin-4-yl)phenyl)methanesulfonamide,
N-(3-(1-((1-(pyridin-2-ylmethyl)-1H-imidazol-4-yl)methyl)piperidin-4-yl)phenyl)propane-2-sulfonamide,
N-(3-(1-((1-(pyridin-2-ylmethyl)-1H-imidazol-5-yl)methyl)piperidin-4-yl)phenyl)propane-2-sulfonamide,
3-(1-((1-(pyridin-2-ylmethyl)-1H-imidazol-4-yl)methyl)piperidin-4-yl)phenol,
3-(1-((1-((3-fluoropyridin-2-yl)methyl)-1H-imidazol-4-yl)methyl)piperidin-4-yl)phenol,
N-(6-(1-((1-phenyl-1H-1,2,3-triazol-4-yl)methyl)piperidin-4-yl)pyridin-2-yl)propionamide,
N-(6-(1-((1-phenyl-1H-1,2,3-triazol-4-yl)methyl)piperidin-4-yl)pyridin-2-yl)methanesulfonamide
N-(2-(1-((1-phenyl-1H-1,2,3-triazol-4-yl)methyl)piperidin-4-yl)pyridin-4-yl)propionamide,
N-(2-(1-((1-phenyl-1H-1,2,3-triazol-4-yl)methyl)piperidin-4-yl)pyridin-4-yl)methanesulfonamide
N-(5-(1-((1-phenyl-1H-1,2,3-triazol-4-yl)methyl)piperidin-4-yl)pyridin-3-yl)methanesulfonamide
N-(5-(1-((1-phenyl-1H-1,2,3-triazol-4-yl)methyl)piperidin-4-yl)pyridin-3-yl)propionamide,
N-(4-(1-((1-phenyl-1H-1,2,3-triazol-4-yl)methyl)piperidin-4-yl)pyridin-2-yl)propionamide,
N-(4-(1-((1-phenyl-1H-1,2,3-triazol-4-yl)methyl)piperidin-4-yl)pyridin-2-yl)methanesulfonamide,
6-(1-((1-phenyl-1H-1,2,3-triazol-4-yl)methyl)piperidin-4-yl)pyridin-2-ol,
N-(6-(1-((1-benzyl-1H-1,2,3-triazol-4-yl)methyl)piperidin-4-yl)pyridin-2-yl)propionamide,
N-(6-(1-((3-phenylisoxazol-5-yl)methyl)piperidin-4-yl)pyridin-2-yl)methanesulfonamide,
N-(6-(1-((3-phenylisoxazol-5-yl)methyl)piperidin-4-yl)pyridin-2-yl)propionamide,
N-(6-(1-((1-phenyl-1H-pyrazol-4-yl)methyl)piperidin-4-yl)pyridin-2-yl)propionamide,
N-(6-(1-((1-phenyl-1H-pyrazol-4-yl)methyl)piperidin-4-yl)pyridin-2-yl)methanesulfonamide,
N-(6-(1-((1-((1R,2R)-2-hydroxy-2,3-dihydro-1H-inden-1-yl)-1H-1,2,3-triazol-4-yl)methyl)piperidin-4-yl)pyridin-2-yl)propionamide,
3-(1-((1-phenyl-1H-1,2,3-triazol-4-yl)methyl)piperidin-4-yl)pyridin-2-ol (not for Formula II),
N-(6-(1-((1-(pyridin-2-ylmethyl)-1H-1,2,3-triazol-4-yl)methyl)piperidin-4-yl)pyridin-2-yl)propane-2-sulfonamide,
N-(6-(1-((1-phenyl-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propane-2-sulfonamide,
N-(6-(1-((1-((3-fluoropyridin-2-yl)methyl)-1H-1,2,3-triazol-4-yl)methyl)piperidin-4-yl)pyridin-2-yl)propane-2-sulfonamide,
N-(6-(1-((1-((5-fluoropyridin-2-yl)methyl)-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propionamide,
N-(6-(1-((1-((3-chloropyridin-2-yl)methyl)-1H-1,2,3-triazol-4-yl)methyl)piperidin-4-yl)pyridin-2-yl)propane-2-sulfonamide, and
N-(6-(1-((1-((5-chloropyridin-2-yl)methyl)-1H-1,2,3-triazol-4-yl)methyl)piperidin-4-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to Formula I or II the compound is selected from
N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-((1R,2R)-2-hydroxycyclopentyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
4-(1-((1-phenyl-1H-1,2,3-triazol-4-yl)methyl)piperidin-4-yl)-1H-benzo[d]imidazole,
3-(1-((1-phenyl-1H-1,2,3-triazol-4-yl)methyl)piperidin-4-yl)-4-(trifluoromethyl)phenol,
4-(1-((1-phenyl-1H-1,2,3-triazol-4-yl)methyl)piperidin-4-yl)-1H-benzo[d]imidazol-2(3H)-one,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide, N-methyl-3-(1-((1-phenyl-1H-1,2,3-triazol-4-yl)methyl)piperidin-4-yl)benzenesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
N-(3-(1-((1-phenyl-1H-1,2,3-triazol-4-yl)methyl)piperidin-4-yl)-4-(trifluoromethyl)phenyl)methanesulfonamide,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
N-(3-(1-((1-isopropyl-1H-1,2,3-triazol-4-yl)methyl)piperidin-4-yl)phenyl)methanesulfonamide,
3-(1-((1-isobutyl-1H-1,2,3-triazol-4-yl)methyl)piperidin-4-yl)phenol,
6-(1-((1-phenyl-1H-1,2,3-triazol-4-yl)methyl)piperidin-4-yl)-1H-indazole,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-N-(3-(1-((1-phenyl-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)indolin-2-one,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea,
N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
N,N-diethyl-2-(4-((4-(3-hydroxyphenyl)piperidin-1-yl)methyl)-1H-1,2,3-triazol-1-yl)acetamide,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine,
N-(3-(1-((1-(2,3-dihydro-1H-inden-1-yl)-1H-1,2,3-triazol-4-yl)methyl)piperidin-4-yl)phenyl)methanesulfonamide,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
N-(3-(1-((1-(4,4-difluorocyclohexyl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propionamide,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
N-(6-(1-((1-phenyl-1H-1,2,3-triazol-4-yl)methyl)piperidin-4-yl)benzo[d]thiazol-2-yl)acetamide,
3-(1-((1-(1-(pyridin-2-yl)ethyl)-1H-1,2,3-triazol-4-yl)methyl)piperidin-4-yl)phenol,
N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol, 3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
N-(3-(1-((1-(1-(pyridin-2-yl)ethyl)-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(5-(1-((1-benzyl-1H-1,2,3-triazol-4-yl)methyl)piperidin-4-yl)-2-fluorophenyl)methanesulfonamide,
N-(3-(1-((1-((1S,2S)-2-hydroxy-2,3-dihydro-1H-inden-1-yl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-((1S,2R)-1-hydroxy-2,3-dihydro-1H-inden-2-yl)-1H-1,2,3-triazol-4-yl)methyl)piperidin-4-yl)phenyl)methanesulfonamide,
N-(3-(1-((1-(pyridin-2-ylmethyl)-1H-1,2,3-triazol-4-yl)methyl)piperidin-4-yl)phenyl)methanesulfonamide,
N-(3-(1-((1-(pyridin-3-ylmethyl)-1H-1,2,3-triazol-4-yl)methyl)piperidin-4-yl)phenyl)methanesulfonamide,
N-(3-(1-((1-((1R,2R)-1-hydroxy-2,3-dihydro-1H-inden-2-yl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-2-methoxyphenyl)methanesulfonamide,
N-(3-(1-((1-(pyridin-2-ylmethyl)-1H-1,2,3-triazol-4-yl)methyl)piperidin-4-yl)phenyl)propionamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-((1S,2S)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-(2-hydroxy-2-methylpropoxy)phenyl)-1H-1,2,3-triazol-4-yl)methyl)piperidin-4-yl)phenol,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
3-(1-((1-(4-(2-hydroxyethoxy)phenyl)-1H-1,2,3-triazol-4-yl)methyl)piperidin-4-yl)phenol,
N-(3-((3R,4S)-3-hydroxy-1-((1-phenyl-1H-1,2,3-triazol-4-yl)methyl)piperidin-4-yl)phenyl)methanesulfonamide,
1-ethyl-3-(3-(1-((1-(pyridin-2-ylmethyl)-1H-1,2,3-triazol-4-yl)methyl)piperidin-4-yl)phenyl)urea,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-(1-((1-((6-(trifluoromethyl)pyridin-2-yl)methyl)-1H-1,2,3-triazol-4-yl)methyl)piperidin-4-yl)phenyl)propane-2-sulfonamide,
N-(3-(1-((1-((6-methylpyridin-2-yl)methyl)-1H-1,2,3-triazol-4-yl)methyl)piperidin-4-yl)phenyl)propane-2-sulfonamide,
N-(3-(1-((8H-[1,2,3]triazolo[5,1-a]isoindol-3-yl)methyl)piperidin-4-yl)phenyl)methanesulfonamide,
3-(1-((8H-[1,2,3]triazolo[5,1-a]isoindol-3-yl)methyl)piperidin-4-yl)phenol,
N-(3-(1-((1-((3-(trifluoromethyl)pyridin-2-yl)methyl)-1H-1,2,3-triazol-4-yl)methyl)piperidin-4-yl)phenyl)propane-2-sulfonamide,
N-(3-(1-((1-((5-(trifluoromethyl)pyridin-2-yl)methyl)-1H-1,2,3-triazol-4-yl)methyl)piperidin-4-yl)phenyl)propane-2-sulfonamide,
N-(3-((3R,4S)-1-((1-benzyl-1H-1,2,3-triazol-4-yl)methyl)-3-hydroxypiperidin-4-yl)phenyl)propane-2-sulfonamide,
N-(3-(1-((1-((6-(trifluoromethyl)pyridin-3-yl)methyl)-1H-1,2,3-triazol-4-yl)methyl)piperidin-4-yl)phenyl)propane-2-sulfonamide,
N-(3-((3R,4S)-3-hydroxy-1-((1-(pyridin-2-ylmethyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide,
N-(3-(1-((1-((4-azidopyridin-2-yl)methyl)-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)methanesulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol,
3-(1-((1-((3-fluoropyridin-2-yl)methyl)-1H-1,2,3-triazol-4-yl)methyl)piperidin-4-yl)phenol,
N-(3-(1-((1-((5-fluoropyridin-2-yl)methyl)-1H-1,2,3-triazol-4-yl)methyl)piperidin-4-yl)phenyl)propane-2-sulfonamide,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol, 3-(1-((1-((3-chloropyridin-2-yl)methyl)-1H-1,2,3-triazol-4-yl)methyl)piperidin-4-yl)phenol,
3-(1-((1-(pyridin-3-ylmethyl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol,
3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
(R)-3-(1-((1-(2-hydroxy-1-phenylethyl)-1H-1,2,3-triazol-4-yl)methyl)piperidin-4-yl)phenol,
(S)-3-(1-((1-(2-hydroxy-1-phenylethyl)-1H-1,2,3-triazol-4-yl)methyl)piperidin-4-yl)phenol,
3-(1-((1-((3-(trifluoromethyl)pyridin-2-yl)methyl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(3-fluoropyridin-2-yl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
2-((4-((4-(3-hydroxyphenyl)piperidin-1-yl)methyl)-1H-1,2,3-triazol-1-yl)methyl)pyridin-3-ol,
3-(1-((1-(4-(trifluoromethyl)pyridin-2-yl)-1H-1,2,3-triazol-4-yl)methyl)piperidin-4-yl)phenol,
3-(1-((1-((3-methoxypyridin-2-yl)methyl)-1H-1,2,3-triazol-4-yl)methyl)piperidin-4-yl)phenol,
6-((4-((4-(3-hydroxyphenyl)piperidin-1-yl)methyl)-1H-1,2,3-triazol-1-yl)methyl)pyridin-3-ol,
3-(1-((1-((4-(trifluoromethyl)pyridin-2-yl)methyl)-1H-1,2,3-triazol-4-yl)methyl)piperidin-4-yl)phenol,
3-(1-((1-(3-chloropyridin-2-yl)-1H-1,2,3-triazol-4-yl)methyl)piperidin-4-yl)phenol,
3-(1-(2-(1-phenyl-1H-1,2,3-triazol-4-yl)ethyl)piperidin-4-yl)phenol,
N-(3-(1-((1-phenyl-1H-pyrazol-4-yl)methyl)piperidin-4-yl)phenyl)methanesulfonamide,
3-(1-((1-phenyl-1H-pyrazol-4-yl)methyl)piperidin-4-yl)phenol,
N-(3-((3R,4S)-3-hydroxy-1-((1-phenyl-1H-pyrazol-4-yl)methyl)piperidin-4-yl)phenyl)methanesulfonamide,
N-(3-(1-((1-((1R,2R)-2-hydroxy-2,3-dihydro-1H-inden-1-yl)-1H-pyrazol-4-yl)methyl)piperidin-4-yl)phenyl)methanesulfonamide,
N-(3-(1-((1-(pyridin-2-ylmethyl)-1H-pyrazol-4-yl)methyl)piperidin-4-yl)phenyl)propane-2-sulfonamide,
N-(3-(1-((1-(pyridin-2-ylmethyl)-1H-pyrazol-4-yl)methyl)piperidin-4-yl)phenyl)methanesulfonamide,
N-(3-((3R,4S)-3-hydroxy-1-((1-(pyridin-2-yl)-1H-pyrazol-4-yl)methyl)piperidin-4-yl)phenyl)propane-2-sulfonamide,
N-(3-(1-((1-((6-fluoropyridin-2-yl)methyl)-1H-pyrazol-4-yl)methyl)piperidin-4-yl)phenyl)propane 2-sulfonamide,
3-(1-((1-(pyridin-2-ylmethyl)-1H-pyrazol-4-yl)methyl)piperidin-4-yl)phenol,
3-(1-((1-((3-fluoropyridin-2-yl)methyl)-1H-pyrazol-4-yl)methyl)piperidin-4-yl)phenol,
3-(1-((1-((5-fluoropyridin-2-yl)methyl)-1H-pyrazol-4-yl)methyl)piperidin-4-yl)phenol,
N-(3-(1-((3-phenylisoxazol-5-yl)methyl)piperidin-4-yl)phenyl)methanesulfonamide,
N-(3-(1-((5-phenyl-1,3,4-oxadiazol-2-yl)methyl)piperidin-4-yl)phenyl)methanesulfonamide,
3-(1-((3-phenylisoxazol-5-yl)methyl)piperidin-4-yl)phenol,
3-(1-((3-benzylisoxazol-5-yl)methyl)piperidin-4-yl)phenol,
N-(3-(1-((3-benzylisoxazol-5-yl)methyl)piperidin-4-yl)phenyl)methanesulfonamide,
N-(4-fluoro-3-(1-((3-phenylisoxazol-5-yl)methyl)piperidin-4-yl)phenyl)methanesulfonamide,
N-(2-fluoro-5-(1-((3-phenylisoxazol-5-yl)methyl)piperidin-4-yl)phenyl)methanesulfonamide,
N-(3-(1-((3-(pyridin-2-yl)isoxazol-5-yl)methyl)piperidin-4-yl)phenyl)propane-2-sulfonamide,
N-(3-(1-((1-phenyl-1H-1,2,4-triazol-3-yl)methyl)piperidin-4-yl)phenyl)methanesulfonamide,
N-(3-(1-((1-benzyl-1H-imidazol-4-yl)methyl)piperidin-4-yl)phenyl)methanesulfonamide,
3-(1-((1-benzyl-1H-imidazol-4-yl)methyl)piperidin-4-yl)phenol,
N-(3-(1-((1-benzyl-1H-imidazol-5-yl)methyl)piperidin-4-yl)phenyl)methanesulfonamide,
N-(3-(1-((1-(pyridin-2-ylmethyl)-1H-imidazol-4-yl)methyl)piperidin-4-yl)phenyl)propane-2-sulfonamide,
N-(3-(1-((1-(pyridin-2-ylmethyl)-1H-imidazol-5-yl)methyl)piperidin-4-yl)phenyl)propane-2-sulfonamide,
3-(1-((1-(pyridin-2-ylmethyl)-1H-imidazol-4-yl)methyl)piperidin-4-yl)phenol,
3-(1-((1-((3-fluoropyridin-2-yl)methyl)-1H-imidazol-4-yl)methyl)piperidin-4-yl)phenol,
N-(6-(1-((1-phenyl-1H-1,2,3-triazol-4-yl)methyl)piperidin-4-yl)pyridin-2-yl)propionamide,
N-(6-(1-((1-phenyl-1H-1,2,3-triazol-4-yl)methyl)piperidin-4-yl)pyridin-2-yl)methanesulfonamide
N-(2-(1-((1-phenyl-1H-1,2,3-triazol-4-yl)methyl)piperidin-4-yl)pyridin-4-yl)propionamide,
N-(5-(1-((1-phenyl-1H-1,2,3-triazol-4-yl)methyl)piperidin-4-yl)pyridin-3-yl)propionamide,
N-(4-(1-((1-phenyl-1H-1,2,3-triazol-4-yl)methyl)piperidin-4-yl)pyridin-2-yl)propionamide,
N-(6-(1-((1-benzyl-1H-1,2,3-triazol-4-yl)methyl)piperidin-4-yl)pyridin-2-yl)propionamide,
N-(6-(1-((3-phenylisoxazol-5-yl)methyl)piperidin-4-yl)pyridin-2-yl)methanesulfonamide,
N-(6-(1-((3-phenylisoxazol-5-yl)methyl)piperidin-4-yl)pyridin-2-yl)propionamide,
N-(6-(1-((1-phenyl-1H-pyrazol-4-yl)methyl)piperidin-4-yl)pyridin-2-yl)propionamide,
N-(6-(1-((1-phenyl-1H-pyrazol-4-yl)methyl)piperidin-4-yl)pyridin-2-yl)methanesulfonamide,
N-(6-(1-((1-((1R,2R)-2-hydroxy-2,3-dihydro-1H-inden-1-yl)-1H-1,2,3-triazol-4-yl)methyl)piperidin-4-yl)pyridin-2-yl)propionamide,
3-(1-((1-phenyl-1H-1,2,3-triazol-4-yl)methyl)piperidin-4-yl)pyridin-2-ol,
N-(6-(1-((1-(pyridin-2-ylmethyl)-1H-1,2,3-triazol-4-yl)methyl)piperidin-4-yl)pyridin-2-yl)propane-2-sulfonamide,
N-(6-(1-((1-phenyl-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propane-2-sulfonamide,
N-(6-(1-((1-((3-fluoropyridin-2-yl)methyl)-1H-1,2,3-triazol-4-yl)methyl)piperidin-4-yl)pyridin-2-yl)propane-2-sulfonamide,
N-(6-(1-((1-((5-fluoropyridin-2-yl)methyl)-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propionamide, N-(6-(1-((1-((3-chloropyridin-2-yl)methyl)-1H-1,2,3-triazol-4-yl)methyl)piperidin-4-yl)pyridin-2-yl)propane-2-sulfonamide, and
N-(6-(1-((1-((5-chloropyridin-2-yl)methyl)-1H-1,2,3-triazol-4-yl)methyl)piperidin-4-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to Formula I or II the compound is selected from N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
3-(1-((1-isobutyl-1H-1,2,3-triazol-4-yl)methyl)piperidin-4-yl)phenol,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea,
N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine,
N-(3-(1-((1-(2,3-dihydro-1H-inden-1-yl)-1H-1,2,3-triazol-4-yl)methyl)piperidin-4-yl)phenyl)methanesulfonamide,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
3-(1-((1-(1-(pyridin-2-yl)ethyl)-1H-1,2,3-triazol-4-yl)methyl)piperidin-4-yl)phenol, N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-(pyridin-3-ylmethyl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol,
3-(1-((1-((3-fluoropyridin-2-yl)methyl)-1H-1,2,3-triazol-4-yl)methyl)piperidin-4-yl)phenol,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-((3-chloropyridin-2-yl)methyl)-1H-1,2,3-triazol-4-yl)methyl)piperidin-4-yl)phenol,
3-(1-((1-(pyridin-3-ylmethyl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol,
3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
(R)-3-(1-((1-(2-hydroxy-1-phenylethyl)-1H-1,2,3-triazol-4-yl)methyl)piperidin-4-yl)phenol,
(S)-3-(1-((1-(2-hydroxy-1-phenylethyl)-1H-1,2,3-triazol-4-yl)methyl)piperidin-4-yl)phenol,
3-(1-((1-((3-(trifluoromethyl)pyridin-2-yl)methyl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(3-fluoropyridin-2-yl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
3-(1-((1-(4-(trifluoromethyl)pyridin-2-yl)-1H-1,2,3-triazol-4-yl)methyl)piperidin-4-yl)phenol,
6-((4-((4-(3-hydroxyphenyl)piperidin-1-yl)methyl)-1H-1,2,3-triazol-1-yl)methyl)pyridin-3-ol,
3-(1-((1-(4-(trifluoromethyl)pyridin-2-yl)methyl)-1H-1,2,3-triazol-4-yl)methyl)piperidin-4-yl)phenol,
3-(1-((1-(3-chloropyridin-2-yl)-1H-1,2,3-triazol-4-yl)methyl)piperidin-4-yl)phenol,
3-(1-(2-(1-phenyl-1H-1,2,3-triazol-4-yl)ethyl)piperidin-4-yl)phenol,
N-(3-(1-((1-phenyl-1H-pyrazol-4-yl)methyl)piperidin-4-yl)phenyl)methanesulfonamide,
3-(1-((1-phenyl-1H-pyrazol-4-yl)methyl)piperidin-4-yl)phenol,
N-(3-((3R,4S)-3-hydroxy-1-((1-phenyl-1H-pyrazol-4-yl)methyl)piperidin-4-yl)phenyl)methanesulfonamide,
N-(3-(1-((1-(pyridin-2-ylmethyl)-1H-pyrazol-4-yl)methyl)piperidin-4-yl)phenyl)propane-2-sulfonamide,
N-(3-(1-((1-(pyridin-2-ylmethyl)-1H-pyrazol-4-yl)methyl)piperidin-4-yl)phenyl)methanesulfonamide,
N-(3-(1-((1-((6-fluoropyridin-2-yl)methyl)-1H-pyrazol-4-yl)methyl)piperidin-4-yl)phenyl)propane 2-sulfonamide,
3-(1-((1-(pyridin-2-ylmethyl)-1H-pyrazol-4-yl)methyl)piperidin-4-yl)phenol, 3-(1-((1-((5-fluoropyridin-2-yl)methyl)-1H-pyrazol-4-yl)methyl)piperidin-4-yl)phenol,
N-(3-(1-((3-phenylisoxazol-5-yl)methyl)piperidin-4-yl)phenyl)methanesulfonamide,
3-(1-((3-phenylisoxazol-5-yl)methyl)piperidin-4-yl)phenol,
3-(1-((3-benzylisoxazol-5-yl)methyl)piperidin-4-yl)phenol,
N-(3-(1-((3-benzylisoxazol-5-yl)methyl)piperidin-4-yl)phenyl)methanesulfonamide,
N-(4-fluoro-3-(1-((3-phenylisoxazol-5-yl)methyl)piperidin-4-yl)phenyl)methanesulfonamide,
N-(2-fluoro-5-(1-((3-phenylisoxazol-5-yl)methyl)piperidin-4-yl)phenyl)methanesulfonamide,
N-(3-(1-((1-phenyl-1H-1,2,4-triazol-3-yl)methyl)piperidin-4-yl)phenyl)methanesulfonamide,
N-(3-(1-((1-benzyl-1H-imidazol-4-yl)methyl)piperidin-4-yl)phenyl)methanesulfonamide,
3-(1-((1-benzyl-1H-imidazol-4-yl)methyl)piperidin-4-yl)phenol,
N-(3-(1-((1-benzyl-1H-imidazol-5-yl)methyl)piperidin-4-yl)phenyl)methanesulfonamide,
N-(3-(1-((1-(pyridin-2-ylmethyl)-1H-imidazol-4-yl)methyl)piperidin-4-yl)phenyl)propane-2-sulfonamide,
N-(3-(1-((1-(pyridin-2-ylmethyl)-1H-imidazol-5-yl)methyl)piperidin-4-yl)phenyl)propane-2-sulfonamide,
3-(1-((1-(pyridin-2-ylmethyl)-1H-imidazol-4-yl)methyl)piperidin-4-yl)phenol,
3-(1-((1-((3-fluoropyridin-2-yl)methyl)-1H-imidazol-4-yl)methyl)piperidin-4-yl)phenol,
N-(6-(1-((1-phenyl-1H-1,2,3-triazol-4-yl)methyl)piperidin-4-yl)pyridin-2-yl)propionamide,
N-(6-(1-((1-phenyl-1H-1,2,3-triazol-4-yl)methyl)piperidin-4-yl)pyridin-2-yl)methanesulfonamide
N-(6-(1-((3-phenylisoxazol-5-yl)methyl)piperidin-4-yl)pyridin-2-yl)methanesulfonamide,
N-(6-(1-((3-phenylisoxazol-5-yl)methyl)piperidin-4-yl)pyridin-2-yl)propionamide,
N-(6-(1-((1-phenyl-1H-pyrazol-4-yl)methyl)piperidin-4-yl)pyridin-2-yl)propionamide,
N-(6-(1-((1-phenyl-1H-pyrazol-4-yl)methyl)piperidin-4-yl)pyridin-2-yl)methanesulfonamide,
N-(6-(1-((1-(pyridin-2-ylmethyl)-1H-1,2,3-triazol-4-yl)methyl)piperidin-4-yl)pyridin-2-yl)propane-2-sulfonamide,
N-(6-(1-((1-phenyl-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propane-2-sulfonamide, and
N-(6-(1-((1-(2-fluorophenyl)-1H-1,2,3-triazol-4-yl)methyl)piperidin-4-yl)pyridin-2-yl)propionamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another preferred embodiment of the compound according to the invention according to Formula I or II the compound is selected from
N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-benzyl-1H-1,2,3-triazol-4-yl)methyl)piperidin-4-yl)phenol,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
3-(1-((1-isobutyl-1H-1,2,3-triazol-4-yl)methyl)piperidin-4-yl)phenol,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
3-(1-((1-(2,3-dihydro-1H-inden-1-yl)-1H-1,2,3-triazol-4-yl)methyl)piperidin-4-yl)phenol,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
3-(1-((1-(1-phenylethyl)-1H-1,2,3-triazol-4-yl)methyl)piperidin-4-yl)phenol,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
3-(1-((1-(benzofuran-3-yl)-1H-1,2,3-triazol-4-yl)methyl)piperidin-4-yl)phenol,
3-(1-((1-phenyl-1H-1,2,3-triazol-4-yl)methyl)piperidin-4-yl)aniline,
3-(1-((1-(4-hydroxyphenyl)-1H-1,2,3-triazol-4-yl)methyl)piperidin-4-yl)phenol,
N-(3-(1-((1-((6-methoxypyridin-2-yl)methyl)-1H-1,2,3-triazol-4-yl)methyl)piperidin-4-yl)phenyl)propane-2-sulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol, 3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
3-(1-(2-(1-phenyl-1H-1,2,3-triazol-4-yl)ethyl)piperidin-4-yl)phenol,
N-(3-(1-((1-phenyl-1H-pyrazol-4-yl)methyl)piperidin-4-yl)phenyl)methanesulfonamide,
3-(1-((1-phenyl-1H-pyrazol-4-yl)methyl)piperidin-4-yl)phenol,
N-(3-(1-((1-((6-fluoropyridin-2-yl)methyl)-1H-pyrazol-4-yl)methyl)piperidin-4-yl)phenyl)propane-2-sulfonamide,
N-(3-(1-((3-phenylisoxazol-5-yl)methyl)piperidin-4-yl)phenyl)methanesulfonamide,
3-(1-((3-phenylisoxazol-5-yl)methyl)piperidin-4-yl)phenol,
3-(1-((3-benzylisoxazol-5-yl)methyl)piperidin-4-yl)phenol,
3-(1-((1-benzyl-1H-imidazol-4-yl)methyl)piperidin-4-yl)phenol,
N-(6-(1-((1-phenyl-1H-pyrazol-4-yl)methyl)piperidin-4-yl)pyridin-2-yl)propionamide, and
N-(6-(1-((1-phenyl-1H-pyrazol-4-yl)methyl)piperidin-4-yl)pyridin-2-yl)methanesulfonamide;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In general the compounds according to the invention may be selected from the following table. The Table lists the compounds by name (Compound) giving the number (Ex) which refers to the corresponding compound in the experimental part. In addition, the table gives an overview which compound would fall under which General Formula with their given definition that are reflected in the claims below. A box with a "0" indicates that this compound would not fall under the definitions of this General Formula.

In addition, the other numbers in the table indicate whether the corresponding compound:
1=would be selected,
2=would be preferably selected,
3=would be more preferably selected,
4=would be the most preferably selected
if falling under the general formula. This allows forming corresponding lists of selected compounds for further preferred embodiments.

| | | General Formula | | | | | | |
|---|---|---|---|---|---|---|---|---|
| Ex. | Compound | I | II | III | IV | V | VI | VII |
| 1. | N-(3-(1-((1-phenyl-1H-1,2,3-triazol-4-yl)methyl)piperidin-4-yl)phenyl)propane-2-sulfonamide, | 4 | 4 | 4 | 4 | 0 | 4 | 4 |
| 2. | 3-(1-((1-phenyl-1H-1,2,3-triazol-4-yl)methyl)piperidin-4-yl)phenol, | 4 | 4 | 4 | 4 | 0 | 4 | 4 |
| 3. | 3-(1-((1-propyl-1H-1,2,3-triazol-4-yl)methyl)piperidin-4-yl)phenol, | 3 | 3 | 3 | 3 | 0 | 0 | 3 |
| 4. | 3-(1-((1-(2-fluorobenzyl)-1H-1,2,3-triazol-4-yl)methyl)piperidin-4-yl)phenol, | 4 | 4 | 4 | 4 | 0 | 4 | 4 |
| 5. | 3-(1-((1-(((1R,2R)-2-hydroxycyclopentyl)-1H-1,2,3-triazol-4-yl)methyl)piperidin-4-yl)phenol, | 2 | 2 | 2 | 2 | 0 | 2 | 2 |
| 6. | 3-(1-((1-phenyl-1H-1,2,3-triazol-4-yl)methyl)piperidin-4-yl)benzamide, | 3 | 3 | 3 | 3 | 0 | 3 | 3 |
| 7. | N-(3-(1-((1-phenyl-1H-1,2,3-triazol-4-yl)methyl)piperidin-4-yl)phenyl)propionamide, | 3 | 3 | 3 | 3 | 0 | 3 | 3 |
| 8. | 3-(1-((1-benzyl-1H-1,2,3-triazol-4-yl)methyl)piperidin-4-yl)phenol, | 4 | 4 | 4 | 4 | 0 | 4 | 4 |
| 9. | N-(3-(1-((1-phenyl-1H-1,2,3-triazol-4-yl)methyl)piperidin-4-yl)phenyl)acetamide, | 3 | 3 | 3 | 3 | 0 | 3 | 3 |
| 10. | 3-(1-((1-(pyridin-3-yl)-1H-1,2,3-triazol-4-yl)methyl)piperidin-4-yl)phenol, | 3 | 3 | 3 | 3 | 0 | 3 | 3 |
| 11. | 4-(1-((1-phenyl-1H-1,2,3-triazol-4-yl)methyl)piperidin-4-yl)-1H-benzo[d]imidazole, | 2 | 2 | 2 | 2 | 0 | 2 | 2 |
| 12. | 3-(1-((1-phenyl-1H-1,2,3-triazol-4-yl)methyl)piperidin-4-yl)-4-(trifluoromethyl)phenol, | 2 | 2 | 2 | 2 | 0 | 2 | 2 |
| 13. | 4-(1-((1-phenyl-1H-1,2,3-triazol-4-yl)methyl)piperidin-4-yl)-1H-benzo[d]imidazol-2(3H)-one, | 2 | 2 | 2 | 2 | 0 | 2 | 2 |
| 14. | 3-(1-((1-(pyridin-4-yl)-1H-1,2,3-triazol-4-yl)methyl)piperidin-4-yl)phenol, | 3 | 3 | 3 | 3 | 0 | 3 | 3 |
| 15. | (1R,2R)-1-(4-((4-(3-hydroxyphenyl)piperidin-1-yl)methyl)-1H-1,2,3-triazol-1-yl)-2,3-dihydro-1H-inden-2-ol, | 3 | 3 | 3 | 3 | 0 | 3 | 3 |
| 16. | N-(3-(1-((1-(4-fluorophenyl)-1H-1,2,3-triazol-4-yl)methyl)piperidin-4-yl)phenyl)methanesulfonamide, | 3 | 3 | 3 | 3 | 0 | 3 | 3 |
| 17. | N-methyl-3-(1-((1-phenyl-1H-1,2,3-triazol-4-yl)methyl)piperidin-4-yl)benzenesulfonamide, | 2 | 2 | 2 | 2 | 0 | 2 | 2 |
| 18. | N-(4-fluoro-3-(1-((1-phenyl-1H-1,2,3-triazol-4-yl)methyl)piperidin-4-yl)phenyl)methanesulfonamide, | 4 | 4 | 4 | 4 | 0 | 4 | 4 |
| 19. | 3-(1-((1-cyclohexyl-1H-1,2,3-triazol-4-yl)methyl)piperidin-4-yl)phenol, | 4 | 4 | 4 | 4 | 0 | 4 | 4 |

-continued

| Ex. | Compound | General Formula | | | | | | |
|---|---|---|---|---|---|---|---|---|
| | | I | II | III | IV | V | VI | VII |
| 20. | N-(3-(1-((1-phenyl-1H-1,2,3-triazol-4-yl)methyl)piperidin-4-yl)-4-(trifluoromethyl)phenyl)methanesulfonamide, | 2 | 2 | 2 | 2 | 0 | 2 | 2 |
| 21. | 6-(1-((1-phenyl-1H-1,2,3-triazol-4-yl)methyl)piperidin-4-yl)-1H-benzo[d]imidazole, | 3 | 3 | 3 | 3 | 0 | 3 | 3 |
| 22. | N-(3-(1-((1-cyclohexyl-1H-1,2,3-triazol-4-yl)methyl)piperidin-4-yl)phenyl)methanesulfonamide, | 3 | 3 | 3 | 3 | 0 | 3 | 3 |
| 23. | 3-(1-((1-isopropyl-1H-1,2,3-triazol-4-yl)methyl)piperidin-4-yl)phenol, | 3 | 3 | 3 | 3 | 0 | 0 | 3 |
| 24. | N-(3-(1-((1-isopropyl-1H-1,2,3-triazol-4-yl)methyl)piperidin-4-yl)phenyl)methanesulfonamide, | 2 | 2 | 2 | 2 | 0 | 0 | 2 |
| 25. | 3-(1-((1-isobutyl-1H-1,2,3-triazol-4-yl)methyl)piperidin-4-yl)phenol, | 4 | 4 | 4 | 4 | 0 | 0 | 4 |
| 26. | 6-(1-((1-phenyl-1H-1,2,3-triazol-4-yl)methyl)piperidin-4-yl)-1H-indazole, | 2 | 2 | 2 | 2 | 0 | 2 | 2 |
| 27. | N-(3-(1-((1-(2-fluorophenyl)-1H-1,2,3-triazol-4-yl)methyl)piperidin-4-yl)phenyl)methanesulfonamide, | 4 | 4 | 4 | 4 | 0 | 4 | 4 |
| 28. | N-(3-(1-((1-(3-fluorophenyl)-1H-1,2,3-triazol-4-yl)methyl)piperidin-4-yl)phenyl)methanesulfonamide, | 4 | 4 | 4 | 4 | 0 | 4 | 4 |
| 29. | 4-(1-((1-phenyl-1H-1,2,3-triazol-4-yl)methyl)piperidin-4-yl)-1H-indazole, | 3 | 3 | 3 | 3 | 0 | 3 | 3 |
| 30. | 4-(3-(1H-imidazol-2-yl)phenyl)-1-((1-phenyl-1H-1,2,3-triazol-4-yl)methyl)piperidine, | 3 | 3 | 3 | 3 | 0 | 3 | 3 |
| 31. | N-methyl-N-(3-(1-((1-phenyl-1H-1,2,3-triazol-4-yl)methyl)piperidin-4-yl)phenyl)methanesulfonamide, | 2 | 2 | 2 | 2 | 0 | 2 | 2 |
| 32. | 4-(1-((1-phenyl-1H-1,2,3-triazol-4-yl)methyl)piperidin-4-yl)indolin-2-one, | 2 | 2 | 2 | 2 | 0 | 2 | 2 |
| 33. | N-methyl-3-(1-((1-phenyl-1H-1,2,3-triazol-4-yl)methyl)piperidin-4-yl)benzamide, | 3 | 3 | 3 | 3 | 0 | 3 | 3 |
| 34. | N-(2-fluoro-5-(1-((1-phenyl-1H-1,2,3-triazol-4-yl)methyl)piperidin-4-yl)phenyl)methanesulfonamide, | 3 | 3 | 3 | 3 | 0 | 3 | 3 |
| 35. | N-(3-fluoro-5-(1-((1-phenyl-1H-1,2,3-triazol-4-yl)methyl)piperidin-4-yl)phenyl)methanesulfonamide, | 4 | 4 | 4 | 4 | 0 | 4 | 4 |
| 36. | 3-(1-((1-(4-fluorophenyl)-1H-1,2,3-triazol-4-yl)methyl)piperidin-4-yl)phenol, | 3 | 3 | 3 | 3 | 0 | 3 | 3 |
| 37. | N-(3-(1-((1-benzyl-1H-1,2,3-triazol-4-yl)methyl)piperidin-4-yl)phenyl)methanesulfonamide, | 3 | 3 | 3 | 3 | 0 | 3 | 3 |
| 38. | 1,1-dimethyl-3-(3-(1-((1-phenyl-1H-1,2,3-triazol-4-yl)methyl)piperidin-4-yl)phenyl)urea, | 3 | 3 | 3 | 3 | 0 | 3 | 3 |
| 39. | N-(3-fluoro-5-(1-((1-phenyl-1H-1,2,3-triazol-4-yl)methyl)piperidin-4-yl)phenyl)acetamide, | 3 | 3 | 3 | 3 | 0 | 3 | 3 |
| 40. | 3-(1-((1-(3,4-dichlorophenyl)-1H-1,2,3-triazol-4-yl)methyl)piperidin-4-yl)phenol, | 4 | 4 | 4 | 4 | 0 | 4 | 4 |
| 41. | 3-(1-((1-(2,4-dichlorophenyl)-1H-1,2,3-triazol-4-yl)methyl)piperidin-4-yl)phenol, | 4 | 4 | 4 | 4 | 0 | 4 | 4 |
| 42. | 2-methyl-5-(3-(1-((1-phenyl-1H-1,2,3-triazol-4-yl)methyl)piperidin-4-yl)phenyl)-1,3,4-oxadiazole, | 3 | 3 | 3 | 3 | 0 | 3 | 3 |
| 43. | 4-((4-((4-(3-hydroxyphenyl)piperidin-1-yl)methyl)-1H-1,2,3-triazol-1-yl)methyl)benzonitrile, | 4 | 4 | 4 | 4 | 0 | 4 | 4 |
| 44. | 3-(1-((1-(3-methoxyphenyl)-1H-1,2,3-triazol-4-yl)methyl)piperidin-4-yl)phenol, | 4 | 4 | 4 | 4 | 0 | 4 | 4 |
| 45. | N,N-diethyl-2-(4-((4-(3-hydroxyphenyl)piperidin-1-yl)methyl)-1H-1,2,3-triazol-1-yl)acetamide, | 2 | 2 | 2 | 2 | 0 | 0 | 2 |
| 46. | 3-(1-((1-(2,3-dihydro-1H-inden-1-yl)-1H-1,2,3-triazol-4-yl)methyl)piperidin-4-yl)phenol, | 4 | 4 | 4 | 4 | 0 | 4 | 4 |
| 47. | 4-(3-(methylsulfonyl)phenyl)-1-((1-phenyl-1H-1,2,3-triazol-4-yl)methyl)piperidine, | 3 | 3 | 3 | 3 | 0 | 3 | 3 |
| 48. | N-(3-(1-((1-(2,3-dihydro-1H-inden-1-yl)-1H-1,2,3-triazol-4-yl)methyl)piperidin-4-yl)phenyl)methanesulfonamide, | 3 | 3 | 3 | 3 | 0 | 3 | 3 |
| 49. | N-(4-((1-(1-phenyl-1H-1,2,3-triazol-4-yl)methyl)piperidin-4-yl)benzo[d]thiazol-2-yl)acetamide, | 4 | 4 | 4 | 4 | 0 | 4 | 4 |
| 50. | 4-(1-((1-phenyl-1H-1,2,3-triazol-4-yl)methyl)piperidin-4-yl)benzo[d]thiazol-2-amine, | 4 | 4 | 4 | 4 | 0 | 4 | 4 |
| 51. | 3-(1-((1-benzyl-1H-1,2,3-triazol-4-yl)methyl)piperidin-4-yl)-N-isopropylbenzamide, | 1 | 1 | 1 | 1 | 0 | 1 | 1 |

-continued

| | | General Formula | | | | | | |
|---|---|---|---|---|---|---|---|---|
| Ex. | Compound | I | II | III | IV | V | VI | VII |
| 52. | 2-methyl-5-(1-((1-phenyl-1H-1,2,3-triazol-4-yl)methyl)piperidin-4-yl)phenol, | 4 | 4 | 4 | 4 | 0 | 4 | 4 |
| 53. | N-(2-fluoro-3-(1-((1-phenyl-1H-1,2,3-triazol-4-yl)methy)piperidin-4-yl)phenyl)methanesulfonamide, | 4 | 4 | 4 | 4 | 0 | 4 | 4 |
| 54. | 3-(1-((1-(pyridin-4-ylmethyl)-1H-1,2,3-triazol-4-yl)methyl)piperidin-4-yl)phenol, | 3 | 3 | 3 | 3 | 0 | 3 | 3 |
| 55. | 3-(1-((1-(pyridin-2-ylmethyl)-1H-1,2,3-triazol-4-yl)methyl)piperidin-4-yl)phenol, | 3 | 3 | 3 | 3 | 0 | 3 | 3 |
| 56. | 1-ethyl-3-(3-(1-((1-phenyl-1H-1,2,3-triazol-4-yl)methyl)piperidin-4-yl)phenyl)urea, | 3 | 3 | 3 | 3 | 0 | 3 | 3 |
| 57. | N-(3-(1-((1-(4-(trifluoromethyl)benzyl)-1H-1,2,3-triazol-4-yl)methyl)piperidin-4-yl)phenyl)methanesulfonamide, | 3 | 3 | 3 | 3 | 0 | 3 | 3 |
| 58. | 2-(4-((4-(3-hydroxyphenyl)piperidin-1-yl)methyl)-1H-1,2,3-triazol-1-yl)phenol, | 3 | 3 | 3 | 3 | 0 | 3 | 3 |
| 59. | 3-(1-((1-(6-methoxypyridin-3-yl)-1H-1,2,3-triazol-4-yl)methyl)piperidin-4-yl)phenol, | 4 | 4 | 4 | 4 | 0 | 4 | 4 |
| 60. | 3-(1-((1-(6-(trifluoromethyl)pyridin-3-yl)-1H-1,2,3-triazol-4-yl)methyl)piperidin-4-yl)phenol, | 4 | 4 | 4 | 4 | 0 | 4 | 4 |
| 61. | 3-(1-((1-((1R,2R)-2-methoxy-2,3-dihydro-1H-inden-1-yl)-1H-1,2,3-triazol-4-yl)methyl)piperidin-4-yl)phenol, | 4 | 4 | 4 | 4 | 0 | 4 | 4 |
| 62. | N-(3-(1-((1-phenyl-1H-1,2,3-triazol-4-yl)methyl)piperidin-4-yl)phenyl)methanesulfonamide, | 4 | 4 | 4 | 4 | 0 | 4 | 4 |
| 63. | 3-(1-((1-(3-fluorobenzyl)-1H-1,2,3-triazol-4-yl)methyl)piperidin-4-yl)phenol, | 4 | 4 | 4 | 4 | 0 | 4 | 4 |
| 64. | 3-(1-((1-(4,4-difluorocyclohexyl)-1H-1,2,3-triazol-4-yl)methyl)piperidin-4-yl)phenol, | 4 | 4 | 4 | 4 | 0 | 4 | 4 |
| 65. | (1S,2S)-1-(4-((4-(3-hydroxyphenyl)piperidin-1-yl)methyl)-1H-1,2,3-triazol-1-yl)-2,3-dihydro-1H-inden-2-ol, | 3 | 3 | 3 | 3 | 0 | 3 | 3 |
| 66. | 3-(1-((1-((1R,2R)-2-hydroxycyclohexyl)-1H-1,2,3-triazol-4-yl)methyl)piperidin-4-yl)phenol, | 3 | 3 | 3 | 3 | 0 | 3 | 3 |
| 67. | 3-(1-((1-(2-hydroxy-1-phenylethyl)-1H-1,2,3-triazol-4-yl)methyl)piperidin-4-yl)phenol, | 3 | 3 | 3 | 3 | 0 | 3 | 3 |
| 68. | N-(3-(1-((1-(4,4-difluorocyclohexyl)-1H-1,2,3-triazol-4-yl)methyl)piperidin-4-yl)phenyl)methanesulfonamide, | 2 | 2 | 2 | 2 | 0 | 2 | 2 |
| 69. | N-(3-(1-((1-((1R,2R)-2-hydroxy-2,3-dihydro-1H-inden-1-yl)-1H-1,2,3-triazol-4-yl)methyl)piperidin-4-yl)phenyl)propionamide, | 2 | 2 | 2 | 2 | 0 | 2 | 2 |
| 70. | N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide, | 2 | 2 | 2 | 2 | 0 | 2 | 2 |
| 71. | 3-(1-((1-((1S,2R)-1-fluoro-2,3-dihydro-1H-inden-2-yl)-1H-1,2,3-triazol-4-yl)methyl)piperidin-4-yl)phenol, | 4 | 4 | 4 | 4 | 0 | 4 | 4 |
| 72. | 3-(1-((1-((1R,2R)-1-fluoro-2,3-dihydro-1H-inden-2-yl)-1H-1,2,3-triazol-4-yl)methyl)piperidin-4-yl)phenol, | 4 | 4 | 4 | 4 | 0 | 4 | 4 |
| 73. | 6-(1-((1-phenyl-1H-1,2,3-triazol-4-yl)methyl)piperidin-4-yl)benzo[d]thiazol-2-amine, | 3 | 3 | 3 | 3 | 0 | 3 | 3 |
| 74. | N-(6-(1-((1-phenyl-1H-1-1,2,3-triazol-4-yl)methyl)piperidin-4-yl)benzo[d]thiazol-2-yl)acetamide, | 2 | 2 | 2 | 2 | 0 | 2 | 2 |
| 75. | 3-(1-((1-(1-(pyridin-2-yl)ethyl)-1H-1,2,3-triazol-4-yl)methyl)piperidin-4-yl)phenol, | 3 | 3 | 3 | 3 | 0 | 3 | 3 |
| 76. | N-(3-(1-((1-(1-phenylethyl)-1H-1,2,3-triazol-4-yl)methyl)piperidin-4-yl)phenyl)methanesulfonamide, | 3 | 3 | 3 | 3 | 0 | 3 | 3 |
| 77. | 3-(1-((1-(1-phenylethyl)-1H-1,2,3-triazol-4-yl)methyl)piperidin-4-yl)phenol, | 4 | 4 | 4 | 4 | 0 | 4 | 4 |
| 78. | (1R,2R)-1-(4-((4-(3-hydroxyphenyl)piperidin-1-yl)methyl)-1H-1,2,3-triazol-1-yl)-2,3-dihydro-1H-inden-2-ol, | 3 | 3 | 3 | 3 | 0 | 3 | 3 |
| 79. | N-(3-(1-((1-benzyl-1H-1,2,3-triazol-4-yl)methyl)piperidin-4-yl)phenyl)propane-2-sulfonamide, | 3 | 3 | 3 | 3 | 0 | 3 | 3 |
| 80. | N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide, | 3 | 3 | 3 | 3 | 0 | 3 | 3 |

| Ex. | Compound | General Formula | | | | | | |
|---|---|---|---|---|---|---|---|---|
| | | I | II | III | IV | V | VI | VII |
| 81. | N-(3-(1-((1-(pyridin-2-ylmethyl)-1H-1,2,3-triazol-4-yl)methyl)piperidin-4-yl)phenyl)propane-2-sulfonamide, | 3 | 3 | 3 | 3 | 0 | 3 | 3 |
| 82. | 3-(1-((1-((1s,4s)-4-(trifluoromethyl)cyclohexyl)-1H-1,2,3-triazol-4-yl)methyl)piperidin-4-yl)phenol, | 4 | 4 | 4 | 4 | 0 | 4 | 4 |
| 83. | 3-(1-((1-((1r,4r)-4-(trifluoromethyl)cyclohexyl)-1H-1,2,3-triazol-4-yl)methyl)piperidin-4-yl)phenol, | 4 | 4 | 4 | 4 | 0 | 4 | 4 |
| 84. | 3-(1-((1-(pyridin-2-yl)-1H-1,2,3-triazol-4-yl)methyl)piperidin-4-yl)phenol, | 4 | 4 | 4 | 4 | 0 | 4 | 4 |
| 85. | 4-(3-(1H-tetrazol-5-yl)phenyl)-1-((1-phenyl-1H-1,2,3-triazol-4-yl)methyl)piperidine, | 1 | 1 | 1 | 1 | 0 | 1 | 1 |
| 86. | N-(3-(1-((1-(1-(pyridin-2-yl)ethyl)-1H-1,2,3-triazol-4-yl)methyl)piperidin-4-yl)phenyl)methanesulfonamide, | 2 | 2 | 2 | 2 | 0 | 2 | 2 |
| 87. | N-(3-(1-((1-benzyl-1H-1,2,3-triazol-4-yl)methyl)piperidin-4-yl)-4-fluorophenyl)methanesulfonamide, | 3 | 3 | 3 | 3 | 0 | 3 | 3 |
| 88. | (1R,2S)-1-(4-((4-(3-hydroxyphenyl)piperidin-1-yl)methyl)-1H-1,2,3-triazol-1-yl)-2,3-dihydro-1H-inden-2-ol, | 3 | 3 | 3 | 3 | 0 | 3 | 3 |
| 89. | 3-(1-((1-(benzofuran-3-yl)-1H-1,2,3-triazol-4-yl)methyl)piperidin-4-yl)phenol, | 4 | 4 | 4 | 4 | 0 | 4 | 4 |
| 90. | N-(5-(1-((1-benzyl-1H-1,2,3-triazol-4-yl)methyl)piperidin-4-yl)-2-fluorophenyl)methanesulfonamide, | 2 | 2 | 2 | 2 | 0 | 2 | 2 |
| 91. | N-(3-(1-((1-((1S,2S)-2-hydroxy-2,3-dihydro-1H-inden-1-yl)-1H-1,2,3-triazol-4-yl)methyl)piperidin-4-yl)phenyl)methanesulfonamide, | 2 | 2 | 2 | 2 | 0 | 2 | 2 |
| 92. | N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide, | 3 | 3 | 3 | 3 | 0 | 3 | 3 |
| 93. | N-(3-(1-((1-(pyridin-2-yl)-1H-1,2,3-triazol-4-yl)methyl)piperidin-4-phenyl)methanesulfonamide, | 3 | 3 | 3 | 3 | 0 | 3 | 3 |
| 94. | 3-(1-((1-phenyl-1H-1,2,3-triazol-4-yl)methyl)piperidin-4-yl)aniline, | 4 | 4 | 4 | 4 | 0 | 4 | 4 |
| 95. | 3-(4-((4-(3-hydroxyphenyl)piperidin-1-yl)methyl)-1H-1,2,3-triazol-1-yl)-3-methylindolin-2-one, | 3 | 3 | 3 | 3 | 0 | 3 | 3 |
| 96. | (1S,2R)-2-(4-((4-(3-hydroxyphenyl)piperidin-1-yl)methyl)-1H-1,2,3-triazol-1-yl)-2,3-dihydro-1H-inden-1-ol, | 3 | 3 | 3 | 3 | 0 | 3 | 3 |
| 97. | N-(3-(1-((1-((1S,2R)-1-hydroxy-2,3-dihydro-1H-inden-2-yl)-1H-1,2,3-triazol-4-yl)methyl)piperidin-4-yl)phenyl)methanesulfonamide, | 2 | 2 | 2 | 2 | 0 | 2 | 2 |
| 98. | N-(3-(1-((1-(pyridin-2-ylmethyl)-1H-1,2,3-triazol-4-yl)methyl)piperidin-4-yl)phenyl)methanesulfonamide, | 2 | 2 | 2 | 2 | 0 | 2 | 2 |
| 99. | N-(3-(1-((1-(pyridin-3-ylmethyl)-1H-1,2,3-triazol-4-yl)methyl)piperidin-4-yl)phenyl)methanesulfonamide, | 3 | 3 | 3 | 3 | 0 | 3 | 3 |
| 100. | N-(3-(1-((1-((1R,2R)-1-hydroxy-2,3-dihydro-1H-inden-2-yl)-1H-1,2,3-triazol-4-yl)methyl)piperidin-4-yl)phenyl)methanesulfonamide, | 2 | 2 | 2 | 2 | 0 | 2 | 2 |
| 101. | N-(2-methoxy-3-(1-((1-phenyl-1H-1,2,3-triazol-4-yl)methyl)piperidin-4-yl)phenyl)methanesulfonamide, | 3 | 3 | 3 | 3 | 0 | 3 | 3 |
| 102. | N-(3-(1-((1-benzyl-1H-1,2,3-triazol-4-yl)methyl)piperidin-4-yl)-2-methoxyphenyl)methanesulfonamide, | 2 | 2 | 2 | 2 | 0 | 2 | 2 |
| 103. | N-(3-(1-((1-(pyridin-2-ylmethyl)-1H-1,2,3-triazol-4-yl)methyl)piperidin-4-yl)phenyl)propionamide, | 2 | 2 | 2 | 2 | 0 | 2 | 2 |
| 104. | N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide, | 3 | 3 | 3 | 3 | 0 | 3 | 3 |
| 105. | N-(3-(1-((1-((1S,2S)-2-hydroxy-2,3-dihydro-1H-inden-1-yl)-1H-1,2,3-triazol-4-yl)methyl)piperidin-4-yl)phenyl)propane-2-sulfonamide, | 2 | 2 | 2 | 2 | 0 | 2 | 2 |
| 106. | 3-(1-((1-(4-(2-hydroxy-2-methylpropoxy)phenyl)-1H-1,2,3-triazol-4-yl)methyl)piperidin-4-yl)phenol, | 2 | 2 | 2 | 2 | 0 | 2 | 2 |
| 107. | 3-(1-((1-(4-hydroxyphenyl)-1H-1,2,3-triazol-4-yl)methyl)piperidin-4-yl)phenol, | 4 | 4 | 4 | 4 | 0 | 4 | 4 |
| 108. | 3-(1-((1-(4-(2-hydroxyethyl)phenyl)-1H-1,2,3-triazol-4-yl)methyl)piperidin-4-yl)phenol, | 3 | 3 | 3 | 3 | 0 | 3 | 3 |
| 109. | 3-(1-((1-(4-(2-hydroxyethoxy)phenyl)-1H-1,2,3-triazol-4-yl)methyl)piperidin-4-yl)phenol, | 2 | 2 | 2 | 2 | 0 | 2 | 2 |

-continued

| Ex. | Compound | General Formula | | | | | | |
|---|---|---|---|---|---|---|---|---|
| | | I | II | III | IV | V | VI | VII |
| 110. | N-(3-((3R,4S)-3-hydroxy-1-((1-phenyl-1H-1,2,3-triazol-4-yl)methyl)piperidin-4-yl)phenyl)methanesulfonamide, | 2 | 2 | 2 | 2 | 0 | 2 | 2 |
| 111. | 1-ethyl-3-(3-(1-((1-(pyridin-2-ylmethyl)-1H-1,2,3-triazol-4-yl)methyl)piperidin-4-yl)phenyl)urea, | 2 | 2 | 2 | 2 | 0 | 2 | 2 |
| 112. | N-(3-(1-((1-(pyridin-2-ylmethyl)-1H-1,2,3-triazol-4-yl)methyl)piperidin-4-yl)phenyl)ethanesulfonamide, | 3 | 3 | 3 | 3 | 0 | 3 | 3 |
| 113. | N-(3-(1-((1-((6-methoxypyridin-2-yl)methyl)-1H-1,2,3-triazol-4-yl)methyl)piperidin-4-yl)phenyl)propane-2-sulfonamide, | 4 | 4 | 4 | 4 | 0 | 4 | 4 |
| 114. | N-(3-(1-((1-((3-fluoropyridin-2-yl)methyl)-1H-1,2,3-triazol-4-yl)methyl)piperidin-4-yl)phenyl)propane-2-sulfonamide, | 3 | 3 | 3 | 3 | 0 | 3 | 3 |
| 115. | N-(3-((3R,4S)-3-hydroxy-1-((1-phenyl-1H-1,2,3-triazol-4-yl)methyl)piperidin-4-yl)phenyl)propane-2-sulfonamide, | 3 | 3 | 3 | 3 | 0 | 3 | 3 |
| 116. | N-(3-(1-((1-((6-fluoropyridin-2-yl)methyl)-1H-1,2,3-triazol-4-yl)methyl)piperidin-4-yl)phenyl)propane-2-sulfonamide, | 3 | 3 | 3 | 3 | 0 | 3 | 3 |
| 117. | N-(3-(1-((1-((6-(trifluoromethyl)pyridin-2-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 118. | N-(3-(1-((1-((6-methylpyridin-2-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 119. | N-(3-(1-((8H-[1,2,3]triazolo[5,1-a]isoindol-3-yl)methyl)piperidin-4-yl)phenyl)methanesulfonamide, | 2 | 2 | 2 | 0 | 0 | 0 | 0 |
| 120. | 3-(1-((8H-[1,2,3]triazolo[5,1-a]isoindol-3-yl)methyl)piperidin-4-yl)phenol, | 2 | 2 | 2 | 0 | 0 | 0 | 0 |
| 121. | N-(3-(1-((1-((3-(trifluoromethyl)pyridin-2-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 122. | N-(3-(1-((1-((5-(trifluoromethyl)pyridin-2-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 123. | N-(3-((3R,4S)-1-((1-benzyl-1H-1,2,3-triazol-4-yl)methyl)-3-hydroxypiperidin-4-yl)phenyl)propane-2-sulfonamide, | 2 | 2 | 2 | 2 | 0 | 2 | 2 |
| 124. | N-(3-(1-((1-((6-(trifluoromethyl)pyridin-3-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 125. | N-(3-((3R,4S)-3-hydroxy-1-((1-(pyridin-2-ylmethyl)-1H-1,2,3-triazol-4-yl)methyl)piperidin-4-yl)phenyl)propane-2-sulfonamide, | 2 | 2 | 2 | 2 | 0 | 2 | 2 |
| 126. | N-(3-((3R,4S)-3-hydroxy-1-((1-phenyl-1H-1,2,3-triazol-4-yl)methyl)piperidin-4-yl)phenyl)propane-2-sulfonamide, | 3 | 3 | 3 | 3 | 0 | 3 | 3 |
| 127. | N-(3-((3S,4R)-3-hydroxy-1-((1-phenyl-1H-1,2,3-triazol-4-yl)methyl)piperidin-4-yl)phenyl)propane-2-sulfonamide, | 3 | 3 | 3 | 3 | 0 | 3 | 3 |
| 128. | N-(3-(1-((1-((4-azidopyridin-2-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 129. | N-(3-(1-((1-((2-(trifluoromethyl)pyrimidin-5-yl)methyl)-1H-1,2,3-triazol-4-yl)methyl)piperidin-4-yl)phenyl)propane-2-sulfonamide, | 3 | 3 | 3 | 3 | 0 | 3 | 3 |
| 130. | N-(3-(1-((1-(2-hydroxy-1-phenylethyl)-1H-1,2,3-triazol-4-yl)methyl)piperidin-4-yl)phenyl)propane-2-sulfonamide, | 2 | 2 | 2 | 2 | 0 | 2 | 2 |
| 131. | N-(3-(1-((1-(2-hydroxy-1-phenylethyl)-1H-1,2,3-triazol-4-yl)methyl)piperidin-4-yl)phenyl)methanesulfonamide, | 2 | 2 | 2 | 2 | 0 | 2 | 2 |
| 132. | 3-(1-((1-((6-fluoropyridin-2-yl)methyl)-1H-1,2,3-triazol-4-yl)methyl)piperidin-4-yl)phenol, | 3 | 3 | 3 | 3 | 0 | 3 | 3 |
| 133. | 3-(1-((1-((5-fluoropyridin-2-yl)methyl)-1H-1,2,3-triazol-4-yl)methyl)piperidin-4-yl)phenol, | 3 | 3 | 3 | 3 | 0 | 3 | 3 |
| 134. | 3-(1-((1-((3-fluoropyridin-2-yl)methyl)-1H-1,2,3-triazol-4-yl)methyl)piperidin-4-yl)phenol, | 3 | 3 | 3 | 3 | 0 | 3 | 3 |
| 135. | N-(3-(1-((1-((5-fluoropyridin-2-yl)methyl)-1H-1,2,3-triazol-4-yl)methyl)piperidin-4-yl)phenyl)propane-2-sulfonamide, | 2 | 2 | 2 | 2 | 0 | 2 | 2 |
| 136. | 2-fluoro-5-(1-((1-(pyridin-2-ylmethyl)-1H-1,2,3-triazol-4-yl)methyl)piperidin-4-yl)phenol, | 3 | 3 | 3 | 3 | 0 | 3 | 3 |

|     |                                                                                                                     | General Formula |||||||
| --- | ------------------------------------------------------------------------------------------------------------------- | - | - | - | - | - | - | - |
| Ex. | Compound                                                                                                            | I | II | III | IV | V | VI | VII |
| 137. | 4-fluoro-3-(1-((1-(pyridin-2-ylmethyl)-1H-1,2,3-triazol-4-yl)methyl)piperidin-4-yl)phenol,                         | 3 | 3 | 3 | 3 | 0 | 3 | 3 |
| 138. | N-methyl-3-(1-((1-(pyridin-2-ylmethyl)-1H-1,2,3-triazol-4-yl)methyl)piperidin-4-yl)benzenesulfonamide,             | 1 | 1 | 1 | 1 | 0 | 1 | 1 |
| 139. | 2-((4-((4-(3-(1H-imidazol-2-yl)phenyl)piperidin-1-yl)methyl)-1H-1,2,3-triazol-1-yl)methyl)pyridine,                | 3 | 3 | 3 | 3 | 0 | 3 | 3 |
| 140. | 3-(1-((1-phenyl-1H-1,2,3-triazol-4-yl)methyl)piperidin-4-yl)benzenesulfonamide,                                    | 3 | 3 | 3 | 3 | 0 | 3 | 3 |
| 141. | 3-(1-((1-(pyridin-2-ylmethyl)-1H-1,2,3-triazol-4-yl)methyl)piperidin-4-yl)benzenesulfonamide,                      | 1 | 1 | 1 | 1 | 0 | 1 | 1 |
| 142. | 3-(1-((1-(2-fluorophenyl)-1H-1,2,3-triazol-4-yl)methyl)piperidin-4-yl)phenol,                                      | 4 | 4 | 4 | 4 | 0 | 4 | 4 |
| 143. | 3-(1-((1-(5-fluoropyridin-2-yl)-1H-1,2,3-triazol-4-yl)methyl)piperidin-4-yl)phenol,                                | 4 | 4 | 4 | 4 | 0 | 4 | 4 |
| 144. | 3-(1-((1-((3-chloropyridin-2-yl)methyl)-1H-1,2,3-triazol-4-yl)methyl)piperidin-4-yl)phenol,                        | 3 | 3 | 3 | 3 | 0 | 3 | 3 |
| 145. | 3-(1-((1-(pyridin-3-ylmethyl)-1H-1,2,3-triazol-4-yl)methyl)piperidin-4-yl)phenol,                                  | 3 | 3 | 3 | 3 | 0 | 3 | 3 |
| 146. | 3-(1-((1-(2,6-difluorophenyl)-1H-1,2,3-triazol-4-yl)methyl)piperidin-4-yl)phenol,                                  | 4 | 4 | 4 | 4 | 0 | 4 | 4 |
| 147. | 3-(1-((1-(3,4-difluorophenyl)-1H-1,2,3-triazol-4-yl)methyl)piperidin-4-yl)phenol,                                  | 4 | 4 | 4 | 4 | 0 | 4 | 4 |
| 148. | 3-(1-((1-(5-chloropyridin-2-yl)-1H-1,2,3-triazol-4-yl)methyl)piperidin-4-yl)phenol,                                | 4 | 4 | 4 | 4 | 0 | 4 | 4 |
| 149. | (R)-3-(1-((1-(2-hydroxy-1-phenylethyl)-1H-1,2,3-triazol-4-yl)methyl)piperidin-4-yl)phenol,                         | 3 | 3 | 3 | 3 | 0 | 3 | 3 |
| 150. | (S)-3-(1-((1-(2-hydroxy-1-phenylethyl)-1H-1,2,3-triazol-4-yl)methyl)piperidin-4-yl)phenol,                         | 3 | 3 | 3 | 3 | 0 | 3 | 3 |
| 151. | 3-(1-((1-((3-(trifluoromethyl)pyridin-2-yl)methyl)-1H-1,2,3-triazol-4-yl)methyl)piperidin-4-yl)phenol,             | 3 | 3 | 3 | 3 | 0 | 3 | 3 |
| 152. | 3-(1-(1-((5-(trifluoromethyl)pyridin-2-yl)methyl)-1H-1,2,3-triazol-4-yl)methyl)piperidin-4-yl)phenol,              | 4 | 4 | 4 | 4 | 0 | 4 | 4 |
| 153. | 3-(1-((1-((5-chloropyridin-2-yl)methyl)-1H-1,2,3-triazol-4-yl)methyl)piperidin-4-yl)phenol,                        | 4 | 4 | 4 | 4 | 0 | 4 | 4 |
| 154. | 3-(1-((1-(3-fluoropyridin-2-yl)-1H-1,2,3-triazol-4-yl)methyl)piperidin-4-yl)phenol,                                | 3 | 3 | 3 | 3 | 0 | 3 | 3 |
| 155. | 3-(1-((1-(2,4-difluorophenyl)-1H-1,2,3-triazol-4-yl)methyl)piperidin-4-yl)phenol,                                  | 4 | 4 | 4 | 4 | 0 | 4 | 4 |
| 156. | 2-((4-((4-(3-hydroxyphenyl)piperidin-1-yl)methyl)-1H-1,2,3-triazol-1-yl)methyl)pyridin-3-ol,                       | 2 | 2 | 2 | 2 | 0 | 2 | 2 |
| 157. | 3-(1-((1-(4-(trifluoromethyl)pyridin-2-yl)-1H-1,2,3-triazol-4-yl)methyl)piperidin-4-yl)phenol,                     | 3 | 3 | 3 | 3 | 0 | 3 | 3 |
| 158. | 3-(1-((1-((3-methoxypyridin-2-yl)methyl)-1H-1,2,3-triazol-4-yl)methyl)piperidin-4-yl)phenol,                       | 2 | 2 | 2 | 2 | 0 | 2 | 2 |
| 159. | 6-((4-((4-(3-hydroxyphenyl)piperidin-1-yl)methyl)-1H-1,2,3-triazol-1-yl)methyl)pyridin-3-ol,                       | 3 | 3 | 3 | 3 | 0 | 3 | 3 |
| 160. | 3-(1-((1-((4-(trifluoromethyl)pyridin-2-yl)methyl)-1H-1,2,3-triazol-4-yl)methyl)piperidin-4-yl)phenol,             | 3 | 3 | 3 | 3 | 0 | 3 | 3 |
| 161. | 3-(1-((1-(3-chloropyridin-2-yl)-1H-1,2,3-triazol-4-yl)methyl)piperidin-4-yl)phenol,                                | 3 | 3 | 3 | 3 | 0 | 3 | 3 |
| 162. | 3-(1-(2-(1-phenyl-1H-1,2,3-triazol-4-yl)ethyl)piperidin-4-yl)phenol,                                               | 4 | 4 | 4 | 4 | 0 | 4 | 4 |
| 163. | N-(3-(1-((1-phenyl-1H-pyrazol-4-yl)methyl)piperidin-4-yl)phenyl)methanesulfonamide,                                | 4 | 4 | 4 | 0 | 0 | 4 | 0 |
| 164. | 3-(1-((1-phenyl-1H-pyrazol-4-yl)methyl)piperidin-4-yl)phenol,                                                      | 4 | 4 | 4 | 0 | 0 | 4 | 0 |
| 165. | N-(3-((3R,4S)-3-hydroxy-1-((1-phenyl-1H-pyrazol-4-yl)methyl)piperidin-4-yl)phenyl)methanesulfonamide,              | 3 | 3 | 3 | 0 | 0 | 3 | 0 |
| 166. | N-(3-(1-((1-((1R,2R)-2-hydroxy-2,3-dihydro-1H-inden-1-yl)-1H-pyrazol-4-yl)methyl)piperidin-4-yl)phenyl)methanesulfonamide, | 2 | 2 | 2 | 0 | 0 | 2 | 0 |
| 167. | N-(3-(1-((1-(pyridin-2-ylmethyl)-1H-pyrazol-4-yl)methyl)piperidin-4-yl)phenyl)propane-2-sulfonamide,               | 3 | 3 | 3 | 0 | 0 | 3 | 0 |
| 168. | N-(3-(1-((1-(pyridin-2-ylmethyl)-1H-pyrazol-4-yl)methyl)piperidin-4-yl)phenyl)methanesulfonamide,                  | 3 | 3 | 3 | 0 | 0 | 3 | 0 |
| 169. | N-(3-((3R,4S)-3-hydroxy-1-((1-(pyridin-2-yl)-1H-pyrazol-4-yl)methyl)piperidin-4-yl)phenyl)propane-2-sulfonamide,   | 2 | 2 | 2 | 0 | 0 | 2 | 0 |

-continued

| | | General Formula | | | | | | |
|---|---|---|---|---|---|---|---|---|
| Ex. | Compound | I | II | III | IV | V | VI | VII |
| 170. | N-(3-(1-((1-((6-fluoropyridin-2-yl)methyl)-1H-pyrazol-4-yl)methyl)piperidin-4-yl)phenyl)propane-2-sulfonamide, | 4 | 4 | 4 | 0 | 0 | 4 | 0 |
| 171. | 3-(1-((1-(pyridin-2-ylmethyl)-1H-pyrazol-4-yl)methyl)piperidin-4-yl)phenol, | 3 | 3 | 3 | 0 | 0 | 3 | 0 |
| 172. | 3-(1-((1-((3-fluoropyridin-2-yl)methyl)-1H-pyrazol-4-yl)methyl)piperidin-4-yl)phenol, | 2 | 2 | 2 | 0 | 0 | 2 | 0 |
| 173. | 3-(1-((1-((5-fluoropyridin-2-yl)methyl)-1H-pyrazol-4-yl)methyl)piperidin-4-yl)phenol, | 3 | 3 | 3 | 0 | 0 | 3 | 0 |
| 174. | N-(3-(1-((3-phenylisoxazol-5-yl)methyl)piperidin-4-yl)phenyl)methanesulfonamide, | 4 | 4 | 4 | 0 | 4 | 0 | 0 |
| 175. | N-(3-(1-((5-phenyl-1,3,4-oxadiazol-2-yl)methyl)piperidin-4-yl)phenyl)methanesulfonamide, | 2 | 2 | 2 | 0 | 2 | 0 | 0 |
| 176. | 3-(1-((3-phenylisoxazol-5-yl)methyl)piperidin-4-yl)phenol, | 4 | 4 | 4 | 0 | 4 | 0 | 0 |
| 177. | 3-(1-((3-benzylisoxazol-5-yl)methyl)piperidin-4-yl)phenol, | 4 | 4 | 4 | 0 | 4 | 0 | 0 |
| 178. | N-(3-(1-((3-benzylisoxazol-5-yl)methyl)piperidin-4-yl)phenyl)methanesulfonamide, | 3 | 3 | 3 | 0 | 3 | 0 | 0 |
| 179. | N-(4-fluoro-3-(1-((3-phenylisoxazol-5-yl)methyl)piperidin-4-yl)phenyl)methanesulfonamide, | 3 | 3 | 3 | 0 | 3 | 0 | 0 |
| 180. | N-(2-fluoro-5-(1-((3-phenylisoxazol-5-yl)methyl)piperidin-4-yl)phenyl)methanesulfonamide, | 3 | 3 | 3 | 0 | 3 | 0 | 0 |
| 181. | N-(3-(1-((3-(pyridin-2-yl)isoxazol-5-yl)methyl)piperidin-4-yl)phenyl)propane-2-sulfonamide, | 2 | 2 | 2 | 0 | 2 | 0 | 0 |
| 182. | N-(3-(1-((1-phenyl-1H-1,2,4-triazol-3-yl)methyl)piperidin-4-yl)phenyl)methanesulfonamide, | 3 | 3 | 3 | 3 | 0 | 3 | 0 |
| 183. | N-(3-(1-((1-benzyl-1H-imidazol-4-yl)methyl)piperidin-4-yl)phenyl)methanesulfonamide, | 3 | 3 | 3 | 0 | 0 | 3 | 0 |
| 184. | 3-(1-((1-benzyl-1H-imidazol-4-yl)methyl)piperidin-4-yl)phenol, | 4 | 4 | 4 | 0 | 0 | 4 | 0 |
| 185. | N-(3-(1-((1-benzyl-1H-imidazol-5-yl)methyl)piperidin-4-yl)phenyl)methanesulfonamide, | 3 | 3 | 3 | 0 | 0 | 3 | 0 |
| 186. | N-(3-(1-((1-(pyridin-2-ylmethyl)-1H-imidazol-4-yl)methyl)piperidin-4-yl)phenyl)propane-2-sulfonamide, | 3 | 3 | 3 | 0 | 0 | 3 | 0 |
| 187. | N-(3-(1-((1-(pyridin-2-ylmethyl)-1H-imidazol-5-yl)methyl)piperidin-4-yl)phenyl)propane-2-sulfonamide, | 3 | 3 | 3 | 0 | 0 | 3 | 0 |
| 188. | 3-(1-((1-(pyridin-2-ylmethyl)-1H-imidazol-4-yl)methyl)piperidin-4-yl)phenol, | 3 | 3 | 3 | 0 | 0 | 3 | 0 |
| 189. | 3-(1-((1-((3-fluoropyridin-2-yl)methyl)-1H-imidazol-4-yl)methyl)piperidin-4-yl)phenol, | 3 | 3 | 3 | 0 | 0 | 3 | 0 |
| 190. | N-(6-(1-((1-phenyl-1H-1,2,3-triazol-4-yl)methyl)piperidin-4-yl)pyridin-2-yl)propionamide, | 3 | 3 | 3 | 3 | 0 | 3 | 3 |
| 191. | N-(6-(1-((1-phenyl-1H-1,2,3-triazol-4-yl)methyl)piperidin-4-yl)pyridin-2-yl)methanesulfonamide, | 3 | 3 | 3 | 3 | 0 | 3 | 3 |
| 192. | N-(2-(1-((1-phenyl-1H-1,2,3-triazol-4-yl)methyl)piperidin-4-yl)pyridin-4-yl)propionamide, | 2 | 2 | 0 | 0 | 0 | 0 | 0 |
| 193. | N-(2-(1-((1-phenyl-1H-1,2,3-triazol-4-yl)methyl)piperidin-4-yl)pyridin-4-yl)methanesulfonamide, | 1 | 1 | 0 | 0 | 0 | 0 | 0 |
| 194. | N-(5-(1-((1-phenyl-1H-1,2,3-triazol-4-yl)methyl)piperidin-4-yl)pyridin-3-yl)methanesulfonamide, | 1 | 1 | 0 | 0 | 0 | 0 | 0 |
| 195. | N-(5-(1-((1-phenyl-1H-1,2,3-triazol-4-yl)methyl)piperidin-4-yl)pyridin-3-yl)propionamide, | 2 | 2 | 0 | 0 | 0 | 0 | 0 |
| 196. | N-(4-(1-((1-phenyl-1H-1,2,3-triazol-4-yl)methyl)piperidin-4-yl)pyridin-2-yl)propionamide, | 2 | 2 | 0 | 0 | 0 | 0 | 0 |
| 197. | N-(4-(1-((1-phenyl-1H-1,2,3-triazol-4-yl)methyl)piperidin-4-yl)pyridin-2-yl)methanesulfonamide, | 1 | 1 | 0 | 0 | 0 | 0 | 0 |

-continued

| Ex. | Compound | General Formula | | | | | | |
|---|---|---|---|---|---|---|---|---|
| | | I | II | III | IV | V | VI | VII |
| 198. | 6-(1-((1-phenyl-1H-1,2,3-triazol-4-yl)methyl)piperidin-4-yl)pyridin-2-ol, | 1 | 1 | 0 | 0 | 0 | 0 | 0 |
| 199. | N-(6-(1-((1-benzyl-1H-1,2,3-triazol-4-yl)methyl)piperidin-4-yl)pyridin-2-yl)propionamide, | 2 | 2 | 2 | 2 | 0 | 2 | 2 |
| 200. | N-(6-(1-((3-phenylisoxazol-5-yl)methyl)piperidin-4-yl)pyridin-2-yl)methanesulfonamide, | 3 | 3 | 3 | 0 | 3 | 0 | 0 |
| 201. | N-(6-(1-((3-phenylisoxazol-5-yl)methyl)piperidin-4-yl)pyridin-2-yl)propionamide, | 3 | 3 | 3 | 0 | 3 | 0 | 0 |
| 202. | N-(6-(1-((1-phenyl-1H-pyrazol-4-yl)methyl)piperidin-4-yl)pyridin-2-yl)propionamide, | 4 | 4 | 4 | 0 | 0 | 4 | 0 |
| 203. | N-(6-(1-((1-phenyl-1H-pyrazol-4-yl)methyl)piperidin-4-yl)pyridin-2-yl)methanesulfonamide, | 4 | 4 | 4 | 0 | 0 | 4 | 0 |
| 204. | N-(6-(1-((1-((1R,2R)-2-hydroxy-2,3-dihydro-1H-inden-1-yl)-1H-1,2,3-triazol-4-yl)methyl)piperidin-4-yl)pyridin-2-yl)propionamide, | 2 | 2 | 2 | 2 | 0 | 2 | 2 |
| 205. | 3-(1-((1-phenyl-1H-1,2,3-triazol-4-yl)methyl)piperidin-4-yl)pyridin-2-ol, | 2 | 0 | 0 | 0 | 0 | 0 | 0 |
| 206. | N-(6-(1-((1-(pyridin-2-ylmethyl)-1H-1,2,3-triazol-4-yl)methyl)piperidin-4-yl)pyridin-2-yl)propane-2-sulfonamide, | 3 | 3 | 3 | 3 | 0 | 3 | 3 |
| 207. | N-(6-(1-((1-phenyl-1H-1,2,3-triazol-4-yl)methyl)piperidin-4-yl)pyridin-2-yl)propane-2-sulfonamide, | 3 | 3 | 3 | 3 | 0 | 3 | 3 |
| 208. | N-(6-(1-((1-(2-fluorophenyl)-1H-1,2,3-triazol-4-yl)methyl)piperidin-4-yl)pyridin-2-yl)propane-2-sulfonamide, | 3 | 3 | 3 | 3 | 0 | 3 | 3 |
| 209. | N-(6-(1-((1-((3-fluoropyridin-2-yl)methyl)-1H-1,2,3-triazol-4-yl)methyl)piperidin-4-yl)pyridin-2-yl)propane-2-sulfonamide, | 2 | 2 | 2 | 2 | 0 | 2 | 2 |
| 210. | N-(6-(1-((1-((5-fluoropyridin-2-yl)methyl)-1H-1,2,3-triazol-4-yl)methyl)piperidin-4-yl)pyridin-2-yl)propane-2-sulfonamide, | 2 | 2 | 2 | 2 | 0 | 2 | 2 |
| 211. | N-(6-(1-((1-(2-fluorophenyl)-1H-1,2,3-triazol-4-yl)methyl)piperidin-4-yl)pyridin-2-yl)propionamide, | 3 | 3 | 3 | 3 | 0 | 3 | 3 |
| 212. | N-(6-(1-((1-((3-chloropyridin-2-yl)methyl)-1H-1,2,3-triazol-4-yl)methyl)piperidin-4-yl)pyridin-2-yl)propane-2-sulfonamide, and | 2 | 2 | 2 | 2 | 0 | 2 | 2 |
| 213. | N-(6-(1-((1-((5-chloropyridin-2-yl)methyl)-1H-1,2,3-triazol-4-yl)methyl)piperidin-4-yl)pyridin-2-yl)propane-2-sulfonamide. | 2 | 2 | 2 | 2 | 0 | 2 | 2 |

In another preferred embodiment of the compound according to the invention according to Formula I or II the compound is a compound according to Formula III,

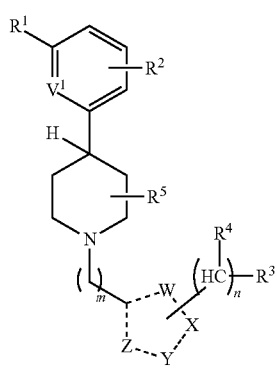

(III)

wherein m is 1 or 2;

n is 0 or 1;

$V^1$ is selected from nitrogen or carbon;

$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;

$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;

or $R^1$ and $R^2$ are bonded to neighbouring atoms in the ring and together with these atoms form a saturated or unsaturated, substituted or unsubstituted ring, fused to the ring

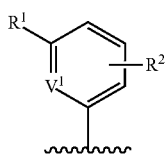

of the corestructure of formula III, which may be condensed with a further unsubstituted or substituted ring system;

R³ is substituted or unsubstituted alkyl, CONR⁶R⁷, substituted or unsubstituted cycloalkyl, substituted or unsubstituted alkenyl, substituted or unsubstituted alkynyl, substituted or unsubstituted aryl and substituted or unsubstituted heterocyclyl;

R⁴ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

R⁵ is hydrogen, halogen, hydroxy, substituted or unsubstituted O-alkyl, substituted or unsubstituted alkyl;

R⁶, R⁷ and R⁸ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or R⁶, R⁷ or R⁸ together with their respective connecting carbon or nitrogen atom may form a cycloalkylic or heterocyclic 4 to 7-membered ring; and

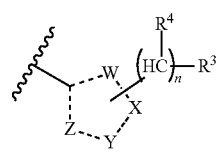

is selected from:

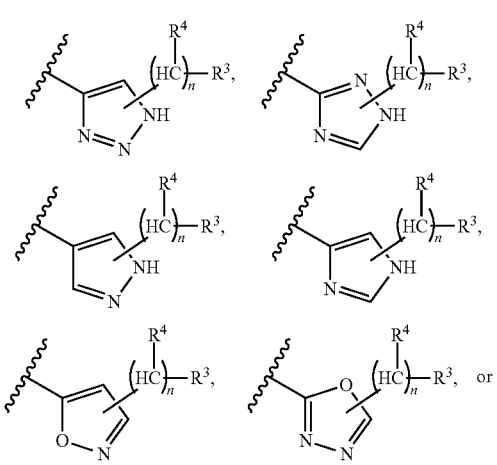

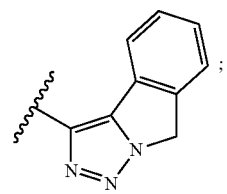

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In one embodiment one or more of the following provisos apply:

with the proviso that if V¹ is nitrogen and

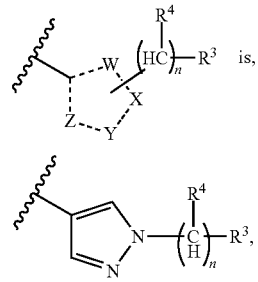

or with n=0 and R³ being alkyl, then R¹ may not be —NR⁶R⁷;

and/or with the proviso that if V¹ is carbon and

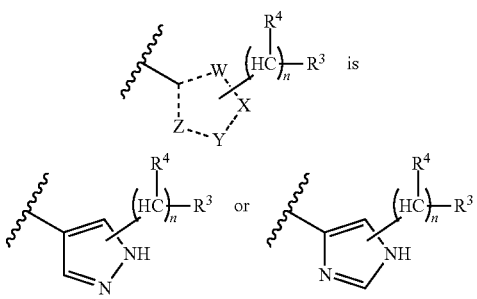

with n being 0, then R¹ may not be —NHC(O)-alkyl in meta position;

In another preferred embodiment of the compound according to the invention according to Formula III

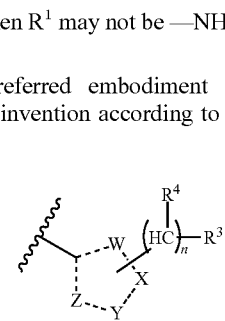

is selected from

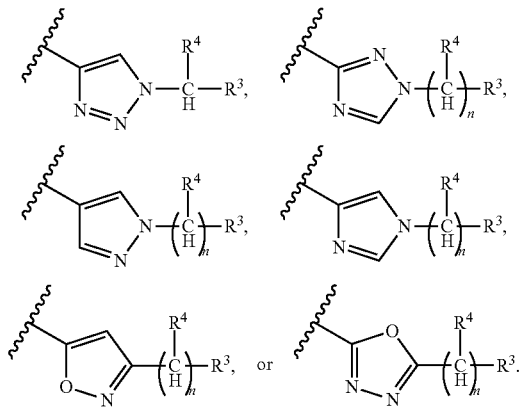

In another preferred embodiment of the compound according to the invention according to Formula I or II has a general formula IV,

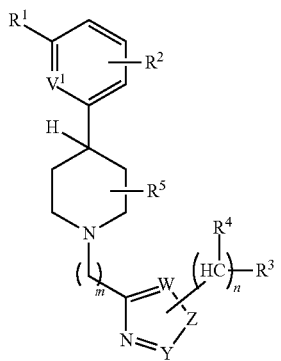

IV wherein m is 1 or 2;

n is 0 or 1;

$V^1$ is selected from carbon or nitrogen;

one of W, X and Y is carbon, while the other two are nitrogen;

$R^1$ is selected from hydroxy, $NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;

$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;

or $R^1$ and $R^2$ are bonded to neighbouring atoms in the ring and together with these atoms form a saturated or unsaturated, substituted or unsubstituted ring, fused to the ring

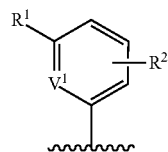

of the corestructure of formula IV, which may be condensed with a further unsubstituted or substituted ring system;

$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl, wherein said cycloalkyl, aryl or heteroaryl groups can be optionally fused to an additional aryl or heteroaryl group;

$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

$R^5$ is hydrogen, halogen, hydroxy, substituted or unsubstituted O-alkyl, substituted or unsubstituted alkyl;

$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to Formula IV

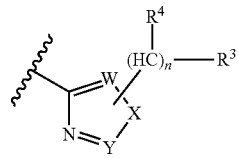

is selected from

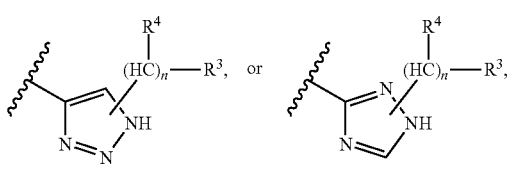

preferably is selected from

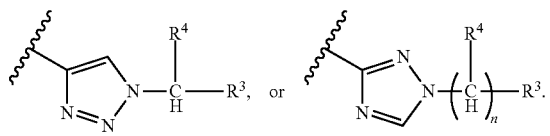

In another preferred embodiment of the compound according to the invention according to Formula I or II the compound has a general formula V,

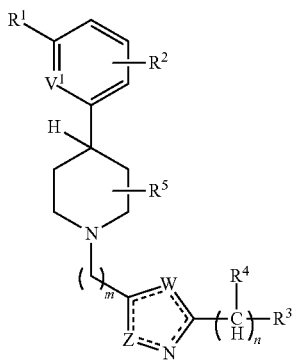

wherein
m is 1 or 2;
n is 0 or 1;
$V^1$ is selected from CH or N;
W being selected from CH or O and Z being selected from N or O, with a maximum of one of them being O;
$R^1$ is selected from hydroxy, $NR^6R^7$, $—NR^6S(O)_2R^7$, $—NR^6COR^7$, $—NR^6CONR^7R^8$, $—SR^6$, $—S(O)_2R^6$, $—S(O)_2NR^6R^7$, $—CONR^6R^7$, substituted or unsubstituted aryl and substituted or unsubstituted heterocyclyl;
$R^2$ is hydrogen, halogen, $—NR^6R^7$, $—SR^6$, $—OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

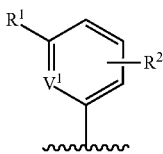

of the corestructure of formula V, which may be condensed with a further unsubstituted or substituted ring system;
$R^3$ is substituted or unsubstituted cycloalkyl, substituted or unsubstituted aryl and substituted or unsubstituted heterocyclyl, wherein said cycloalkyl, aryl or heteroaryl groups can be optionally fused to an additional aryl or heteroaryl group;

$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
$R^5$ is hydrogen, halogen, hydroxy, substituted or unsubstituted O-alkyl, substituted or unsubstituted alkyl;
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof or a corresponding solvate thereof.

In another preferred embodiment of the compound according to the invention according to Formula V

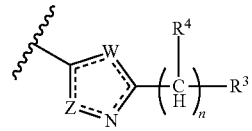

is selected from

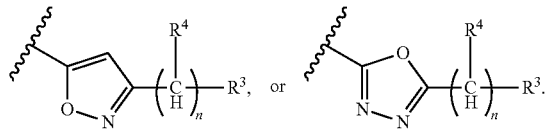

In another preferred embodiment of the compound according to the invention according to general formulas I or II the compound is having a general formula VI

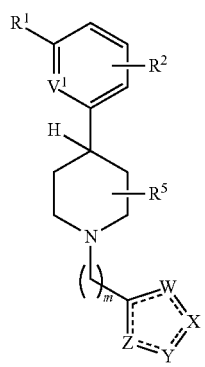

wherein
m is 1 or 2;
$V^1$ is a nitrogen or carbon atom;
n is 0 or 1;

one of W and X is N or CH, while the other is

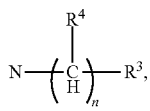

and
one of Y and Z is selected from N or CH, while the other is N, with only a maximum of 2 of W, X, Y or Z being N;

$R^1$ is selected from hydroxy, $NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl, and substituted or unsubstituted heterocyclyl;

$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;

or $R^1$ and $R^2$ are bonded to neighbouring atoms in the ring and together with these atoms form a saturated or unsaturated, substituted or unsubstituted ring, fused to the ring

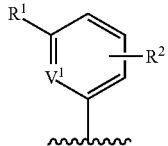

of the corestructure of formula IV, which may be condensed with a further unsubstituted or substituted ring system;

$R^3$ is substituted or unsubstituted cycloalkyl, substituted or unsubstituted aryl and substituted or unsubstituted heterocyclyl, wherein said cycloalkyl, aryl or heteroaryl groups can be optionally fused to an additional aryl or heteroaryl group;

$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

$R^5$ is hydrogen, halogen, hydroxy, substituted or unsubstituted O-alkyl, substituted or unsubstituted alkyl;

$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof or a corresponding solvate thereof.

In another preferred embodiment of the compound according to the invention according to general formulas I, II, III, IV, V and VI $R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl, wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or most preferably $R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, —$CONR^6R^7$, substituted or unsubstituted aryl like phenyl and substituted or unsubstituted heterocyclyl like imidazol;

and/or $R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl;

and/or halogen is any of fluorine, chlorine, iodine or bromine, preferably chlorine or fluorine;

and/or most preferably $R^2$ is selected from hydrogen, halogen like fluorine, or $C_{1-4}$alkyl like $CH_3$ or $CF_3$;

and/or $R^1$ and $R^2$ are bonded to neighbouring atoms in the ring and together with these atoms form a saturated or unsaturated, substituted or unsubstituted ring, fused to the ring

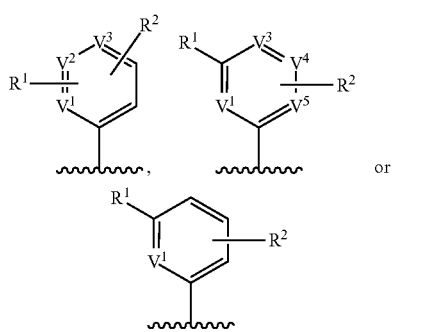

of the corestructure of formulas I, II, III, IV, V or VI respectively, which may be condensed with a further unsubstituted or substituted ring system, wherein the ring is either unsubstituted or substituted by one or more of halogen, —OH, —NH$_2$, —SH, =O, —OC$_{1-4}$alkyl being unsubstituted or substituted by one or more of OH or halogen, —CN, or C$_{1-4}$alkyl being unsubstituted or substituted by one or more of OH or halogen;

preferably the ring being formed with $V^1$, $V^2$, $V^3$, $V^4$ and $V^5$ all being carbon is fused with a phenyl ring on the corestructure

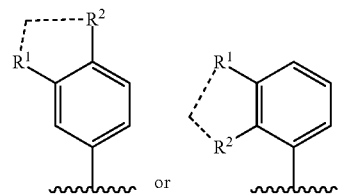

forming a double ring, more preferably forming a heterocyclic double ring, most preferably the heterocyclic double ring formed by $R^1$ and $R^2$ with the corestructure is selected from benzoimidazole, indazole, indoline and benzothiazole being unsubstituted or being substituted by one or more of halogen, —OH, —NH$_2$, —SH, =O, —OC$_{1-4}$alkyl being unsubstituted or substituted by one or more of OH or halogen, —CN, or C$_{1-4}$alkyl being unsubstituted or substituted by one or more of OH or halogen;

and/or $R^3$ is substituted or unsubstituted alkyl, CONR$^6$R$^7$, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl or $R^3$ is not alkyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or
- the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or
preferably $R^3$ is not alkyl;

and/or
- most preferably $R^3$ is selected from substituted or unsubstituted alkyl like propyl or butyl, $CONR^6R^7$ like diethylacetamide, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine,
- or most preferably $R^3$ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine;

and/or
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl, wherein
- the aryl is phenyl, naphtyl or anthracene; preferably is napthyl and phenyl; more preferable is phenyl;

and/or
- the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or
- the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or
- the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or
- the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or
- the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or
most preferably $R^4$ is selected from hydrogen or from substituted or unsubstituted $C_{1-4}$alkyl like $CH_3$ or $CH_2OH$;

and/or
$R^5$ is hydrogen, halogen, hydroxy, substituted or unsubstituted O-alkyl, substituted or unsubstituted alkyl, wherein
- the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or
- the O-alkyl is —O—$C_{1-8}$alkyl like —Omethyl, —O-ethyl, —O-propyl, —O-butyl, —O-pentyl, —O-hexyl, —O-heptyl, or —O-octyl; preferably is —O—$C_{1-6}$alkyl like —O-methyl, —O-ethyl, —O-propyl, —O-butyl, —O-pentyl, or —O-hexyl; more preferably is —O—$C_{1-4}$alkyl like —O-methyl, —O-ethyl, —O-propyl or —O-butyl;

and/or
halogen is any of fluorine, chlorine, iodine or bromine, preferably chlorine or fluorine;

and/or
most preferably $R^5$ is selected from hydrogen or hydroxy;

and/or
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring, wherein
- the aryl is phenyl, naphtyl or anthracene; preferably is napthyl and phenyl; more preferably is phenyl;

and/or
- the alkyl-aryl is $C_{1-4}$-alkyl-aryl; preferably is benzyl;

and/or
- the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or when $R^6$, $R^7$ or $R^8$ together with their respective connecting carbon or nitrogen atom form a cycloalkylic or heterocyclic ring this ring is 5 or 6 membered, preferably form a saturated cycloalkylic ring of 5 or 6 members, like saturated, unsubstituted cyclohexyl;

and/or most preferably $R^6$, $R^7$, and $R^8$ are independently from each other selected from hydrogen, from substituted or unsubstituted $C_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkyl-aryl like benzyl, or $R^6$ and $R^7$ together with their connecting carbon atom form a cycloalkylic 5 or 6-membered ring like cyclohexyl.

In another preferred embodiment of the compound according to the invention according to general formulas I, II, III, IV, V and VI $V^1$ is CH or N;
m is 1 or 2;
n is 0 or 1;
$R^1$ is selected from hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, —$CONR^6R^7$, substituted or unsubstituted aryl like phenyl and substituted or unsubstituted heterocyclyl like imidazol;
$R^2$ is selected from hydrogen, halogen like fluorine, or $C_{1-4}$alkyl like $CH_3$ or $CF_3$; or $R^1$ and $R^2$ are bonded to neighbouring atoms in the ring and together with these atoms form a saturated or unsaturated, substituted or unsubstituted ring, fused to the—with $V^1$ being carbon—phenyl ring

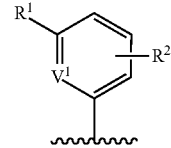

of the corestructure of formula VII

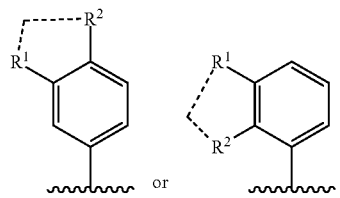

forming a double ring, preferably forming a heterocyclic double ring, more preferably the heterocyclic double ring formed by $R^1$ and $R^2$ with the corestructure is selected from benzoimidazole, indazole, indoline and benzothiazole being unsubstituted or being substituted by one or more of halogen, —OH, —$NH_2$, —SH, =O, —$OC_{1-4}$alkyl being unsubstituted or substituted by one or more of OH or halogen, —CN, or $C_{1-4}$alkyl being unsubstituted or substituted by one or more of OH or halogen;

$R^3$ is selected from substituted or unsubstituted alkyl like methyl, propyl, isopropyl, isobutyl or butyl, from $CONR^6R^7$ like diethylacetamide, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, indoline, 2,3-dihydroindene, benzofuran, pyrimidine, quinoline;

$R^4$ is hydrogen or substituted or unsubstituted $C_{1-4}$alkyl, preferably is hydrogen, $CH_3$ or $CH_2OH$;

$R^5$ is hydrogen, halogen, hydroxy, substituted or unsubstituted O-alkyl, substituted or unsubstituted alkyl preferably is hydrogen or hydroxy;

$R^6$, $R^7$ and $R^8$ are independently from each other selected from hydrogen, from substituted or unsubstituted $C_{1-4}$alkyl like methyl, ethyl, propyl, isopropyl or butyl, from substituted or unsubstituted aryl like phenyl, from substituted or unsubstituted heterocyclyl like pyrrolidine, thiazole, or pyridine, or from substituted or unsubstituted cycloalkyl like cyclopropyl or from substituted or unsubstituted alkyl-aryl like benzyl, or $R^6$ and $R^7$ together with their connecting carbon atom form a cycloalkylic 5 or 6-membered ring like cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formulas I, II, and III has a general formula VII,

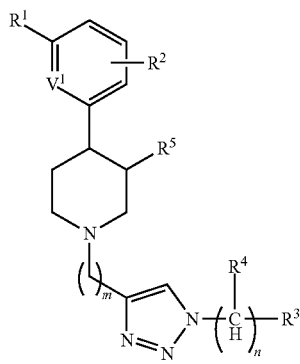

wherein
m is 1 or 2;
n is 0 or 1;
$V^1$ is selected from nitrogen or carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;
$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

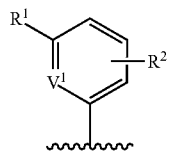

of the corestructure of formula III, which may be condensed with a further unsubstituted or substituted ring system;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
$R^5$ is hydrogen, halogen, hydroxy, substituted or unsubstituted O-alkyl, substituted or unsubstituted alkyl;
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formulas I, II, and III has a general formula VII,

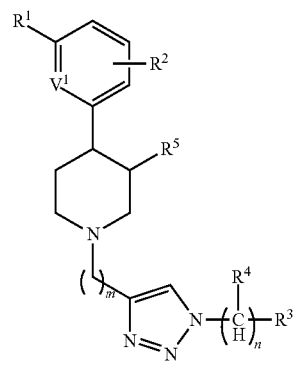

wherein
$V^1$ is CH or N;
m is 1 or 2;
n is 0 or 1;
$R^1$ is selected from hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, —$CONR^6R^7$, substituted or unsubstituted aryl like phenyl and substituted or unsubstituted heterocyclyl like imidazol;
$R^2$ is selected from hydrogen, halogen like fluorine, or $C_{1-4}$alkyl like $CH_3$ or $CF_3$;
or
$R^1$ and $R^2$ are bonded to neighbouring atoms in the ring and together with these atoms form a saturated or unsaturated, substituted or unsubstituted ring, fused to the—with $V^1$ being carbon—phenyl ring

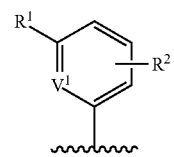

of the corestructure of formula VII

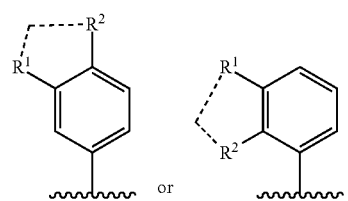

forming a double ring, preferably forming a heterocyclic double ring, more preferably the heterocyclic double ring formed by $R^1$ and $R^2$ with the corestructure is selected from benzoimidazole, indazole, indoline and benzothiazole being unsubstituted or being substituted by one or more of halogen, —OH, —NH$_2$, —SH, ═O, —OC$_{1-4}$alkyl being unsubstituted or substituted by one or more of OH or halogen, —CN, or C$_{1-4}$alkyl being unsubstituted or substituted by one or more of OH or halogen;

$R^3$ is selected from substituted or unsubstituted alkyl like methyl, propyl, isopropyl, isobutyl or butyl, from CONR$^6$R$^7$ like diethylacetamide, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, indoline, 2,3-dihydroindene, benzofuran, pyrimidine, quinoline;

$R^4$ is hydrogen or substituted or unsubstituted C$_{1-4}$alkyl, preferably is hydrogen, CH$_3$ or CH$_2$OH;

$R^5$ is hydrogen, halogen, hydroxy, substituted or unsubstituted O-alkyl, substituted or unsubstituted alkyl preferably is hydrogen or hydroxy;

$R^6$, $R^7$ and $R^8$ are independently from each other selected from hydrogen, from substituted or unsubstituted C$_{1-4}$alkyl like methyl, ethyl, propyl, isopropyl or butyl, from substituted or unsubstituted aryl like phenyl, from substituted or unsubstituted heterocyclyl like pyrrolidine, thiazole or pyridine, or from substituted or unsubstituted cycloalkyl like cyclopropyl or from substituted or unsubstituted alkyl-aryl like benzyl, or $R^6$ and $R^7$ together with their connecting carbon atom form a cycloalkylic 5 or 6-membered ring like cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formulas I, II, III, IV, V, VI and VII, any aryl which is substituted is substituted by one or more of halogen, —OH, —NH$_2$, —SH, —C(O)OH, —OC$_{1-4}$alkyl being unsubstituted or substituted by one or more of OH or halogen, —CN, or —C$_{1-4}$alkyl being unsubstituted or substituted by one or more of OH or halogen, any cycloalkyl or heterocyclyl which is substituted is substituted by one or more of halogen, —OH, —NH$_2$, —SH, ═O, —C(O)OH, —OC$_{1-4}$alkyl being unsubstituted or substituted by one or more of OH or halogen, —CN, or —C$_{1-4}$alkyl being unsubstituted or substituted by one or more of OH or halogen, and any alkyl, alkenyl, alkynyl or O-alkyl which is substituted is substituted by one or more of halogen, —OH, —NH$_2$, —SH, —C(O)OH, or —OC$_{1-4}$alkyl being unsubstituted or substituted by one or more of OH or halogen.

In a preferred embodiment of the compound according to the invention according to general formula VII being selected from N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
3-(1-((1-isobutyl-1H-1,2,3-triazol-4-yl)methyl)piperidin-4-yl)phenol,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea,
N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine, N-(3-(1-((1-(2,3-dihydro-1H-inden-1-yl)-1H-1,2,3-triazol-4-yl)methyl)piperidin-4-yl)phenyl)methanesulfonamide,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
3-(1-(1-(pyridin-2-yl)ethyl)-1H-1,2,3-triazol-4-yl)methyl)piperidin-4-yl)phenol,
N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-(pyridin-3-ylmethyl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol,
3-(1-((1-((3-fluoropyridin-2-yl)methyl)-1H-1,2,3-triazol-4-yl)methyl)piperidin-4-yl)phenol,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-((3-chloropyridin-2-yl)methyl)-1H-1,2,3-triazol-4-yl)methyl)piperidin-4-yl)phenol, 3-(1-((1-(pyridin-3-ylmethyl)-1H-1,2,3-triazol-4-yl)methyl)
    piperidin-4-yl)phenol,
3-(1-((1-(2,6-difluorophenyl)-1H-1,2,3-triazol-4-yl)methyl)
    piperidin-4-yl)phenol,
3-(1-((1-(3,4-difluorophenyl)-1H-1,2,3-triazol-4-yl)methyl)
    piperidin-4-yl)phenol,
3-(1-((1-(5-chloropyridin-2-yl)-1H-1,2,3-triazol-4-yl)
    methyl)piperidin-4-yl)phenol,
(R)-3-(1-((1-(2-hydroxy-1-phenylethyl)-1H-1,2,3-triazol-4-
    yl)methyl)piperidin-4-yl)phenol,
(S)-3-(1-((1-(2-hydroxy-1-phenylethyl)-1H-1,2,3-triazol-4-
    yl)methyl)piperidin-4-yl)phenol,
3-(1-((1-((3-(trifluoromethyl)pyridin-2-yl)methyl)-1H-1,2,
    3-triazol-4-yl)methyl)piperidin-4-yl)phenol,
3-(1-((1-((5-(trifluoromethyl)pyridin-2-yl)methyl)-1H-1,2,
    3-triazol-4-yl)methyl)piperidin-4-yl)phenol,
3-(1-((1-((5-chloropyridin-2-yl)methyl)-1H-1,2,3-triazol-4-
    yl)methyl)piperidin-4-yl)phenol,
3-(1-((1-(3-fluoropyridin-2-yl)-1H-1,2,3-triazol-4-yl)
    methyl)piperidin-4-yl)phenol,
3-(1-((1-(2,4-difluorophenyl)-1H-1,2,3-triazol-4-yl)methyl)
    piperidin-4-yl)phenol,
3-(1-((1-(4-(trifluoromethyl)pyridin-2-yl)-1H-1,2,3-triazol-
    4-yl)methyl)piperidin-4-yl)phenol,
6-((4-((4-(3-hydroxyphenyl)piperidin-1-yl)methyl)-1H-1,2,
    3-triazol-1-yl)methyl)pyridin-3-ol,
3-(1-((1-((4-(trifluoromethyl)pyridin-2-yl)methyl)-1H-1,2,
    3-triazol-4-yl)methyl)piperidin-4-yl)phenol,
3-(1-((1-(3-chloropyridin-2-yl)-1H-1,2,3-triazol-4-yl)
    methyl)piperidin-4-yl)phenol,
3-(1-(2-(1-phenyl-1H-1,2,3-triazol-4-yl)ethyl)piperidin-4-
    yl)phenol,
N-(6-(1-((1-phenyl-1H-1,2,3-triazol-4-yl)methyl)piperidin-
    4-yl)pyridin-2-yl)methanesulfonamide,
N-(6-(1-((1-(pyridin-2-ylmethyl)-1H-1,2,3-triazol-4-yl)
    methyl)piperidin-4-yl)pyridin-2-yl)propane-2-sulfona-
    mide,
N-(6-(1-((1-phenyl-1H-1,2,3-triazol-4-yl)methyl)piperidin-
    4-yl)pyridin-2-yl)propane-2-sulfonamide,
N-(6-(1-((1-(2-fluorophenyl)-1H-1,2,3-triazol-4-yl)methyl)
    piperidin-4-yl)pyridin-2-yl)propane-2-sulfonamide,
N-(6-(1-((1-(2-fluorophenyl)-1H-1,2,3-triazol-4-yl)methyl)
    piperidin-4-yl)pyridin-2-yl)propionamide,
    optionally in form of one of the stereoisomers, preferably
    enantiomers or diastereomers, a racemate or in form of
    a mixture of at least two of the stereoisomers, prefer-
    ably enantiomers and/or diastereomers, in any mixing
    ratio, or a corresponding salt thereof, or—option-
    ally—a corresponding solvate thereof.
  In a very preferred embodiment of the compound accord-
ing to the invention according to general formula VII being
selected from
N-(3-(1-((1-phenyl-1H-1,2,3-triazol-4-yl)methyl)piperidin-
    4-yl)phenyl)propane-2-sulfonamide,
3-(1-((1-phenyl-1H-1,2,3-triazol-4-yl)methyl)piperidin-4-
    yl)phenol,
3-(1-((1-(2-fluorobenzyl)-1H-1,2,3-triazol-4-yl)methyl)pip-
    eridin-4-yl)phenol,
3-(1-((1-benzyl-1H-1,2,3-triazol-4-yl)methyl)piperidin-4-
    yl)phenol,
N-(4-fluoro-3-(1-((1-phenyl-1H-1,2,3-triazol-4-yl)methyl)
    piperidin-4-yl)phenyl)methanesulfonamide,
3-(1-((1-cyclohexyl-1H-1,2,3-triazol-4-yl)methyl)piperidin-
    4-yl)phenol,
3-(1-((1-isobutyl-1H-1,2,3-triazol-4-yl)methyl)piperidin-4-
    yl)phenol,
N-(3-(1-((1-(2-fluorophenyl)-1H-1,2,3-triazol-4-yl)methyl)
    piperidin-4-yl)phenyl)methanesulfonamide,
N-(3-(1-((1-(3-fluorophenyl)-1H-1,2,3-triazol-4-yl)methyl)
    piperidin-4-yl)phenyl)methanesulfonamide,
N-(3-fluoro-5-(1-((1-phenyl-1H-1,2,3-triazol-4-yl)methyl)
    piperidin-4-yl)phenyl)methanesulfonamide,
3-(1-((1-(3,4-dichlorophenyl)-1H-1,2,3-triazol-4-yl)methyl)
    piperidin-4-yl)phenol,
3-(1-((1-(2,4-dichlorophenyl)-1H-1,2,3-triazol-4-yl)methyl)
    piperidin-4-yl)phenol,
4-((4-((4-(3-hydroxyphenyl)piperidin-1-yl)methyl)-1H-1,2,
    3-triazol-1-yl)methyl)benzonitrile,
3-(1-((1-(3-methoxyphenyl)-1H-1,2,3-triazol-4-yl)methyl)
    piperidin-4-yl)phenol,
3-(1-((1-(2,3-dihydro-1H-inden-1-yl)-1H-1,2,3-triazol-4-yl)
    methyl)piperidin-4-yl)phenol,
N-(4-(1-((1-phenyl-1H-1,2,3-triazol-4-yl)methyl)piperidin-
    4-yl)benzo[d]thiazol-2-yl)acetamide,
4-(1-((1-phenyl-1H-1,2,3-triazol-4-yl)methyl)piperidin-4-
    yl)benzo[d]thiazol-2-amine,
2-methyl-5-(1-((1-phenyl-1H-1,2,3-triazol-4-yl)methyl)pip-
    eridin-4-yl)phenol,
N-(2-fluoro-3-(1-((1-phenyl-1H-1,2,3-triazol-4-yl)methyl)
    piperidin-4-yl)phenyl)methanesulfonamide,
3-(1-((1-(6-methoxypyridin-3-yl)-1H-1,2,3-triazol-4-yl)
    methyl)piperidin-4-yl)phenol,
3-(1-((1-(6-(trifluoromethyl)pyridin-3-yl)-1H-1,2,3-triazol-
    4-yl)methyl)piperidin-4-yl)phenol,
3-(1-((1-((1R,2R)-2-methoxy-2,3-dihydro-1H-inden-1-yl)-
    1H-1,2,3-triazol-4-yl)methyl)piperidin-4-yl)phenol,
N-(3-(1-((1-phenyl-1H-1,2,3-triazol-4-yl)methyl)piperidin-
    4-yl)phenyl)methanesulfonamide,
3-(1-((1-(3-fluorobenzyl)-1H-1,2,3-triazol-4-yl)methyl)pip-
    eridin-4-yl)phenol,
3-(1-((1-(4,4-difluorocyclohexyl)-1H-1,2,3-triazol-4-yl)
    methyl)piperidin-4-yl)phenol,
3-(1-((1-((1S,2R)-1-fluoro-2,3-dihydro-1H-inden-2-yl)-1H-
    1,2,3-triazol-4-yl)methyl)piperidin-4-yl)phenol,
3-(1-((1-((1R,2R)-1-fluoro-2,3-dihydro-1H-inden-2-yl)-1H-
    1,2,3-triazol-4-yl)methyl)piperidin-4-yl)phenol,
3-(1-((1-(1-phenylethyl)-1H-1,2,3-triazol-4-yl)methyl)pip-
    eridin-4-yl)phenol,
3-(1-((1-((1s,4s)-4-(trifluoromethyl)cyclohexyl)-1H-1,2,3-
    triazol-4-yl)methyl)piperidin-4-yl)phenol,
3-(1-((1-((1r,4r)-4-(trifluoromethyl)cyclohexyl)-1H-1,2,3-
    triazol-4-yl)methyl)piperidin-4-yl)phenol,
3-(1-((1-(pyridin-2-yl)-1H-1,2,3-triazol-4-yl)methyl)piperi-
    din-4-yl)phenol,
3-(1-((1-(benzofuran-3-yl)-1H-1,2,3-triazol-4-yl)methyl)pi-
    peridin-4-yl)phenol,
3-(1-((1-phenyl-1H-1,2,3-triazol-4-yl)methyl)piperidin-4-
    yl)aniline,
3-(1-((1-(4-hydroxyphenyl)-1H-1,2,3-triazol-4-yl)methyl)
    piperidin-4-yl)phenol,
N-(3-(1-((1-((6-methoxypyridin-2-yl)methyl)-1H-1,2,3-tri-
    azol-4-yl)methyl)piperidin-4-yl)phenyl)propane-2-sulfo-
    namide,
3-(1-((1-(2-fluorophenyl)-1H-1,2,3-triazol-4-yl)methyl)pip-
    eridin-4-yl)phenol,
3-(1-((1-(5-fluoropyridin-2-yl)-1H-1,2,3-triazol-4-yl)
    methyl)piperidin-4-yl)phenol,
3-(1-((1-(2,6-difluorophenyl)-1H-1,2,3-triazol-4-yl)methyl)
    piperidin-4-yl)phenol,
3-(1-((1-(3,4-difluorophenyl)-1H-1,2,3-triazol-4-yl)methyl)
    piperidin-4-yl)phenol,
3-(1-((1-(5-chloropyridin-2-yl)-1H-1,2,3-triazol-4-yl)
    methyl)piperidin-4-yl)phenol, 3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol, and
3-(1-(2-(1-phenyl-1H-1,2,3-triazol-4-yl)ethyl)piperidin-4-yl)phenol, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another very preferred embodiment of the invention the compound according to Formula VII is having a general formula of general Formula VIII

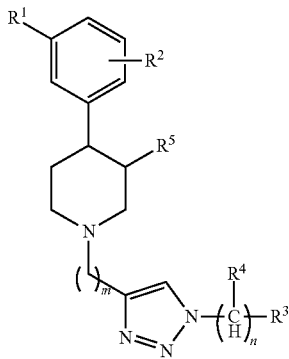

(VIII)

In another preferred embodiment of the compound according to the invention according to general formula VIII being selected from
N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-((1R,2R)-2-hydroxycyclopentyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
4-(1-((1-phenyl-1H-1,2,3-triazol-4-yl)methyl)piperidin-4-yl)-1H-benzo[d]imidazole,
3-(1-((1-phenyl-1H-1,2,3-triazol-4-yl)methyl)piperidin-4-yl)-4-(trifluoromethyl)phenol,
4-(1-((1-phenyl-1H-1,2,3-triazol-4-yl)methyl)piperidin-4-yl)-1H-benzo[d]imidazol-2(3H)-one,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide,
N-methyl-3-(1-((1-phenyl-1H-1,2,3-triazol-4-yl)methyl)piperidin-4-yl)benzenesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
N-(3-(1-((1-phenyl-1H-1,2,3-triazol-4-yl)methyl)piperidin-4-yl)-4-(trifluoromethyl)phenyl)methanesulfonamide,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
N-(3-(1-((1-isopropyl-1H-1,2,3-triazol-4-yl)methyl)piperidin-4-yl)phenyl)methanesulfonamide,
3-(1-((1-isobutyl-1H-1,2,3-triazol-4-yl)methyl)piperidin-4-yl)phenol,
6-(1-((1-phenyl-1H-1,2,3-triazol-4-yl)methyl)piperidin-4-yl)-1H-indazole,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-N-(3-(1-((1-phenyl-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)indolin-2-one,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea,
N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
N,N-diethyl-2-(4-((4-(3-hydroxyphenyl)piperidin-1-yl)methyl)-1H-1,2,3-triazol-1-yl)acetamide,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine, N-(3-(1-((1-(2,3-dihydro-1H-inden-1-yl)-1H-1,2,3-triazol-4-yl)methyl)piperidin-4-yl)phenyl)methanesulfonamide,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
3-(1-((1-benzyl-1H-1,2,3-triazol-4-yl)methyl)piperidin-4-yl)-N-isopropylbenzamide,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
N-(3-(1-((1-(4,4-difluorocyclohexyl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propionamide,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
N-(6-(1-((1-phenyl-1H-1,2,3-triazol-4-yl)methyl)piperidin-4-yl)benzo[d]thiazol-2-yl)acetamide,
3-(1-((1-(1-(pyridin-2-yl)ethyl)-1H-1,2,3-triazol-4-yl)methyl)piperidin-4-yl)phenol,
N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
4-(3-(1H-tetrazol-5-yl)phenyl)-1-((1-phenyl-1H-1,2,3-triazol-4-yl)methyl)piperidine,
N-(3-(1-((1-(1-(pyridin-2-yl)ethyl)-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(5-(1-((1-benzyl-1H-1,2,3-triazol-4-yl)methyl)piperidin-4-yl)-2-fluorophenyl)methanesulfonamide,
N-(3-(1-((1-((1S,2S)-2-hydroxy-2,3-dihydro-1H-inden-1-yl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-((1S,2R)-1-hydroxy-2,3-dihydro-1H-inden-2-yl)-1H-1,2,3-triazol-4-yl)methyl)piperidin-4-yl)phenyl)methanesulfonamide,
N-(3-(1-((1-(pyridin-2-ylmethyl)-1H-1,2,3-triazol-4-yl)methyl)piperidin-4-yl)phenyl)methanesulfonamide,
N-(3-(1-((1-(pyridin-3-ylmethyl)-1H-1,2,3-triazol-4-yl)methyl)piperidin-4-yl)phenyl)methanesulfonamide,
N-(3-(1-((1-((1R,2R)-1-hydroxy-2,3-dihydro-1H-inden-2-yl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-2-methoxyphenyl)methanesulfonamide,
N-(3-(1-((1-(pyridin-2-ylmethyl)-1H-1,2,3-triazol-4-yl)methyl)piperidin-4-yl)phenyl)propionamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-((1S,2S)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-(2-hydroxy-2-methylpropoxy)phenyl)-1H-1,2,3-triazol-4-yl)methyl)piperidin-4-yl)phenol,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
3-(1-((1-(4-(2-hydroxyethoxy)phenyl)-1H-1,2,3-triazol-4-yl)methyl)piperidin-4-yl)phenol, N-(3-((3R,4S)-3-hydroxy-1-((1-phenyl-1H-1,2,3-triazol-4-yl)methyl)piperidin-4-yl)phenyl)methanesulfonamide,
1-ethyl-3-(3-(1-((1-(pyridin-2-ylmethyl)-1H-1,2,3-triazol-4-yl)methyl)piperidin-4-yl)phenyl)urea,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-(1-((1-((6-(trifluoromethyl)pyridin-2-yl)methyl)-1H-1,2,3-triazol-4-yl)methyl)piperidin-4-yl)phenyl)propane-2-sulfonamide,
N-(3-(1-((1-((6-methylpyridin-2-yl)methyl)-1H-1,2,3-triazol-4-yl)methyl)piperidin-4-yl)phenyl)propane-2-sulfonamide,
N-(3-(1-((8H-[1,2,3]triazolo[5,1-a]isoindol-3-yl)methyl)piperidin-4-yl)phenyl)methanesulfonamide,
3-(1-((8H-[1,2,3]triazolo[5,1-a]isoindol-3-yl)methyl)piperidin-4-yl)phenol,
N-(3-(1-((1-((3-(trifluoromethyl)pyridin-2-yl)methyl)-1H-1,2,3-triazol-4-yl)methyl)piperidin-4-yl)phenyl)propane-2-sulfonamide,
N-(3-(1-((1-((5-(trifluoromethyl)pyridin-2-yl)methyl)-1H-1,2,3-triazol-4-yl)methyl)piperidin-4-yl)phenyl)propane-2-sulfonamide,
N-(3-((3R,4S)-1-((1-benzyl-1H-1,2,3-triazol-4-yl)methyl)-3-hydroxypiperidin-4-yl)phenyl)propane-2-sulfonamide,
N-(3-(1-((1-((6-(trifluoromethyl)pyridin-3-yl)methyl)-1H-1,2,3-triazol-4-yl)methyl)piperidin-4-yl)phenyl)propane-2-sulfonamide,
N-(3-((3R,4S)-3-hydroxy-1-((1-(pyridin-2-ylmethyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide,
N-(3-(1-((1-((4-azidopyridin-2-yl)methyl)-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)methanesulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol,
3-(1-((1-((3-fluoropyridin-2-yl)methyl)-1H-1,2,3-triazol-4-yl)methyl)piperidin-4-yl)phenol,
N-(3-(1-((1-((5-fluoropyridin-2-yl)methyl)-1H-1,2,3-triazol-4-yl)methyl)piperidin-4-yl)phenyl)propane-2-sulfonamide,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
N-methyl-3-(1-((1-(pyridin-2-ylmethyl)-1H-1,2,3-triazol-4-yl)methyl)piperidin-4-yl)benzenesulfonamide,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(pyridin-2-ylmethyl)-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-((3-chloropyridin-2-yl)methyl)-1H-1,2,3-triazol-4-yl)methyl)piperidin-4-yl)phenol,
3-(1-((1-(pyridin-3-ylmethyl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol,
3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
(R)-3-(1-((1-(2-hydroxy-1-phenylethyl)-1H-1,2,3-triazol-4-yl)methyl)piperidin-4-yl)phenol,
(S)-3-(1-((1-(2-hydroxy-1-phenylethyl)-1H-1,2,3-triazol-4-yl)methyl)piperidin-4-yl)phenol,
3-(1-((1-((3-(trifluoromethyl)pyridin-2-yl)methyl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(3-fluoropyridin-2-yl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
2-((4-((4-(3-hydroxyphenyl)piperidin-1-yl)methyl)-1H-1,2,3-triazol-1-yl)methyl)pyridin-3-ol,
3-(1-((1-(4-(trifluoromethyl)pyridin-2-yl)-1H-1,2,3-triazol-4-yl)methyl)piperidin-4-yl)phenol,
3-(1-((1-((3-methoxypyridin-2-yl)methyl)-1H-1,2,3-triazol-4-yl)methyl)piperidin-4-yl)phenol,
6-((4-((4-(3-hydroxyphenyl)piperidin-1-yl)methyl)-1H-1,2,3-triazol-1-yl)methyl)pyridin-3-ol,
3-(1-((1-((4-(trifluoromethyl)pyridin-2-yl)methyl)-1H-1,2,3-triazol-4-yl)methyl)piperidin-4-yl)phenol,
3-(1-((1-(3-chloropyridin-2-yl)-1H-1,2,3-triazol-4-yl)methyl)piperidin-4-yl)phenol, and
3-(1-(2-(1-phenyl-1H-1,2,3-triazol-4-yl)ethyl)piperidin-4-yl)phenol,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formula VIII being selected from
N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol, 3-(1-((1-(2-fluorobenzyl)-1H-1,2,3-triazol-4-yl)methyl)piperidin-4-yl)phenol,
3-(1-((1-((1R,2R)-2-hydroxycyclopentyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
4-(1-((1-phenyl-1H-1,2,3-triazol-4-yl)methyl)piperidin-4-yl)-1H-benzo[d]imidazole,
3-(1-((1-phenyl-1H-1,2,3-triazol-4-yl)methyl)piperidin-4-yl)-4-(trifluoromethyl)phenol,
4-(1-((1-phenyl-1H-1,2,3-triazol-4-yl)methyl)piperidin-4-yl)-1H-benzo[d]imidazol-2(3H)-one,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide,
N-methyl-3-(1-((1-phenyl-1H-1,2,3-triazol-4-yl)methyl)piperidin-4-yl)benzenesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
N-(3-(1-((1-phenyl-1H-1,2,3-triazol-4-yl)methyl)piperidin-4-yl)-4-(trifluoromethyl)phenyl)methanesulfonamide,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
N-(3-(1-((1-isopropyl-1H-1,2,3-triazol-4-yl)methyl)piperidin-4-yl)phenyl)methanesulfonamide,
3-(1-((1-isobutyl-1H-1,2,3-triazol-4-yl)methyl)piperidin-4-yl)phenol,
6-(1-((1-phenyl-1H-1,2,3-triazol-4-yl)methyl)piperidin-4-yl)-1H-indazole,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-N-(3-(1-((1-phenyl-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)indolin-2-one,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea,
N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
N,N-diethyl-2-(4-((4-(3-hydroxyphenyl)piperidin-1-yl)methyl)-1H-1,2,3-triazol-1-yl)acetamide,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine,
N-(3-(1-((1-(2,3-dihydro-1H-inden-1-yl)-1H-1,2,3-triazol-4-yl)methyl)piperidin-4-yl)phenyl)methanesulfonamide,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
N-(3-(1-((1-(4,4-difluorocyclohexyl)-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propionamide, N-(3-(1-((1-(((1R,2R)-2-hydroxy-2,3-dihydro-1H-inden-1-yl)-1H-1,2,3-triazol-4-yl)methyl)piperidin-4-yl)phenyl)methanesulfonamide,
3-(1-((1-(((1S,2R)-1-fluoro-2,3-dihydro-1H-inden-2-yl)-1H-1,2,3-triazol-4-yl)methyl)piperidin-4-yl)phenol,
3-(1-((1-(((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
N-(6-(1-((1-phenyl-1H-1,2,3-triazol-4-yl)methyl)piperidin-4-yl)benzo[d]thiazol-2-yl)acetamide,
3-(1-((1-(1-(pyridin-2-yl)ethyl)-1H-1,2,3-triazol-4-yl)methyl)piperidin-4-yl)phenol,
N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-(((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
N-(3-(1-((1-(1-(pyridin-2-yl)ethyl)-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(5-(1-((1-benzyl-1H-1,2,3-triazol-4-yl)methyl)piperidin-4-yl)-2-fluorophenyl)methanesulfonamide,
N-(3-(1-((1-(((1S,2S)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-(((1S,2R)-1-hydroxy-2,3-dihydro-1H-inden-2-yl)-1H-1,2,3-triazol-4-yl)methyl)piperidin-4-yl)phenyl)methanesulfonamide,
N-(3-(1-((1-(pyridin-2-ylmethyl)-1H-1,2,3-triazol-4-yl)methyl)piperidin-4-yl)phenyl)methanesulfonamide,
N-(3-(1-((1-(pyridin-3-ylmethyl)-1H-1,2,3-triazol-4-yl)methyl)piperidin-4-yl)phenyl)methanesulfonamide,
N-(3-(1-((1-(((1R,2R)-1-hydroxy-2,3-dihydro-1H-inden-2-yl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-benzyl-1H-1,2,3-triazol-4-yl)methyl)piperidin-4-yl)-2-methoxyphenyl)methanesulfonamide,
N-(3-(1-((1-(pyridin-2-ylmethyl)-1H-1,2,3-triazol-4-yl)methyl)piperidin-4-yl)phenyl)propionamide,
N-(3-(1-((1-(((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(((1S,2S)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-(2-hydroxy-2-methylpropoxy)phenyl)-1H-1,2,3-triazol-4-yl)methyl)piperidin-4-yl)phenol,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
3-(1-((1-(4-(2-hydroxyethoxy)phenyl)-1H-1,2,3-triazol-4-yl)methyl)piperidin-4-yl)phenol,
N-(3-((3R,4S)-3-hydroxy-1-((1-phenyl-1H-1,2,3-triazol-4-yl)methyl)piperidin-4-yl)phenyl)methanesulfonamide,
1-ethyl-3-(3-(1-((1-(pyridin-2-ylmethyl)-1H-1,2,3-triazol-4-yl)methyl)piperidin-4-yl)phenyl)urea,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-(1-((1-((6-(trifluoromethyl)pyridin-2-yl)methyl)-1H-1,2,3-triazol-4-yl)methyl)piperidin-4-yl)phenyl)propane-2-sulfonamide,
N-(3-(1-((1-((6-methylpyridin-2-yl)methyl)-1H-1,2,3-triazol-4-yl)methyl)piperidin-4-yl)phenyl)propane-2-sulfonamide,
N-(3-(1-((8H-[1,2,3]triazolo[5,1-a]isoindol-3-yl)methyl)piperidin-4-yl)phenyl)methanesulfonamide,
3-(1-((8H-[1,2,3]triazolo[5,1-a]isoindol-3-yl)methyl)piperidin-4-yl)phenol,
N-(3-(1-((1-((3-(trifluoromethyl)pyridin-2-yl)methyl)-1H-1,2,3-triazol-4-yl)methyl)piperidin-4-yl)phenyl)propane-2-sulfonamide,
N-(3-(1-((1-((5-(trifluoromethyl)pyridin-2-yl)methyl)-1H-1,2,3-triazol-4-yl)methyl)piperidin-4-yl)phenyl)propane-2-sulfonamide,
N-(3-((3R,4S)-1-((1-benzyl-1H-1,2,3-triazol-4-yl)methyl)-3-hydroxypiperidin-4-yl)phenyl)propane-2-sulfonamide,
N-(3-(1-((1-((6-(trifluoromethyl)pyridin-3-yl)methyl)-1H-1,2,3-triazol-4-yl)methyl)piperidin-4-yl)phenyl)propane-2-sulfonamide,
N-(3-((3R,4S)-3-hydroxy-1-((1-(pyridin-2-ylmethyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide, N-(3-(1-((1-((4-azidopyridin-2-yl)methyl)-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)propane-2-sulfonamide,
N-(3-(1-((1-(2-hydroxy-1-phenylethyl)-1H-1,2,3-triazol-4-yl)methyl)piperidin-4-yl)phenyl)methanesulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol,
3-(1-((1-((3-fluoropyridin-2-yl)methyl)-1H-1,2,3-triazol-4-yl)methyl)piperidin-4-yl)phenol,
N-(3-(1-((1-((5-fluoropyridin-2-yl)methyl)-1H-1,2,3-triazol-4-yl)methyl)piperidin-4-yl)phenyl)propane-2-sulfonamide,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-((3-chloropyridin-2-yl)methyl)-1H-1,2,3-triazol-4-yl)methyl)piperidin-4-yl)phenol,
3-(1-((1-(pyridin-3-ylmethyl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol,
3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
(R)-3-(1-((1-(2-hydroxy-1-phenylethyl)-1H-1,2,3-triazol-4-yl)methyl)piperidin-4-yl)phenol,
(S)-3-(1-((1-(2-hydroxy-1-phenylethyl)-1H-1,2,3-triazol-4-yl)methyl)piperidin-4-yl)phenol,
3-(1-((1-((3-(trifluoromethyl)pyridin-2-yl)methyl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(3-fluoropyridin-2-yl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
2-((4-((4-(3-hydroxyphenyl)piperidin-1-yl)methyl)-1H-1,2,3-triazol-1-yl)methyl)pyridin-3-ol,
3-(1-((1-(4-(trifluoromethyl)pyridin-2-yl)-1H-1,2,3-triazol-4-yl)methyl)piperidin-4-yl)phenol,
3-(1-((1-((3-methoxypyridin-2-yl)methyl)-1H-1,2,3-triazol-4-yl)methyl)piperidin-4-yl)phenol,
6-((4-((4-(3-hydroxyphenyl)piperidin-1-yl)methyl)-1H-1,2,3-triazol-1-yl)methyl)pyridin-3-ol,
3-(1-((1-((4-(trifluoromethyl)pyridin-2-yl)methyl)-1H-1,2,3-triazol-4-yl)methyl)piperidin-4-yl)phenol,
3-(1-((1-(3-chloropyridin-2-yl)-1H-1,2,3-triazol-4-yl)methyl)piperidin-4-yl)phenol, and
3-(1-(2-(1-phenyl-1H-1,2,3-triazol-4-yl)ethyl)piperidin-4-yl)phenol;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formula VIII being selected from
N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-propyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-phenyl-1H-1,2,3-triazol-4-yl)methyl)piperidin-4-yl)benzamide,
N-(3-(1-((1-phenyl-1H-1,2,3-triazol-4-yl)methyl)piperidin-4-yl)phenyl)propionamide,
3-(1-((1-benzyl-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)acetamide,
3-(1-((1-(pyridin-3-yl)-1H-1,2,3-triazol-4-yl)methyl)piperidin-4-yl)phenol,
3-(1-((1-(pyridin-4-yl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-(4-fluorophenyl)-1H-1,2,3-triazol-4-yl)methyl)piperidin-4-yl)phenyl)methanesulfonamide,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
6-(1-((1-phenyl-1H-1,2,3-triazol-4-yl)methyl)piperidin-4-yl)-1H-benzo[d]imidazole,
N-(3-(1-((1-cyclohexyl-1H-1,2,3-triazol-4-yl)methyl)piperidin-4-yl)phenyl)methanesulfonamide,
3-(1-((1-isopropyl-1H-1,2,3-triazol-4-yl)methyl)piperidin-4-yl)phenol,
3-(1-((1-isobutyl-1H-1,2,3-triazol-4-yl)methyl)piperidin-4-yl)phenol,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
4-(1-((1-phenyl-1H-1,2,3-triazol-4-yl)methyl)piperidin-4-yl)-1H-indazole,
4-(3-(1H-imidazol-2-yl)phenyl)-1-((1-phenyl-1H-1,2,3-triazol-4-yl)methyl)piperidine,
N-methyl-3-(1-((1-phenyl-1H-1,2,3-triazol-4-yl)methyl)piperidin-4-yl)benzamide,
N-(2-fluoro-5-(1-((1-phenyl-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(4-fluorophenyl)-1H-1,2,3-triazol-4-yl)methyl)piperidin-4-yl)phenol,
N-(3-(1-((1-benzyl-1H-1,2,3-triazol-4-yl)methyl)piperidin-4-yl)phenyl)methanesulfonamide,
1,1-dimethyl-3-(3-(1-((1-phenyl-1H-1,2,3-triazol-4-yl)methyl)piperidin-4-yl)phenyl)urea, N-(3-fluoro-5-(1-((1-phenyl-1H-1,2,3-triazol-4-yl)methyl)piperidin-4-yl)phenyl)acetamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
2-methyl-5-(3-(1-((1-phenyl-1H-1,2,3-triazol-4-yl)methyl)piperidin-4-yl)phenyl)-1,3,4-oxadiazole,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
3-(1-((1-(2,3-dihydro-1H-inden-1-yl)-1H-1,2,3-triazol-4-yl)methyl)piperidin-4-yl)phenol,
4-(3-(methylsulfonyl)phenyl)-1-((1-phenyl-1H-1,2,3-triazol-4-yl)methyl)piperidine,
N-(3-(1-((1-(2,3-dihydro-1H-inden-1-yl)-1H-1,2,3-triazol-4-yl)methyl)piperidin-4-yl)phenyl)methanesulfonamide,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(pyridin-4-ylmethyl)-1H-1,2,3-triazol-4-yl)methyl)piperidin-4-yl)phenol,
3-(1-((1-(pyridin-2-ylmethyl)-1H-1,2,3-triazol-4-yl)methyl)piperidin-4-yl)phenol,
1-ethyl-3-(3-(1-((1-phenyl-1H-1,2,3-triazol-4-yl)methyl)piperidin-4-yl)phenyl)urea,
N-(3-(1-((1-(4-(trifluoromethyl)benzyl)-1H-1,2,3-triazol-4-yl)methyl)piperidin-4-yl)phenyl)methanesulfonamide,
2-(4-((4-(3-hydroxyphenyl)piperidin-1-yl)methyl)-1H-1,2,3-triazol-1-yl)phenol,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
(1S,2S)-1-(4-((4-(3-hydroxyphenyl)piperidin-1-yl)methyl)-1H-1,2,3-triazol-1-yl)-2,3-dihydro-1H-inden-2-ol,
3-(1-((1-((1R,2R)-2-hydroxycyclohexyl)-1H-1,2,3-triazol-4-yl)methyl)piperidin-4-yl)phenol,
3-(1-((1-(2-hydroxy-1-phenylethyl)-1H-1,2,3-triazol-4-yl)methyl)piperidin-4-yl)phenol,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
6-(1-((1-phenyl-1H-1,2,3-triazol-4-yl)methyl)piperidin-4-yl)benzo[d]thiazol-2-amine,
3-(1-((1-(1-(pyridin-2-yl)ethyl)-1H-1,2,3-triazol-4-yl)methyl)piperidin-4-yl)phenol,
N-(3-(1-((1-(1-phenylethyl)-1H-1,2,3-triazol-4-yl)methyl)piperidin-4-yl)phenyl)methanesulfonamide,
3-(1-((1-(1-phenylethyl)-1H-1,2,3-triazol-4-yl)methyl)piperidin-4-yl)phenol,
(1R,2R)-1-(4-((4-(3-hydroxyphenyl)piperidin-1-yl)methyl)-1H-1,2,3-triazol-1-yl)-2,3-dihydro-1H-inden-2-ol,
N-(3-(1-((1-benzyl-1H-1,2,3-triazol-4-yl)methyl)piperidin-4-yl)phenyl)propane-2-sulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
N-(3-(1-((1-(pyridin-2-ylmethyl)-1H-1,2,3-triazol-4-yl)methyl)piperidin-4-yl)phenyl)propane-2-sulfonamide,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
N-(3-(1-((1-benzyl-1H-1,2,3-triazol-4-yl)methyl)piperidin-4-yl)-4-fluorophenyl)methanesulfonamide,
(1R,2S)-1-(4-((4-(3-hydroxyphenyl)piperidin-1-yl)methyl)-1H-1,2,3-triazol-1-yl)-2,3-dihydro-1H-inden-2-ol,
3-(1-((1-(benzofuran-3-yl)-1H-1,2,3-triazol-4-yl)methyl)piperidin-4-yl)phenol,
N-(3-(1-((1-((1R,2R)-2-hydroxy-2,3-dihydro-1H-inden-1-yl)-1H-1,2,3-triazol-4-yl)methyl)piperidin-4-yl)phenyl)methanesulfonamide,
N-(3-(1-((1-(pyridin-2-yl)-1H-1,2,3-triazol-4-yl)methyl)piperidin-4-yl)phenyl)methanesulfonamide,
3-(1-((1-phenyl-1H-1,2,3-triazol-4-yl)methyl)piperidin-4-yl)aniline,
3-(4-((4-(3-hydroxyphenyl)piperidin-1-yl)methyl)-1H-1,2,3-triazol-1-yl)-3-methylindolin-2-one,
(1S,2R)-2-(4-((4-(3-hydroxyphenyl)piperidin-1-yl)methyl)-1H-1,2,3-triazol-1-yl)-2,3-dihydro-1H-inden-1-ol,
N-(3-(1-((1-(pyridin-3-ylmethyl)-1H-1,2,3-triazol-4-yl)methyl)piperidin-4-yl)phenyl)methanesulfonamide,
N-(2-methoxy-3-(1-((1-phenyl-1H-1,2,3-triazol-4-yl)methyl)piperidin-4-yl)phenyl)methanesulfonamide,
N-(3-(1-((1-((1R,2R)-2-hydroxy-2,3-dihydro-1H-inden-1-yl)-1H-1,2,3-triazol-4-yl)methyl)piperidin-4-yl)phenyl)propane-2-sulfonamide,
3-(1-((1-(4-hydroxyphenyl)-1H-1,2,3-triazol-4-yl)methyl)piperidin-4-yl)phenol,
3-(1-((1-(4-(2-hydroxyethyl)phenyl)-1H-1,2,3-triazol-4-yl)methyl)piperidin-4-yl)phenol,
N-(3-(1-((1-(pyridin-2-ylmethyl)-1H-1,2,3-triazol-4-yl)methyl)piperidin-4-yl)phenyl)ethanesulfonamide,
N-(3-(1-((1-((6-methoxypyridin-2-yl)methyl)-1H-1,2,3-triazol-4-yl)methyl)piperidin-4-yl)phenyl)propane-2-sulfonamide,
N-(3-(1-((1-((3-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-(1-((1-((6-fluoropyridin-2-yl)methyl)-1H-1,2,3-triazol-4-yl)methyl)piperidin-4-yl)phenyl)propane-2-sulfonamide,
N-(3-((3R,4S)-3-hydroxy-1-((1-phenyl-1H-1,2,3-triazol-4-yl)methyl)piperidin-4-yl)phenyl)propane-2-sulfonamide,
N-(3-((3S,4R)-3-hydroxy-1-((1-phenyl-1H-1,2,3-triazol-4-yl)methyl)piperidin-4-yl)phenyl)propane-2-sulfonamide,
N-(3-(1-((1-((2-(trifluoromethyl)pyrimidin-5-yl)methyl)-1H-1,2,3-triazol-4-yl)methyl)piperidin-4-yl)phenyl)propane-2-sulfonamide,
3-(1-((1-((6-fluoropyridin-2-yl)methyl)-1H-1,2,3-triazol-4-yl)methyl)piperidin-4-yl)phenol,
3-(1-((1-((5-fluoropyridin-2-yl)methyl)-1H-1,2,3-triazol-4-yl)methyl)piperidin-4-yl)phenol, 3-(1-((1-((3-fluoropyridin-2-yl)methyl)-1H-1,2,3-triazol-4-yl)methyl)piperidin-4-yl)phenol,
2-fluoro-5-(1-((1-(pyridin-2-ylmethyl)-1H-1,2,3-triazol-4-yl)methyl)piperidin-4-yl)phenol,
4-fluoro-3-(1-((1-(pyridin-2-ylmethyl)-1H-1,2,3-triazol-4-yl)methyl)piperidin-4-yl)phenol,
2-((4-((4-(3-(1H-imidazol-2-yl)phenyl)piperidin-1-yl)methyl)-1H-1,2,3-triazol-1-yl)methyl)pyridine,
3-(1-((1-phenyl-1H-1,2,3-triazol-4-yl)methyl)piperidin-4-yl)benzenesulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-((3-chloropyridin-2-yl)methyl)-1H-1,2,3-triazol-4-yl)methyl)piperidin-4-yl)phenol,
3-(1-((1-(pyridin-3-ylmethyl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol,
3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
(R)-3-(1-((1-(2-hydroxy-1-phenylethyl)-1H-1,2,3-triazol-4-yl)methyl)piperidin-4-yl)phenol,
(S)-3-(1-((1-(2-hydroxy-1-phenylethyl)-1H-1,2,3-triazol-4-yl)methyl)piperidin-4-yl)phenol,
3-(1-((1-((3-(trifluoromethyl)pyridin-2-yl)methyl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(3-fluoropyridin-2-yl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol,
3-(1-((1-(4-(trifluoromethyl)pyridin-2-yl)-1H-1,2,3-triazol-4-yl)methyl)piperidin-4-yl)phenol,
6-((4-((4-(3-hydroxyphenyl)piperidin-1-yl)methyl)-1H-1,2,3-triazol-1-yl)methyl)pyridin-3-ol,
3-(1-((1-((4-(trifluoromethyl)pyridin-2-yl)methyl)-1H-1,2,3-triazol-4-yl)methyl)piperidin-4-yl)phenol,
3-(1-((1-(3-chloropyridin-2-yl)-1H-1,2,3-triazol-4-yl)methyl)piperidin-4-yl)phenol, and
3-(1-(2-(1-phenyl-1H-1,2,3-triazol-4-yl)ethyl)piperidin-4-yl)phenol,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formula VIII being selected from
N-(3-(1-((1-phenyl-1H-1,2,3-triazol-4-yl)methyl)piperidin-4-yl)phenyl)propane-2-sulfonamide,
3-(1-((1-phenyl-1H-1,2,3-triazol-4-yl)methyl)piperidin-4-yl)phenol,
3-(1-((1-(2-fluorobenzyl)-1H-1,2,3-triazol-4-yl)methyl)piperidin-4-yl)phenol,
3-(1-((1-benzyl-1H-1,2,3-triazol-4-yl)methyl)piperidin-4-yl)phenol,
N-(4-fluoro-3-(1-((1-phenyl-1H-1,2,3-triazol-4-yl)methyl)piperidin-4-yl)phenyl)methanesulfonamide,
3-(1-((1-cyclohexyl-1H-1,2,3-triazol-4-yl)methyl)piperidin-4-yl)phenol,
3-(1-((1-isobutyl-1H-1,2,3-triazol-4-yl)methyl)piperidin-4-yl)phenol,
N-(3-(1-((1-(2-fluorophenyl)-1H-1,2,3-triazol-4-yl)methyl)piperidin-4-yl)phenyl)methanesulfonamide,
N-(3-(1-((1-(3-fluorophenyl)-1H-1,2,3-triazol-4-yl)methyl)piperidin-4-yl)phenyl)methanesulfonamide,
N-(3-fluoro-5-(1-((1-phenyl-1H-1,2,3-triazol-4-yl)methyl)piperidin-4-yl)phenyl)methanesulfonamide,
3-(1-((1-(3,4-dichlorophenyl)-1H-1,2,3-triazol-4-yl)methyl)piperidin-4-yl)phenol,
3-(1-((1-(2,4-dichlorophenyl)-1H-1,2,3-triazol-4-yl)methyl)piperidin-4-yl)phenol,
4-((4-((4-(3-hydroxyphenyl)piperidin-1-yl)methyl)-1H-1,2,3-triazol-1-yl)methyl)benzonitrile,
3-(1-((1-(3-methoxyphenyl)-1H-1,2,3-triazol-4-yl)methyl)piperidin-4-yl)phenol,
3-(1-((1-(2,3-dihydro-1H-inden-1-yl)-1H-1,2,3-triazol-4-yl)methyl)piperidin-4-yl)phenol,
N-(4-(1-((1-phenyl-1H-1,2,3-triazol-4-yl)methyl)piperidin-4-yl)benzo[d]thiazol-2-yl)acetamide,
4-(1-((1-phenyl-1H-1,2,3-triazol-4-yl)methyl)piperidin-4-yl)benzo[d]thiazol-2-amine,
2-methyl-5-(1-((1-phenyl-1H-1,2,3-triazol-4-yl)methyl)piperidin-4-yl)phenol,
N-(2-fluoro-3-(1-((1-phenyl-1H-1,2,3-triazol-4-yl)methyl)piperidin-4-yl)phenyl)methanesulfonamide,
3-(1-((1-(6-methoxypyridin-3-yl)-1H-1,2,3-triazol-4-yl)methyl)piperidin-4-yl)phenol,
3-(1-((1-(6-(trifluoromethyl)pyridin-3-yl)-1H-1,2,3-triazol-4-yl)methyl)piperidin-4-yl)phenol,
3-(1-((1-((1R,2R)-2-methoxy-2,3-dihydro-1H-inden-1-yl)-1H-1,2,3-triazol-4-yl)methyl)piperidin-4-yl)phenol,
N-(3-(1-((1-phenyl-1H-1,2,3-triazol-4-yl)methyl)piperidin-4-yl)phenyl)methanesulfonamide,
3-(1-((1-(3-fluorobenzyl)-1H-1,2,3-triazol-4-yl)methyl)piperidin-4-yl)phenol,
3-(1-((1-(4,4-difluorocyclohexyl)-1H-1,2,3-triazol-4-yl)methyl)piperidin-4-yl)phenol,
3-(1-((1-((1S,2R)-1-fluoro-2,3-dihydro-1H-inden-2-yl)-1H-1,2,3-triazol-4-yl)methyl)piperidin-4-yl)phenol,
3-(1-((1-((1R,2R)-1-fluoro-2,3-dihydro-1H-inden-2-yl)-1H-1,2,3-triazol-4-yl)methyl)piperidin-4-yl)phenol,
3-(1-((1-(1-phenylethyl)-1H-1,2,3-triazol-4-yl)methyl)piperidin-4-yl)phenol,
3-(1-((1-((1s,4s)-4-(trifluoromethyl)cyclohexyl)-1H-1,2,3-triazol-4-yl)methyl)piperidin-4-yl)phenol,
3-(1-((1-((1r,4r)-4-(trifluoromethyl)cyclohexyl)-1H-1,2,3-triazol-4-yl)methyl)piperidin-4-yl)phenol,
3-(1-((1-(pyridin-2-yl)-1H-1,2,3-triazol-4-yl)methyl)piperidin-4-yl)phenol,
3-(1-((1-(benzofuran-3-yl)-1H-1,2,3-triazol-4-yl)methyl)piperidin-4-yl)phenol,
3-(1-((1-phenyl-1H-1,2,3-triazol-4-yl)methyl)piperidin-4-yl)aniline,
3-(1-((1-(4-hydroxyphenyl)-1H-1,2,3-triazol-4-yl)methyl)piperidin-4-yl)phenol,
N-(3-(1-((1-((6-methoxypyridin-2-yl)methyl)-1H-1,2,3-triazol-4-yl)methyl)piperidin-4-yl)phenyl)propane-2-sulfonamide,
3-(1-((1-(2-fluorophenyl)-1H-1,2,3-triazol-4-yl)methyl)piperidin-4-yl)phenol,
3-(1-((1-(5-fluoropyridin-2-yl)-1H-1,2,3-triazol-4-yl)methyl)piperidin-4-yl)phenol,
3-(1-((1-(2,6-difluorophenyl)-1H-1,2,3-triazol-4-yl)methyl)piperidin-4-yl)phenol, 3-(1-((1-(3,4-difluorophenyl)-1H-1,2,3-triazol-4-yl)methyl)piperidin-4-yl)phenol,
3-(1-((1-(5-chloropyridin-2-yl)-1H-1,2,3-triazol-4-yl)methyl)piperidin-4-yl)phenol,
3-(1-((1-((5-(trifluoromethyl)pyridin-2-yl)methyl)-1H-1,2,3-triazol-4-yl)methyl)piperidin-4-yl)phenol,
3-(1-((1-((5-chloropyridin-2-yl)methyl)-1H-1,2,3-triazol-4-yl)methyl)piperidin-4-yl)phenol,
3-(1-((1-(2,4-difluorophenyl)-1H-1,2,3-triazol-4-yl)methyl)piperidin-4-yl)phenol, and
3-(1-(2-(1-phenyl-1H-1,2,3-triazol-4-yl)ethyl)piperidin-4-yl)phenol,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another very preferred embodiment of the invention the compound according to Formula VII is having a general formula of general Formula IX

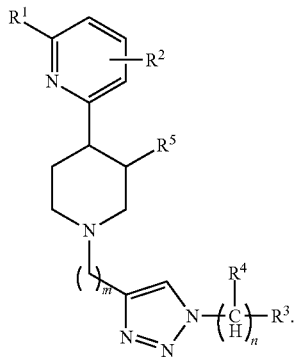

(IX)

In another preferred embodiment of the compound according to the invention according to general formula IX being selected from
N-(6-(1-((1-phenyl-1H-1,2,3-triazol-4-yl)methyl)piperidin-4-yl)pyridin-2-yl)methanesulfonamide,
N-(6-(1-((1-benzyl-1H-1,2,3-triazol-4-yl)methyl)piperidin-4-yl)pyridin-2-yl)propionamide,
N-(6-(1-((1-((1R,2R)-2-hydroxy-2,3-dihydro-1H-inden-1-yl)-1H-1,2,3-triazol-4-yl)methyl)piperidin-4-yl)pyridin-2-yl)propionamide,
N-(6-(1-((1-(pyridin-2-ylmethyl)-1H-1,2,3-triazol-4-yl)methyl)piperidin-4-yl)pyridin-2-yl)propane-2-sulfonamide,
N-(6-(1-((1-phenyl-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propane-2-sulfonamide,
N-(6-(1-((1-((3-fluoropyridin-2-yl)methyl)-1H-1,2,3-triazol-4-yl)methyl)piperidin-4-yl)pyridin-2-yl)propane-2-sulfonamide,
N-(6-(1-((1-((5-fluoropyridin-2-yl)methyl)-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propionamide,
N-(6-(1-((1-((3-chloropyridin-2-yl)methyl)-1H-1,2,3-triazol-4-yl)methyl)piperidin-4-yl)pyridin-2-yl)propane-2-sulfonamide, and
N-(6-(1-((1-((5-chloropyridin-2-yl)methyl)-1H-1,2,3-triazol-4-yl)methyl)piperidin-4-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

In another preferred embodiment of the compound according to the invention according to general formula IX being selected from
N-(6-(1-((1-phenyl-1H-1,2,3-triazol-4-yl)methyl)piperidin-4-yl)pyridin-2-yl)methanesulfonamide,
N-(6-(1-((1-(pyridin-2-ylmethyl)-1H-1,2,3-triazol-4-yl)methyl)piperidin-4-yl)pyridin-2-yl)propane-2-sulfonamide,
N-(6-(1-((1-phenyl-1H-1,2,3-triazol-4-yl)methyl)piperidin-4-yl)pyridin-2-yl)propane-2-sulfonamide,
N-(6-(1-((1-(2-fluorophenyl)-1H-1,2,3-triazol-4-yl)methyl)piperidin-4-yl)pyridin-2-yl)propane-2-sulfonamide, and
N-(6-(1-((1-(2-fluorophenyl)-1H-1,2,3-triazol-4-yl)methyl)piperidin-4-yl)pyridin-2-yl)propionamide,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or—optionally—a corresponding solvate thereof.

As this invention is aimed at providing a compound or a chemically related series of compounds which act as dual ligands of the $\sigma_1$ receptor and the µ-opiod receptor it is a very preferred embodiment in which the compounds are selected which act as dual ligands of the $\sigma_1$ receptor and the µ-opiod receptor and especially compounds which have a binding expressed as $K_i$ which is <100 nm for both receptors.

In the following the phrase "compound of the invention" is used. This is to be understood as any compound according to the invention as described above according to general formulas I, II, III, IV, or V.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

Another preferred aspect of the invention is a process for the production of a compound according to the invention, wherein a compound of formula I

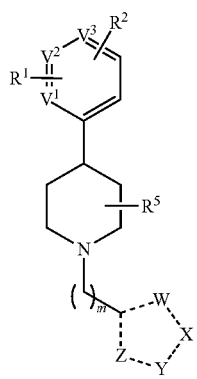

wherein $R^1$, $R^2$, $R^5$, $V^1$, $V^2$, $V^3$, W, X, Y, Z and m are as defined for Formula I or according to formula Ia

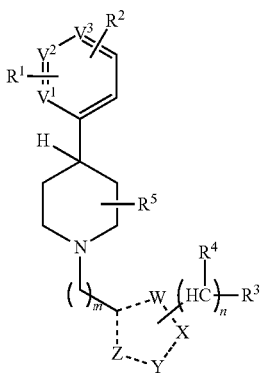

wherein $R^1$, $R^2$, $R^3$, $R^4$, $R^5$, $V^1$, $V^2$, $V^3$, W, X, Y, Z, n and m are as defined for Formula I wherein a compound of formula X or its suitable salt like the hydrochloride

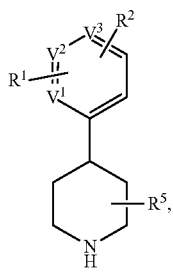

wherein $R^1$, $R^2$, $R^5$, $V^1$, $V^2$, and $V^3$ are as defined for Formula I, is reacted with a compound according to formula XI (for a compound according to formula I) or according to formula XIa (for a compound according to formula Ia) under the conditions of Step 1

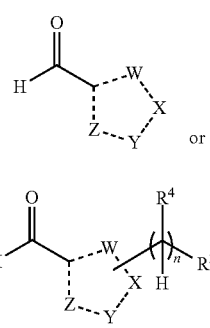

wherein $R^3$, $R^4$, W, X, Y, Z and n are as defined for Formula I, leading to a compound according to formula (I) or formula (Ia) respectively, wherein the reductive amination reaction of the compounds of formula (X) and (XI or XIa) of Step 1 is carried out with a reductive reagent in an aprotic solvent in the presence of an organic base.

In a preferred embodiment of Step 1 the reductive reagent is sodium triacetoxyborohydride, the aprotic solvent is dichloroethane and/or the organic base is diisopropylethylamine.

A preferred aspect of the invention is also a process for the production of a compound according to formula VII,

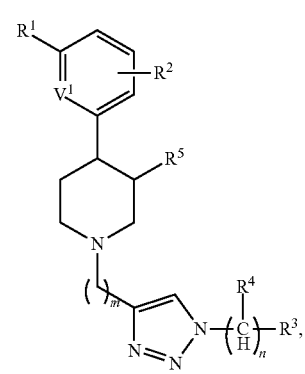

wherein $R^1$, $R^2$, $R^3$, $R^4$, $R^5$, n and m are as defined for Formula VII, wherein a compound of formula XII or its suitable salt like the hydrochloride

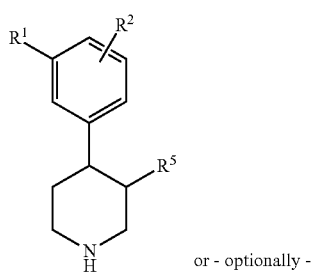

or - optionally -

(XIIa)

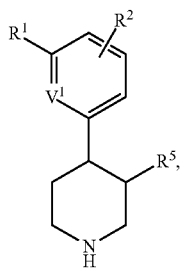

wherein $R^1$, $R^2$, and $R^5$ are as defined for Formula VII, is reacted with a compound according to formula XIV under the conditions of Step 2

(XIV)

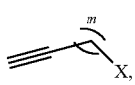

wherein m is as defined for Formula VII, leading to a compound according to formula XIII, (XIII)

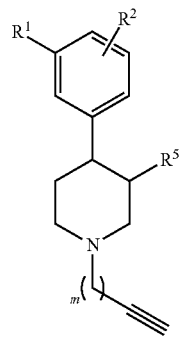

wherein $R^1$, $R^2$, $R^5$ and m are as defined for Formula VII, followed by reacting said compound according to formula XIII with a compound according to formula XV under the conditions of Step 3

(XV)

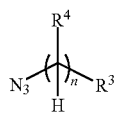

wherein $R^3$, $R^4$ and n are as defined for Formula VII, under the conditions of Step 3, leading to a compound according to formula (VII), wherein X is a leaving group like a halogen or sulphate like chlorine, wherein the reaction of Step 2 of said compounds of general formula (XII) (or—optionally—(XIIa)) with said compounds of formula (XIV) is carried out in the presence of a base in an aprotic solvent wherein the reaction of Step 3 of said compounds of general formula (XIII) with said compounds of formula (XV) is carried out in the presence of a copper salt and sodium ascorbate in a mixture of protic organic solvent and water.

In a preferred embodiment of Step 2 the base is $Et_3N$, the aprotic solvent is tetrahydrofurane (THF) and/or the reaction is preferably carried out at a temperature range of 25-75° C., preferably either by standard heating or through microwave.

In a preferred embodiment of Step 3 the copper salt is $CuSO_4.5H_2O$, the mixture of protic organic solvent and water is a mixture of t-BuOH:$H_2O$ 1:1 and/or the reaction is preferably carried out at room temperature.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I, II, III, IV, V, VI, VII, VIII or IX or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to a compound of the invention or a pharmaceutically acceptable salt or isomer thereof for use as a medicament.

Another aspect of the invention refers to the use of a compound of the invention or a pharmaceutically acceptable salt or isomer thereof in the manufacture of a medicament.

Another aspect of the invention refers to a compound of the invention as described above according to general formulas I, II, III, IV, V, VI, VII, VIII or IX or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

All solvents used for synthesis were p. a. quality.
General Formula ($I_{ex}$)

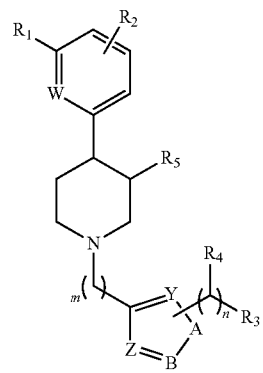

Method I

A process is described for the preparation of compounds of general formula ($I_{ex}$) where $R_1$, $R_2$, $R_3$, $R_4$, $R_5$, A, B, Y, Z, W, n and m have the meanings as defined above (with "A", "B", "Y", and "Z" being "X", "Y", "W", "Z" in the above description, respectively, and "W" being "$V^1$" in the above description), comprising the reaction of compound of formula ($II_{ex}$), or its suitable salt such as hydrochloride, with a compound of general formula ($III_{ex}$) as described in scheme 1:

Scheme 1:

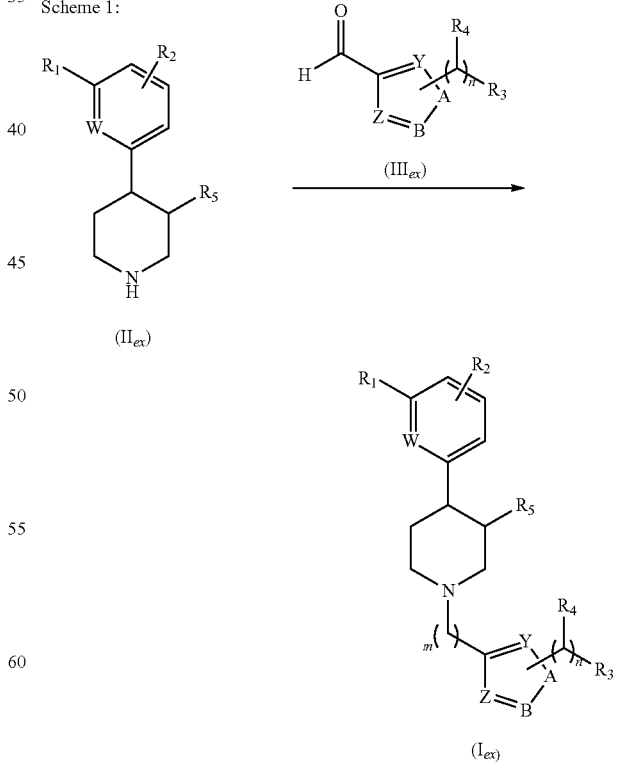

The reductive amination reaction of compounds of formula ($II_{ex}$) and ($III_{ex}$) is preferably carried out with a reductive reagent, preferably sodium triacetoxyborohydride, in an aprotic solvent, preferably dichloroethane, in the presence of an organic base preferably diisopropylethylamine.

Method II

A process is described for the preparation of compounds of general formula (Ia$_{ex}$ and Ib$_{ex}$) where R$_1$, R$_2$, R$_3$, R$_4$, R$_5$, the intermediate (V$_{ex}$) can be isolated but in other cases the two steps may be carried out one-pot. The compounds of formula (IV$_{ex}$) and the reagents of formula (VI$_{ex}$), (VII$_{ex}$) or (VIII$_{ex}$) are either commercially available or can be prepared following conventional methods reported in the literature. Alternately, some of the azides can be prepared in situ.

Scheme 2:

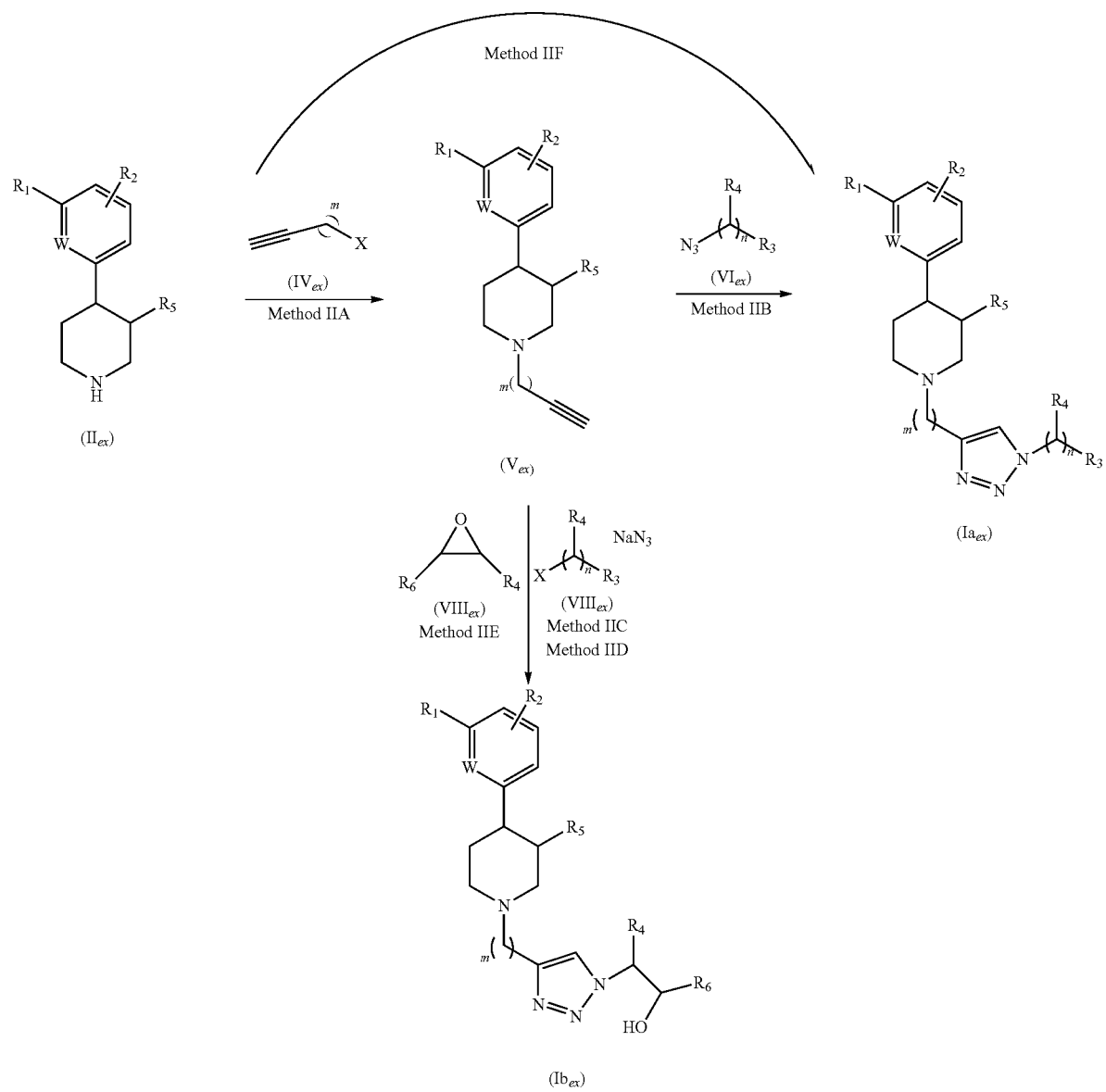

W, n and m have the meanings as defined above (with "W" being "V$^1$" in the above description), comprising the reaction of compound of formula (II$_{ex}$) with a compound of formula (IV$_{ex}$), where X is a suitable leaving group such as a halogen or sulfonate, and the reaction of the resulting intermediate (V$_{ex}$) with convenient reagents such as (VI$_{ex}$), (VII$_{ex}$) or (VIII$_{ex}$) to give the triazoles (Ia$_{ex}$) and (Ib$_{ex}$). As indicated in Scheme 2 different methods can be used in the practical realization of these two reactions. In some cases, In Method IIA the reaction of compounds of general formula (II$_{ex}$) with compounds of formula (IV$_{ex}$) where X is a suitable leaving group, such as a halogen or sulfonate, is carried out in the presence of a base, preferably Et$_3$N, in an aprotic solvent such as tetrahydrofurane (THF) at a temperature range of 25-75° C., using conventional heating or a microwave reactor.

In Method IIB the reaction of compounds of formula (V$_{ex}$) with azides of general formula (VI$_{ex}$) is carried out in the presence of a copper salt, preferably CuSO$_4$.5H$_2$O and sodium ascorbate, in a mixture of protic organic solvent and water, preferably a mixture of t-BuOH:H$_2$O 1:1 at room temperature.

In Method IIC the azide is generated in situ. The precursor of the azide (VII$_{ex}$), where X is a suitable leaving group such as a halogen or sulfonate, is treated with sodium azide and a copper salt, preferably CuI, in an organic solvent, preferably dimethylformamide, at 100° C. using microwave irradiation. Alternatively, some additives such as N$_1$,N$_2$-dimethylethane-1,2-diamine (DMEDA) and sodium ascorbate can be added to the reaction mixture.

In Method IID the precursor of the azide of general formula (VII$_{ex}$) is treated with sodium azide in a mixture of a protic organic solvent and water, preferably a mixture of t-BuOH:H$_2$O 1:1, at 100° C. using microwave irradiation for a suitable time, such as 1 h or until completed reaction. The in situ formed azide is then treated with compounds of general formula (V$_{ex}$) in the presence of a copper salt, preferably CuSO$_4$.5H$_2$O and sodium ascorbate at room temperature.

In Method IIE the compounds of general formula (Ib$_{ex}$) where R$_1$, R$_2$, R$_4$, R$_5$, R$_6$, W and m have the meanings as defined above (with "W" being "V$^1$" in the above description), comprises the reaction of compounds of general formula (V$_{ex}$) with an epoxide of general formula (VIII$_{ex}$) in the presence of sodium azide and a copper salt, preferably CuSO$_4$.5H$_2$O and sodium ascorbate, in a mixture of a protic organic solvent and water, preferably a mixture of t-BuOH: H$_2$O 1:1, heating at 100° C. using microwave irradiation.

In Method IIF the intermediates of general formula (Ia$_{ex}$) are prepared in a one-pot procedure comprising the reaction of compounds of general formula (II$_{ex}$) and propargyl bromide in the presence of a base, preferably Et$_3$N, in water at room temperature for 1 h or until completed reaction, after which compounds of general formula (VI$_{ex}$) are added in the presence of a copper salt, preferably CuI, at room temperature (*Tetrahedron* 2005, 61, 9331-9337).

Additionally the compounds of formula I$_{ex}$ can be prepared by interconversion of functional groups present in the final molecules. In this, functional groups that are present on some part of the final molecule could be converted into other related functional groups either with or without an intermediate product by inducing a chemical reaction.

If desired, racemic intermediates of general formula (II$_{ex}$) or final compounds of general formula (I$_{ex}$) may be resolved into their enantiomers by conventional resolution methods as for example, chiral chromatography, crystallization of the diastereomeric salts, etc.

The obtained reaction products may, if the above described processes for the preparation of compounds of the invention give rise to mixtures of stereoisomers, be separated in the isomers. These isomers may be separated by conventional techniques such as preparative or chiral chromatography. It is also possible to use crystallization of the diastereomeric salts as a way to obtain single isomers sometimes already during the prifiation step of the obtained reaction products. If there are chiral centers the compounds may be prepared in racemic form, or individual enantiomers may be prepared either by enantiospecific synthesis or by resolution. Standard conventional resolution methods are for example, chiral chromatography, crystallization of the diastereomeric salts.

Synthesis of Intermediates of General Formula (II$_{ex}$)

In some cases, compounds of formula (II$_{ex}$) are commercially available or they can be obtained by conventional methods. Alternatively compound of formula (II$_{ex}$) can be obtained following different methods:

Method III

Scheme 3

The process for the preparation of intermediates of general formula (IIa$_{ex}$) where W, R$_1$ and R$_2$ have the meanings as defined above (with "W" being "V$^1$" in the above description), according to the reaction sequence shown in scheme 3 and comprises:

a) The coupling reaction of an aromatic bromide of general formula (IX$_{ex}$) with 3,6-dihydro-2H-pyridine-1-tert-butoxycarbonyl-4-boronic acid pinacol ester in the presence of a palladium catalyst, such as Pd(PPh$_3$)$_4$ and an inorganic base, preferably K$_2$CO$_3$ or Na$_2$CO$_3$ in a mixture of organic solvents and water, preferably a mixture of dimethoxyethane/ethanol/water or dioxane/ethanol/water at a temperature range of 90-160° C. Alternatively, the reaction can be carried out in a microwave reactor. The bromides of general formula (IX$_{ex}$) are commercially available or can be prepared by conventional methods.

b) The reduction of compounds of formula (X$_{ex}$), by any suitable method such as a hydrogenation using a palladium catalyst, preferably Pd(OH)$_2$, in a protic solvent preferably MeOH.

c) The deprotection of the resulting compounds of formula (XI$_{ex}$) in an acidic medium, preferably HCl in an organic solvent preferably 1,4-dioxane.

Method IV

Scheme 4

Method IVa

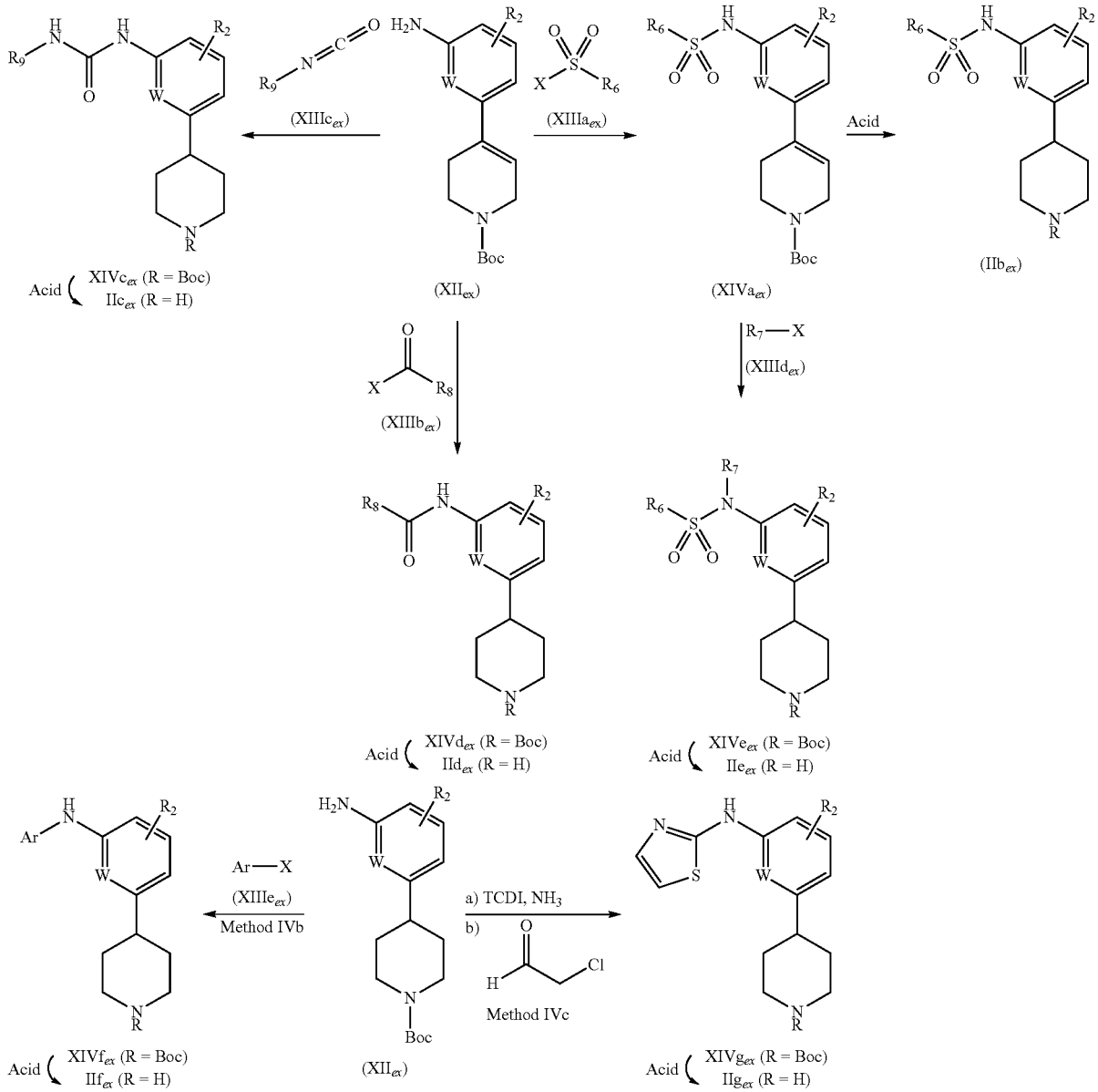

The process for the preparation of intermediates of general formula ($IIb_{ex}$-$g_{ex}$) where W, $R_2$, $R_6$, $R_7$, $R_8$, and $R_9$ have the meanings as defined above (with "W" being "$V^1$" in the above description), and Ar is an aryl or heteroaryl, according to the reaction sequence shown in scheme 4.

Method IVa Comprises:
 a) The reaction of intermediate ($XII_{ex}$) with a compound of formula ($XIIIa_{ex}$-$c_{ex}$, where X is a suitable leaving group, such as halogen) in the presence of a base, preferably pyridine, $Et_3N$, NaH, $K_2CO_3$ or $Cs_2CO_3$ at a range of temperature of 0 to 120° C. in the presence of a suitable solvent, such as dichloromethane or alternatively, the reactions can be carried out in a microwave reactor.

b) The reaction of intermediate $XIVa_{ex}$ with a compound of formula $XIIId_{ex}$ in the presence of a base, preferably $K_2CO_3$, in the presence of a suitable solvent, such as acetonitrile at a range of temperature of 0 to 120° C. and alternatively, the reaction can be carried out in a microwave reactor.

The deprotection of the resulting compounds ($XIVa_{ex}$-$d_{ex}$) in an acidic medium, preferably HCl in an organic solvent, preferably 1,4-dioxane.

Method IVb Comprises:
 a) The reaction of intermediate ($XII_{ex}$) with a compound of formula ($XIIIe_{ex}$, where X is a suitable leaving group, such as halogen, and Ar is an aryl or heteroaryl group) in the presence of a base, preferably NaOtBu, and a palladium catalyst, preferably Pd$_2$(dba)$_3$ and DPPF as ligand, at a range of temperature of 80 to 100° C. in the presence of a suitable solvent, such as toluene.

b) The deprotection of the resulting compounds (XIVf$_{ex}$) in an acidic medium, preferably HCl in an organic solvent, preferably 1,4-dioxane.

Method IVc Comprises:

a) The reaction of intermediate (XII$_{ex}$) with thiocarbonyl-diimidazole and a solution of ammonia in methanol, in the presence of a suitable solvent, such as dichloromethane at a range of temperature of 0 to 30° C., and subsequent reaction with chloroacetaldehyde in the presence of a suitable solvent, such a mixture of ethanol and water, at a range of temperature of 80 to 100° C.

b) The deprotection of the resulting compounds (XIVg$_{ex}$) in an acidic medium, preferably HCl in an organic solvent, preferably 1,4-dioxane.

Method V

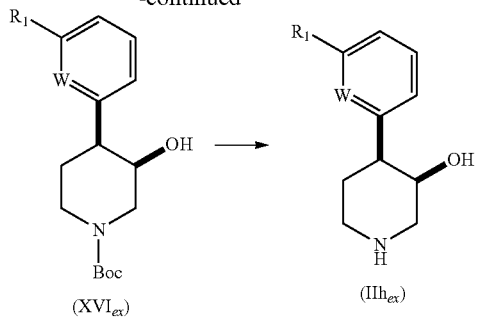

The process for the preparation of intermediates of general formula (IIh$_{ex}$) where R$_1$ and W have the meanings as defined above (with W being V$^1$ in the description above), according to the reaction sequence shown in scheme 5, which comprises:

a) The oxidation of compounds of formula (X$_{ex}$) with a suitable oxidizing agent such as m-chloroperbenzoic acid in an organic solvent, such as dichloromethane.

b) The reduction of the resulting intermediate (XV$_{ex}$), preferably under hydrogenation conditions, and more preferably at 50 psi, in the presence of a catalyst, preferably Pd/C, in a suitable organic solvent, such as mixtures of ethyl acetate and methanol.

c) The deprotection of the resulting compound of formula (XVI$_{ex}$) in an acidic medium, preferably HCl in an organic solvent, preferably 1,4-dioxane.

Synthesis of Intermediates of General Formula III$_{ex}$

The aldehydes of general formula (III$_{ex}$) where R$_3$, R$_4$, A, B, Y, Z and n have the meanings as defined above (with "A", "B", "Y", and "Z" being "X", "Y", "W", "Z" in the above description, respectively), are commercially available or can be prepared by methods described in the bibliography (for example, WO2010046780 A2, WO2008157844 A1) or by the methods described below and summarized in Scheme 6.

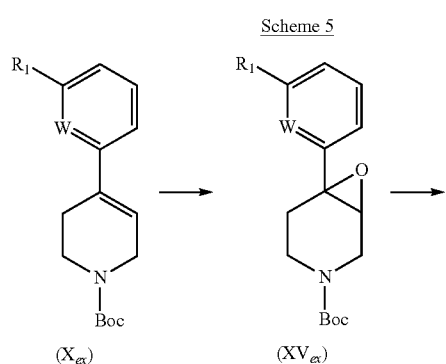

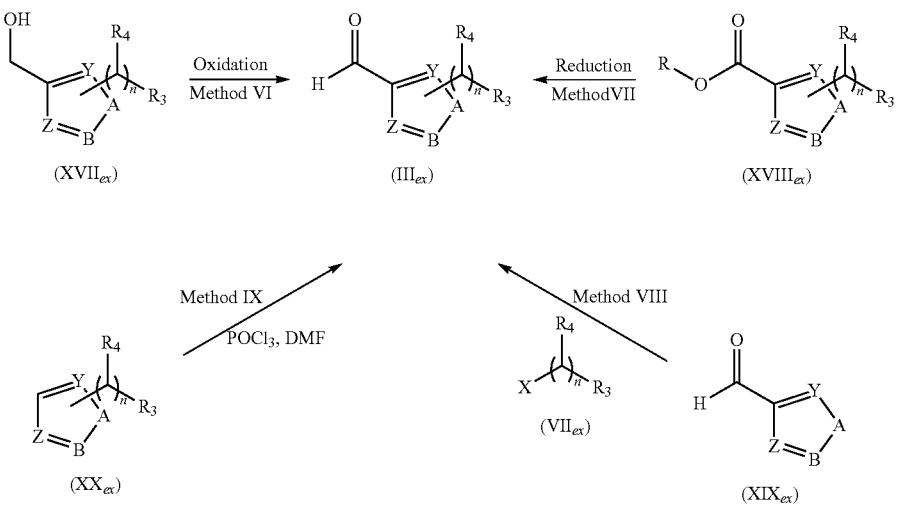

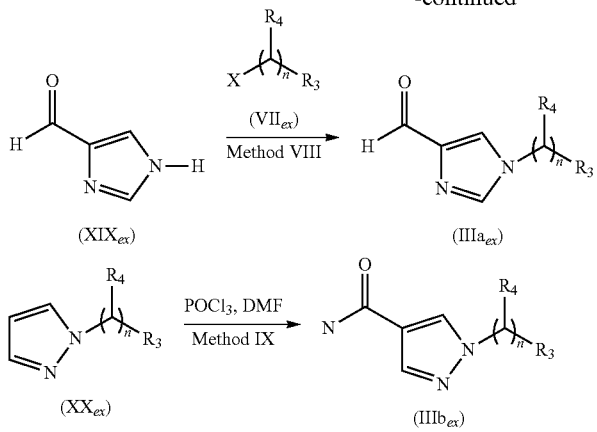

Method VI involves the oxidation of compounds of general formula (XVII$_{ex}$), using a suitable oxidizing reagent, such as MnO$_2$, in an aprotic solvent such as dichloromethane.

Method VII involves the reduction of compounds of general formula (XVIII$_{ex}$) with a suitable reducing agent such as DIBAL-H at −78° C. in an aprotic solvent, preferably dichloromethane.

Method VIII, which is exemplified for the preparation of compounds of formula IIIa, comprises the reaction between compounds of formula (XIX$_{ex}$) with compounds of general formula (VII$_{ex}$) where X is a suitable leaving group as an halogen or sulfonate, in the presence of an inorganic base, preferably an aqueous solution of NaOH and a catalyst, preferably tetra-n-butylammonium bromide, in a aprotic solvent preferably toluene at room temperature.

Method IX, which is exemplified for the preparation of compounds of formula IIIb, comprises the reaction between the compounds of general formula (XX$_{ex}$) with POCl$_3$ in DMF as solvent at 105° C.

Synthesis of Intermediates of General Formula XVII$_{ex}$

The alcohols of general formula (XVII$_{ex}$) where R$_3$, R$_4$, A, B, Y, Z and n have the meanings as defined above (with "A", "B", "Y", and "Z" being "X", "Y", "W", "Z" in the above description, respectively), are commercially available or can be prepared by methods described in the bibliography (for example *J. Org. Chem.* 2010, 75, 6540-6548, WO2010080864, *Org. Lett.* 2009, 21, 4954-4957, *J. Med. Chem.* 2011, 54, 5988-5999). In particular, alcohols of formula XVIIa$_{ex}$ and XVIIb$_{ex}$ can be prepared by the methods outlined in Scheme 7.

Scheme 7

Method X

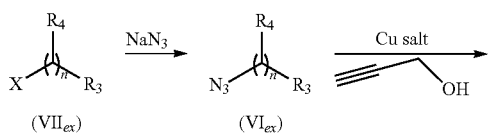

Method XI

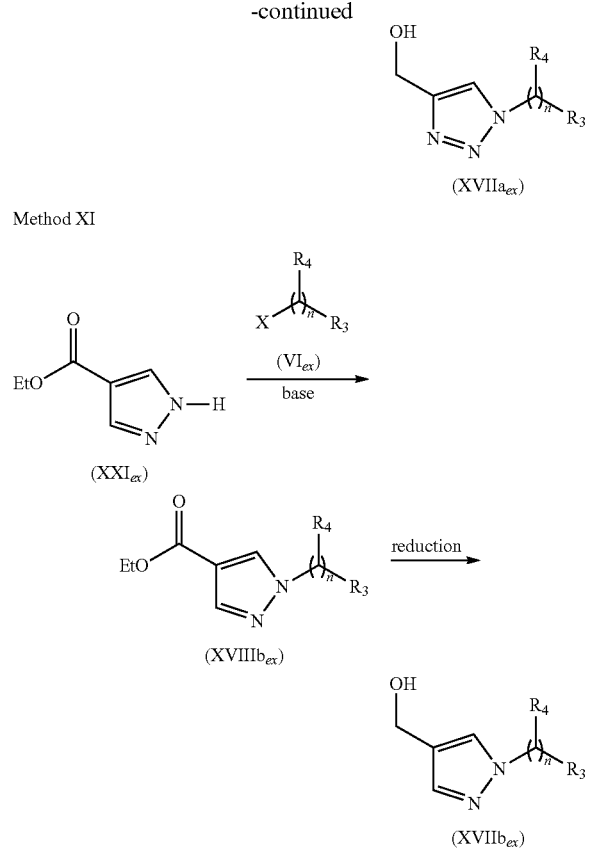

Method X comprises the cycloaddition reaction of an azide of general formula (VI$_{ex}$) with propargyl alcohol in the presence of a copper salt as catalys. The azides of general formula (VI$_{ex}$) are commercially available or may be prepared following conventional methods reported in the literature; alternately, some of the azides can be prepared in situ. Thus, Method XA comprises the reaction of compounds of general formula (VI$_{ex}$) and propargyl alcohol in the presence of a copper salt, preferably CuSO$_4$.5H$_2$O and sodium ascorbate in a mixture of protic organic solvent and water, preferably a mixture of t-BuOH:H$_2$O 1:1 at room temperature Alternatively, CuI can be used as copper salt in a polar solvent as dimethylformamide at 100° C. using microwave irradiation or Cu(OAc)$_2$ can be used as copper salt in a polar solvent, such as tert-butanol at room temperature.

Method XB comprises a one-pot procedure, involving the reaction of compounds of general formula (VII$_{ex}$) where X is a suitable leaving group such as a halogen or tosylate with sodium azide in a mixture of protic organic solvent and water, preferably a mixture of t-BuOH:H$_2$O 1:1, heating at 100° C. using microwave irradiation for 1 h or until completed reaction, followed by the reaction with propargyl alcohol in the presence of a copper salt, preferably CuSO$_4$.5H$_2$O and sodium ascorbate at room temperature. Alternatively, CuI is used as copper salt in a polar solvent, such as dimethylformamide and at 90° C. using microwave irradiation.

Compounds of general formula (XVIIb$_{ex}$), where R$_3$, R$_4$, and n have the meanings as defined above can be prepared using Method XI. This process comprises:

a) The reaction between compound of formula (XXI$_{ex}$) with a compound of general formula (VII$_{ex}$) where X is a suitable leaving group such as an halogen or sulfonate, in the presence of a base, preferably K$_2$CO$_3$, in a polar solvent, preferably acetone at 60° C.

b) The reduction of the resulting compound (XVIIIb$_{ex}$) with a suitable hydride reagent, preferably LiAlH$_4$ at 0° C., in an aprotic solvent, preferably THF.

Synthesis of Intermediate XVIIc$_{ex}$

Alcohol of formula (XVIIc$_{ex}$) may be prepared according to the reaction sequence shown in scheme 8 (Method XII). This process comprises:

a) The reaction between compound (XXI$_{ex}$) with indene oxide in the presence of an inorganic base, preferably Cs$_2$CO$_3$ in a polar solvent, preferably acetonitrile, at 90° C. with microwave irradiation.

b) The protection of the hydroxyl group in compound (XXII$_{ex}$), preferably with tert-butyldimethylchlorosilane, in the presence of an organic base preferably imidazole in an aprotic solvent such as dichloromethane.

c) The reduction of the resulting intermediate (XXIII$_{ex}$), with a suitable hydride reagent, preferably LiAlH$_4$, at 0° C. in an aprotic solvent, preferably THF.

Scheme 8

Method XII

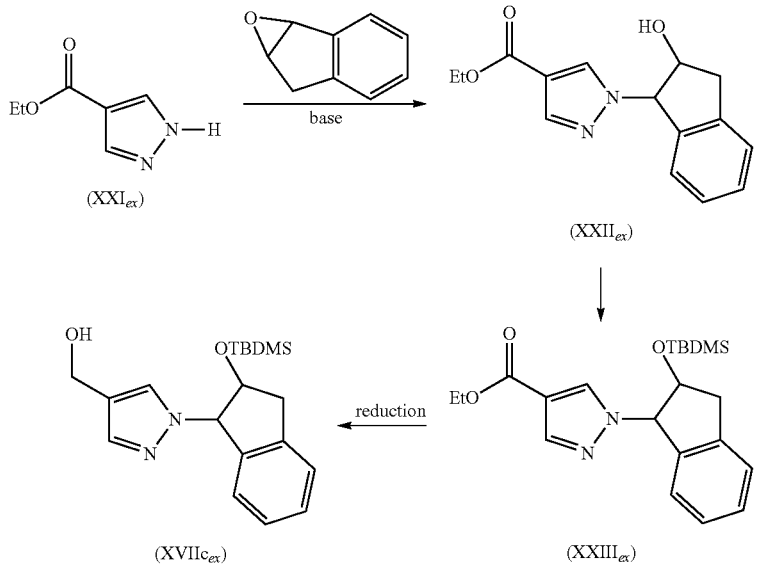

(XXI$_{ex}$)

(XXII$_{ex}$)

(XVIIc$_{ex}$)

(XXIII$_{ex}$)

Synthesis of Intermediate XVIId$_{ex}$

Alcohol of formula (XVIId$_{ex}$) may be prepared according to the reaction sequence shown in scheme 9 (Method XIII), which comprises:

a) The reaction between 2-chlorobenzyl chloride and Sodium azide in a mixture of a polar organic solvent and water, preferably a mixture of t-BuOH:H$_2$O 1:1, at 100° C. using microwave irradiation for 1 h or until completed reaction, followed by the reaction with propargyl alcohol and a copper salt, preferably CuSO$_4$.5H$_2$O and sodium ascorbate at room temperature to give intermediate (XXIV$_{ex}$).

b) The protection of the hydroxyl group of compound (XXIV$_{ex}$) preferably with tert-butyldimethylchlorosilane (ClTBDMS) in the presence of an organic base, preferably imidazole, in an aprotic solvent such as dichloromethane.

c) The Intramolecular palladium-catalyzed arylation of compound XXV$_{ex}$ using a palladium catalyst, preferably Pd(OAc)$_2$, in the presence of an inorganic base, preferably K$_2$CO$_3$, and a phosphine as ligand, preferably tricyclohexylphosphine and an additive, preferably pivalic acid in an aprotic solvent, preferably toluene, at 130° C.

d) The deprotection reaction of compound (XXVI$_{ex}$), preferably with tetrabutylammonium fluoride, in a polar solvent, preferably tetrahydrofurane.

Scheme 9

Method XIII

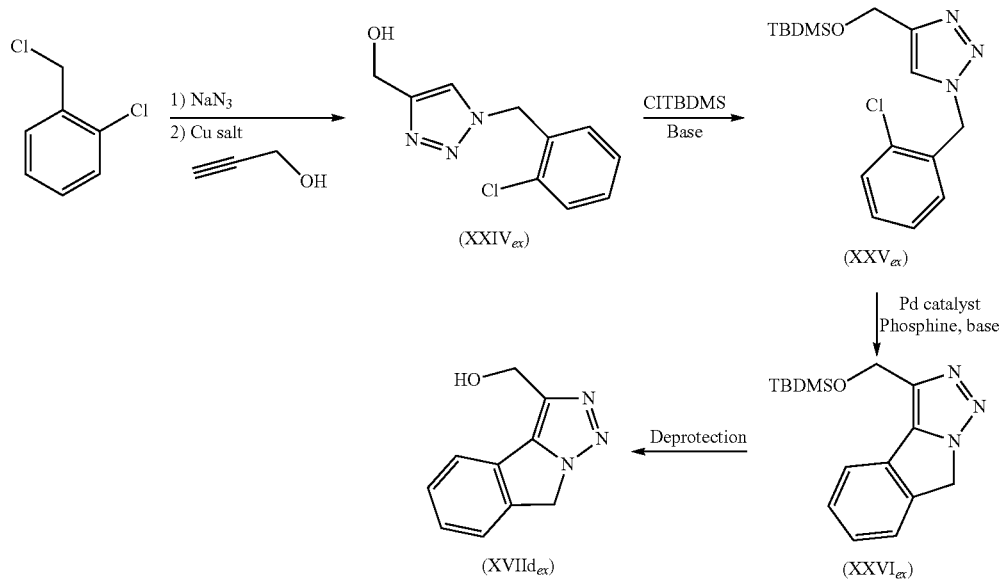

Synthesis of Intermediates of General Formula $XVIII_{ex}$

The esters of general formula ($XVIII_{ex}$), where $R_3$, $R_4$, A, B, Y, Z and n have the meanings as defined above (with "A", "B", "Y", and "Z" being "X", "Y", "W", "Z" in the above description, respectively), are commercially available or can be prepared by methods described in the bibliography (*Synthesis*, 1975, 9, 609-610; WO2011098904; *Org. Lett.* 2010, 12, 9, 2166-2169)

The esters of general formula $XVIIIa_{ex}$, where $R_3$, $R_4$, and n have the meanings as defined above, can be prepared by Method XIV, which involves the cycloaddition reaction of an azide of general formula ($VI_{ex}$) with ethyl propiolate in the presence of a copper salt as catalyst, preferably Cu(OTf)$_2$*C$_6$H$_6$ in an aprotic solvent, preferably toluene, at 70-100° C. (Scheme 10).

Method XIV

Scheme 10

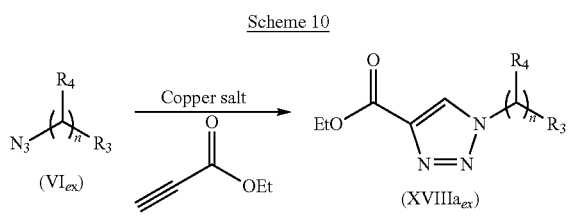

Synthesis of Intermediates

Example of Preparation of an Intermediate of Formula ($IIa_{ex}$), Method III

Synthesis of N-(3-(piperidin-4-yl)phenyl)propane-2-sulfonamide

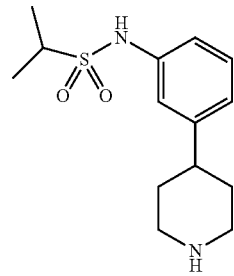 [SMILES: CC(C)S(=O)(=O)Nc1cccc(C2CCNCC2)c1]

N-(3-Bromophenyl)propane-2-sulfonamide

To a solution of 3-bromoaniline (250 mg, 1.45 mmol) in pyridine (1.7 ml) isopropylsulfonyl chloride (0.2 ml, 1.7 mmol) was added. The reaction mixture was stirred at 50° C. overnight. Solvent was removed under vacuum and the residue was purified by flash chromatography, silica gel, gradient hexane to ethyl acetate to give the titled compound (262 mg, 65% yield) as white solid. $^1$H-NMR (300 MHz, CDCl$_3$), δ ppm: 7.40 (s, 1H), 7.27 (m, 1H), 7.18 (m, 1H), 6.69 (s, 1H), 3.32 (septet, J=7 Hz, 1H), 1.41 (d, J=7 Hz, 6H).

tert-Butyl 4-(3-(1-methylethylsulfonamido)phenyl)-5,6-dihydropyridine-1 (2H)-carboxylate A solution containing N-(3-bromophenyl)propane-2-sulfonamide (500 mg, 1.8 mmol), 3,6-dihydro-2H-pyridine-1- tert-butoxycarbonyl-4-boronic acid pinacol ester (556 mg, 1.8 mmol), Pd(PPh$_3$)$_4$ (100 mg, 0.09 mmol) and Na$_2$CO$_3$ (2.7 ml of 2 M aqueous solution, 5.4 mmol) in 10 ml of dioxane:ethanol:water (7:3:1) under argon atmosphere was heated at 160° C. under microwave heating for 30 minutes. The crude was cooled, ethyl acetate was added and the reaction mixture was washed with water, dried over Na$_2$SO$_4$ and concentrated under vacuum. The residue was purified by flash chromatography, silica gel, gradient hexane to hexane: ethyl acetate 7:3 to give the titled compound (498 mg, 73% yield) as a white solid. $^1$H-NMR (400 MHz, CDCl$_3$), δ ppm: 7.28 (t, J=8 Hz, 1H), 7.24 (t, J=2 Hz, 1H), 7.15 (dt, J=8, 1 Hz, 1H), 7.11 (ddd, J=8, 2, 1 Hz, 1H), 6.51 (s, 1H), 6.05 (s, 1H), 4.07 (m, 2H), 3.63 (t, J=6 Hz, 2H), 3.30 (septet, J=7 Hz, 1H), 2.50 (m, 2H), 1.49 (s, 9H), 1.40 (d, J=7 Hz, 6H).

tert-Butyl 4-(3-(1-methylethylsulfonamido)phenyl) piperidine-1-carboxylate

A solution of the tert-butyl 4-(3-(1-methylethylsulfonamido)phenyl)-5,6-dihydropyridine-1(2H)-carboxylate (1.10 g, 2.86 mmol) in MeOH (70 ml) was added to a flask containing Pd(OH)$_2$ 20% mol under H$_2$ atmosphere. The reaction mixture was stirred at rt overnight. The crude was filtered through a plug of Celite and then the solvent was removed under vacuum. The product (1.08 g, 99% yield) was obtained as white foam. $^1$H-NMR (400 MHz, CDCl$_3$), δ ppm: 7.25 (t, J=8 Hz, 1H), 7.06 (m, 2H), 6.98 (d, J=8 Hz, 1H), 6.61 (bs, 1H), 4.24 (d, J=13 Hz, 2H), 3.29 (septet, J=7 Hz, 1H), 2.79 (td, J=13, 3 Hz, 2H), 2.63 (tt, J=13, 2 Hz, 1H), 1.80 (d, J=13 Hz, 2H), 1.59 (qd, J=13, 4 Hz, 2H), 1.49 (s, 9H), 1.40 (d, J=7 Hz, 6H).

N-(3-(Piperidin-4-yl)phenyl)propane-2-sulfonamide

To a solution of tert-butyl 4-(3-(1-methylethylsulfonamido)phenyl)piperidine-1-carboxylate (1.10 g, 2.28 mmol) in dioxane (5 ml), a solution of HCl in 4M dioxane (10 ml, 39.5 mmol) was added, and the mixture was stirred at rt for 4 h. The solution was concentrated to dryness to afford the titled compound (895 mg, 99% yield) as hydrochloride. $^1$H-NMR (400 MHz, MeOD), δ ppm: 7.31 (t, J=8 Hz, 1H), 7.27 (t, J=2 Hz, 1H), 7.13 (ddd, J=8, 2, 1 Hz, 1H), 7.06 (d, J=8 Hz, 1H), 3.53 (d, J=13 Hz, 2H), 3.27 (septet, J=7 Hz, 1H), 3.17 (td, J=13, 3 Hz, 2H), 2.93 (tt, J=13, 2 Hz, 1H), 2.10 (d, J=14 Hz, 2H), 1.95 (qd, J=13, 4 Hz, 2H), 1.35 (d, J=7 Hz, 6H).

This method was used for the preparation of intermediates of formula (IIa) in the synthesis of examples of formula (I) 1, 6, 11-13, 17-18, 20-21, 26, 29-30, 32-35, 39, 42, 47, 49-53, 73-74, 79-81, 85, 87, 90, 101-102, 104, 112-114, 116-118, 121-122, 124, 128-130, 135-141, 167, 170, 179, 180-181, 186-187, 190-213, 228.

Example of Preparation of an Intermediate of Formula (IIb$_{ex}$), Method IVa

Synthesis of N-(3-(piperidin-4-yl)phenyl)methanesulfonamide

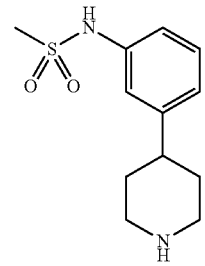 [SMILES: CS(=O)(=O)Nc1cccc(C2CCNCC2)c1]

tert-Butyl 4-(3-(methylsulfonamido)phenyl)piperidine-1-carboxylate

Pyridine (160 µL, 1.96 mmol) was added to a stirred solution of tert-butyl 4-(3-aminophenyl)piperidine-1-carboxylate (180 mg, 0.65 mmol) and methane sulfonyl chloride (76 µl, 0.98 mmol) in dichloromethane (13 ml), and the reaction mixture was stirred at ambient temperature overnight. Dichloromethane was added and the mixture was washed with brine, dried over Na$_2$SO$_4$, filtered and concentrated. Purification by flash chromatography, silica gel, gradient hexane to hexane:ethyl acetate 6:4 afforded the desired product (225 mg, 97% yield) as a white solid. $^1$H-NMR (400 MHz, CDCl$_3$), δ ppm: 7.28 (m, 1H), 7.08 (m, 2H), 7.02 (d, J=7 Hz, 1H), 6.93 (bs, 1H), 4.24 (s, 2H), 3.00 (s, 3H), 2.79 (t, J=11 Hz, 2H), 2.64 (tt, J=12, 3 Hz, 1H), 1.81 (d, J=13 Hz, 2H), 1.60 (qd, J=13, 4 Hz, 2H), 1.48 (s, 9H).

N-(3-(Piperidin-4-yl)phenyl)methanesulfonamide

To a solution of tert-butyl 4-(3-methylsulfonamido)phenyl)piperidine-1-carboxylate (250 mg, 0.70 mmol) in dioxane (1.2 ml), a solution of HCl in 4M dioxane (2.5 ml, 9.8 mmol) was added and stirred at room temperature for 4 h. The mixture was concentrated to dryness to afford the titled compound (185 mg, 90% yield) as hydrochloride. $^1$H-NMR (300 MHz, MeOD) δ ppm: 7.32 (t, J=7 Hz, 1H), 7.22 (m, 1H), 7.09 (m, 2H), 3.51 (d, J=12 Hz, 2H), 3.15 (t, J=12 Hz, 2H), 2.95 (s, 3H), 2.92 (m, 1H), 2.10 (d, J=14 Hz, 2H), 1.93 (qd, J=13, 3 Hz, 2H).

This method was used for the preparation of intermediates of formula (IIc) in the synthesis of examples of formula (I) 16, 22, 24, 27-28, 37, 48, 57, 62, 68, 70, 76, 86, 91-93, 97-100, 119, 163, 166, 168, 174-175, 178, 182-183, 185.

Example of Preparation of an Intermediate of Formula (IIe$_{ex}$), Method IVa Synthesis of N-methyl-N-(3-(piperidin-4-yl)phenyl)methanesulfonamide

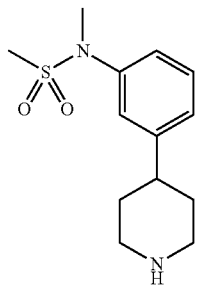 [SMILES: CN(c1cccc(C2CCNCC2)c1)S(C)(=O)=O]

tert-Butyl 4-(3-(N-methylmethylsulfonamido)phenyl)piperidine-1-carboxylate

A microwave vial was charged with tert-butyl 4-(3-(methylsulfonamido)phenyl)piperidine-1-carboxylate (150 mg, 0.42 mmol) and K$_2$CO$_3$ (175 mg, 1.27 mmol) and then evacuated and backfilled with argon before acetonitrile (6 ml) was added. MeI (80 µl, 1.27 mmol) was added and the reaction mixture was irradiated with microwaves at 120° C. for 10 min. The mixture was cooled and was filtered in order to remove K$_2$CO$_3$, and then, the solvent was removed under vacuum. Purification by flash chromatography, silica gel, gradient hexane to ethyl acetate afforded the titled product (146 mg, 94% yield) as white solid. $^1$H-NMR (400 MHz, CDCl$_3$), δ ppm: 7.33 (t, J=8 Hz, 1H), 7.23 (t, J=2 Hz, 1H), 7.20 (ddd, J=8, 2, 1 Hz, 1H), 7.14 (d, J=8 Hz, 1H), 4.25 (s, 2H), 3.32 (s, 3H), 2.84 (s, 3H), 2.79 (t, J=11 Hz, 2H), 2.66 (tt, J=12, 4 Hz, 1H), 1.83 (d, J=13 Hz, 2H), 1.61 (qd, J=13, 4 Hz, 2H), 1.48 (s, 9H).

N-(3-(Piperidin-4-yl)phenyl)methanesulfonamide

To a solution of tert-butyl 4-(3-(N-methylmethylsulfonamido)phenyl)piperidine-1-carboxylate (150 mg, 0.41 mmol) in dioxane (0.5 ml), a solution of HCl in 4M dioxane (1.53 ml, 6.11 mmol) was added, and the mixture stirred at room temperature overnight. The solution was concentrated to dryness to afford the titled compound (122 mg, 99% yield) as hydrochloride. $^1$H-NMR (300 MHz, MeOD) δ ppm: 7.38 (m, 3H), 7.28 (d, J=7 Hz, 1H), 3.54 (d, J=12 Hz, 2H), 3.34 (s, 3H), 3.18 (t, J=12 Hz, 2H), 2.98 (m, 1H), 2.92 (s, 3H), 2.13 (d, J=14 Hz, 2H), 1.94 (qd, J=13, 3 Hz, 2H).

This method was used for the preparation of intermediates of formula (IIe) in the synthesis of example of formula (I) 31.

Example of Preparation of an Intermediate of Formula (IId$_{ex}$), Method IVa Synthesis of N-(3-(piperidin-4-yl)phenyl)propionamide

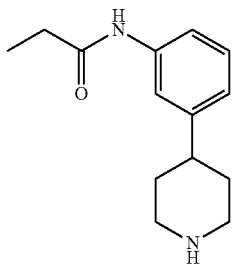 [SMILES: CCC(=O)Nc1cccc(C2CCNCC2)c1]

tert-Butyl 4-(3-propionamidophenyl)piperidine-1-carboxylate

To a solution of tert-butyl 4-(3-aminophenyl)piperidine-1-carboxylate (171 mg, 0.62 mmol) in THF (6 ml) cooled at 0° C., Et$_3$N (260 µl, 1.86 mmol) and propionyl chloride (59 µl, 0.68 mmol) were slowly added. The reaction mixture was stirred at rt for 3 h. Dichloromethane was added and the reaction mixture was washed with brine, dried over Na$_2$SO$_4$, filtered and concentrated to provide a residue that was purified by flash chromatography, silica gel, gradient hexane to ethyl acetate afforded the desired product (186 mg, 90% yield) as white solid. $^1$H-NMR (500 MHz, CDCl$_3$), δ ppm: 8.34 (s, 1H), 7.49 (s, 1H), 7.32 (d, J=8 Hz, 1H), 7.16 (t, J=8 Hz, 1H), 6.86 (d, J=8 Hz, 1H), 4.17 (s, 2H), 2.72 (s, 2H), 2.54 (tt, J=12, 3 Hz, 1H), 2.34 (q, J=8 Hz, 2H), 1.73 (d, J=13 Hz, 2H), 1.53 (qd, J=13, 4 Hz, 2H), 1.45 (s, 9H), 1.17 (t, J=8 Hz, 3H).

N-(3-(Piperidin-4-yl)phenyl)propionamide

To a solution of tert-butyl 4-(3-propionamidophenyl)piperidine-1-carboxylate (250 mg, 0.75 mmol) in dioxane (2.8 ml), a solution of HCl in 4M dioxane (1.88 ml, 7.52 mmol) was added and stirred at room temperature for 3 h. The mixture was concentrated and suspended in dichloromethane, washed with Na$_2$CO$_3$ 10% solution and water, dried over Na$_2$SO$_4$, filtered and concentrated to provide the titled compound (152 mg, 87% yield) as a white solid. $^1$H-NMR (400 MHz, CDCl3) δ ppm: 8.11 (s, 1H), 7.45 (s, 1H), 7.32 (d, J=8 Hz, 1H), 7.19 (t, J=8 Hz, 1H), 6.92 (d, J=8 Hz, 1H), 3.13 (d, J=12 Hz, 2H), 2.67 (td, J=12, 2 Hz, 2H), 2.55 (tt, J=12, 3 Hz, 1H), 2.35 (q, J=7 Hz, 2H), 1.91 (bs, 1H), 1.77 (d, J=13 Hz, 2H), 1.56 (qd, J=13, 4 Hz, 2H), 1.20 (t, J=7 Hz, 3H).

This method was used for the preparation of intermediate of formula (IId) in the synthesis of examples of formula (I) 7, 9, 38, 69, 103.

Example of Preparation of an Intermediate of Formula (IIc$_{ex}$), Method IVa

Synthesis of
1-ethyl-3-(3-(piperidin-4-yl)phenyl)urea

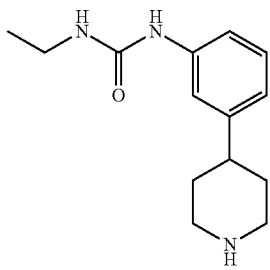 [SMILES: CCNC(=O)Nc1cccc(C2CCNCC2)c1]

tert-Butyl 4-(3-(3-ethylureido)phenyl)piperidine-1-carboxylate

To a solution of tert-butyl 4-(3-aminophenyl)piperidine-1-carboxylate (80 mg, 0.29 mmol) in dichloromethane (5 ml), pyridine (100 µl, 1.24 mmol) and ethyl isocyanate (77 µl, 0.99 mmol) were added. The reaction mixture was stirred at rt overnight. Dichloromethane was added and the reaction mixture was washed with NaHCO$_3$ saturated solution and brine, dried over Na$_2$SO$_4$, filtered and concentrated to provide a residue that was purified by flash chromatography, silica gel, gradient hexane to ethyl acetate to afford the desired product (90 mg, 89% yield) as white solid. $^1$H-NMR (300 MHz, CDCl$_3$), δ ppm: 7.78 (s, 1H), 7.26 (s, 1H), 7.08 (m, 2H), 6.77 (d, J=7 Hz, 1H), 5.80 (t, J=5 Hz, 1H), 4.18 (s, 2H), 3.20 (m, 2H), 2.71 (t, J=12 Hz, 2H), 2.50 (tt, J=12, 3 Hz, 1H), 1.71 (d, J=12 Hz, 2H), 1.51 (qd, J=12, 4 Hz, 2H), 1.47 (s, 9H), 1.06 (t, J=7 Hz, 3H).

1-Ethyl-3-(3-(piperidin-4-yl)phenyl)urea

To a solution of tert-butyl 4-(3-(3-ethylureido)phenyl) piperidine-1-carboxylate (89 mg, 0.26 mmol) in dioxane (0.6 ml), a solution of HCl in 4M dioxane (0.64 ml, 2.56 mmol) was added and stirred at room temperature for 3 h. The mixture was concentrated and suspended in dichlormethane, washed with Na$_2$CO$_3$ 10% solution and water, dried over Na$_2$SO$_4$, filtered and concentrated to provide the titled compound (49 mg, 77% yield) as white solid. $^1$H-NMR (500 MHz, MeOD) δ ppm: 7.26 (s, 1H), 7.19 (m, 2H), 6.87 (d, J=7 Hz, 1H), 3.24 (q, J=7 Hz, 2H), 3.12 (d, J=12 Hz, 2H), 2.70 (td, J=12, 2 Hz, 2H), 2.60 (tt, J=12, 3 Hz, 1H), 1.80 (d, J=13 Hz, 2H), 1.64 (qd, J=13, 4 Hz, 2H), 1.16 (t, J=7 Hz, 3H).

This method was used for the preparation of intermediate of formula (IIc) in the synthesis of examples of formula (I) 56, 111.

Example of Preparation of an Intermediate of Formula (IIf$_{ex}$), Method IVb

Synthesis of 5-fluoro-N-(3-(piperidin-4-yl)phenyl) pyridin-2-amine, hydrochloride

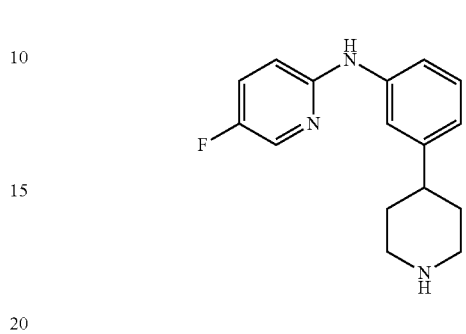

a) tert-butyl 4-(3-((5-fluoropyridin-2-yl)amino)phenyl)piperidine-1-carboxylate

A dried flask, under argon atmosphere, was charged with Pd$_2$(dba)$_3$ (21 mg, 0.023 mmol), 1,1'-Bis(diphenylphosphino)ferrocene (38 mg, 0.068 mmol), NaO$^t$Bu (44 mg, 0.455 mmol), tert-butyl 4-(3-aminophenyl)piperidine-1-carboxylate (126 mg, 0.455 mmol) and 2-bromo-5-fluoropyridine (80 mg, 0.455 mmol). Degassed dry toluene (4 mL) was added and the mixture was heated at 80° C. for 4.5 h. The reaction mixture was cooled at rt, dichloromethane was added and filtered through a pad of Celite. Purification by flash chromatography, silica gel, gradient hexane to ethyl acetate afforded the desired product (127 mg, 75% yield). $^1$H-NMR (500 MHz, CDCl$_3$) δ ppm: 8.09 (m, 1H), 7.29 (m, 2H), 7.17 (m, 1H), 7.14 (m, 1H), 6.91 (m, 1H), 6.84 (m, 1H), 6.53 (bs, 1H), 4.26 (m, 2H), 2.82 (m, 2H), 2.65 (m, 1H), 1.85 (m, 2H), 1.64 (m, 2H), 1.45 (s, 9H).

b) Title Compound

To a solution of tert-butyl 4-(3-((5-fluoropyridin-2-yl) amino)phenyl)piperidine-1-carboxylate (126 mg, 0.339 mmol) in dioxane (0.6 ml), a solution of HCl in 4M dioxane (1.18 ml, 4.75 mmol) was added and stirred at room temperature for 16 h. The mixture was concentrated to dryness to afford the titled compound (115 mg, 98% yield). $^1$H-NMR (400 MHz, MeOD) δ ppm: 8.12 (m, 1H), 8.04 (m, 1H), 7.60 (m, 1H), 7.39 (m, 4H), 3.60 (m, 2H), 3.25 (m, 2H), 3.10 (m, 1H), 2.20 (m, 2H), 2.09 (m, 2H).

This method was used for the preparation of intermediate of formula (IIf) in the synthesis of examples of formula (I) 231, 232.

Example of Preparation of an Intermediate of Formula (IIg$_{ex}$), Method IVc

Synthesis of N-(3-(piperidin-4-yl)phenyl)thiazol-2-amine, hydrochloride

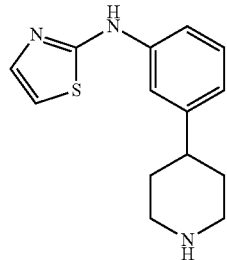 [SMILES: c1cc(Nc2nccs2)cc(C2CCNCC2)c1]

a) tert-butyl 4-(3-thioureidophenyl)piperidine-1-carboxylate

To a suspension of thiocarbonyldiimidazole (206 mg, 1.10 mmol) in DCM (3 mL) at 0° C., a solution of tert-butyl 4-(3-aminophenyl)piperidine-1-carboxylate (160 mg, 0.58 mmol) in DCM (2 mL) was added dropwise and the mixture was stirred at rt for 3 h. The reaction mixture was cooled again to 0° C. and a solution of ammonia in MeOH 7N (2 mL) was added dropwise. The reaction mixture was stirred at rt for 16 h. Water was added and extracted with DCM. Purification by flash chromatography, silica gel, gradient hexane to 50% acetone afforded the desired product (180 mg, 93% yield) as white foam. $^1$H-NMR (400 MHz, CDCl$_3$) δ ppm: 8.16 (bs, 1H), 7.39 (t, J=7.6 Hz, 1H), 7.18 (d, J=7.6 Hz, 1H), 7.12 (d, J=7.6 Hz, 1H), 7.09 (m, 1H), 6.17 (bs, 2H), 4.26 (m, 2H), 2.81 (m, 2H), 2.68 (m, 1H), 1.83 (m, 2H (1.62 (m, 2H), 1.50 (m, 9H).

b) tert-butyl 4-(3-(thiazol-2-ylamino)phenyl)piperidine-1-carboxylate

To a suspension of tert-butyl 4-(3-thioureidophenyl)piperidine-1-carboxylate (170 mg, 0.51 mmol) in EtOH (5 mL) a 50% solution of chloroacetaldehyde in water (0.32 mL, 2.5 mmol) was added and the mixture was heated at reflux for 2 hours. The reaction mixture was concentrated and the residue was dissolved in DCM, the organic phase was washed with aq NaHCO$_3$ sat solution and water. The organic phase was dried over Na$_2$SO$_4$, filtered and concentrated. Purification by flash chromatography, silica gel, gradient hexane to 50% acetone afforded the desired product (118 mg, 65% yield) as white foam. $^1$H-NMR (500 MHz, CDCl$_3$) δ ppm: 8.29 (bs, 1H), 7.31 (m, 2H), 7.24 (m, 1H), 7.21 (m, 1H), 6.93 (d, J=7.5 Hz, 1H), 6.65 (d, J=3.6 Hz, 1H), 4.27 (m, 2H), 2.83 (m, 2H), 2.67 (m, 1H), 1.87 (m, 2H), 1.65 (m, 2H), 1.51 (s, 9H).

c) Title Compound

To a solution of tert-butyl 4-(3-(thiazol-2-ylamino)phenyl)piperidine-1-carboxylate (118 mg, 0.33 mmol) in dioxane (0.8 mL), a solution of HCl in 4M dioxane (1.06 ml, 4.27 mmol) was added and stirred at room temperature for 16 h. The mixture was concentrated to dryness to afford the title compound (103 mg, 94% yield). $^1$H-NMR (400 MHz, MeOD) δ ppm: 7.60 (t, J=7.9 Hz, 1H), 7.44 (m, 4H), 7.15 (m, 1H), 3.60 (m, 2H), 3.25 (m, 2H), 3.10 (m, 1H), 2.20 (m, 2H), 2.08 (m, 2H).

This method was used for the preparation of intermediate of formula (IIg) in the synthesis of examples of formula (I) 225, 229, 230.

Example of Preparation of an Intermediate of Formula (IIh$_{ex}$), Method V

Synthesis of (±)-(cis)-N-(3-((3-hydroxypiperidin-4-yl)phenyl) propane-2-sulfonamide

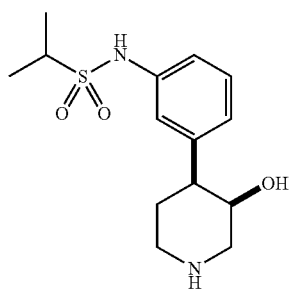

tert-Butyl 6-(3-(1-methylethylsulfonamido)phenyl)-7-oxa-3-azabicyclo[4.1.0]heptane-3-carboxylate To a solution of tert-butyl 4-(3-(1-methylethylsulfonamido)phenyl)-5,6-dihydropyridine-1(2H)-carboxylate (0.21 g, 0.54 mmol) in dichloromethane (2.7 ml), m-chloroperoxybenzoic acid (196 mg, 0.82 mmol) was added and the mixture was stirred at rt under argon atmosphere for 16 h. The reaction was quenched by the addition of saturated aqueous sodium thiosulfate solution followed by NaHCO$_3$ saturated solution and stirred for 45 min. Dichloromethane was added and the mixture was washed with NaHCO$_3$ saturated solution, dried over Na$_2$SO$_4$ and concentrated. The crude was then purified by flash chromatography, silica gel, gradient from hexane to ethyl acetate afforded the desired product (169 mg, 79% yield) as colorless oil. $^1$H-NMR (400 MHz, CDCl$_3$), δ ppm: 7.29 (t, J=8 Hz, 1H), 7.20 (m, 2H), 7.12 (d, J=8 Hz, 1H), 4.04 (bs, 1H), 3.77 (bs, 1H), 3.65 (bs, 1H), 3.29 (septet, J=7 Hz, 1H), 3.15 (m, 2H), 2.43 (m, 1H), 2.12 (d, J=13 Hz, 1H), 1.47 (s, 9H), 1.38 (d, J=7 Hz, 6H).

(±)-(cis)-(3R,4S)-tert-Butyl 3-hydroxy-4-(3-(1-methylethyl sulfonamido)phenyl) piperidine-1-carboxylate A mixture of tert-butyl 6-(3-(1-methylethylsulfonamido) phenyl)-7-oxa-3-azabicyclo[4.1.0]heptane-3-carboxylate (1.20 g, 3.04 mmol) and Pd/C (10% w/w, 0.12 g) in EtOAc:MeOH (2:1, 25.5 ml) was hydrogenated with H$_2$ at 50 psi overnight. The reaction mixture was purged with argon, filtered through a pad of celite, washed with MeOH and EtOAc and concentrated. Purification by flash chromatography, silica gel, gradient hexane to ethyl acetate afforded the desired product (1.12 g, 93% yield) as white foam. $^1$H-NMR (400 MHz, CDCl$_3$), δ ppm: 7.26 (t, J=8 Hz, 1H), 7.17 (s, 1H), 7.12 (dd, J=8, 2 Hz, 1H), 7.07 (s, 1H), 7.05 (d, J=8 Hz, 1H), 4.29 (d, J=12 Hz, 2H), 3.94 (s, 1H), 3.29 (septet, J=7 Hz, 1H), 2.98 (d, J=13 Hz, 1H), 2.80 (m, 2H), 2.21 (qd, J=13, 4 Hz, 1H), 1.60 (d, J=13 Hz, 1H), 1.47 (s, 9H), 1.37 (dd, J=7, 2 Hz, 6H).

(±)-(cis)-N-(3-((3-Hydroxypiperidin-4-yl)phenyl)propane-2-sulfonamide

To a solution of (±)-(cis)-(3R,4S)-tert-butyl 3-hydroxy-4-(3-(1-methylethyl sulfonamido)phenyl)piperidine-1-carboxylate (1.11 g, 2.79 mmol) in dioxane (6.3 ml), a solution of HCl in 4M dioxane (9.7 ml, 39.1 mmol) was added and stirred at rt for 4 h. The mixture was concentrated to dryness to afford the titled compound (0.92 mg, 99% yield) as hydrochloride. $^1$H-NMR (400 MHz, MeOD) δ ppm: 7.35 (s, 1H), 7.28 (t, J=8 Hz, 1H), 7.14 (m, 2H), 4.15 (s, 1H), 3.48 (d, J=12 Hz, 1H), 3.36 (m, 2H), 3.30 (septet, J=7 Hz, 1H), 3.18 (td, J=13, 3 Hz, 1H), 3.03 (d, J=12 Hz, 1H), 2.55 (qd, J=13, 4 Hz, 1H), 1.86 (d, J=13 Hz, 1H), 1.36 (dd, J=7, 2 Hz, 6H).

This method was used for the preparation of intermediates of formula (IIh) in the synthesis of examples of formula (I) 110, 115, 123, 125-127, 165, 169.

Examples of Preparation of an Intermediate of Formula (V$_{ex}$), Method IIA Synthesis of 3-(1-(prop-2-yn-1-yl)piperidin-4-yl)phenol

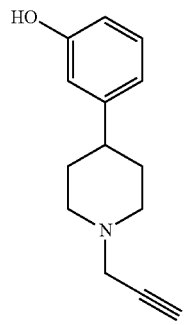 [SMILES: C#CCN1CCC(c2cccc(O)c2)CC1]

A suspension of 4-(3-hydroxyphenyl)piperidine (403 mg, 2.23 mmol), Et$_3$N (404 μl, 2.90 mmol) and propargyl bromide (273 μL, 80% wt in toluene, 2.45 mmol) in THF (20 ml) was irradiated with microwaves at 75° C. for 1 h. The reaction mixture was cooled and the solvent evaporated. Purification by flash chromatography, silica gel, gradient hexane to ethyl acetate afforded the desired product (352 mg, 73% yield) as a white solid. $^1$H-NMR (400 MHz, CDCl$_3$), δ ppm: 7.16 (t, J=8 Hz, 1H), 6.78 (d, J=8 Hz, 1H), 6.77 (m, 2H), 3.37 (d, J=2 Hz, 2H), 3.02 (d, J=11 Hz, 2H), 2.46 (m, 1H), 2.36 (td, J=11, 3 Hz, 2H), 2.28 (t, J=2 Hz, 1H), 1.84 (m, 4H).

Synthesis of 3-(1-(but-3-yn-1-yl)piperidin-4-yl)phenol

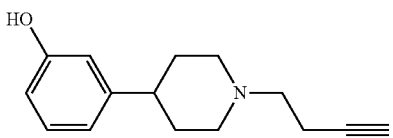 [SMILES: C#CCCN1CCC(c2cccc(O)c2)CC1]

A mixture of 4-(3-Hydroxyphenyl)piperidine (307 mg, 1.73 mmol) and 3-butynyl tosylate (201 mg, 0.90 mmol) and THF (3 ml) was refluxed overnight. Then, the crude was partitioned between 2N NaOH (1.5 ml) and dichloromethane (6 ml). The organic layer was isolated and the aqueous phase extracted again with dichloromethane. The extracts were combined, dried over Na$_2$SO$_4$, filtered, and evaporated to provide a residue that was purified by flash chromatography, silica gel, gradient hexane to ethyl acetate to afford the desired product (86 mg, 44% yield) as a white solid. $^1$H-NMR (500 MHz, CDCl$_3$), δ ppm: 7.15 (t, J=8 Hz, 1H), 6.76 (d, J=8 Hz, 1H), 6.65 (m, 2H), 3.06 (d, J=11 Hz, 2H), 2.66 (t, J=8 Hz, 2H), 2.44 (m, 3H), 2.15 (td, J=11, 3 Hz, 2H), 1.99 (t, J=3 Hz, 1H), 1.78 (m, 4H).

Examples of Preparation of an Intermediate of Formula (III$_{ex}$), Method VI Synthesis of 1-(2-fluorophenyl)-1H-1,2,3-triazole-4-carbaldehyde

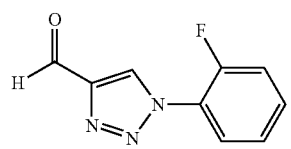 [SMILES: O=Cc1cn(-c2ccccc2F)nn1]

To a solution of (1-(2-fluorophenyl)-1H-1,2,3-triazol-4-yl)methanol (100 mg, 0.52 mmol) in dry dichloromethane (5 ml), MnO$_2$ (465 mg, 4.70 mmol) was added at rt. The resulting dark solution was stirred during 4 hours at rt. Then, the reaction mixture was filtered on Celite, and the solvent was removed under vacuum to afford the desired product (84 mg, 74% yield) as an orange solid. $^1$H-NMR (400 MHz, CDCl$_3$), δ ppm: 10.24 (s, 1H), 8.64 (d, J=2 Hz, 1H), 8.00 (td, J=8, 1 Hz, 1H), 7.52 (m, 1H), 7.32-7.41 (m, 2H).

Synthesis of (±)-(trans)-1-((1S,2S)-2-((tert-butyldimethylsilyl)oxy)-2,3-dihydro-1H-inden-1-yl)-1H-pyrazole-4-carbaldehyde

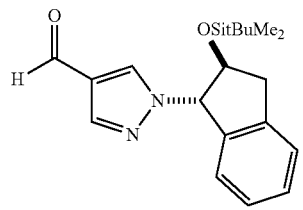

To a solution of (±)-(trans)-1-((1S,2S)-2-((tert-butyldimethylsilyl)oxy)-2,3-dihydro-1H-inden-1-yl)-1H-pyrazol-4-yl)methanol (96 mg, 0.28 mmol) in dichloromethane (4.5 ml), MnO$_2$ (0.48 g, 5.6 mmol) was added and the mixture stirred at r.t. overnight. The mixture was filtered through a plug of celite and washed with dichloromethane. The solvent was removed. The crude was purified by flash chromatography, silica gel, gradient hexane to ethyl acetate to afford the desired product (89 mg, 93% yield). $^1$H-NMR (300 MHz, CDl$_3$), δ ppm: 9.89 (s, 1H), 8.05 (s, 1H), 8.01 (s, 1H), 7.26 (m, 3H), 6.92 (d, J=7 Hz, 1H), 5.57 (d, J=7 Hz, 1H), 4.84 (q, J=7 Hz, 1H), 3.29 (dd, J=15, 8 Hz, 1H), 2.96 (dd, J=15, 8 Hz, 1H), 0.83 (s, 9H), −0.05 (s, 3H), −0.13 (s, 3H).

Synthesis of 8H-[1,2,3]triazolo[5,1-a]isoindole-3-carbaldehyde

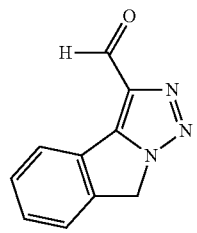 [SMILES: O=Cc1nnn2c1-c1ccccc1C2]

To a solution of 3-(((tert-butyldimethylsilyl)oxy)methyl)-8H-[1,2,3]triazolo[5,1-a]isoindole (83 mg, 0.44 mmol) in dichloromethane (8 ml), MnO$_2$ (540 mg, 6.21 mmol) was added and the mixture stirred at rt for 6 h. The black suspension was filtered through a pad of celite, washed with dichloromethane and concentrated to afford the desired aldehyde (70 mg, 85% yield) as orange solid. $^1$H-NMR (300 MHz, CDCl$_3$), δ ppm: 10.16 (s, 1H), 8.19 (m, 1H), 7.50 (m, 3H), 5.35 (s, 2H).

Examples of Preparation of an Intermediate of Formula (III$_{ex}$), Method VII

Synthesis of 1-(5-fluoropyridin-2-yl)-1H-1,2,3-triazole-4-carbaldehyde

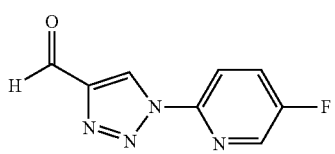 [SMILES: O=Cc1cn(-c2ccc(F)cn2)nn1]

DIBAL-H (0.95 ml, 1 M in dichloromethane, 0.95 mmol) was added dropwise to a solution of 1-(5-fluoropyridin-2-yl)-1H-1,2,3-triazole-4-carboxylate (204 mg, 0.86 mmol) in dichloromethane (9.0 ml) at −78° C. under argon atmosphere. The resulting mixture was stirred for 1 hour at this temperature and then DIBAL-H (0.95 ml, 1 M in dichloromethane, 0.95 mmol) was added again. After stirring for 1 h at −78° C., the mixture was then quenched with MeOH and water at −78° C. Then, the reaction mixture was filtered on Celite and the filtrate was washed with dichloromethane. The solvent was removed under vacuum and the resuidue was purified by flash chromatography, silica gel, gradient hexane to ethyl acetate to provide the desired product (146 mg, 88% yield) as white solid. $^1$H-NMR (500 MHz, CDCl3), δ ppm: 10.24 (s, 1H), 9.04 (s, 1H), 8.40 (d, J=3 Hz, 1H), 8.28 (dd, J=9, 4 Hz, 1H), 7.71 (ddd, J=9, 7, 3 Hz, 1H).

Examples of Preparation of an Intermediate of Formula (IIIa$_{ex}$), Method VIII Synthesis of 1-(pyridin-2-ylmethyl)-1H-imidazole-4-carbaldehyde

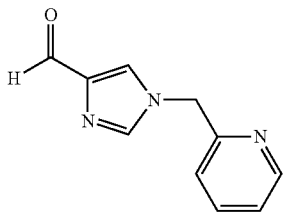 [SMILES: O=Cc1cn(Cc2ccccn2)cn1]

1H-imidazole-4-carbaldehyde (500 mg, 5.20 mmol) and 2-(chloromethyl)pyridine hydrochloride (871 mg, 5.20 mmol) were dissolved in dry toluene (19 ml), then tetra-n-butylammonium bromide (671 mg, 2.01 mmol) was added, followed by 10% aqueous solution of NaOH (6 ml, 15 mmol). The mixture was stirred at 80° C. overnight with vigorous stirring. A saturated aqueous solution of NH$_4$Cl was added at −78° C., followed by the addition of a saturated aqueous solution of Rochelle salt and the mixture was stirred at room temperature for 1 hour and then extracted with ethyl acetate. The organic phase was dried over Na$_2$SO$_4$ and the solvent was removed. Purification by flash chromatography, silica gel, gradient dichloromethane to dichloromethane:methanol 8:2 afforded two products: the desired product, (1-(pyridin-2-ylmethyl)-1H-imidazole-4-carbaldehyde), (24 mg, 5% yield), but also 1-(pyridin-2-ylmethyl)-1H-imidazole-5-carbaldehyde (59 mg, 12% yield). $^1$H-NMR (400 MHz, CDl$_3$), δ ppm: (1-(pyridin-2-ylmethyl)-1H-imidazole-4-carbaldehyde) 9.85 (d, J=2 Hz, 1H), 8.59 (d, J=5 Hz, 1H), 7.72 (s, 1H), 7.69 (m, 2H), 7.27 (dd, J=8, 5 Hz, 1H), 7.11 (d, J=8 Hz, 1H), 5.26 (s, 2H); (1-(pyridin-2-ylmethyl)-1H-imidazole-5-carbaldehyde) 9.72 (d, J=1 Hz, 1H), 8.53 (d, J=5 Hz, 1H), 7.89 (s, 1H), 7.81 (s, 1H), 7.63 (td, J=8, 2 Hz, 1H), 7.19 (m, 2H), 5.60 (s, 2H).

Examples of Preparation of an Intermediate of Formula (IIIb$_{ex}$), Method IX

Synthesis of 1-(pyridin-2-yl)-1H-pyrazole-4-carbaldehyde

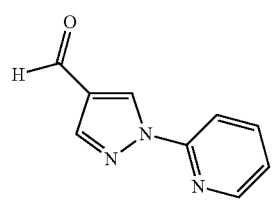 [SMILES: O=Cc1cnn(-c2ccccn2)c1]

2-(1H-pyrazol-1-yl)pyridine (155 mg, 1.07 mmol) was dissolved in DMF (0.8 ml) at 0° C. and POCl$_3$ (0.8 ml, 9.08 mmol) was added. The mixture was stirred at this temperature for 10 min and then heated at 105° C. for 3 h. Purification by flash chromatography, silica gel, gradient hexane to ethyl acetate afforded the desired product (53 mg, 29% yield) as a yellow oil. $^1$H-NMR (400 MHz, CDl$_3$), δ ppm: 10.00, (s, 1H), 9.10 (d, J=1 Hz, 1H), 8.46 (ddd, J=5, 2, 1 Hz, 1H), 8.17 (s, 1H), 8.03 (dt, J=8, 1 Hz, 1H), 7.22 (ddd, J=8, 8, 5 Hz, 1H), 7.30 (ddd, J=8, 5, 1 Hz, 1H).

Examples of Preparation of an Intermediate of Formula (XVIIa$_{ex}$), Method XA

Synthesis of (1-(2-fluorophenyl)-1H-1,2,3-triazol-4-yl)methanol

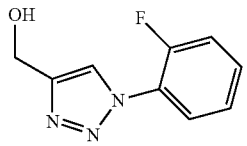 [SMILES: OCc1cn(-c2ccccc2F)nn1]

Propargyl alcohol (64 mg, 1.12 mmol) was added to a mixture of 1-azido-2-fluorobenzene (143 mg, 0.94 mmol), CuSO$_4$.5H$_2$O (29 mg, 0.12 mmol) and sodium ascorbate (40 mg, 0.2 mmol) in t-BuOH:H$_2$O 1:1 (10 ml) and the reaction mixture was stirred at rt overnight. NH$_4$Cl was added and the mixture was extracted with EtOAc; the organic phase was washed with NH$_4$Cl, brine, dried over Na$_2$SO$_4$ filtered and concentrated. Purification was carried out by flash chromatography, silica gel, gradient dichloromethane to dichloromethane:methanol 9:1 to afford the desired product (101 mg g, 56% yield) as a brown oil. $^1$H-NMR (500 MHz, CDCl$_3$), δ ppm: 8.08 (d, J=2 Hz, 1H), 7.93 (td, J=8, 1 Hz, 1H), 7.43 (m, 1H), 7.26-7.35 (m, 2H), 4.90 (s, 2H), 2.94 (bs, 1H).

Synthesis of (1-cyclohexyl-1H-1,2,3-triazol-4-yl)methanol

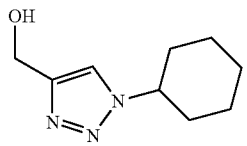 [SMILES: OCc1cn(C2CCCCC2)nn1]

A solution of azidocyclohexane (200 mg, 1.12 mmol) in DMF (2 ml) was added to a microwave tube under Argon atmosphere. To this mixture CuI (43 mg, 0.22 mmol) and propargyl alcohol (63 mg, 1.12 mmol) were added, and the mixture was irradiated with microwaves at 100° C. for 1 h. Ethyl acetate was added and the mixture was washed with NH$_4$Cl. The organic layer was washed with water and brine, dried over Na$_2$SO$_4$, filtered and the solvent was removed under vacuum. No further purification of the desired product (135 mg, 67% yield) was carried out. $^1$H-NMR (300 MHz, CDCl$_3$), δ ppm: 7.54 (s, 1H), 4.80 (s, 2H), 4.45 (tt, J=12, 4 Hz, 1H), 2.21 (d, J=12 Hz, 2H), 1.93 (dt, J=13, 3 Hz, 2H), 1.74 (m, 3H), 1.46 (qt, J=13, 3 Hz, 2H), 1.28 (m, 2H).

Synthesis of (1-((6-methylpyridin-2-yl)methyl)-1H-1,2,3-triazol-4-yl)methanol

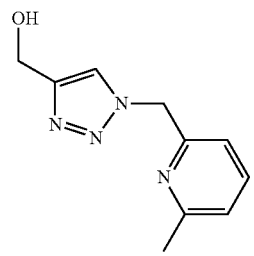

2-(Azidomethyl)-6-methylpyridine

Sodium azide (48 mg, 0.73 mmol) was added to a solution of 2-(bromomethyl)-6-methylpyridine (91 mg, 0.49 mmol) in dry DMF (1.8 ml). The reaction mixture was irradiated with microwaves 90° C. for 30 min. After cooling, water was added and the reaction mixture was extracted with Et$_2$O. The organic phase was dried over Na$_2$SO$_4$ and the solvent removed to yield the desired product (33 mg, 46%). $^1$H-NMR (300 MHz, CDCl3), δ ppm: 7.58 (t, J=8 Hz, 1H), 7.13 (d, J=8 Hz, 1H), 7.08 (d, J=8 Hz, 1H), 4.43 (s, 2H), 2.54 (s, 3H).

(1-((6-Methylpyridin-2-yl)methyl)-1H-1,2,3-triazol-4-yl)methanol

A mixture of 2-(azidomethyl)-6-methylpyridine (33 mg, 0.23 mmol), propargyl alcohol (32 µl, 0.56 mmol), Cu(OAc)$_2$ (solution of 2 mg in 0.15 ml of water, 0.01 mmol) in tBuOH (0.45 ml) was stirred at rt overnight. Most of the tBuOH was removed in vacuum and the residue was filtered through a short plug of celite. The solvent was removed to afford the desired product (44 mg, 85% yield). $^1$H-NMR (300 MHz, CDCl3), δ ppm: 7.82 (s, 1H), 7.57 (t, J=7 Hz, 1H), 7.12 (d, J=7 Hz, 1H), 6.99 (s, 1H), 5.63 (s, 2H), 4.83 (s, 2H), 2.57 (s, 3H).

Examples of Preparation of an Intermediate of Formula (XVIIa$_{ex}$), Method XB

Synthesis of (1-(4-(trifluoromethyl)benzyl)-1H-1,2,3-triazol-4-yl) methanol

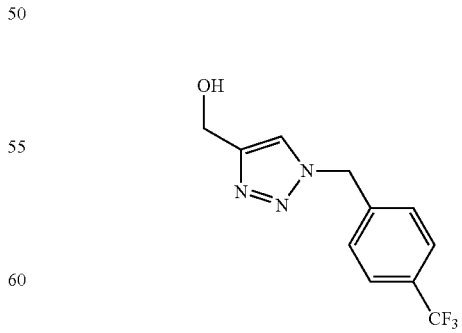

A solution of 4(trifluoromethyl)benzyl chloride (50 µl, 0.34 mmol) and sodium azide (27 mg, 0.41 mmol) in tBuOH:H$_2$O 1:1 (1 ml) was irradiated with microwaves at 100° C. for 30 min. Propargyl alcohol (24 µl, 0.041 mmol), CuSO$_4$.5H$_2$O (9 mg, 0.03 mmol) and sodium ascorbate (14 mg, 0.07 mmol) were added and the mixture was stirred at rt for 3 days. EtOAc was added and the mixture was washed with NH$_4$Cl saturated solution and water, dried over Na$_2$SO$_4$, filtered and concentrated. Purification by flash chromatography, silica gel, gradient dichloromethane to dichloromethane: methanol 9:1 afforded the desired product (52 mg, 60% yield) as a white solid. $^1$H-NMR (300 MHz, CDCl3), δ ppm: 7.58 (d, J=8 Hz, 2H), 7.51 (s, 1H), 7.33 (d, J=8 Hz, 2H), 5.54 (s, 2H), 4.71 (d, J=5 Hz, 2H), 4.04 (bs, 1H).

Synthesis of (1-(1-(pyridin-2-yl)ethyl)-1H-1,2,3-triazol-4-yl)methanol

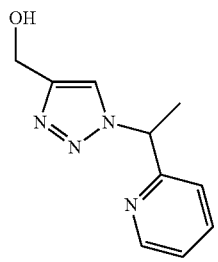

Sodium azide (208 mg, 3.2 mmol) was added to a solution of 1-(pyridin-2-yl)ethyl 4-methylbenzenesulfonate (286 mg, 1.0 mmol) in dry DMF (6 ml). The reaction mixture was irradiated by MW at 90° C. for 30 min. After cooling, CuI (39 mg, 0.2 mmol) and propargyl alcohol (186 µl, 3.2 mmol) were added and the mixture was irradiated again at 100° C. for 1 hour. Dichloromethane was added and the reaction mixture was washed with a solution of saturated NH$_4$Cl/NH$_3$. The organic phase was dried over Na$_2$SO$_4$ and the solvent was removed to give the desired product as a brown oil (129 mg, 58% yield). The product was used in the next step without further purification. $^1$H-NMR (400 MHz, CDCl3), δ ppm: 8.54 (d, J=5 Hz, 1H), 7.76 (s, 1H), 7.64 (td, J=8, 2 Hz, 1H), 7.21 (ddd, J=8, 5, 1 Hz, 1H), 7.16 (d, J=8 Hz, 1H), 5.90 (q, J=7 Hz, 1H), 4.74 (s, 2H), 1.95 (d, J=7 Hz, 3H).

Example of Preparation of an Intermediate of Formula (XVIIb$_{ex}$), Method XI

Synthesis of 1-(pyridin-2-ylmethyl)-1H-pyrazol-4-yl)methanol

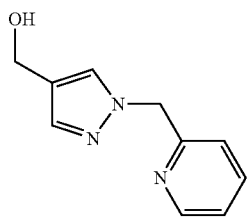 [SMILES: OCc1cnn(Cc2ccccn2)c1]

Ethyl 1-(pyridin-2-ylmethyl)-1H-pyrazole-4-carboxylate

To a solution of ethyl-1H-pyrazole-4-carboxylate (450 mg, 3.15 mmol) in acetone (6.3 ml) K$_2$CO$_3$ (976 mg, 7.06 mmol), 2-(chloromethyl)pyridine hydrochloride (516 mg, 3.15 mmol) and TBAI (119 mg, 0.32 mmol) was added. The mixture was heated at 60° C. overnight. The reaction mixture was cooled and filtered to remove any solids. The filtrate was concentrated. Purification by flash chromatography, silica gel, gradient hexane to ethyl acetate afforded the desired product (605 mg, 83% yield) as yellow oil. $^1$H-NMR (300 MHz, CDl$_3$), δ ppm: 8.57 (d, J=5 Hz, 1H), 8.03 (s, 1H), 7.94 (s, 1H), 7.65 (td, J=8, 2 Hz, 1H), 7.22 (dd, J=8, 5 Hz, 1H), 7.11 (d, J=8 Hz, 1H), 5.45 (s, 2H), 4.30 (q, J=7 Hz, 2H), 1.34 (t, J=7 Hz, 3H).

1-(pyridin-2-ylmethyl)-1H-pyrazol-4-yl)methanol

To a solution of ethyl 1-(pyridin-2-ylmethyl)-1H-pyrazole-4-carboxylate (597 mg, 2.58 mmol) in THF (5 ml) cooled at 0° C. under inert atmosphere, LiAlH$_4$ (1M in THF, 2.58 ml, 2.58 mmol) was added dropwise. The solution was allowed to warm at rt and stirred for 2 h. NH$_4$Cl sat solution was slowly added and the solvent was removed. Water and ethyl acetate were added, the organic phase was decanted, dried over Na$_2$SO$_4$, filtered and the solvent removed to afford the titled product (320 mg, 65% yield). $^1$H-NMR (300 MHz, CDl$_3$), δ ppm: 8.55 (d, J=4.7 Hz, 1H), 7.64 (td, J=7.8, 2 Hz, 1H), 7.54 (d, J=4.7 Hz, 2H), 7.21 (dd, J=7.4, 4.7 Hz, 1H), 7.06 (d, J=7.8 Hz, 1H), 5.40 (s, 2H), 4.59 (s, 2H).

Examples of Preparation of an Intermediate of Formula (XVII$_{ex}$), Method XII

Synthesis of (±)-(trans)-(1-((1S,2S)-2-((tert-butyldimethylsilyl)oxy)-2,3-dihydro-1H-inden-1-yl)-1H-pyrazol-4-yl)methanol

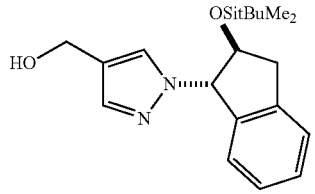

(±)-(trans)-Ethyl 1-((1S,2S)-2-hydroxy-2,3-dihydro-1H-inden-1-yl)-1H-pyrazole-4-carboxylate A mixture of racemic 6,6a-dihydro-1aH-indeno[1,2-b]oxirene (189 mg, 1.43 mmol), ethyl-1H-pyrazole-4-carboxylate (100 mg, 0.71 mmol) and Cs$_2$CO$_3$ (488 mg, 1.5 mmol) in acetonitrile (2 ml) was irradiated with microwaves at 90° C. for 1 h. Ethyl acetate was added and the reaction mixture was washed with brine, dried over Na$_2$SO$_4$, filtered and concentrated. Purification by flash chromatography, silica gel, gradient hexane to ethyl acetate afforded the desired product (135 mg, 70% yield) as a yellow oil. $^1$H-NMR (300 MHz, CDl$_3$), δ ppm: 7.97 (s, 1H), 7.86 (s, 1H), 7.30 (m, 3H), 7.08 (d, J=7 Hz, 1H), 5.66 (d, J=6 Hz, 1H), 4.78 (q, J=6 Hz, 1H), 4.27 (q, J=7 Hz, 2H), 3.38 (dd, J=16, 7 Hz, 1H), 2.99 (dd, J=16, 7 Hz, 1H), 1.33 (t, J=7 Hz, 3H).

(±)-(trans)-Ethyl 1-((1S,2S)-2-((tert-butyldimethylsilyl)oxy)-2,3-dihydro-1H-inden-1-yl)-1H-pyrazole-4-carboxylate To a solution of (±)-(trans)-1-((1S,2S)-2-hydroxy-2,3-dihydro-1H-inden-1-yl)-1H-pyrazole-4-carboxylate (135 mg, 0.50 mmol) in dichloromethane (4.4 ml), imidazole (68 mg, 0.99 mmol) and TBDMSCI (112 mg, 0.74 mmol) were added. The mixture was stirred at rt under argon overnight. Dichloromethane was added and the mixture was washed with water and brine, dried over Na$_2$SO$_4$, filtered and the solvent removed. Purification by flash chromatography, silica gel, gradient hexane to ethyl acetate afforded the desired product (147 mg, 77% yield). $^1$H-NMR (300 MHz, CDl$_3$), δ ppm: 7.97 (s, 1H), 7.86 (s, 1H), 7.30 (m, 3H), 7.08 (d, J=8 Hz, 1H), 5.54 (d, J=7 Hz, 1H), 4.84 (q, J=7 Hz, 1H), 4.30 (q, J=7 Hz, 2H), 3.38 (dd, J=15, 8 Hz, 1H), 2.94 (dd, J=15, 8 Hz, 1H), 1.35 (t, J=7 Hz, 3H), 0.84 (s, 9H), −0.06 (s, 3H), −0.13 (s, 3H).

(±)-(trans)-(1-((1S,2S)-2-((Tert-butyldimethylsilyl)oxy)-2,3-dihydro-1H-inden-1-yl)-1H-pyrazol-4-yl)methanol A solution of (±)-(trans)-ethyl 1-((1S,2S)-2-((tert-butyldimethylsilyl)oxy)-2,3-dihydro-1H-inden-1-yl)-1H-pyrazole-4-carboxylate (108 mg, 0.28 mmol) in THF (0.6 ml) was cooled to 0° C. under nitrogen atmosphere. LiAlH$_4$ (0.28 ml, 1M in THF, 0.28 mmol) was added dropwise. After complete addition, the solution was allowed to warm to rt and stirred for 2 h. NH$_4$Cl saturated solution was slowly added and the solvent was removed. Water and ethyl acetate were added to the residue. The organic phase was dried over Na$_2$SO$_4$ and the solvent was removed to give the desired product (96 mg, 99% yield). No further purification was carried out. $^1$H-NMR (300 MHz, CDl$_3$), δ ppm: 7.58 (s, 1H), 7.48 (s, 1H), 7.24 (m, 3H), 6.93 (d, J=7 Hz, 1H), 5.51 (d, J=7 Hz, 1H), 4.81 (q, J=7 Hz, 1H), 4.60 (s, 2H), 3.26 (dd, J=15, 8 Hz, 1H), 2.93 (dd, J=15, 8 Hz, 1H), 0.83 (s, 9H), −0.07 (s, 3H), −0.13 (s, 3H).

Examples of Preparation of an Intermediate of Formula (XVIId$_{ex}$), Method XIII Synthesis of (8H-[1,2,3]triazolo[5,1-a]isoindol-3-yl)methanol

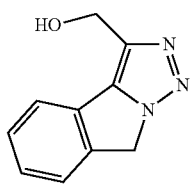 [SMILES: OCc1nnn2c1-c1ccccc1C2]

(1-(2-Chlorobenzyl)-1H-1,2,3-triazol-4-yl)methanol

A solution of 2-chlorobenzyl chloride (200 µl, 1.58 mmol) and sodium azide (123 mg, 1.89 mmol) in tBuOH:H$_2$O 1:1 (4 ml) was irradiated with MW at 100° C. for 1 h. Propargyl alcohol (110 µl, 1.89 mmol), CuSO$_4$.5H$_2$O (40 mg, 0.16 mmol) and sodium ascorbate (62 mg, 0.31 mmol) were added and the mixture was stirred at rt for 16 h. EtOAc was added and the mixture was washed with NH$_4$Cl saturated solution and water, dried over Na$_2$SO$_4$, filtered and concentrated. Purification by flash chromatography, silica gel, gradient dichloromethane to dichloromethane: methanol 9:1 afforded the desired product (217 mg, 61% yield) as a white solid. $^1$H-NMR (300 MHz, CDCl$_3$), δ ppm: 7.55 (s, 1H), 7.44 (dd, J=7, 2 Hz, 1H), 7.27 (m, 3H), 5.67 (s, 2H), 4.79 (d, J=6 Hz, 2H), 2.17 (bs, 1H).

4-(((Tert-butyldimethylsilyl)oxy)methyl)-1-(2-chlorobenzyl)-1H-1,2,3-triazole

To a solution of (1-(2-chlorobenzyl)-1H-1,2,3-triazol-4-yl)methanol (200 mg, 0.89 mmol) in dichloromethane (8 ml), 1H-imidazole (122 mg, 1.79 mmol) and TBDMSCI (148 mg, 0.98 mmol) were added. The mixture was stirred at rt under Argon atmosphere for 1 h. Dichloromethane was added and the reaction mixture was washed with water and brine, dried over Na$_2$SO$_4$, filtered and concentrated. Purification by flash chromatography, silica gel, gradient hexane to ethyl acetate afforded the desired product (280 mg, 93% yield) as a colourless oil. $^1$H-NMR (300 MHz, CDCl3), δ ppm: 7.49 (s, 1H), 7.42 (dd, J=7, 2 Hz, 1H), 7.26 (m, 2H), 7.13 (dd, J=7, 2 Hz, 1H), 5.64 (s, 2H), 4.84 (s, 2H), 0.88 (s, 9H), 0.07 (s, 6H).

3-(((Tert-butyldimethylsilyl)oxy)methyl)-8H-[1,2,3]triazolo[5,1-a]isoindole

A mixture of 4-(((tert-butyldimethylsilyl)oxy)methyl)-1-(2-chlorobenzyl)-1H-1,2,3-triazole (214 mg, 0.63 mmol), K$_2$CO$_3$ (175 mg, 1.27 mmol) and Pd(OAc)$_2$ (14 mg, 0.06 mmol) in toluene (6 ml) was purged with argon and then pivalic acid (19.4 mg, 194 µl of a 10% wt solution in DMF, 0.19 mmol) and tricyclohexylphosphine (89 µl, 20% wt solution in toluene, 0.06 mmol) were added and the mixture was heated at 130° C. for 16 h. Ethyl acetate was added and the mixture was washed with NH$_4$Cl saturated solution and water, dried over Na$_2$SO$_4$, filtered and concentrated. Purification by flash chromatography, silica gel, gradient hexane to ethyl acetate afforded the desired product (134 mg, 70% yield) as a dark-green solid. $^1$H-NMR (300 MHz, CDCl$_3$), δ ppm: 7.82 (d, J=7 Hz, 1H), 7.43 (m, 3H), 5.31 (s, 2H), 5.06 (s, 2H), 0.92 (s, 9H), 0.14 (s, 6H).

(8H-[1,2,3]Triazolo[5,1-a]isoindol-3-yl)methanol

To a solution of 3-(((tert-butyldimethylsilyl)oxy)methyl)-8H-[1,2,3]triazolo[5,1-a]isoindole (159 mg, 0.53 mmol) in THF (5 ml) under argon atmosphere, TBAF (0,791 ml, 1M solution in THF, 0.79 mmol) was added dropwise and the mixture was stirred at rt for 2 h. Some drops of water were added and the reaction mixture was then concentrated. Purification by flash chromatography, silica gel, gradient hexane to ethyl acetate afforded the desired product (86 mg, 87% yield) as a white solid. $^1$H-NMR (400 MHz, MeOD), δ ppm: 7.78 (d, J=7 Hz, 1H), 7.52 (d, J=7 Hz, 1H), 7.39 (m, 2H), 5.27 (s, 2H), 4.88 (d, J=7 Hz, 2H).

Examples of Preparation of an Intermediate of Formula (XVIIIa$_{ex}$), Method XIV Synthesis of ethyl 1-(5-fluoropyridin-2-yl)-1H-1,2,3-triazole-4-carboxylate

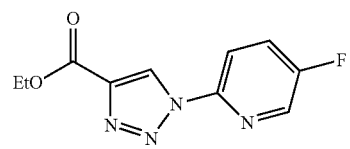 [SMILES: CCOC(=O)c1cn(-c2ccc(F)cn2)nn1]

2-Azido-5-fluoropyridine

A microwave vial was charged with a solution of 2-bromo-5-fluoropyridine (0.52 g, 2.96 mmol), sodium azide (196 mg, 3.01 mmol), sodium ascorbate (31 mg, 0.15 mmol), CuI (57 mg, 0.30 mmol), N,N'-dimethylethylenediamine (49 μL, 0.44 mmol) in EtOH:H$_2$O (7:3) (12.4 mL) and the mixture was irradiated at 100° C. for 60 min. The reaction mixture was cooled, water was added and extracted with ethyl acetate. The organic phase was dried over Na$_2$SO$_4$ and the solvent was removed to obtain the titled product (0.32 g, 78% yield) as a yellow solid, that was used in the next step without further purification. $^1$H-NMR (400 MHz, CDCl3), δ ppm: 8.77 (td, J=3, 1 Hz, 1H), 8.06 (dd, J=12, 6 Hz, 1H), 7.62 (ddd, J=12, 9, 3 Hz, 1H).

Ethyl 1-(5-fluoropyridin-2-yl)-1H-1,2,3-triazole-4-carboxylate

To a mixture of 2-azido-5-fluoropyridine (0.32 g, 1.97 mmol) and (CuOTf)$_2$.C$_6$H$_6$ (112 mg, 0.20 mmol) under argon atmosphere, dry toluene (7.7 ml) was added, followed by ethyl propiolate (240 μL, 2.36 mmol). The reaction mixture was stirred at 100° C. overnight. Toluene was removed under reduced pressure and the reaction mixture was then diluted with dichloromethane, washed with water, brine and dried over Na$_2$SO$_4$. The mixture was filtered and the filtrate was concentrated under reduced pressure. Purification by flash chromatography, silica gel, gradient hexane to ethyl acetate afforded the titled product (450 mg, 97% yield) as a yellowish solid. $^1$H-NMR (500 MHz, CDCl3), δ ppm: 9.00 (s, 1H), 8.38 (d, J=3 Hz, 1H), 8.27 (dd, J=9, 4 Hz, 1H), 7.68 (ddd, J=9, 7, 3 Hz, 1H), 4.47 (q, J=7 Hz, 2H), 1.44 (t, J=7 Hz, 3H).

Synthesis of Examples

Preparation of Compounds of General Formula (I$_{ex}$), Method I

Example 1: N-(3-(1-((1-phenyl-1H-1,2,3-triazol-4-yl)methyl)piperidin-4-yl)phenyl)propane-2-sulfonamide

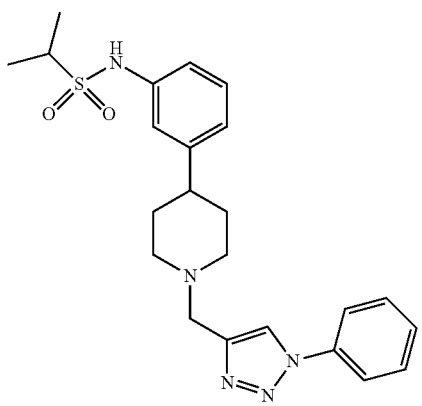 [SMILES: CC(C)S(=O)(=O)Nc1cccc(C2CCN(Cc3cn(-c4ccccc4)nn3)CC2)c1]

To a suspension of N-(3-(piperidin-4-yl)phenyl)propane-2-sulfonamide hydrochloride (69 mg, 0.21 mmol) in dichloroethane (10 ml), DIPEA (226 μl, 1.29 mmol) was added and the mixture was stirred at rt for 5 min. Then, 1-phenyl-1H-1,2,3-triazole-4-carbaldehyde (49 mg, 0.28 mmol) and NaBH(OAc)$_3$ (73 mg, 0.34 mmol) were added and the reaction mixture was stirred at rt overnight. Dichloromethane was added and washed with NaHCO$_3$ sat solution and brine, dried over Na$_2$SO$_4$, filtered and concentrated. Purification by flash chromatography, silica gel, gradient dichloromethane to dichloromethane: methanol 85:15 afforded the desired product (60 mg, 63% yield). HPLC retention time: 5.62 min; HRMS: 440.2141 (M+H).

This method was used for the preparation of examples 1, 7, 11-13, 16-35, 37-39, 42, 47-49, 51-53, 56-57, 62, 64, 68, 73-74, 76, 79, 81-87, 90, 93-94, 98-99, 101-103, 110-125, 128-141, 143-148, 151-154, 157, 161, 163-165, 167-203, 205-222, 224-226, 228-232.

Racemic example 115 was separated using an Agilent 1100 Preparative HPLC. The stationary phase used in the chiral chromatography was a ChiralPak IA column, the mobile phase was a mixture consisting of 50% heptane and 50% ethanol performed at a temperature of 20-25° C. at a flow rate of 7 mL/min of eluent. The extracts were concentrated by evaporation on rotary evaporators and analyzed for purity by HPLC. The analysis determined that the enantiomeric purity of the R,S-enantiomer (example 126) was 99.9% and the S,R-enantiomer (example 127) was 99.4%.

Preparation of Compounds of General Formula (Ia$_{ex}$), Method IIB

Example 2: 3-(1-((1-phenyl-1H-1,2,3-triazol-4-yl)methyl)piperidin-4-yl)phenol

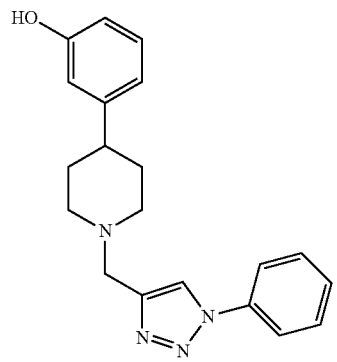

A mixture of 3-(1-(prop-2-yn-1-yl)piperidin-4-yl)phenol (622 mg, 2.89 mmol), phenylazide (490 mg, 3.21 mmol), CuSO$_4$.5H$_2$O (72 mg, 0.29 mmol) and sodium ascorbate (115 mg, 0.58 mmol) in t-BuOH:H$_2$O 1:1 (40 ml) was stirred at rt for 16 h. Water and saturated NH$_4$Cl aqueous solution were added and the mixture extracted with EtOAc. The organic phases were combined, dried over Na$_2$SO$_4$ and concentrated. Purification was carried out by flash chromatography, silica gel, gradient dichloromethane to dichloromethane:methanol 9:1 to afford the desired product (800 mg, 83% yield). HPLC retention time: 5.13 min; HRMS: 335.1882 (M+H).

This method was used for the preparation of the examples of formula (Ia) 2, 8, 10, 14-15, 36, 40-41, 43-46, 54-55, 58-61, 63, 65-67, 71-72, 75, 77-78, 88, 95-96, 106-109, 142, 149-150, 155-156, 158-160, 162, 223, 227, 233.

Racemic example 67 was separated using an Agilent 1100 Preparative HPLC. The stationary phase used in the chiral chromatography was a Chiralcel OD-H column. The mobile Preparation of Compounds of General Formula (Ia$_{ex}$), Method IIC Example 3: 3-(1-((1-propyl-1H-1,2,3-triazol-4-yl)methyl)piperidin-4-yl)phenol

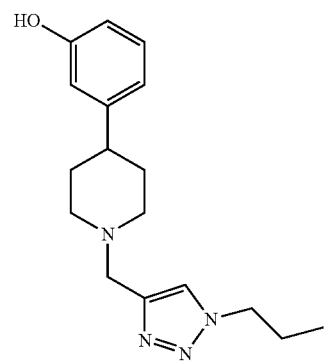

A mixture of 3-(1-(prop-2-yn-1-yl)piperidin-4-yl)phenol (100 mg, 0.46 mmol), sodium azide (39 mg, 0.60 mmol), CuI (18 mg, 0.09 mmol) and iodopropane (59 μl, 0.60 mmol) in DMF (2.0 ml) was irradiated with microwaves at 100° C. for 30 min. Ethyl acetate was added and the mixture was washed with NH$_4$Cl saturated solution and brine, dried over Na$_2$SO$_4$, filtered and concentrated. Purification was carried out by flash chromatography, silica gel, gradient dichloromethane to dichloromethane:methanol 9:1 to yield the desired product (55 mg, 39% yield). HPLC retention time: 4.68 min; HRMS: 301.2015 (M+H).

This method was used for the preparation of the examples of formula (Ia) 3, 9, 89.

Preparation of Compounds of General Formula (Ia$_{ex}$), Method IID

Example 4: 3-(1-((1-(2-fluorobenzyl)-1H-1,2,3-triazol-4-yl)methyl)piperidin-4-yl)phenol

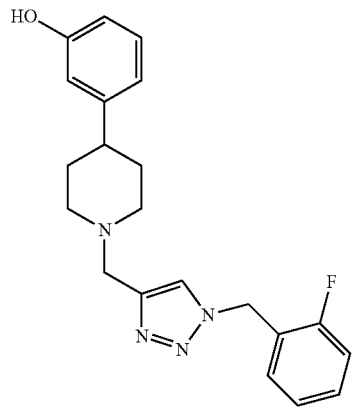

A solution of 2-fluorobenzyl bromide (32 μl, 0.27 mmol) and sodium azide (21 mg, 0.32 mmol) in tBuOH:H$_2$O 1:1 (1 ml) was irradiated with microwaves at 100° C. for 1 h. 3-(1-(prop-2-yn-1-yl)piperidin-4-yl)phenol (46 mg, 0.21 mmol), CuSO$_4$.5H$_2$O (7 mg, 0.03 mmol) and sodium ascorbate (11 mg, 0.05 mmol) were added and the mixture was stirred at rt for 16 h. Ethyl acetate was added and the reaction mixture washed with NH$_4$Cl saturated solution and water, dried over Na$_2$SO$_4$, filtered and concentrated. The crude was purified by flash chromatography, silica gel, gradient dichloromethane to dichloromethane: methanol 9:1 to yield the desired product (63 mg, 65% yield) as a white solid. HPLC retention time: 5.26 min; HRMS: 367.1917 (M+H).

This method was used for the preparation of examples of formula (Ia) 4, 63.

Preparation of Compounds of General Formula (Ib$_{ex}$), Method IIE

Example 5: (±)-(trans)-3-(1-((1-(2-hydroxycyclopentyl)-1H-1,2,3-triazol-4-yl)methyl)piperidin-4-yl)phenol

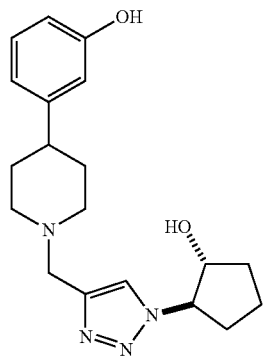

A mixture of 3-(1-(prop-2-yn-1-yl)piperidin-4-yl)phenyl acetate (89 mg, 0.35 mmol), sodium azide (135 mg, 2.07 mmol), CuSO₄.5H₂O (2 mg, 0.07 mmol), sodium ascorbate (10 mg, 0.05 mmol) and cyclopentene oxide (39 μl, 0.45 mmol) in t-BuOH:H₂O 1:1 (3 ml) (2.0 ml) was irradiated with microwaves at 100° C. for 60 min. Ethyl acetate was added and the mixture was washed with NH₄Cl saturated solution and brine, dried over Na₂SO₄, filtered and concentrated. Purification was carried out by flash chromatography, silica gel, gradient dichloromethane to dichloromethane: methanol 7:3 to yield the desired product (45 mg, 34% yield). HPLC retention time: 4.78 min; HRMS: 343.2122 (M+H).

Preparation of Compounds of General Formula (Ia$_{ex}$), Method IIF

Example 6: 3-(1-((1-phenyl-1H-1,2,3-triazol-4-yl) methyl)piperidin-4-yl)benzamide

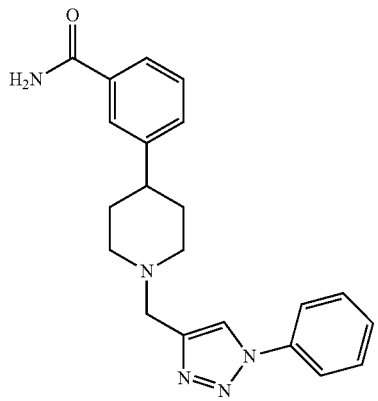

3-(1-((1-Phenyl-1H-1,2,3-triazol-4-yl)methyl)piperidin-4-yl)benzonitrile

A mixture of 3-(piperidin-4-yl)benzonitrile (80 mg, 0.43 mmol), Et₃N (180 μl, 1.30 mmol) and propargyl bromide (48 μl, 0.51 mmol, 80% solution in toluene) in water (1.5 ml) was vigorously stirred at rt for 1 h. Then, phenylazide (54 mg, 0.45 mmol), CuI (9 mg, 0.04 mmol) and THF (1.0 ml) were added, and the mixture was stirred at rt overnight. NH₄Cl saturated solution was added and the mixture was extracted with EtOAc (3×), washed with brine, dried over Na₂SO₄, filtered and concentrated. Purification by flash chromatography silica gel, gradient from hexane to ethyl acetate afforded the desired product (80 mg, 54% yield) as a brown oil. ¹H-NMR (500 MHz, CDCl3), δ ppm: 7.97 (s, 1H), 7.74 (d, J=8 Hz, 1H), 7.54-7.40 (m, 6H), 7.37 (t, J=8 Hz, 1H), 3.80 (s, 2H), 3.13 (d, J=11 Hz, 2H), 2.55 (m, 1H), 2.23 (t, J=11 Hz, 2H), 1.80 (m, 4H).

This method was used for the preparation of examples 6, 69

3-(1-((1-Phenyl-1H-1,2,3-triazol-4-yl)methyl)piperidin-4-yl)benzamide

To a flask containing H₂O₂ (0.7 ml of a 35% solution, 8.15 mmol), water (0.3 ml), acetone (2.0 ml) and K₂CO₃ (0.73 ml of a 10% K₂CO₃ solution, 0.52 mmol), a solution of 3-(1-((1-phenyl-1H-1,2,3-triazol-4-yl)methyl)piperidin-4-yl) benzonitrile (80 mg, 0.23 mmol) in acetone (0.5 ml) was added. The mixture was maintained at 40° C. overnight. Acetone was removed and the mixture was extracted with dichloromethane and water, dried over Na₂SO₄, filtered and concentrated. The crude was purified by flash chromatography, silica gel, gradient dichloromethane to dichloromethane:methanol 9:1 to yield the desired product (28 mg, 33% yield) as a yellowish solid.

Example 49: N-(4-(1-((1-Phenyl-1H-1,2,3-triazol-4-yl)methyl)piperidin-4-yl)benzo[d]thiazol-2-yl)acetamide To a suspension of N-(6-(piperidin-4-yl)benzo[d]thiazol-2-yl)acetamide hydrochloride (91 mg, 0.26 mmol) in dichloroethane (6 ml), DIPEA (137 μl, 0.80 mmol) was added and the mixture was stirred at rt for 5 min. Then, 1-phenyl-1H-1,2,3-triazole-4-carbaldehyde (63 mg, 0.37 mmol) and NaBH(OAc)₃ (111 mg, 0.52 mmol) were added and the reaction mixture was stirred at rt overnight. Dichloromethane was added and washed with NaHCO₃ sat solution and brine, dried over Na₂SO₄, filtered and concentrated. Purification by flash chromatography, silica gel, gradient dichloromethane to dichloromethane: methanol 96:4 afforded the desired product (62 mg, 55% yield). HPLC retention time: 5.79 min; HRMS: 455.1637 (M+Na).

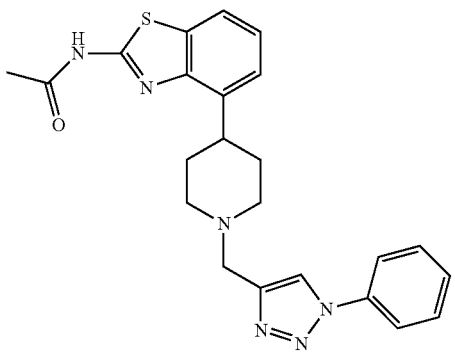 [SMILES: CC(=O)Nc1nc2c(C3CCN(Cc4cn(-c5ccccc5)nn4)CC3)cccc2s1]

Example 50: 4-(1-((1-phenyl-1H-1,2,3-triazol-4-yl)methyl)piperidin-4-yl)benzo[d]thiazol-2-amine To a solution of N-(4-(1-((1-phenyl-1H-1,2,3-triazol-4-yl)methyl)piperidin-4-yl)benzo[d]thiazol-2-yl)acetamide (42 mg, 0.1 mmol) in methanol (0.5 ml), a solution of 10M NaOH (0.1 ml, 1.0 mmol) was added and the reaction mixture was stirred at 80° C. for 90 min. The reaction mixture was cooled to rt and acidified to pH=2 with 1M HCl solution and then washed with dichloromethane. The aqueous phase was neutralized with saturated $NaHCO_3$ and extracted with dichloromethane. The organic phase was dried over $Na_2SO_4$, filtered and concentrated to afford the desired product (23 mg, 61% yield). HPLC retention time: 4.90 min; HRMS: 413.1535 (M+Na) as white solid.

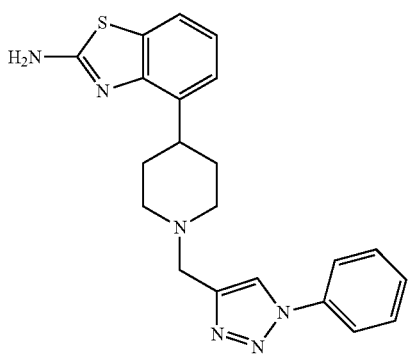 [SMILES: Nc1nc2c(C3CCN(Cc4cn(-c5ccccc5)nn4)CC3)cccc2s1]

Example 70: (±)-(trans)-N-(3-(1-((1-(2-hydroxy-2,3-dihydro-1H-inden-1-yl)-1H-1,2,3-triazol-4-yl)methyl)piperidin-4-yl)phenyl)methanesulfonamide

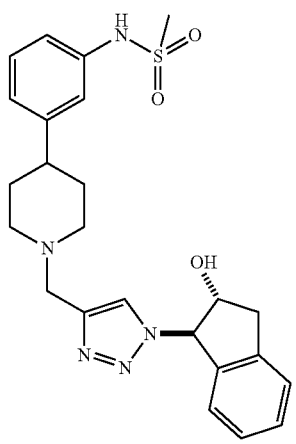

(±)-(trans)-N-(3-(1-((1-(2-((tert-Butyldimethylsilyl)oxy)-2,3-dihydro-1H-inden-1-yl)-1H-1,2,3-triazol-4-yl)methyl)piperidin-4-yl)phenyl)methanesulfonamide To a suspension of N-(3-(piperidin-4-yl)phenyl)methanesulfonamide hydrochloride (32 mg, 0.11 mmol) in dichloroethane (2.2 ml), DIPEA (76 μl, 0.44 mmol) was added and the mixture was stirred at rt for 5 min. Then, (±)-(trans)-1-(2-((tert-butyldimethylsilyl)oxy)-2,3-dihydro-1H-inden-1-yl)-1H-1,2,3-triazole-4-carbaldehyde (42 mg, 0.12 mmol) and $NaBH(OAc)_3$ (47 mg, 0.22 mmol) were added and the reaction mixture was stirred at rt overnight. Dichloromethane was added and washed with $NaHCO_3$ sat solution and brine, dried over $Na_2SO_4$, filtered and concentrated. Purification by flash chromatography, silica gel, gradient hexane to ethyl acetate afforded the desired product (59 mg, 92% yield). $^1$H-NMR (500 MHz, CDCl3), δ ppm: 7.46 (s, 1H), 7.25 (m, 4H), 7.06 (m, 2H), 7.02 (d, J=7 Hz, 1H), 6.93 (d, J=7 Hz, 1H), 5.91 (d, J=7 Hz, 1H), 4.79 (q, J=7 Hz, 1H), 3.74 (s, 2H), 3.31 (dd, J=16, 7 Hz, 1H), 3.01 (m, 3H), 2.99 (s, 3H), 2.48 (m, 1H), 2.16 (m, 2H), 1.77 (m, 4H), 0.83 (s, 9H), −0.06 (s, 3H), −0.11 (s, 3H).

(±)-(trans)-N-(3-(1-((1-(2-Hydroxy-2,3-dihydro-1H-inden-1-yl)-1H-1,2,3-triazol-4-yl)methyl)piperidin-4-yl)phenyl)methanesulfonamide To a solution of (±)-(trans)-N-(3-(1-((1-(2-((tert-butyldimethylsilyl)oxy)-2,3-dihydro-1H-inden-1-yl)-1H-1,2,3-triazol-4-yl)methyl)piperidin-4-yl)phenyl)methanesulfonamide (55 mg, 0.1 mmol) in THF (0.9 ml) under argon atmosphere, TBAF (0.142 ml, 1M solution in THF, 0.14 mmol) was added dropwise and the mixture was stirred at rt for 3 hours. Some drops of water were added and the reaction mixture was concentrated. The crude was purified by flash chromatography, silica gel, gradient dichloromethane to dichloromethane:methanol 9:1 to yield the desired product (39 mg, 87% yield). HPLC retention time: 5.12 min; HRMS: 466.1911 (M−H).

This method was used for the preparation of examples 70, 80, 91-92, 97, 100, 104-105, 166, 204.

Table of Examples

HPLC:

column: Agilent Eclipse XDB-C18, 4.6×150 mm, 5 mm, flux: 1 ml/min.

A:$H_2O$ (0.05% TFA), B:ACN.

Conditions: 1°/gradient 5% to 95% B in 7 min. 2°/isocratic 95% B 5 min.

HRMS:

Source type: ESI; Ion Polarity: Positive or Negative

| EX | Structure | Chemical name | Ret time (min) | HRMS |
|---|---|---|---|---|
| 1 | 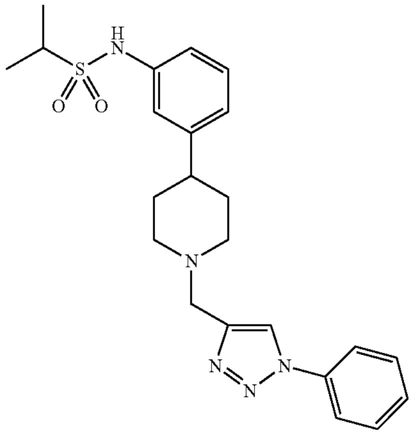 [SMILES: CC(C)S(=O)(=O)Nc1cccc(C2CCN(Cc3cn(-c4ccccc4)nn3)CC2)c1] | N-(3-(1-((1-phenyl-1H-1,2,3-triazol-4-yl)methyl)piperidin-4-yl)phenyl)propane-2-sulfonamide | 5.62 | 440.2141 (M + H) |
| 2 | 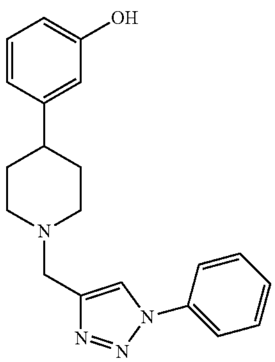 [SMILES: Oc1cccc(C2CCN(Cc3cn(-c4ccccc4)nn3)CC2)c1] | 3-(1-((1-phenyl-1H-1,2,3-triazol-4-yl)methyl)piperidin-4-yl)phenol | 5.13 | 335.1882 (M + H) |
| 3 | 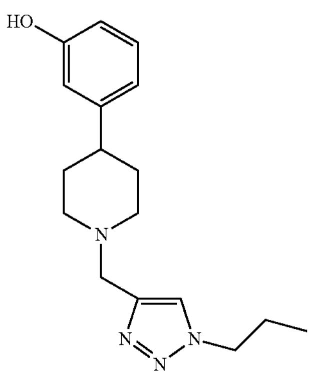 [SMILES: CCCn1cc(CN2CCC(c3cccc(O)c3)CC2)nn1] | 3-(1-((1-propyl-1H-1,2,3-triazol-4-yl)methyl)piperidin-4-yl)phenol | 4.68 | 301.2015 (M + H) |
| 4 | 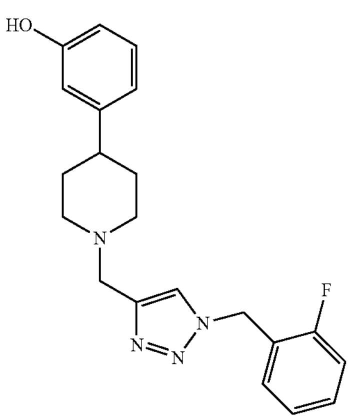 [SMILES: Oc1cccc(C2CCN(Cc3cn(Cc4ccccc4F)nn3)CC2)c1] | 3-(1-((1-(2-fluorobenzyl)-1H-1,2,3-triazol-4-yl)methyl)piperidin-4-yl)phenol | 5.26 | 367.1917 (M + H) |

-continued

| EX | Structure | Chemical name | Ret time (min) | HRMS |
|---|---|---|---|---|
| 5 | 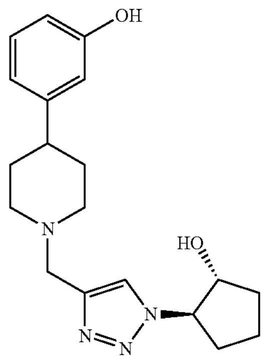 [SMILES: Oc1cccc(C2CCN(Cc3cn([C@@H]4CCC[C@H]4O)nn3)CC2)c1] | 3-(1-((1-((1R,2R)-2-hydroxycyclopentyl)-1H-1,2,3-triazol-4-yl)methyl)piperidin-4-yl)phenol | 4.78 | 343.2122 (M + H) |
| 6 | 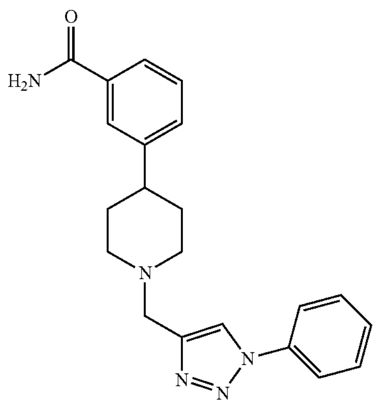 [SMILES: NC(=O)c1cccc(C2CCN(Cc3cn(-c4ccccc4)nn3)CC2)c1] | 3-(1-((1-phenyl-1H-1,2,3-triazol-4-yl)methyl)piperidin-4-yl)benzamide | 4.88 | 362.1997 (M + H) |
| 7 | 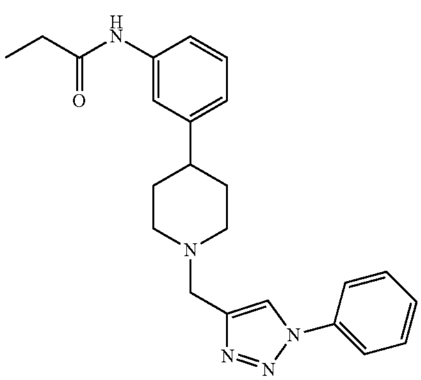 [SMILES: CCC(=O)Nc1cccc(C2CCN(Cc3cn(-c4ccccc4)nn3)CC2)c1] | N-(3-(1-((1-phenyl-1H-1,2,3-triazol-4-yl)methyl)piperidin-4-yl)phenyl)propionamide | 5.47 | 390.2281 (M + H) |
| 8 | 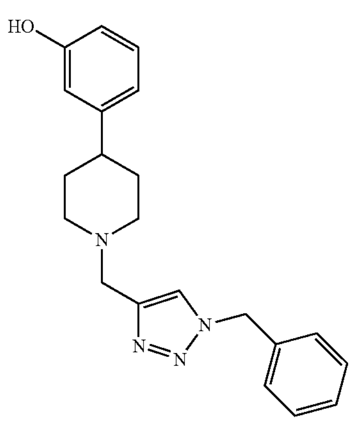 [SMILES: Oc1cccc(C2CCN(Cc3cn(Cc4ccccc4)nn3)CC2)c1] | 3-(1-((1-benzyl-1H-1,2,3-triazol-4-yl)methyl)piperidin-4-yl)phenol | 5.28 | 349.2015 (M + H) |

-continued

| EX | Structure | Chemical name | Ret time (min) | HRMS |
|---|---|---|---|---|
| 9 | 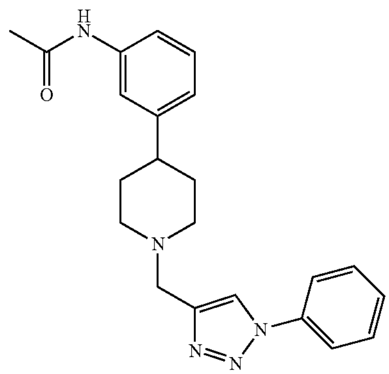 [SMILES: CC(=O)Nc1cccc(C2CCN(Cc3cn(-c4ccccc4)nn3)CC2)c1] | N-(3-(1-((1-phenyl-1H-1,2,3-triazol-4-yl)methyl)piperidin-4-yl)phenyl)acetamide | 5.17 | 376.2136 (M + H) |
| 10 | 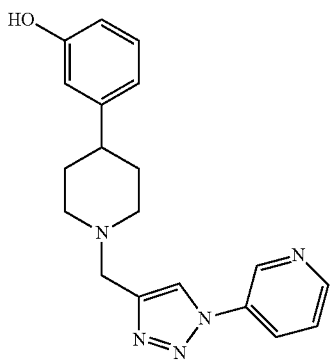 [SMILES: Oc1cccc(C2CCN(Cc3cn(-c4cccnc4)nn3)CC2)c1] | 3-(1-((1-(pyridin-3-yl)-1H-1,2,3-triazol-4-yl)methyl)piperidin-4-yl)phenol | 4.55 | 336.1815 (M + H) |
| 11 | 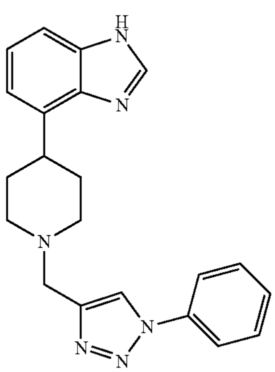 [SMILES: c1ccc(-n2cc(CN3CCC(c4cccc5[nH]cnc45)CC3)nn2)cc1] | 4-(1-((1-phenyl-1H-1,2,3-triazol-4-yl)methyl)piperidin-4-yl)-1H-benzo[d]imidazole | 4.38 | 381.1788 (M + Na) |
| 12 | 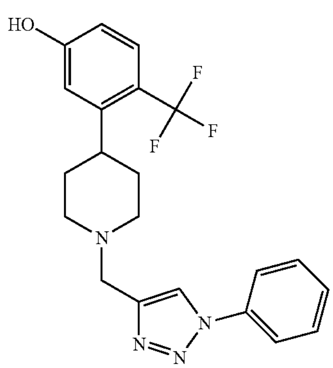 [SMILES: Oc1ccc(C(F)(F)F)c(C2CCN(Cc3cn(-c4ccccc4)nn3)CC2)c1] | 3-(1-((1-phenyl-1H-1,2,3-triazol-4-yl)methyl)piperidin-4-yl)-4-(trifluoromethyl)phenol | 5.87 | 403.1747 (M + H) |

-continued
| EX | Structure | Chemical name | Ret time (min) | HRMS |
|----|-----------|---------------|----------------|------|
| 13 | 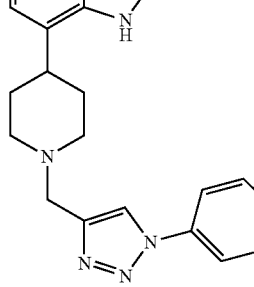 | 4-(1-((1-phenyl-1H-1,2,3-triazol-4-yl)methyl)piperidin-4-yl)-1H-benzo[d]imidazol-2(3H)-one | 4.87 | 375.1916 (M + H) |
| 14 | 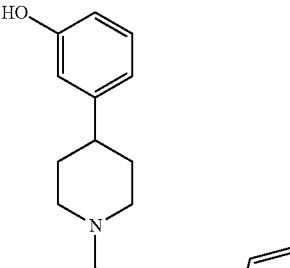 | 3-(1-((1-(pyridin-4-yl)-1H-1,2,3-triazol-4-yl)methyl)piperidin-4-yl)phenol | 4.21 | 336.1811 (M + H) |
| 15 | 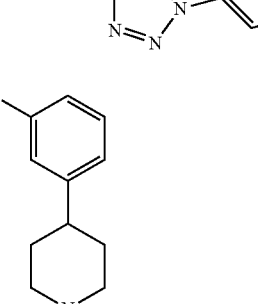 | (1R,2R)-1-(4-((4-(3-hydroxyphenyl)piperidin-1-yl)methyl)-1H-1,2,3-triazol-1-yl)-2,3-dihydro-1H-inden-2-ol | 5.04 | 391.2128 (M + H) |
| 16 | 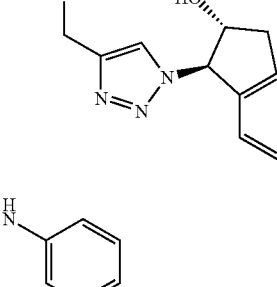 | N-(3-(1-((1-(4-fluorophenyl)-1H-1,2,3-triazol-4-yl)methyl)piperidin-4-yl)phenyl)methanesulfonamide | 5.42 | 430.1708 (M + H) |

| EX | Structure | Chemical name | Ret time (min) | HRMS |
|---|---|---|---|---|
| 17 | 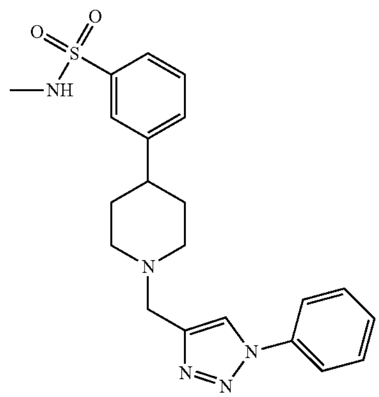 [SMILES: CNS(=O)(=O)c1cccc(C2CCN(Cc3cn(-c4ccccc4)nn3)CC2)c1] | N-methyl-3-(1-((1-phenyl-1H-1,2,3-triazol-4-yl)methyl)piperidin-4-yl)benzenesulfonamide | 5.27 | 412.1805 (M + H) |
| 18 | 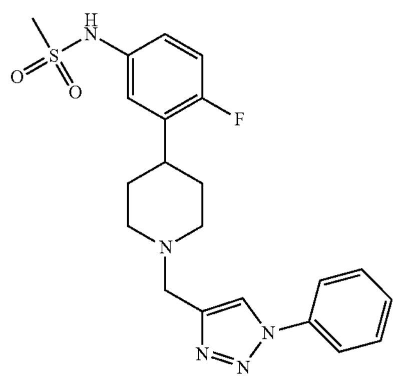 [SMILES: CS(=O)(=O)Nc1ccc(F)c(C2CCN(Cc3cn(-c4ccccc4)nn3)CC2)c1] | N-(4-fluoro-3-(1-((1-phenyl-1H-1,2,3-triazol-4-yl)methyl)piperidin-4-yl)phenyl)methane-sulfonamide | 5.47 | 430.1702 (M + H) |
| 19 | 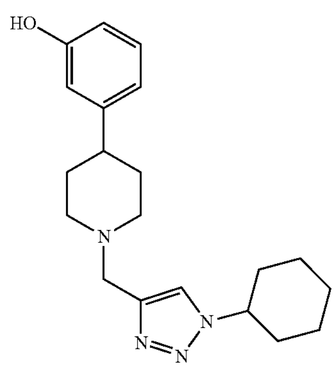 [SMILES: Oc1cccc(C2CCN(Cc3cn(C4CCCCC4)nn3)CC2)c1] | 3-(1-((1-cyclohexyl-1H-1,2,3-triazol-4-yl)methyl)piperidin-4-yl)phenol | 5.07 | 341.2328 (M + H) |
| 20 | 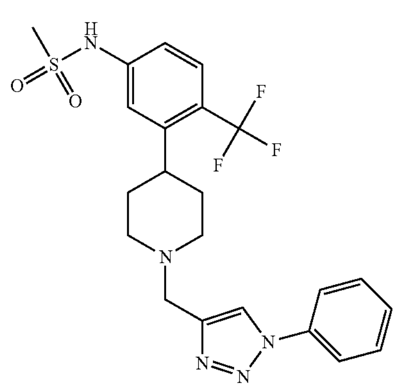 [SMILES: CS(=O)(=O)Nc1ccc(C(F)(F)F)c(C2CCN(Cc3cn(-c4ccccc4)nn3)CC2)c1] | N-(3-(1-((1-phenyl-1H-1,2,3-triazol-4-yl)methyl)piperidin-4-yl)-4-(trifluoromethyl)phenyl)methanesulfonamide | 5.98 | 480.1693 (M + H) |

| EX | Structure | Chemical name | Ret time (min) | HRMS |
|---|---|---|---|---|
| 21 | 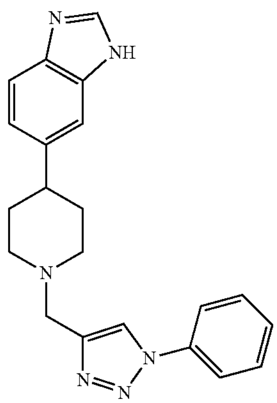 [SMILES: c1ccc(-n2cc(CN3CCC(c4ccc5nc[nH]c5c4)CC3)nn2)cc1] | 6-(1-((1-phenyl-1H-1,2,3-triazol-4-yl)methyl)piperidin-4-yl)-1H-benzo[d]imidazole | 4.34 | 359.1977 (M + H) |
| 22 | 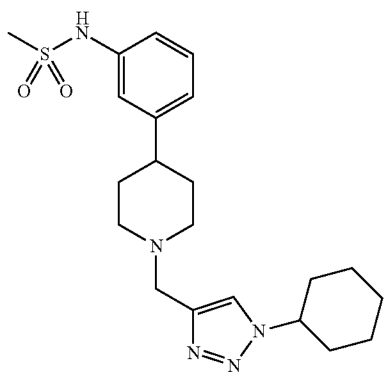 [SMILES: CS(=O)(=O)Nc1cccc(C2CCN(Cc3cn(C4CCCCC4)nn3)CC2)c1] | N-(3-(1-((1-cyclohexyl-1H-1,2,3-triazol-4-yl)methyl)piperidin-4-yl)phenyl)methanesulfonamide | 5.39 | 418.2277 (M + H) |
| 23 | 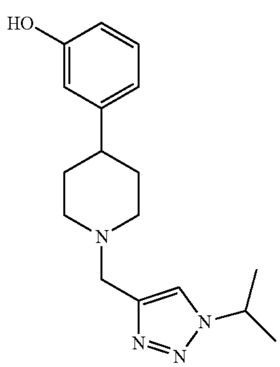 [SMILES: CC(C)n1cc(CN2CCC(c3cccc(O)c3)CC2)nn1] | 3-(1-((1-isopropyl-1H-1,2,3-triazol-4-yl)methyl)piperidin-4-yl)phenol | 4.66 | 301.2023 (M + H) |
| 24 | 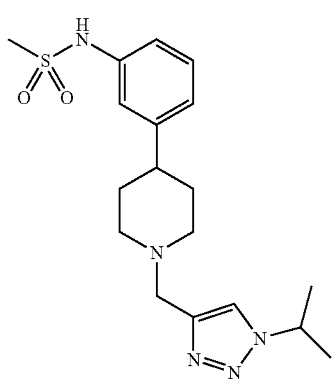 [SMILES: CC(C)n1cc(CN2CCC(c3cccc(NS(C)(=O)=O)c3)CC2)nn1] | N-(3-(1-((1-isopropyl-1H-1,2,3-triazol-4-yl)methyl)piperidin-4-yl)phenyl)methanesulfonamide | 4.73 | 376.1811 (M + H) |

-continued

| EX | Structure | Chemical name | Ret time (min) | HRMS |
|---|---|---|---|---|
| 25 | 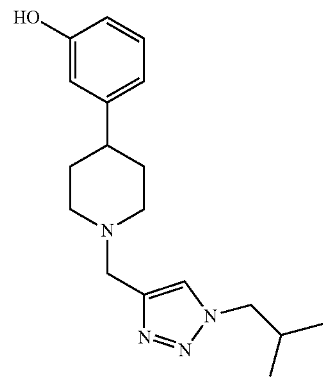 [SMILES: CC(C)Cn1cc(CN2CCC(c3cccc(O)c3)CC2)nn1] | 3-(1-((1-isobutyl-1H-1,2,3-triazol-4-yl)methyl)piperidin-4-yl)phenol | 5.03 | 315.2173 (M + H) |
| 26 | 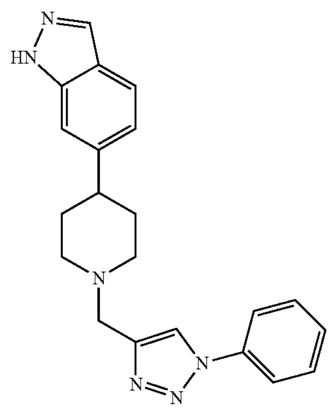 [SMILES: c1ccc(-n2cc(CN3CCC(c4ccc5cn[nH]c5c4)CC3)nn2)cc1] | 6-(1-((1-phenyl-1H-1,2,3-triazol-4-yl)methyl)piperidin-4-yl)-1H-indazole | 5.23 | 359.1978 (M + H) |
| 27 | 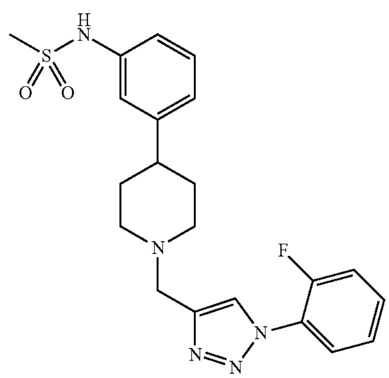 [SMILES: CS(=O)(=O)Nc1cccc(C2CCN(Cc3cn(-c4ccccc4F)nn3)CC2)c1] | N-(3-(1-((1-(2-fluorophenyl)-1H-1,2,3-triazol-4-yl)methyl)piperidin-4-yl)phenyl)methanesulfonamide | 5.29 | 430.1720 (M + H) |
| 28 | 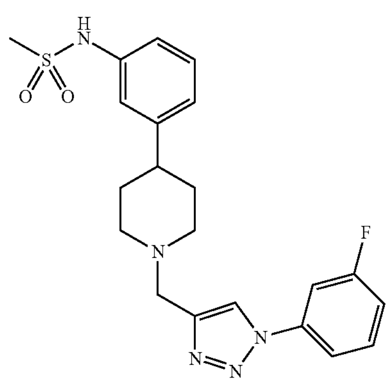 [SMILES: CS(=O)(=O)Nc1cccc(C2CCN(Cc3cn(-c4cccc(F)c4)nn3)CC2)c1] | N-(3-(1-((1-(3-fluorophenyl)-1H-1,2,3-triazol-4-yl)methyl)piperidin-4-yl)phenyl)methanesulfonamide | 5.43 | 430.1733 (M + H) |

-continued

| EX | Structure | Chemical name | Ret time (min) | HRMS |
|---|---|---|---|---|
| 29 | 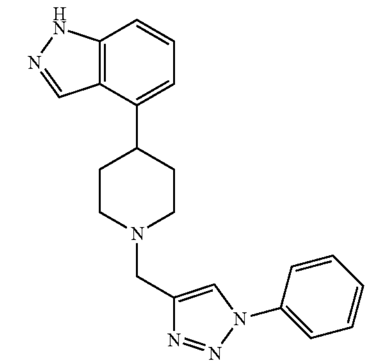 [SMILES: c1ccc(-n2cc(CN3CCC(c4cccc5[nH]ncc45)CC3)nn2)cc1] | 4-(1-((1-phenyl-1H-1,2,3-triazol-4-yl)methyl)piperidin-4-yl)-1H-indazole | 5.22 | 359.1973 (M + H) |
| 30 | 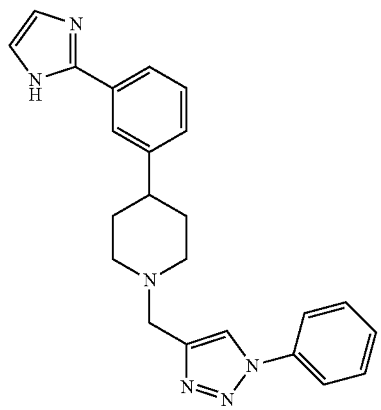 [SMILES: c1ccc(-n2cc(CN3CCC(c4cccc(-c5ncc[nH]5)c4)CC3)nn2)cc1] | 4-(3-(1H-imidazol-2-yl)phenyl)-1-((1-phenyl-1H-1,2,3-triazol-4-yl)methyl)piperidine | 4.54 | 385.2138 (M + H) |
| 31 | 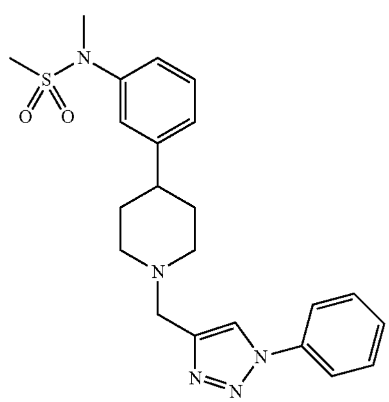 [SMILES: CN(c1cccc(C2CCN(Cc3cn(-c4ccccc4)nn3)CC2)c1)S(C)(=O)=O] | N-methyl-N-(3-(1-((1-phenyl-1H-1,2,3-triazol-4-yl)methyl)piperidin-4-yl)phenyl)methane-sulfonamide | 5.55 | 426.1961 (M + H) |
| 32 | 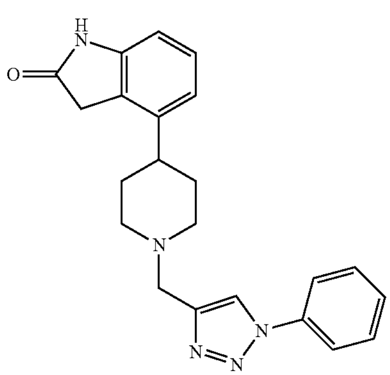 [SMILES: O=C1Cc2c(cccc2C2CCN(Cc3cn(-c4ccccc4)nn3)CC2)N1] | 4-(1-((1-phenyl-1H-1,2,3-triazol-4-yl)methyl)piperidin-4-yl)indolin-2-one | 5.02 | 374.1966 (M + H) |

-continued

| EX | Structure | Chemical name | Ret time (min) | HRMS |
|---|---|---|---|---|
| 33 | 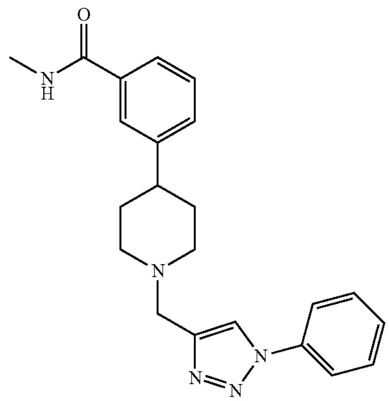 [SMILES: CNC(=O)c1cccc(C2CCN(Cc3cn(-c4ccccc4)nn3)CC2)c1] | N-methyl-3-(1-((1-phenyl-1H-1,2,3-triazol-4-yl)methyl)piperidin-4-yl)benzamide | 4.87 | 374.2150 (M + H) |
| 34 | 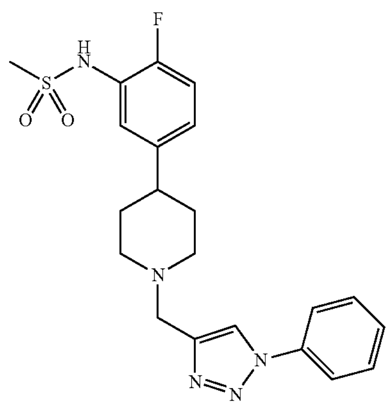 [SMILES: CS(=O)(=O)Nc1cc(C2CCN(Cc3cn(-c4ccccc4)nn3)CC2)ccc1F] | N-(2-fluoro-5-(1-((1-phenyl-1H-1,2,3-triazol-4-yl)methyl)piperidin-4-yl)phenyl)methanesulfonamide | 5.36 | 428.1551 (M − H) |
| 35 | 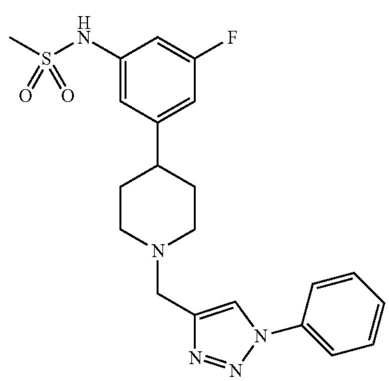 [SMILES: CS(=O)(=O)Nc1cc(F)cc(C2CCN(Cc3cn(-c4ccccc4)nn3)CC2)c1] | N-(3-fluoro-5-(1-((1-phenyl-1H-1,2,3-triazol-4-yl)methyl)piperidin-4-yl)phenyl)methanesulfonamide | 5.52 | 428.1564 (M − H) |
| 36 | 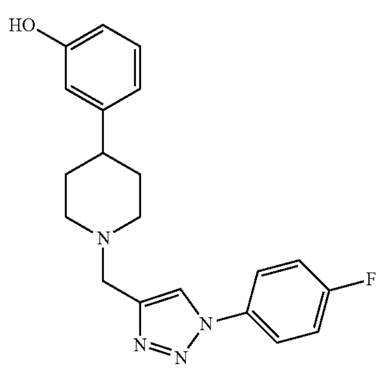 [SMILES: Oc1cccc(C2CCN(Cc3cn(-c4ccc(F)cc4)nn3)CC2)c1] | 3-(1-((1-(4-fluorophenyl)-1H-1,2,3-triazol-4-yl)methyl)piperidin-4-yl)phenol | 5.36 | 353.1790 (M + H) |

-continued

| EX | Structure | Chemical name | Ret time (min) | HRMS |
|---|---|---|---|---|
| 37 | 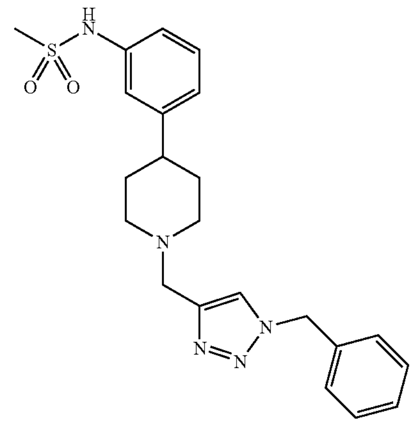 [SMILES: CS(=O)(=O)Nc1cccc(C2CCN(Cc3cn(Cc4ccccc4)nn3)CC2)c1] | N-(3-(1-((1-benzyl-1H-1,2,3-triazol-4-yl)methyl)piperidin-4-yl)phenyl)methane-sulfonamide | 5.33 | 426.1950 (M + H) |
| 38 | 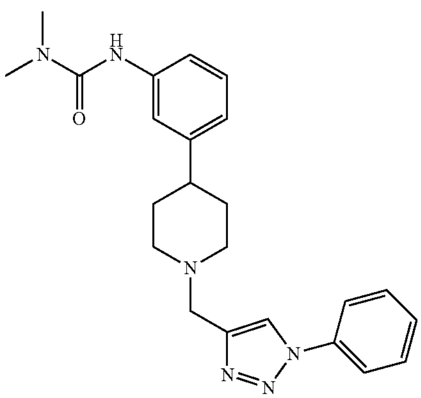 [SMILES: CN(C)C(=O)Nc1cccc(C2CCN(Cc3cn(-c4ccccc4)nn3)CC2)c1] | 1,1-dimethyl-3-(3-(1-((1-phenyl-1H-1,2,3-triazol-4-yl)methyl)piperidin-4-yl)phenyl)urea | 5.32 | 405.2394 (M + H) |
| 39 | 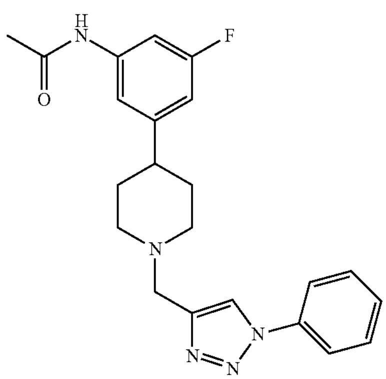 [SMILES: CC(=O)Nc1cc(F)cc(C2CCN(Cc3cn(-c4ccccc4)nn3)CC2)c1] | N-(3-fluoro-5-(1-((1-phenyl-1H-1,2,3-triazol-4-yl)methyl)piperidin-4-yl)phenyl)acetamide | 5.41 | 394.2032 (M + H) |
| 40 | 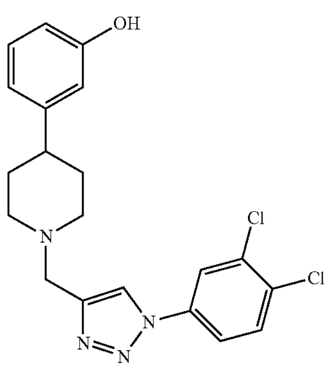 [SMILES: Oc1cccc(C2CCN(Cc3cn(-c4ccc(Cl)c(Cl)c4)nn3)CC2)c1] | 3-(1-((1-(3,4-dichlorophenyl)-1H-1,2,3-triazol-4-yl)methyl)piperidin-4-yl)phenol | 5.81 | 403.1079 (M + H) |

-continued

| EX | Structure | Chemical name | Ret time (min) | HRMS |
|---|---|---|---|---|
| 41 | 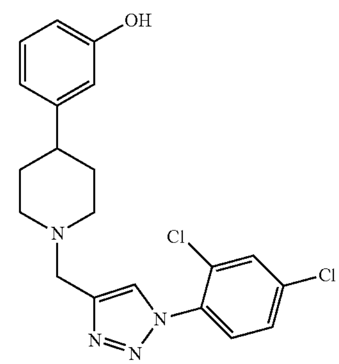 [SMILES: Oc1cccc(C2CCN(Cc3cn(-c4ccc(Cl)cc4Cl)nn3)CC2)c1] | 3-(1-((1-(2,4-dichlorophenyl)-1H-1,2,3-triazol-4-yl)methyl)piperidin-4-yl)phenol | 5.84 | 403.1075 (M + H) |
| 42 | 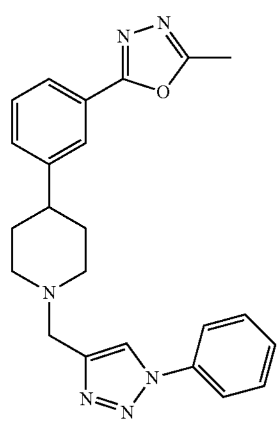 [SMILES: Cc1nnc(-c2cccc(C3CCN(Cc4cn(-c5ccccc5)nn4)CC3)c2)o1] | 2-methyl-5-(3-(1-((1-phenyl-1H-1,2,3-triazol-4-yl)methyl)piperidin-4-yl)phenyl)-1,3,4-oxadiazole | 5.43 | 401.2091 (M + H) |
| 43 | 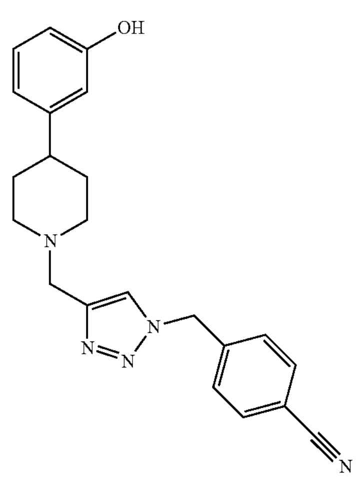 [SMILES: N#Cc1ccc(Cn2cc(CN3CCC(c4cccc(O)c4)CC3)nn2)cc1] | 4-((4-((4-(3-hydroxyphenyl)piperidin-1-yl)methyl)-1H-1,2,3-triazol-1-yl)methyl)benzonitrile | 5.20 | 374.1987 (M + H) |

-continued

| EX | Structure | Chemical name | Ret time (min) | HRMS |
|---|---|---|---|---|
| 44 | 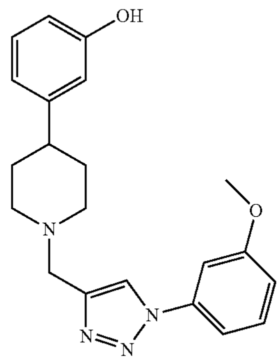 [SMILES: COc1cccc(-n2cc(CN3CCC(c4cccc(O)c4)CC3)nn2)c1] | 3-(1-((1-(3-methoxyphenyl)-1H-1,2,3-triazol-4-yl)methyl)piperidin-4-yl)phenol | 5.47 | 365.1974 (M + H) |
| 45 | 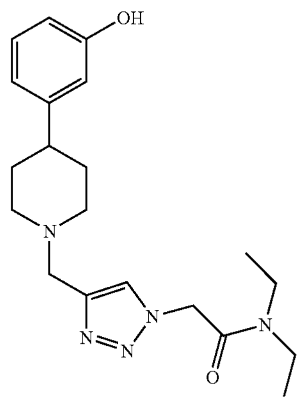 [SMILES: CCN(CC)C(=O)Cn1cc(CN2CCC(c3cccc(O)c3)CC2)nn1] | N,N-diethyl-2-(4-((4-(3-hydroxyphenyl)piperidin-1-yl)methyl)-1H-1,2,3-triazol-1-yl)acetamide | 4.77 | 372.2414 (M + H) |
| 46 | 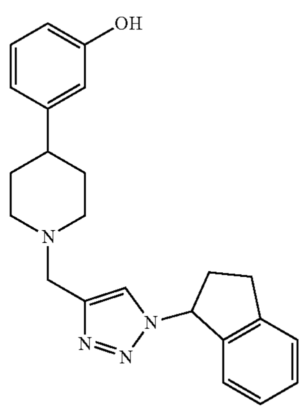 [SMILES: Oc1cccc(C2CCN(Cc3cn(C4CCc5ccccc54)nn3)CC2)c1] | 3-(1-((1-(2,3-dihydro-1H-inden-1-yl)-1H-1,2,3-triazol-4-yl)methyl)piperidin-4-yl)phenol | 5.57 | 375.2128 (M + H) |
| 47 | 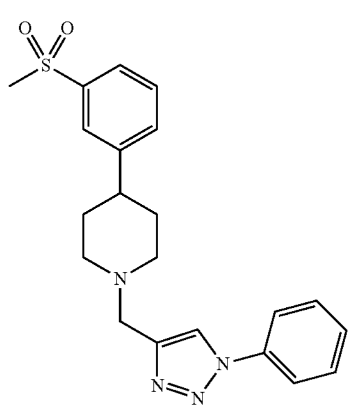 [SMILES: CS(=O)(=O)c1cccc(C2CCN(Cc3cn(-c4ccccc4)nn3)CC2)c1] | 4-(3-(methylsulfonyl)phenyl)-1-((1-phenyl-1H-1,2,3-triazol-4-yl)methyl)piperidine | 5.22 | 397.1707 (M + H) |

-continued

| EX | Structure | Chemical name | Ret time (min) | HRMS |
|---|---|---|---|---|
| 48 | 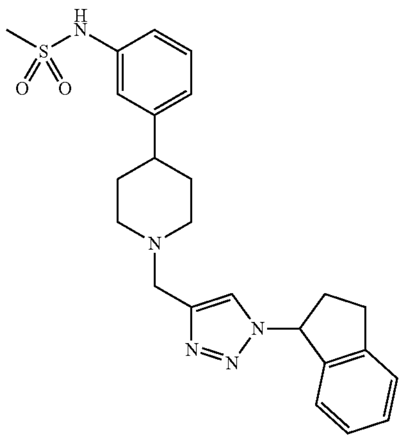 [SMILES: CS(=O)(=O)Nc1cccc(C2CCN(Cc3cn(C4CCc5ccccc54)nn3)CC2)c1] | N-(3-(1-((1-(2,3-dihydro-1H-inden-1-yl)-1H-1,2,3-triazol-4-yl)methyl)piperidin-4-yl)phenyl)methane-sulfonamide | 5.58 | 450.1945 (M − H) |
| 49 | 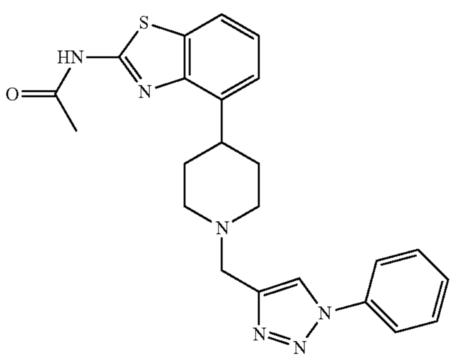 [SMILES: CC(=O)Nc1nc2c(C3CCN(Cc4cn(-c5ccccc5)nn4)CC3)cccc2s1] | N-(4-(1-((1-phenyl-1H-1,2,3-triazol-4-yl)methyl)piperidin-4-yl)benzo[d]thiazol-2-yl)acetamide | 5.79 | 455.1637 (M + Na) |
| 50 | 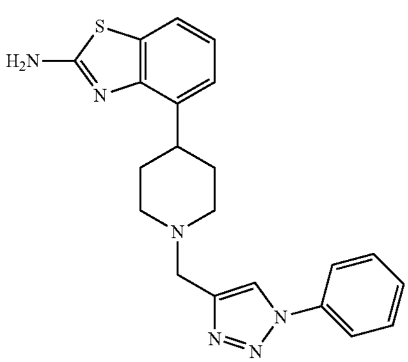 [SMILES: Nc1nc2c(C3CCN(Cc4cn(-c5ccccc5)nn4)CC3)cccc2s1] | 4-(1-((1-phenyl-1H-1,2,3-triazol-4-yl)methyl)piperidin-4-yl)benzo[d]thiazol-2-amine | 4.90 | 4.90 |

| EX | Structure | Chemical name | Ret time (min) | HRMS |
|---|---|---|---|---|
| 51 | 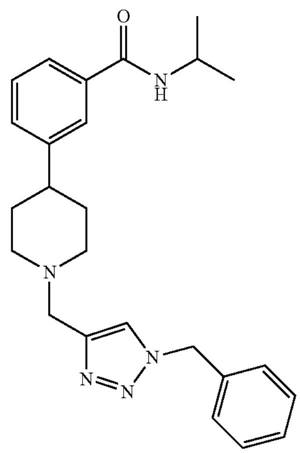 [SMILES: CC(C)NC(=O)c1cccc(C2CCN(Cc3cn(Cc4ccccc4)nn3)CC2)c1] | 3-(1-((1-benzyl-1H-1,2,3-triazol-4-yl)methyl)piperidin-4-yl)-N-isopropylbenzamide | 5.56 | 418.2622 (M + H) |
| 52 | 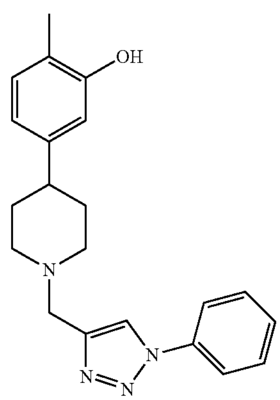 [SMILES: Cc1ccc(C2CCN(Cc3cn(-c4ccccc4)nn3)CC2)cc1O] | 2-methyl-5-(1-((1-phenyl-1H-1,2,3-triazol-4-yl)methyl)piperidin-4-yl)phenol | 5.59 | 349.2013 (M + H) |
| 53 | 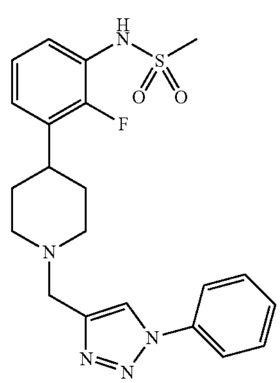 [SMILES: CS(=O)(=O)Nc1cccc(C2CCN(Cc3cn(-c4ccccc4)nn3)CC2)c1F] | N-(2-fluoro-3-(1-((1-phenyl-1H-1,2,3-triazol-4-yl)methyl)piperidin-4-yl)phenyl)methanesulfonamide | 5.35 | 430.1692 (M + H) |

-continued

| EX | Structure | Chemical name | Ret time (min) | HRMS |
|---|---|---|---|---|
| 54 | 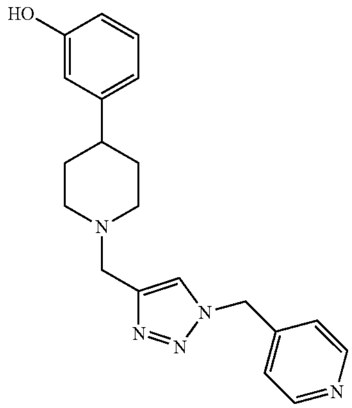 | 3-(1-((1-(pyridin-4-ylmethyl)-1H-1,2,3-triazol-4-yl)methyl)piperidin-4-yl)phenol | 4.25 | 350.1976 (M + H) |
| 55 | 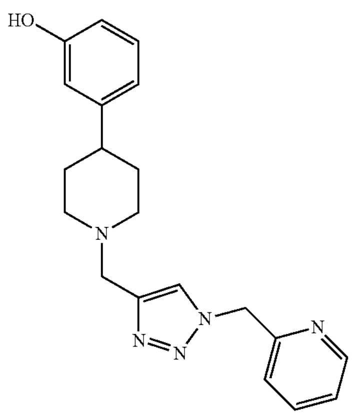 [SMILES: Oc1cccc(C2CCN(Cc3cn(Cc4ccccn4)nn3)CC2)c1] | 3-(1-((1-(pyridin-2-ylmethyl)-1H-1,2,3-triazol-4-yl)methyl)piperidin-4-yl)phenol | 4.44 | 350.1987 (M + H) |
| 56 | 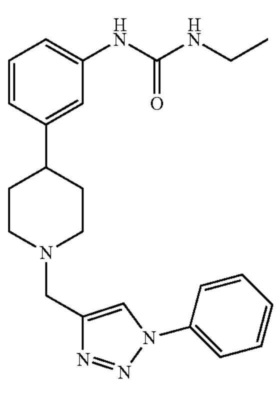 [SMILES: CCNC(=O)Nc1cccc(C2CCN(Cc3cn(-c4ccccc4)nn3)CC2)c1] | 1-ethyl-3-(3-(1-((1-phenyl-1H-1,2,3-triazol-4-yl)methyl)piperidin-4-yl)phenyl)urea | 5.37 | 405.2391 (M + H) |

| EX | Structure | Chemical name | Ret time (min) | HRMS |
|---|---|---|---|---|
| 57 | 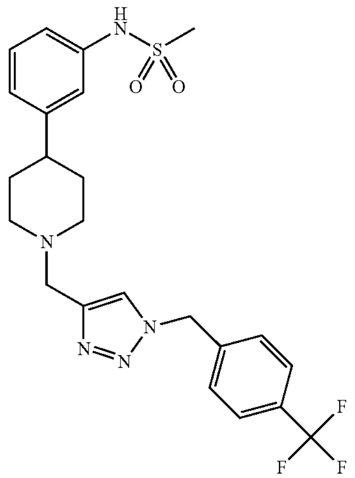 [SMILES: CS(=O)(=O)Nc1cccc(C2CCN(Cc3cn(Cc4ccc(C(F)(F)F)cc4)nn3)CC2)c1] | N-(3-(1-((1-(4-(trifluoromethyl)benzyl)-1H-1,2,3-triazol-4-yl)methyl)piperidin-4-yl)phenyl)methane-sulfonamide | 5.88 | 492.1663 (M − H) |
| 58 | 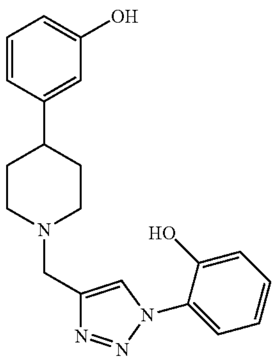 [SMILES: Oc1cccc(C2CCN(Cc3cn(-c4ccccc4O)nn3)CC2)c1] | 2-(4-((4-(3-hydroxyphenyl)piperidin-1-yl)methyl)-1H-1,2,3-triazol-1-yl)phenol | 5.04 | 351.1 (M + H) |
| 59 | 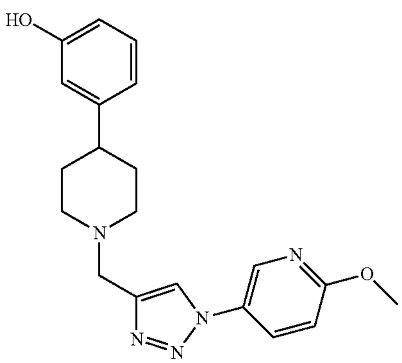 [SMILES: COc1ccc(-n2cc(CN3CCC(c4cccc(O)c4)CC3)nn2)cn1] | 3-(1-((1-(6-methoxypyridin-3-yl)-1H-1,2,3-triazol-4-yl)methyl)piperidin-4-yl)phenol | 5.81 | 364.1782 (M + H) |
| 60 | 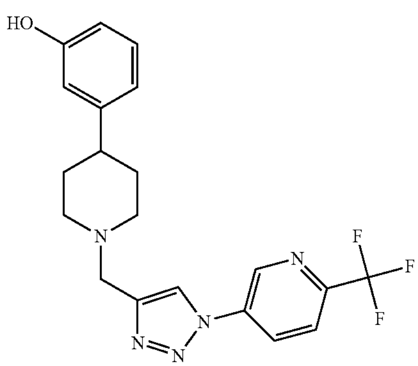 [SMILES: Oc1cccc(C2CCN(Cc3cn(-c4ccc(C(F)(F)F)nc4)nn3)CC2)c1] | 3-(1-((1-(6-(trifluoromethyl)pyridin-3-yl)-1H-1,2,3-triazol-4-yl)methyl)piperidin-4-yl)phenol | 5.56 | 402.1523 (M − H) |

-continued
| EX | Structure | Chemical name | Ret time (min) | HRMS |
|---|---|---|---|---|
| 61 | 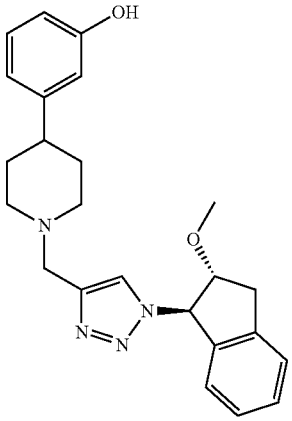 [SMILES: CO[C@@H]1Cc2ccccc2[C@H]1n1cc(CN2CCC(c3cccc(O)c3)CC2)nn1] | 3-(1-((1-((1R,2R)-2-methoxy-2,3-dihydro-1H-inden-1-yl)-1H-1,2,3-triazol-4-yl)methyl)piperidin-4-yl)phenol | 5.54 | 405.2275 (M + H) |
| 62 | 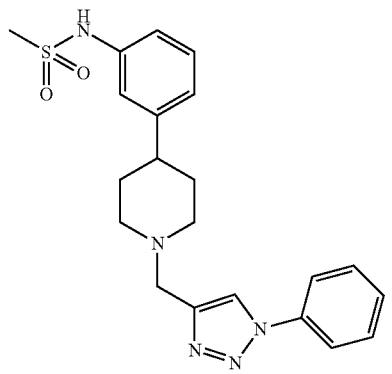 [SMILES: CS(=O)(=O)Nc1cccc(C2CCN(Cc3cn(-c4ccccc4)nn3)CC2)c1] | N-(3-(1-((1-phenyl-1H-1,2,3-triazol-4-yl)methyl)piperidin-4-yl)phenyl)methane-sulfonamide | 5.37 | 412.1805 (M + H) |
| 63 | 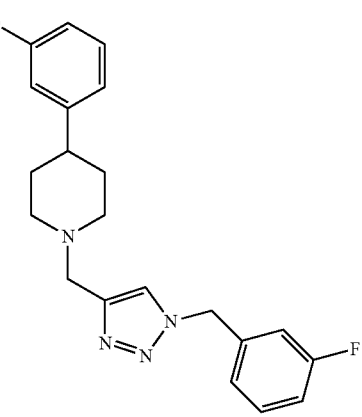 | 3-(1-((1-(3-fluorobenzyl)-1H-1,2,3-triazol-4-yl)methyl)piperidin-4-yl)phenol | 5.30 | 367.1916 (M + H) |

-continued

| EX | Structure | Chemical name | Ret time (min) | HRMS |
|---|---|---|---|---|
| 64 | 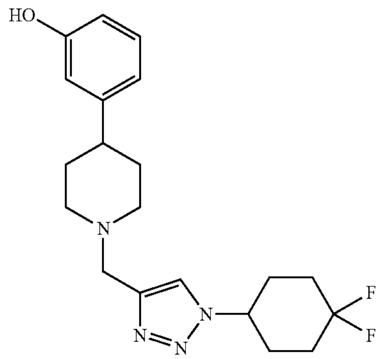 [SMILES: Oc1cccc(C2CCN(Cc3cn(C4CCC(F)(F)CC4)nn3)CC2)c1] | 3-(1-((1-(4,4-difluorocyclohexyl)-1H-1,2,3-triazol-4-yl)methyl)piperidin-4-yl)phenol | 5.32 | 375.1989 (M − H) |
| 65 | 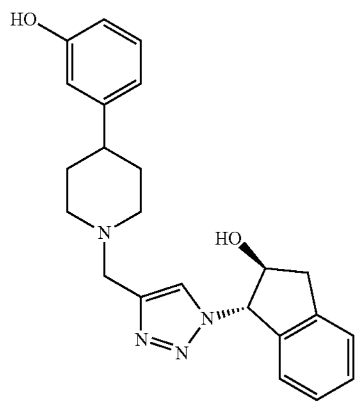 [SMILES: Oc1cccc(C2CCN(Cc3cn([C@H]4c5ccccc5C[C@@H]4O)nn3)CC2)c1] | (1S,2S)-1-(4-((4-(3-hydroxyphenyl)piperidin-1-yl)methyl)-1H-1,2,3-triazol-1-yl)-2,3-dihydro-1H-inden-2-ol | 5.08 | 391.2134 (M + H) |
| 66 | 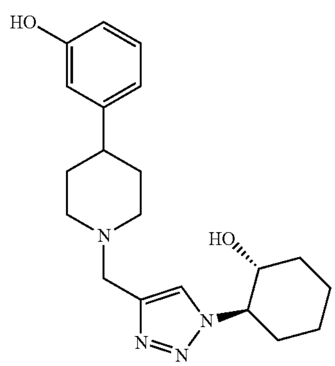 [SMILES: Oc1cccc(C2CCN(Cc3cn([C@@H]4CCCC[C@H]4O)nn3)CC2)c1] | 3-(1-((1-((1R,2R)-2-hydroxycyclohexyl)-1H-1,2,3-triazol-4-yl)methyl)piperidin-4-yl)phenol | 4.69 | 357.2277 (M + H) |
| 67 | 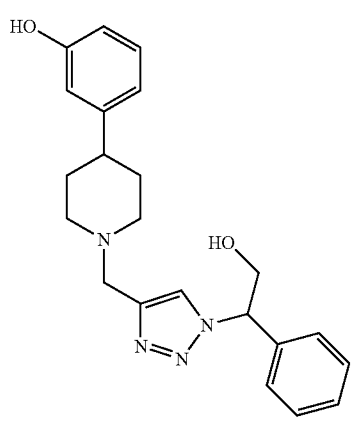 [SMILES: OCC(c1ccccc1)n1cc(CN2CCC(c3cccc(O)c3)CC2)nn1] | 3-(1-((1-(2-hydroxy-1-phenylethyl)-1H-1,2,3-triazol-4-yl)methyl)piperidin-4-yl)phenol | 5.00 | 379.2127 (M + H) |

-continued

| EX | Structure | Chemical name | Ret time (min) | HRMS |
|---|---|---|---|---|
| 68 | 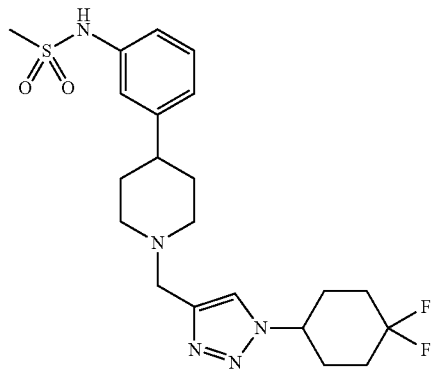 [SMILES: CS(=O)(=O)Nc1cccc(C2CCN(Cc3cn(C4CCC(F)(F)CC4)nn3)CC2)c1] | N-(3-(1-((1-(4,4-difluorocyclohexyl)-1H-1,2,3-triazol-4-yl)methyl)piperidin-4-yl)phenyl)methane-sulfonamide | 5.36 | 452.1910 (M − H) |
| 69 | 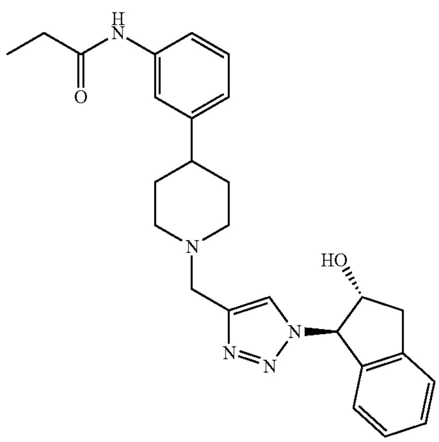 [SMILES: CCC(=O)Nc1cccc(C2CCN(Cc3cn([C@@H]4c5ccccc5C[C@H]4O)nn3)CC2)c1] | N-(3-(1-((1-(((1R,2R)-2-hydroxy-2,3-dihydro-1H-inden-1-yl)-1H-1,2,3-triazol-4-yl)methyl)piperidin-4-yl)phenyl)propionamide | 5.21 | 444.2418 (M − H) |
| 70 | 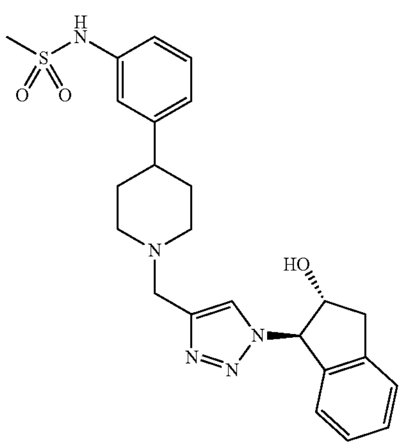 [SMILES: CS(=O)(=O)Nc1cccc(C2CCN(Cc3cn([C@@H]4c5ccccc5C[C@H]4O)nn3)CC2)c1] | N-(3-(1-((1-(((1R,2R)-2-hydroxy-2,3-dihydro-1H-inden-1-yl)-1H-1,2,3-triazol-4-yl)methyl)piperidin-4-yl)phenyl)methane-sulfonamide | 5.12 | 466.1911 (M − H) |

-continued
| EX | Structure | Chemical name | Ret time (min) | HRMS |
|---|---|---|---|---|
| 71 | 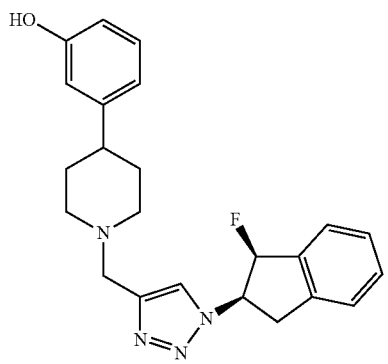 [SMILES: Oc1cccc(C2CCN(Cc3cn([C@@H]4Cc5ccccc5[C@@H]4F)nn3)CC2)c1] | 3-(1-((1-((1S,2R)-1-fluoro-2,3-dihydro-1H-inden-2-yl)-1H-1,2,3-triazol-4-yl)methyl)piperidin-4-yl)phenol | 5.61 | 393.2088 (M + H) |
| 72 | 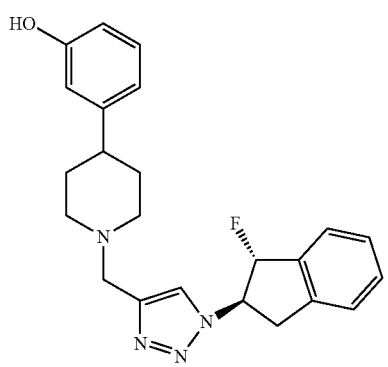 [SMILES: Oc1cccc(C2CCN(Cc3cn([C@@H]4Cc5ccccc5[C@H]4F)nn3)CC2)c1] | 3-(1-((1-((1R,2R)-1-fluoro-2,3-dihydro-1H-inden-2-yl)-1H-1,2,3-triazol-4-yl)methyl)piperidin-4-yl)phenol | 5.62 | 393.2095 (M + H) |
| 73 | 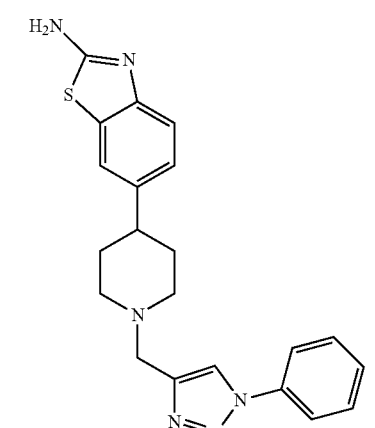 | 6-(1-((1-phenyl-1H-1,2,3-triazol-4-yl)methyl)piperidin-4-yl)benzo[d]thiazol-2-amine | 4.58 | 389.1555 (M + H) |

-continued

| EX | Structure | Chemical name | Ret time (min) | HRMS |
|---|---|---|---|---|
| 74 | 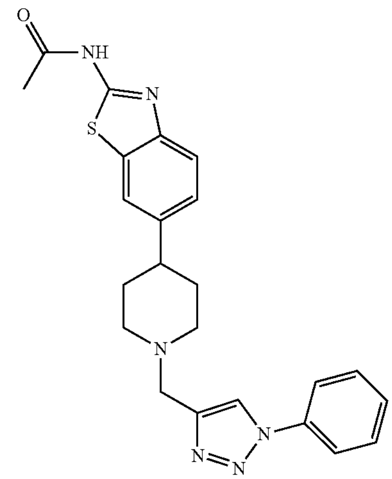 [SMILES: CC(=O)Nc1nc2ccc(C3CCN(Cc4cn(-c5ccccc5)nn4)CC3)cc2s1] | N-(6-(1-((1-phenyl-1H-1,2,3-triazol-4-yl)methyl)piperidin-4-yl)benzo[d]thiazol-2-yl)acetamide | 5.38 | 433.1823 (M + H) |
| 75 | 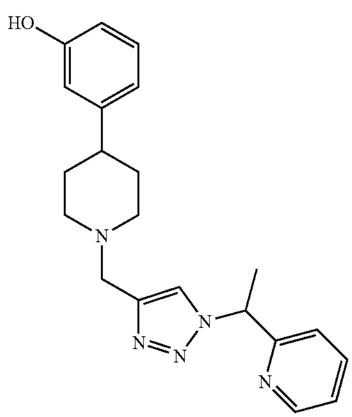 [SMILES: CC(c1ccccn1)n1cc(CN2CCC(c3cccc(O)c3)CC2)nn1] | 3-(1-((1-(1-(pyridin-2-yl)ethyl)-1H-1,2,3-triazol-4-yl)methyl)piperidin-4-yl)phenol | 4.63 | 362.1978 (M − H) |
| 76 | 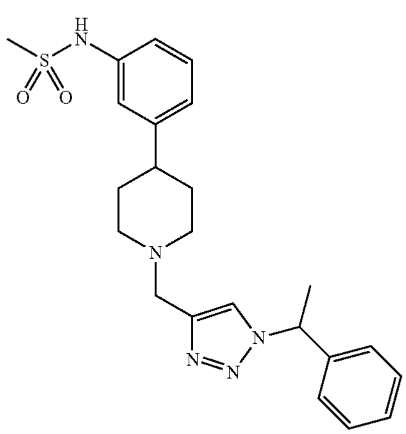 [SMILES: CC(c1ccccc1)n1cc(CN2CCC(c3cccc(NS(C)(=O)=O)c3)CC2)nn1] | N-(3-(1-((1-(1-phenylethyl)-1H-1,2,3-triazol-4-yl)methyl)piperidin-4-yl)phenyl)methanesulfonamide | 5.54 | 440.2117 (M + H) |

-continued

| EX | Structure | Chemical name | Ret time (min) | HRMS |
|---|---|---|---|---|
| 77 | 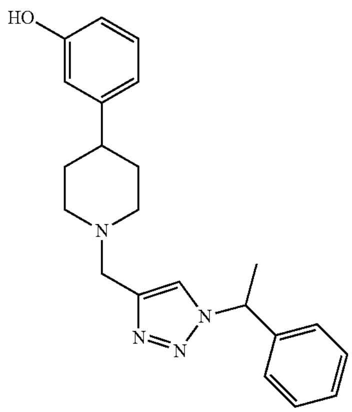 [SMILES: CC(c1ccccc1)n1cc(CN2CCC(c3cccc(O)c3)CC2)nn1] | 3-(1-((1-(1-phenylethyl)-1H-1,2,3-triazol-4-yl)methyl)piperidin-4-yl)phenol | 5.46 | 361.2025 (M + H) |
| 78 | 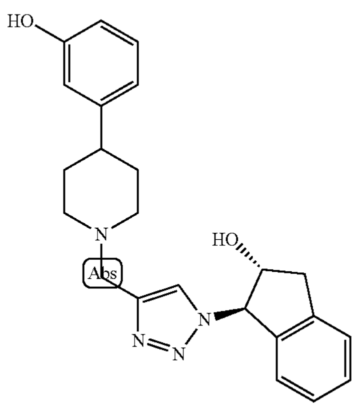 [SMILES: Oc1cccc(C2CCN(Cc3cn([C@@H]4c5ccccc5C[C@H]4O)nn3)CC2)c1] | (1R,2R)-1-(4-((4-(3-hydroxyphenyl)piperidin-1-yl)methyl)-1H-1,2,3-triazol-1-yl)-2,3-dihydro-1H-inden-2-ol | 5.04 | 389.1978 (M − H) |
| 79 | 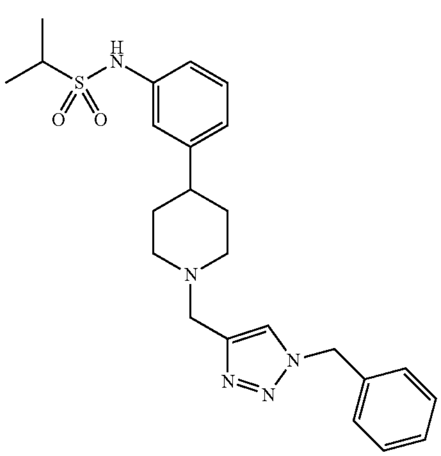 [SMILES: CC(C)S(=O)(=O)Nc1cccc(C2CCN(Cc3cn(Cc4ccccc4)nn3)CC2)c1] | N-(3-(1-((1-benzyl-1H-1,2,3-triazol-4-yl)methyl)piperidin-4-yl)phenyl)propane-2-sulfonamide | 5.65 | 452.2121 (M − H) |

| EX | Structure | Chemical name | Ret time (min) | HRMS |
|---|---|---|---|---|
| 80 | 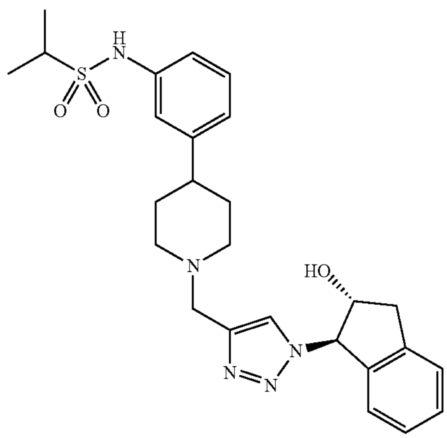 [SMILES: CC(C)S(=O)(=O)Nc1cccc(C2CCN(Cc3cn([C@@H]4c5ccccc5C[C@H]4O)nn3)CC2)c1] | N-(3-(1-((1-((1R,2R)-2-hydroxy-2,3-dihydro-1H-inden-1-yl)-1H-1,2,3-triazol-4-yl)methyl)piperidin-4-yl)phenyl)propane-2- | 5.47 | 494.2239 (M − H) |
| 81 | 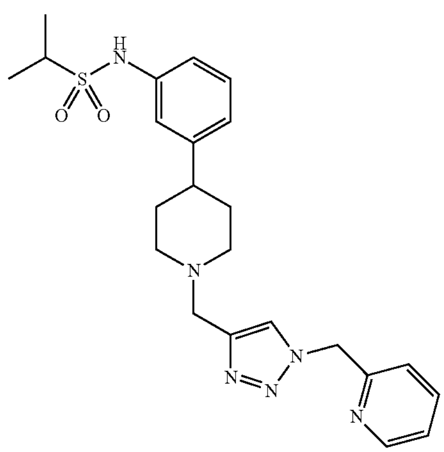 | N-(3-(1-((1-(pyridin-2-ylmethyl)-1H-1,2,3-triazol-4-yl)methyl)piperidin-4-yl)phenyl)propane-2-sulfonamide | 4.96 | 455.2232 (M + H) |
| 82 | 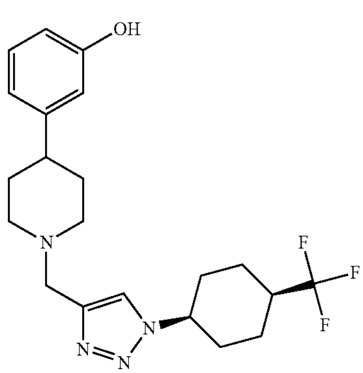 [SMILES: Oc1cccc(C2CCN(Cc3cn([C@H]4CC[C@@H](C(F)(F)F)CC4)nn3)CC2)c1] | 3-(1-((1-((1s,4s)-4-(trifluoromethyl)cyclohexyl)-1H-1,2,3-triazol-4-yl)methyl)piperidin-4-yl)phenol | 5.79 | 431.2014 (M + Na) |

-continued

| EX | Structure | Chemical name | Ret time (min) | HRMS |
|---|---|---|---|---|
| 83 | 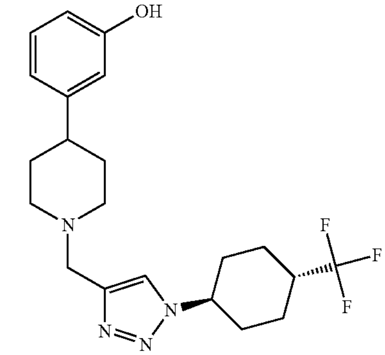 [SMILES: Oc1cccc(C2CCN(Cc3cn([C@H]4CC[C@H](C(F)(F)F)CC4)nn3)CC2)c1] | 3-(1-((1-((1r,4r)-4-(trilfuoromethyl)cyclohexyl)-1H-1,2,3-triazol-4-yl)methyl)piperidin-4-yl)phenol | 5.70 | 431.2032 (M + Na) |
| 84 | 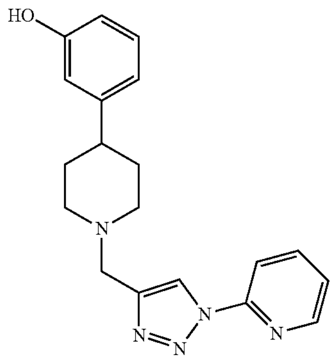 [SMILES: Oc1cccc(C2CCN(Cc3cn(-c4ccccn4)nn3)CC2)c1] | 3-(1-((1-(pyridin-2-yl)-1H-1,2,3-triazol-4-yl)methyl)piperidin-4-yl)phenol | 4.90 | 334.1663 (M − H) |
| 85 | 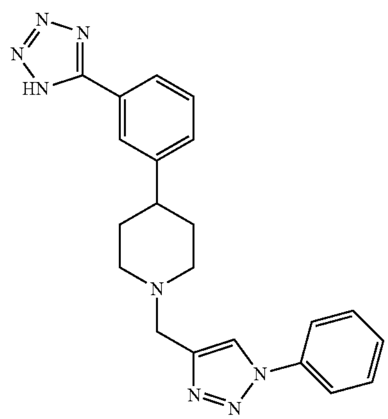 [SMILES: c1ccc(-n2cc(CN3CCC(c4cccc(-c5nnn[nH]5)c4)CC3)nn2)cc1] | 4-(3-(1H-tetrazol-5-yl)phenyl)-1-((1-phenyl-1H-1,2,3-triazol-4-yl)methyl)piperidine | 5.20 | 387.2027 (M + H) |
| 86 | 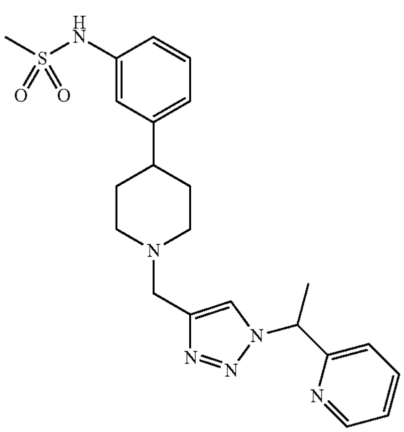 [SMILES: CC(c1ccccn1)n1cc(CN2CCC(c3cccc(NS(C)(=O)=O)c3)CC2)nn1] | N-(3-(1-((1-(1-(pyridin-2-yl)ethyl)-1H-1,2,3-triazol-4-yl)methyl)piperidin-4-yl)phenyl)methanesulfonamide | 4.60 | 441.2072 (M + H) |

-continued

| EX | Structure | Chemical name | Ret time (min) | HRMS |
|---|---|---|---|---|
| 87 | 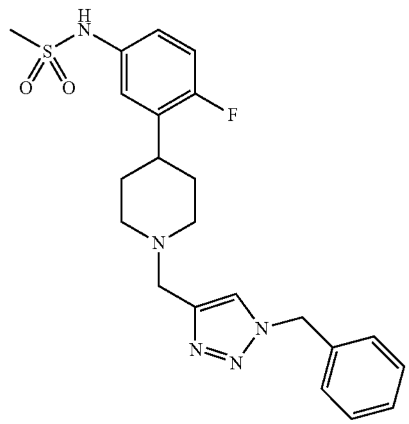 [SMILES: CS(=O)(=O)Nc1ccc(F)c(C2CCN(Cc3cn(Cc4ccccc4)nn3)CC2)c1] | N-(3-(1-(((1-benzyl-1H-1,2,3-triazol-4-yl)methyl)piperidin-4-yl)-4-fluorophenyl)methanesulfonamide | 5.55 | 442.1725 (M − H) |
| 88 | 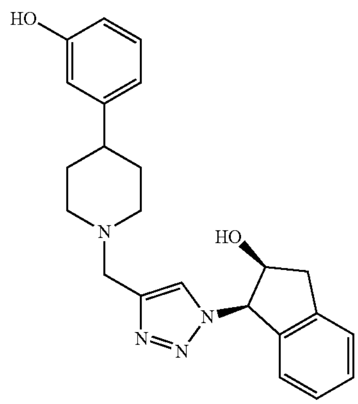 [SMILES: Oc1cccc(C2CCN(Cc3cn([C@@H]4c5ccccc5C[C@@H]4O)nn3)CC2)c1] | (1R,2S)-1-(4-((4-(3-hydroxyphenyl)piperidin-1-yl)methyl)-1H-1,2,3-triazol-1-yl)-2,3-dihydro-1H-inden-2-ol | 5.04 | 389.1996 (M − H) |
| 89 | 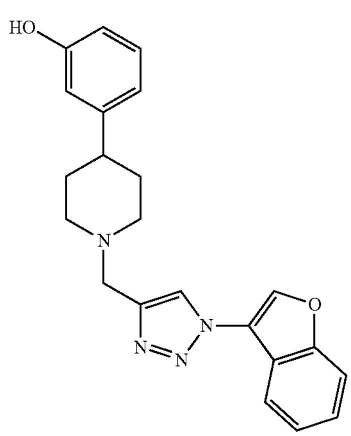 [SMILES: Oc1cccc(C2CCN(Cc3cn(-c4coc5ccccc45)nn3)CC2)c1] | 3-(1-(((1-(benzofuran-3-yl)-1H-1,2,3-triazol-4-yl)methyl)piperidin-4-yl)phenol | 5.69 | 373.1652 (M − H) |

-continued

| EX | Structure | Chemical name | Ret time (min) | HRMS |
|----|-----------|---------------|----------------|------|
| 90 | 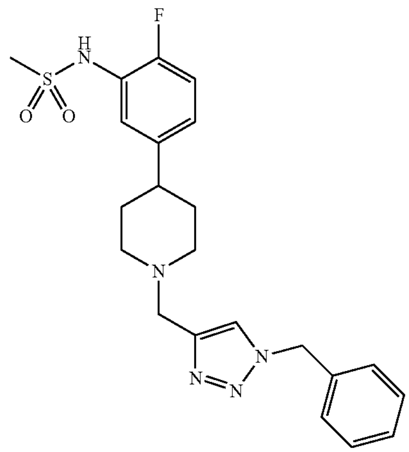 [SMILES: CS(=O)(=O)Nc1cc(C2CCN(Cc3cn(Cc4ccccc4)nn3)CC2)ccc1F] | N-(5-(1-((1-benzyl-1H-1,2,3-triazol-4-yl)methyl)piperidin-4-yl)-2-fluorophenyl)methane-sulfonamide | 5.37 | 442.1719 (M − H) |
| 91 | 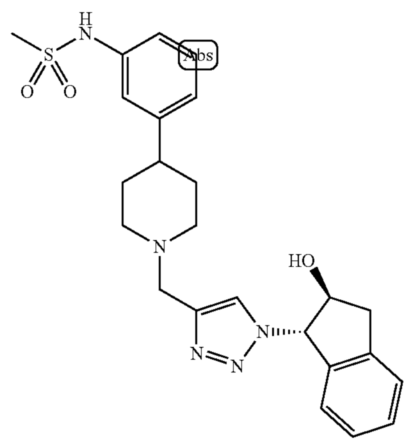 [SMILES: CS(=O)(=O)Nc1cccc(C2CCN(Cc3cn([C@H]4c5ccccc5C[C@@H]4O)nn3)CC2)c1] | N-(3-(1-((1-((1S,2S)-2-hydroxy-2,3-dihydro-1H-inden-1-yl)-1H-1,2,3-triazol-4-yl)methyl)piperidin-4-yl)phenyl)methane-sulfonamide | 5.13 | 466.1932 (M − H) |
| 92 | 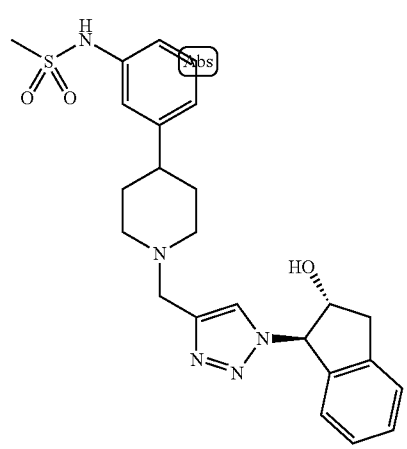 [SMILES: CS(=O)(=O)Nc1cccc(C2CCN(Cc3cn([C@@H]4c5ccccc5C[C@H]4O)nn3)CC2)c1] | N-(3-(1-((1-((1R,2R)-2-hydroxy-2,3-dihydro-1H-inden-1-yl)-1H-1,2,3-triazol-4-yl)methyl)piperidin-4-yl)phenyl)methane-sulfonamide | 5.04 | 466.1932 (M − H) |

-continued

| EX | Structure | Chemical name | Ret time (min) | HRMS |
|---|---|---|---|---|
| 93 | 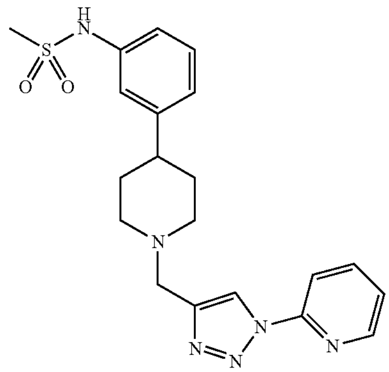 [SMILES: CS(=O)(=O)Nc1cccc(C2CCN(Cc3cn(-c4ccccn4)nn3)CC2)c1] | N-(3-(1-((1-(pyridin-2-yl)-1H-1,2,3-triazol-4-yl)methyl)piperidin-4-yl)phenyl)methane-sulfonamide | 5.01 | 441.1607 (M − H) |
| 94 | 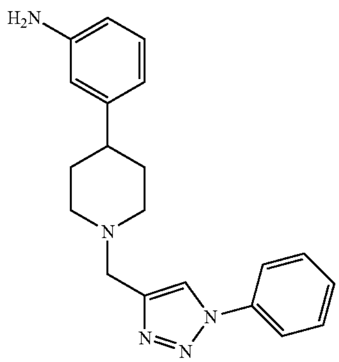 [SMILES: Nc1cccc(C2CCN(Cc3cn(-c4ccccc4)nn3)CC2)c1] | 3-(1-((1-phenyl-1H-1,2,3-triazol-4-yl)methyl)piperidin-4-yl)aniline | 4.39 | 334.2036 (M + H) |
| 95 | 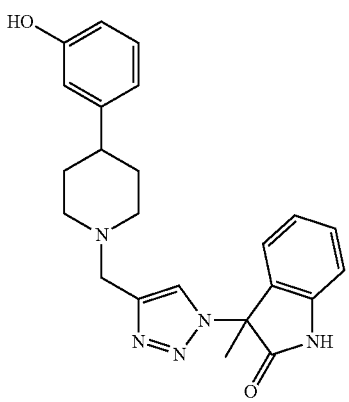 [SMILES: CC1(n2cc(CN3CCC(c4cccc(O)c4)CC3)nn2)C(=O)Nc2ccccc21] | 3-(4-((4-(3-hydroxyphenyl)piperidin-1-yl)methyl)-1H-1,2,3-triazol-1-yl)-3-methylindolin-2-one | 5.01 | 402.1944 (M − H) |
| 96 | 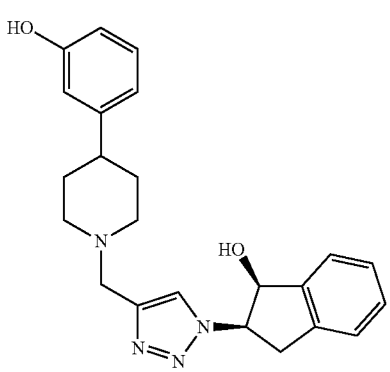 [SMILES: Oc1cccc(C2CCN(Cc3cn([C@@H]4Cc5ccccc5[C@@H]4O)nn3)CC2)c1] | (1S,2R)-2-(4-((4-(3-hydroxyphenyl)piperidin-1-yl)methyl)-1H-1,2,3-triazol-1-yl)-2,3-dihydro-1H-inden-1-ol | 5.06 | 389.1978 (M − H) |

| EX | Structure | Chemical name | Ret time (min) | HRMS |
|---|---|---|---|---|
| 97 | 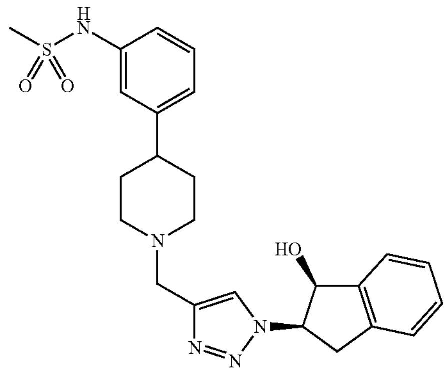 [SMILES: CS(=O)(=O)Nc1cccc(C2CCN(Cc3cn([C@@H]4Cc5ccccc5[C@@H]4O)nn3)CC2)c1] | N-(3-(1-((1-((1S,2R)-1-hydroxy-2,3-dihydro-1H-inden-2-yl)-1H-1,2,3-triazol-4-yl)methyl)piperidin-4-yl)phenyl)methane-sulfonamide | 5.16 | 466.1915 (M − H) |
| 98 | 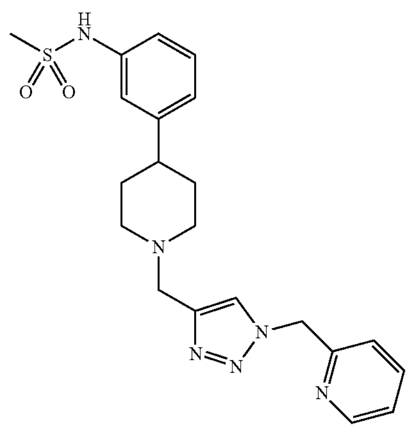 | N-(3-(1-((1-(pyridin-2-ylmethyl)-1H-1,2,3-triazol-4-yl)methyl)piperidin-4-yl)phenyl)methane-sulfonamide | 4.56 | 425.1764 (M − H) |
| 99 | 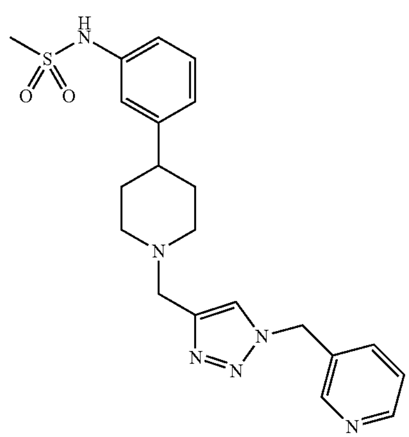 [SMILES: CS(=O)(=O)Nc1cccc(C2CCN(Cc3cn(Cc4cccnc4)nn3)CC2)c1] | N-(3-(1-((1-(pyridin-3-ylmethyl)-1H-1,2,3-triazol-4-yl)methyl)piperidin-4-yl)phenyl)methane-sulfonamide | 4.06 | 425.1755 (M − H) |

| EX | Structure | Chemical name | Ret time (min) | HRMS |
|---|---|---|---|---|
| 100 | 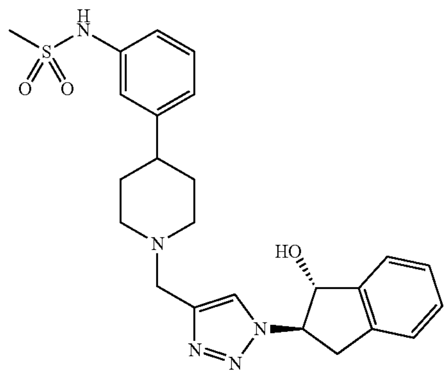 [SMILES: CS(=O)(=O)Nc1cccc(C2CCN(Cc3cn([C@@H]4Cc5ccccc5[C@H]4O)nn3)CC2)c1] | N-(3-(1-((1-((1R,2R)-1-hydroxy-2,3-dihydro-1H-inden-2-yl)-1H-1,2,3-triazol-4-yl)methyl)piperidin-4-yl)phenyl)methanesulfona | 5.23 | 466.1919 (M − H) |
| 101 | 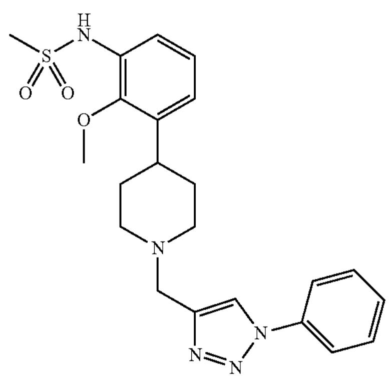 [SMILES: COc1c(NS(C)(=O)=O)cccc1C1CCN(Cc2cn(-c3ccccc3)nn2)CC1] | N-(2-methoxy-3-(1-((1-phenyl-1H-1,2,3-triazol-4-yl)methyl)piperidin-4-yl)phenyl)methane-sulfonamide | 5.37 | 440.1759 (M − H) |
| 102 | 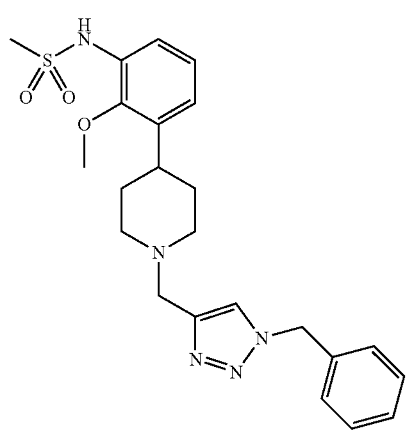 [SMILES: COc1c(NS(C)(=O)=O)cccc1C1CCN(Cc2cn(Cc3ccccc3)nn2)CC1] | N-(3-(1-((1-benzyl-1H-1,2,3-triazol-4-yl)methyl)piperidin-4-yl)-2-methoxyphenyl)methane-sulfonamide | 5.40 | 454.1914 (M − H) |

| EX | Structure | Chemical name | Ret time (min) | HRMS |
|---|---|---|---|---|
| 103 | 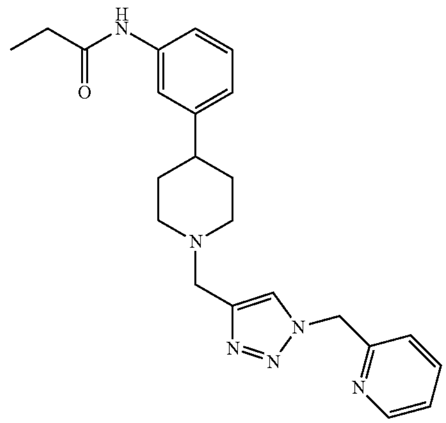 [SMILES: CCC(=O)Nc1cccc(C2CCN(Cc3cn(Cc4ccccn4)nn3)CC2)c1] | N-(3-(1-((1-(pyridin-2-ylmethyl)-1H-1,2,3-triazol-4-yl)methyl)piperidin-4-yl)phenyl)propionamide | 4.71 | 403.2251 (M − H) |
| 104 | 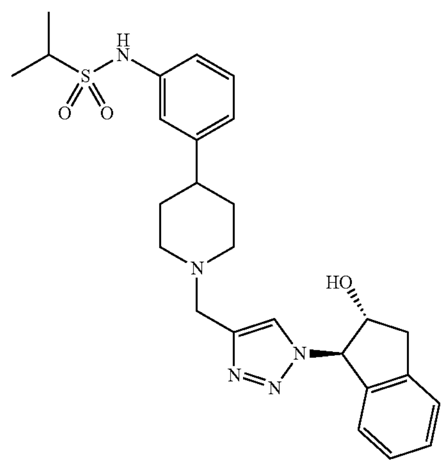 [SMILES: CC(C)S(=O)(=O)Nc1cccc(C2CCN(Cc3cn([C@@H]4c5ccccc5C[C@H]4O)nn3)CC2)c1] | N-(3-(1-((1-(((1R,2R)-2-hydroxy-2,3-dihydro-1H-inden-1-yl)-1H-1,2,3-triazol-4-yl)methyl)piperidin-4-yl)phenyl)propane-2- | 5.47 | 494.2232 (M − H) |
| 105 | 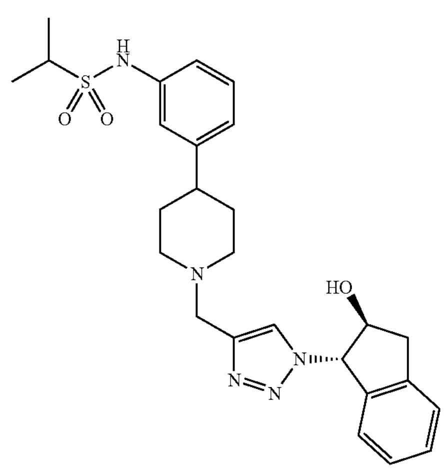 [SMILES: CC(C)S(=O)(=O)Nc1cccc(C2CCN(Cc3cn([C@H]4c5ccccc5C[C@@H]4O)nn3)CC2)c1] | N-(3-(1-((1-(((1S,2S)-2-hydroxy-2,3-dihydro-1H-inden-1-yl)-1H-1,2,3-triazol-4-yl)methyl)piperidin-4-yl)phenyl)propane-2- | 5.48 | 494.2232 (M − H) |

-continued

| EX | Structure | Chemical name | Ret time (min) | HRMS |
|---|---|---|---|---|
| 106 | 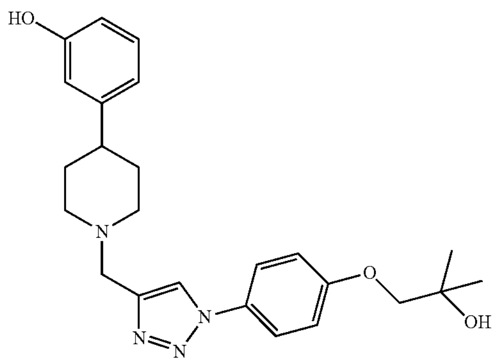 [SMILES: CC(C)(O)COc1ccc(-n2cc(CN3CCC(c4cccc(O)c4)CC3)nn2)cc1] | 3-(1-((1-(4-(2-hydroxy-2-methylpropoxy)phenyl)-1H-1,2,3-triazol-4-yl)methyl)piperidin-4-yl)phenol | 5.19 | 421.2241 (M − H) |
| 107 | 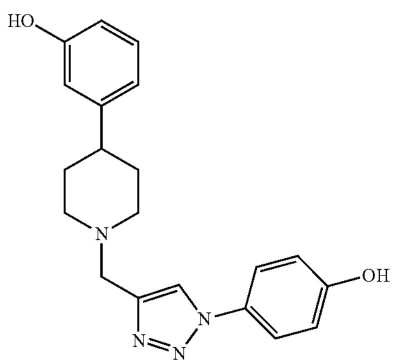 [SMILES: Oc1ccc(-n2cc(CN3CCC(c4cccc(O)c4)CC3)nn2)cc1] | 3-(1-((1-(4-hydroxyphenyl)-1H-1,2,3-triazol-4-yl)methyl)piperidin-4-yl)phenol | 4.83 | 349.1669 (M − H) |
| 108 | 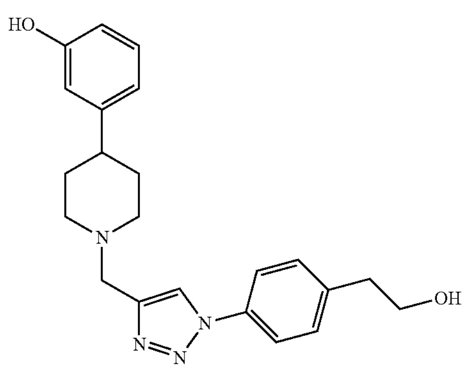 [SMILES: OCCc1ccc(-n2cc(CN3CCC(c4cccc(O)c4)CC3)nn2)cc1] | 3-(1-((1-(4-(2-hydroxyethyl)phenyl)-1H-1,2,3-triazol-4-yl)methyl)piperidin-4-yl)phenol | 4.77 | 395.2085 (M + H) |
| 109 | 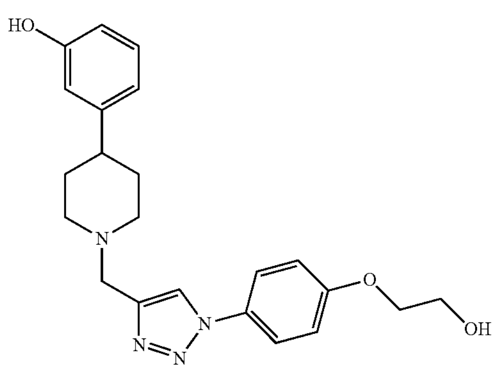 [SMILES: OCCOc1ccc(-n2cc(CN3CCC(c4cccc(O)c4)CC3)nn2)cc1] | 3-(1-((1-(4-(2-hydroxyethoxy)phenyl)-1H-1,2,3-triazol-4-yl)methyl)piperidin-4-yl)phenol | 5.56 | 334.2026 (M + H) |

| EX | Structure | Chemical name | Ret time (min) | HRMS |
|---|---|---|---|---|
| 110 | 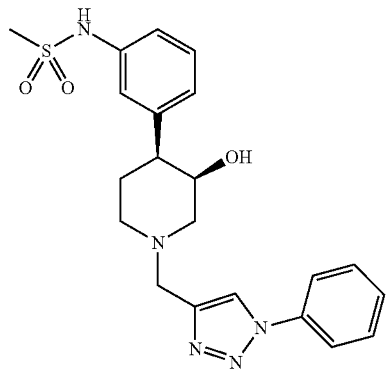 [SMILES: CS(=O)(=O)Nc1cccc([C@@H]2CCN(Cc3cn(-c4ccccc4)nn3)C[C@@H]2O)c1] | N-(3-((3R,4S)-3-hydroxy-1-((1-phenyl-1H-1,2,3-triazol-4-yl)methyl)piperidin-4-yl)phenyl)methane-sulfonamide | 5.13 | 426.1597 (M − H) |
| 111 | 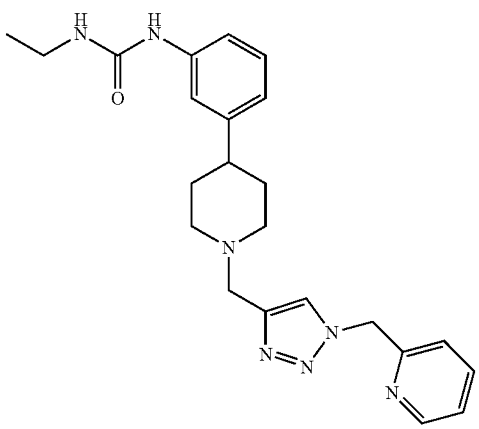 [SMILES: CCNC(=O)Nc1cccc(C2CCN(Cc3cn(Cc4ccccn4)nn3)CC2)c1] | 1-ethyl-3-(3-(1-((1-(pyridin-2-ylmethyl)-1H-1,2,3-triazol-4-yl)methyl)piperidin-4-yl)phenyl)urea | 4.63 | 418.2355 (M − H) |
| 112 | 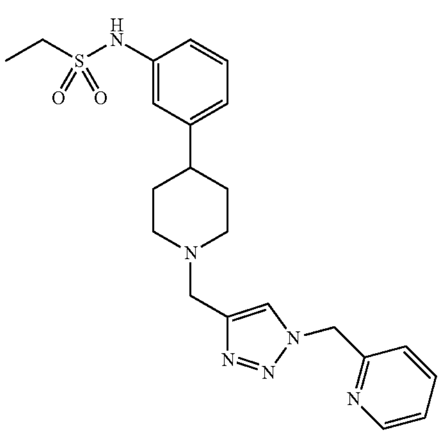 [SMILES: CCS(=O)(=O)Nc1cccc(C2CCN(Cc3cn(Cc4ccccn4)nn3)CC2)c1] | N-(3-(1-((1-(pyridin-2-ylmethyl)-1H-1,2,3-triazol-4-yl)methyl)piperidin-4-yl)phenyl)ethane-sulfonamide | 4.70 | 441.2080 (M + H) |

| EX | Structure | Chemical name | Ret time (min) | HRMS |
|---|---|---|---|---|
| 113 | 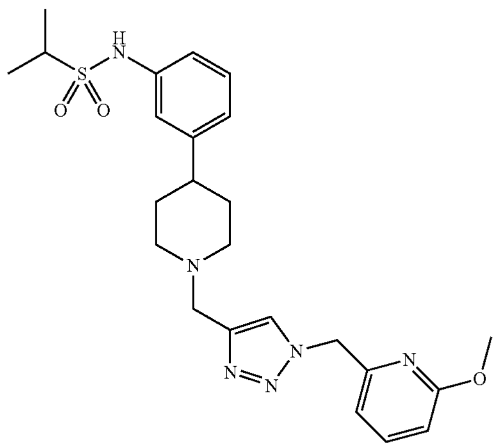 [SMILES: COc1cccc(Cn2cc(CN3CCC(c4cccc(NS(=O)(=O)C(C)C)c4)CC3)nn2)n1] | N-(3-(1-((1-((6-methoxypyridin-2-yl)methyl)-1H-1,2,3-triazol-4-yl)methyl)piperidin-4-yl)phenyl)propane-2-sulfonamide | 5.56 | 485.2331 (M + H) |
| 114 | 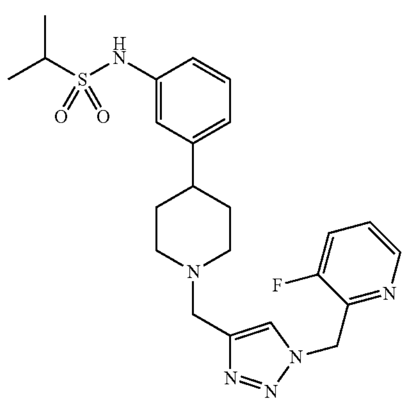 [SMILES: CC(C)S(=O)(=O)Nc1cccc(C2CCN(Cc3cn(Cc4ncccc4F)nn3)CC2)c1] | N-(3-(1-((1-((3-fluoropyridin-2-yl)methyl)-1H-1,2,3-triazol-4-yl)methyl)piperidin-4-yl)phenyl)propane-2-sulfonamide | 5.16 | 473.2136 (M + H) |
| 115 | 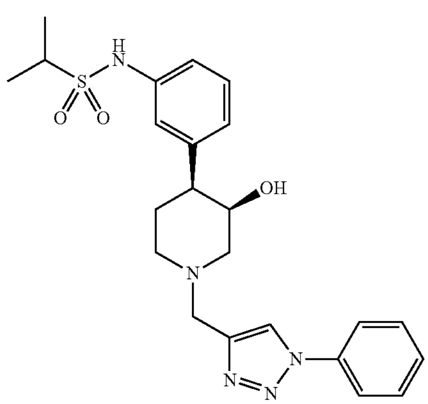 [SMILES: CC(C)S(=O)(=O)Nc1cccc([C@@H]2CCN(Cc3cn(-c4ccccc4)nn3)C[C@@H]2O)c1] | (rac)-N-(3-((3,4-cis)-3-hydroxy-1-((1-phenyl-1H-1,2,3-triazol-4-yl)methyl)piperidin-4-yl)phenyl)propane-2-sulfonamide | 5.42 | 454.1914 (M − H) |

| EX | Structure | Chemical name | Ret time (min) | HRMS |
|---|---|---|---|---|
| 116 | 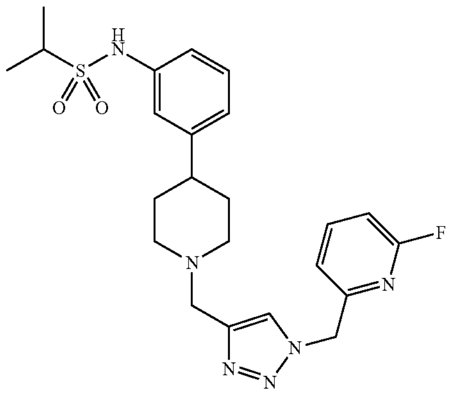 [SMILES: CC(C)S(=O)(=O)Nc1cccc(C2CCN(Cc3cn(Cc4cccc(F)n4)nn3)CC2)c1] | N-(3-(1-((1-((6-fluoropyridin-2-yl)methyl)-1H-1,2,3-triazol-4-yl)methyl)piperidin-4-yl)phenyl)propane-2-sulfonamide | 5.36 | 473.2141 (M + H) |
| 117 | 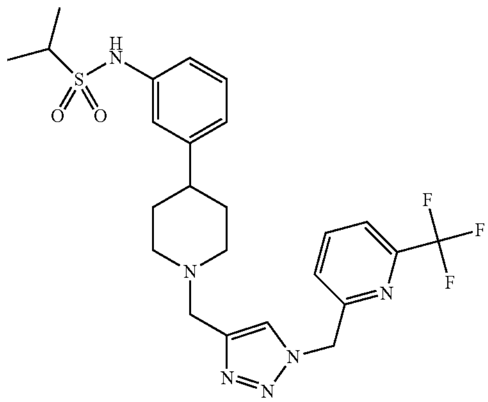 [SMILES: CC(C)S(=O)(=O)Nc1cccc(C2CCN(Cc3cn(Cc4cccc(C(F)(F)F)n4)nn3)CC2)c1] | N-(3-(1-((1-((6-(trifluoromethyl)pyridin-2-yl)methyl)-1H-1,2,3-triazol-4-yl)methyl)piperidin-4-yl)phenyl)propane-2-sulfonamide | 5.78 | 523.2102 (M + H) |
| 118 | 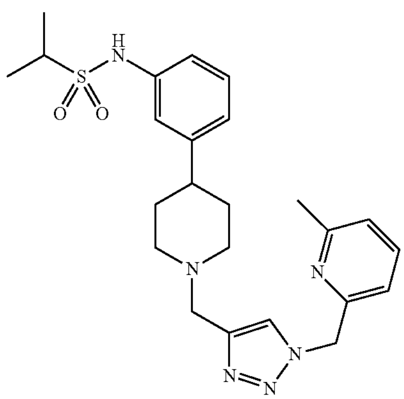 [SMILES: Cc1cccc(Cn2cc(CN3CCC(c4cccc(NS(=O)(=O)C(C)C)c4)CC3)nn2)n1] | N-(3-(1-((1-((6-methylpyridin-2-yl)methyl)-1H-1,2,3-triazol-4-yl)methyl)piperidin-4-yl)phenyl)propane-2-sulfonamide | 4.63 | 469.2380 (M + H) |
| 119 | 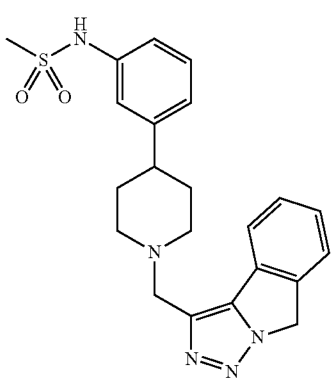 [SMILES: CS(=O)(=O)Nc1cccc(C2CCN(Cc3nnn4c3-c3ccccc3C4)CC2)c1] | N-(3-(1-((8H-[1,2,3]triazolo[5,1-a]isoindol-3-yl)methyl)piperidin-4-yl)phenyl)methanesulfonamide | 5.82 | 422.1649 (M − H) |

| EX | Structure | Chemical name | Ret time (min) | HRMS |
|---|---|---|---|---|
| 120 | 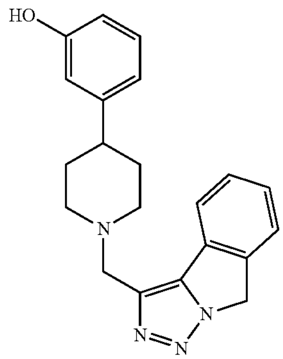 [SMILES: Oc1cccc(C2CCN(Cc3nnn4c3-c3ccccc3C4)CC2)c1] | 3-(1-((8H-[1,2,3]triazolo[5,1-a]isoindol-3-yl)methyl)piperidin-4-yl)phenol | 5.04 | 345.1712 (M − H) |
| 121 | 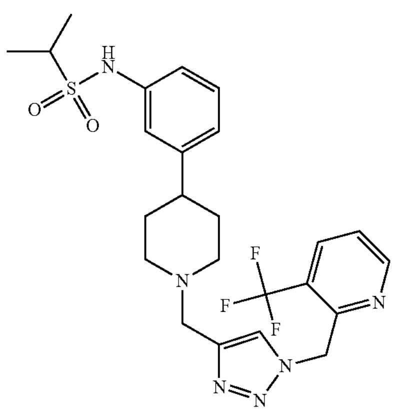 [SMILES: CC(C)S(=O)(=O)Nc1cccc(C2CCN(Cc3cn(Cc4ncccc4C(F)(F)F)nn3)CC2)c1] | N-(3-(1-((1-((3-(trifluoromethyl)pyridin-2-yl)methyl)-1H-1,2,3-triazol-4-yl)methyl)piperidin-4-yl)phenyl)propane-2-sulfonamide | 5.69 | 523.2114 (M + H) |
| 122 | 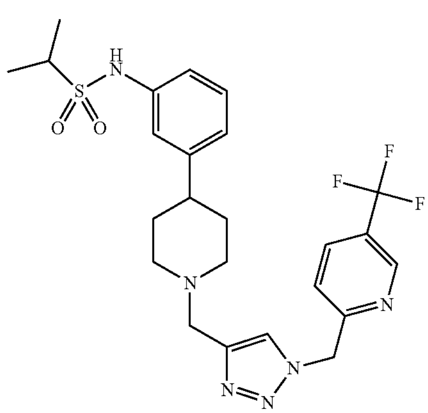 [SMILES: CC(C)S(=O)(=O)Nc1cccc(C2CCN(Cc3cn(Cc4ccc(C(F)(F)F)cn4)nn3)CC2)c1] | N-(3-(1-((1-((5-(trifluoromethyl)pyridin-2-yl)methyl)-1H-1,2,3-triazol-4-yl)methyl)piperidin-4-yl)phenyl)propane-2-sulfonamide | 5.79 | 523.2098 (M + H) |

-continued

| EX | Structure | Chemical name | Ret time (min) | HRMS |
|----|-----------|---------------|----------------|------|
| 123 | 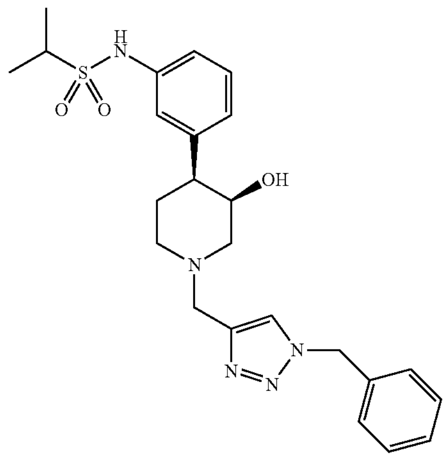 [SMILES: CC(C)S(=O)(=O)Nc1cccc([C@@H]2CCN(Cc3cn(Cc4ccccc4)nn3)C[C@@H]2O)c1] | N-(3-((3R,4S)-1-((1-benzyl-1H-1,2,3-triazol-4-yl)methyl)-3-hydroxypiperidin-4-yl)phenyl)propane-2-sulfonamide | 5.48 | 470.2219 (M + H) |
| 124 | 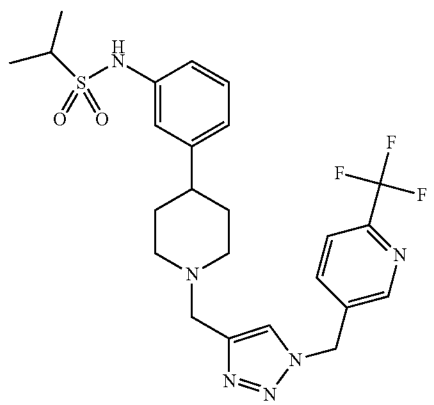 [SMILES: CC(C)S(=O)(=O)Nc1cccc(C2CCN(Cc3cn(Cc4ccc(C(F)(F)F)nc4)nn3)CC2)c1] | N-(3-(1-((1-((6-(trifluoromethyl)pyridin-3-yl)methyl)-1H-1,2,3-triazol-4-yl)methyl)piperidin-4-yl)phenyl)propane-2-sulfonamide | 5.73 | 523.2095 (M + H) |
| 125 | 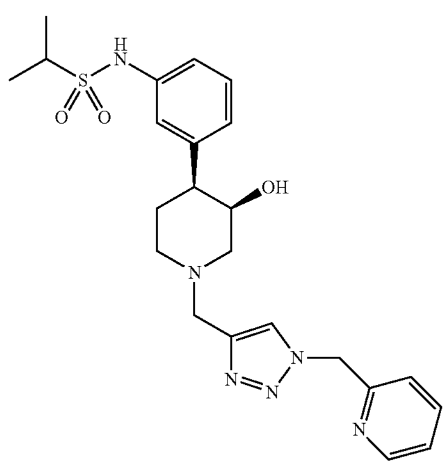 [SMILES: CC(C)S(=O)(=O)Nc1cccc([C@@H]2CCN(Cc3cn(Cc4ccccn4)nn3)C[C@@H]2O)c1] | N-(3-((3R,4S)-3-hydroxy-1-((1-(pyridin-2-ylmethyl)-1H-1,2,3-triazol-4-yl)methyl)piperidin-4-yl)phenyl)propane-2-sulfonamide | 4.73 | 471.2165 (M + H) |

| EX | Structure | Chemical name | Ret time (min) | HRMS |
|---|---|---|---|---|
| 126 | 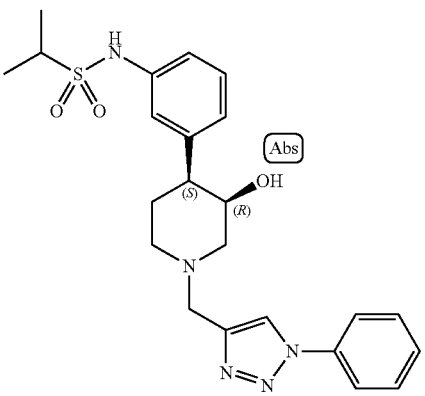 | N-(3-((3R,4S)-3-hydroxy-1-((1-phenyl-1H-1,2,3-triazol-4-yl)methyl)piperidin-4-yl)phenyl)propane-2-sulfonamide | | |
| 127 | 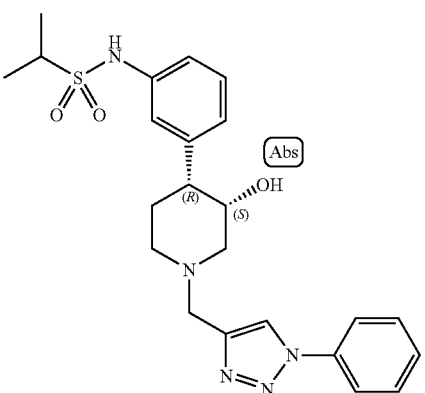 | N-(3-((3S,4R)-3-hydroxy-1-((1-phenyl-1H-1,2,3-triazol-4-yl)methyl)piperidin-4-yl)phenyl)propane-2-sulfonamide | | |
| 128 | 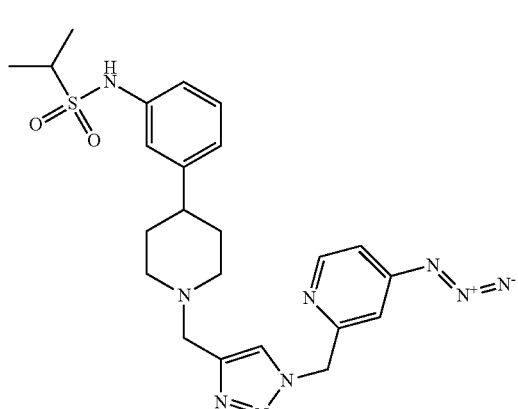 | N-(3-(1-((1-((4-azidopyridin-2-yl)methyl)-1H-1,2,3-triazol-4-yl)methyl)piperidin-4-yl)phenyl)propane-2-sulfonamide | 5.25 | 494.2 (M − H) |

| EX | Structure | Chemical name | Ret time (min) | HRMS |
|---|---|---|---|---|
| 129 | 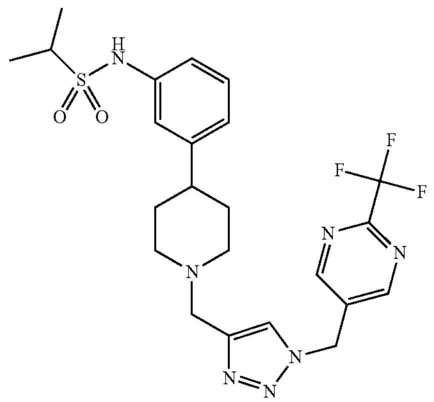 [SMILES: CC(C)S(=O)(=O)Nc1cccc(C2CCN(Cc3cn(Cc4cnc(C(F)(F)F)nc4)nn3)CC2)c1] | N-(3-(1-((1-((2-(trifluoromethyl)pyrimidin-5-yl)methyl)-1H-1,2,3-triazol-4-yl)methyl)piperidin-4-yl)phenyl)propane-2-sulfonamide | 5.66 | 524.2062 (M + H) |
| 130 | 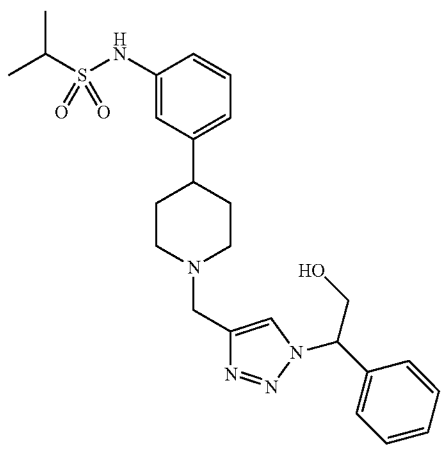 [SMILES: CC(C)S(=O)(=O)Nc1cccc(C2CCN(Cc3cn(C(CO)c4ccccc4)nn3)CC2)c1] | N-(3-(1-((1-(2-hydroxy-1-phenylethyl)-1H-1,2,3-triazol-4-yl)methyl)piperidin-4-yl)phenyl)propane-2-sulfonamide | 5.39 | 484.2377 (M + H) |
| 131 | 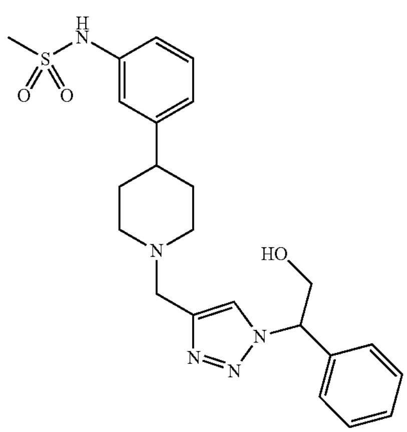 [SMILES: CS(=O)(=O)Nc1cccc(C2CCN(Cc3cn(C(CO)c4ccccc4)nn3)CC2)c1] | N-(3-(1-((1-(2-hydroxy-1-phenylethyl)-1H-1,2,3-triazol-4-yl)methyl)piperidin-4-yl)phenyl)methanesulfonamide | 5.06 | 456.2076 (M + H) |

| EX | Structure | Chemical name | Ret time (min) | HRMS |
|---|---|---|---|---|
| 132 | 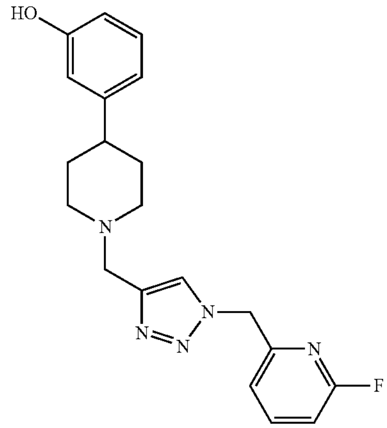 [SMILES: Oc1cccc(C2CCN(Cc3cn(Cc4cccc(F)n4)nn3)CC2)c1] | 3-(1-((1-((6-fluoropyridin-2-yl)methyl)-1H-1,2,3-triazol-4-yl)methyl)piperidin-4-yl)phenol | 4.87 | 368.1896 (M + H) |
| 133 | 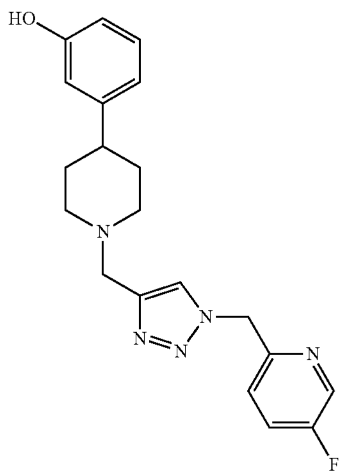 [SMILES: Oc1cccc(C2CCN(Cc3cn(Cc4ccc(F)cn4)nn3)CC2)c1] | 3-(1-((1-((5-fluoropyridin-2-yl)methyl)-1H-1,2,3-triazol-4-yl)methyl)piperidin-4-yl)phenol | 4.76 | 366.1733 (M − H) |
| 134 | 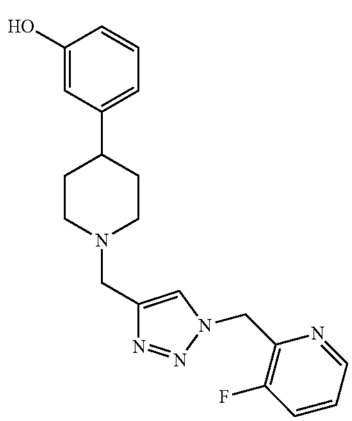 [SMILES: Oc1cccc(C2CCN(Cc3cn(Cc4ncccc4F)nn3)CC2)c1] | 3-(1-((1-((3-fluoropyridin-2-yl)methyl)-1H-1,2,3-triazol-4-yl)methyl)piperidin-4-yl)phenol | 4.75 | 366.1742 (M − H) |

| EX | Structure | Chemical name | Ret time (min) | HRMS |
|---|---|---|---|---|
| 135 | 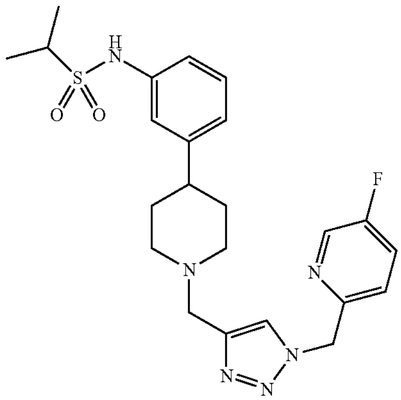 [SMILES: CC(C)S(=O)(=O)Nc1cccc(C2CCN(Cc3cn(Cc4ccc(F)cn4)nn3)CC2)c1] | N-(3-(1-((1-((5-fluoropyridin-2-yl)methyl)-1H-1,2,3-triazol-4-yl)methyl)piperidin-4-yl)phenyl)propane-2-sulfonamide | 5.24 | 473.2133 (M + H) |
| 136 | 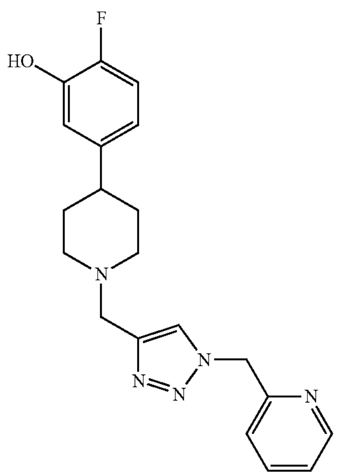 [SMILES: Oc1cc(C2CCN(Cc3cn(Cc4ccccn4)nn3)CC2)ccc1F] | 2-fluoro-5-(1-((1-(pyridin-2-ylmethyl)-1H-1,2,3-triazol-4-yl)methyl)piperidin-4-yl)phenol | 4.60 | 368.1887 (M + H) |
| 137 | 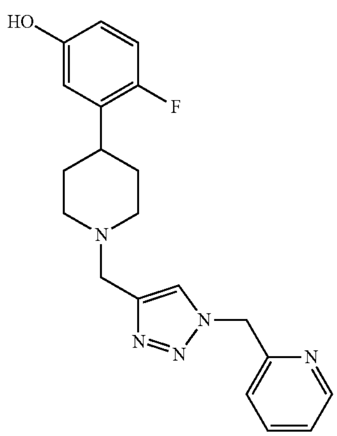 [SMILES: Oc1ccc(F)c(C2CCN(Cc3cn(Cc4ccccn4)nn3)CC2)c1] | 4-fluoro-3-(1-((1-(pyridin-2-ylmethyl)-1H-1,2,3-triazol-4-yl)methyl)piperidin-4-yl)phenol | 4.61 | 368.1878 (M + H) |

| EX | Structure | Chemical name | Ret time (min) | HRMS |
|---|---|---|---|---|
| 138 | 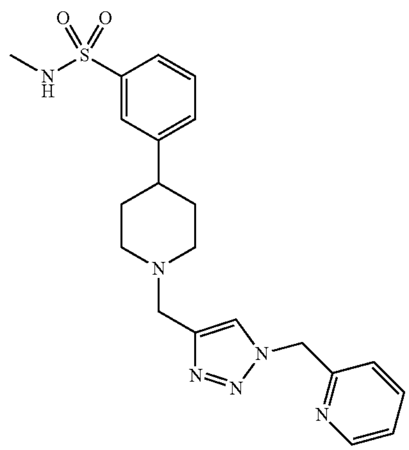 [SMILES: CNS(=O)(=O)c1cccc(C2CCN(Cc3cn(Cc4ccccn4)nn3)CC2)c1] | N-methyl-3-(1-((1-(pyridin-2-ylmethyl)-1H-1,2,3-triazol-4-yl)methyl)piperidin-4-yl)benzenesulfonamide | 4.63 | 427.1911 (M + H) |
| 139 | 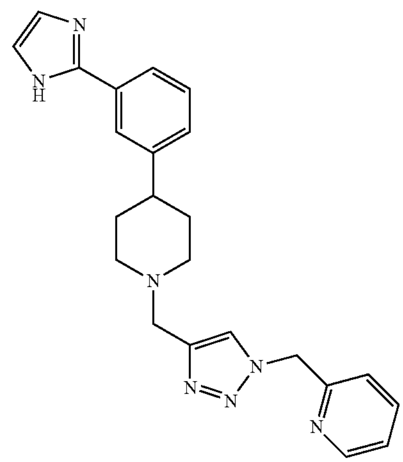 [SMILES: c1ccc(Cn2cc(CN3CCC(c4cccc(-c5ncc[nH]5)c4)CC3)nn2)nc1] | 2-((4-((4-(3-(1H-imidazol-2-yl)phenyl)piperidin-1-yl)methyl)-1H-1,2,3-triazol-1-yl)methyl)pyridine | 3.95 | 400.2246 (M + H) |
| 140 | 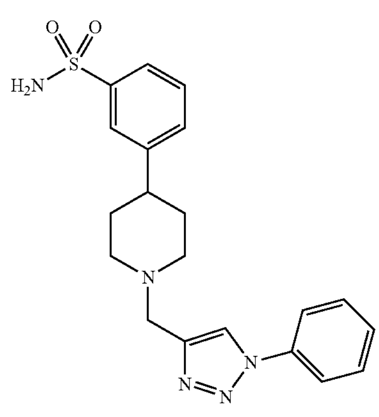 [SMILES: NS(=O)(=O)c1cccc(C2CCN(Cc3cn(-c4ccccc4)nn3)CC2)c1] | 3-(1-((1-phenyl-1H-1,2,3-triazol-4-yl)methyl)piperidin-4-yl)benzenesulfonamide | 5.09 | 398.1 (M + H) |

| EX | Structure | Chemical name | Ret time (min) | HRMS |
|---|---|---|---|---|
| 141 | 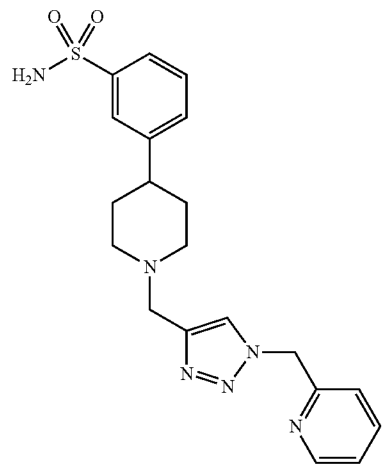 [SMILES: NS(=O)(=O)c1cccc(C2CCN(Cc3cn(Cc4ccccn4)nn3)CC2)c1] | 3-(1-((1-(pyridin-2-ylmethyl)-1H-1,2,3-triazol-4-yl)methyl)piperidin-4-yl)benzenesulfonamide | 4.28 | 413.1 (M + H) |
| 142 | 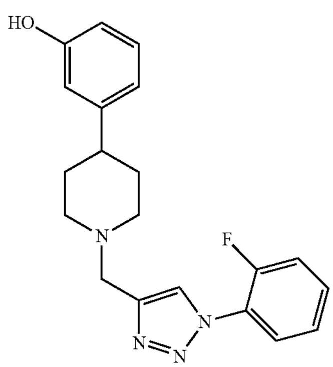 [SMILES: Oc1cccc(C2CCN(Cc3cn(-c4ccccc4F)nn3)CC2)c1] | 3-(1-((1-(2-fluorophenyl)-1H-1,2,3-triazol-4-yl)methyl)piperidin-4-yl)phenol | 5.28 | 353.1770 (M + H) |
| 143 | 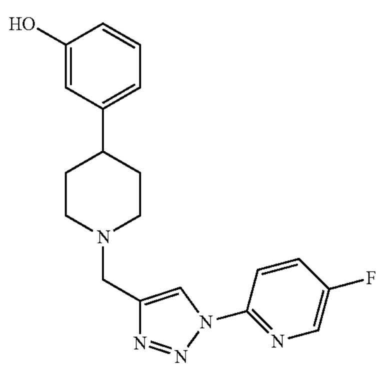 [SMILES: Oc1cccc(C2CCN(Cc3cn(-c4ccc(F)cn4)nn3)CC2)c1] | 3-(1-((1-(5-fluoropyridin-2-yl)-1H-1,2,3-triazol-4-yl)methyl)piperidin-4-yl)phenol | 5.11 | 354.1722 (M + H) |

| EX | Structure | Chemical name | Ret time (min) | HRMS |
|---|---|---|---|---|
| 144 | 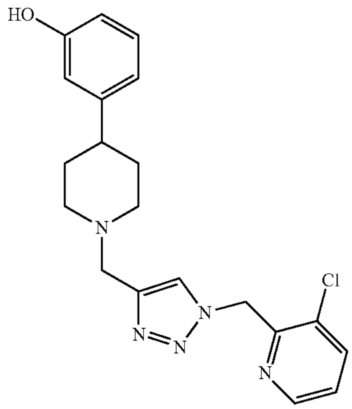 [SMILES: Oc1cccc(C2CCN(Cc3cn(Cc4ncccc4Cl)nn3)CC2)c1] | 3-(1-((1-((3-chloropyridin-2-yl)methyl)-1H-1,2,3-triazol-4-yl)methyl)piperidin-4-yl)phenol | 4.94 | 384.1588 (M + H) |
| 145 | 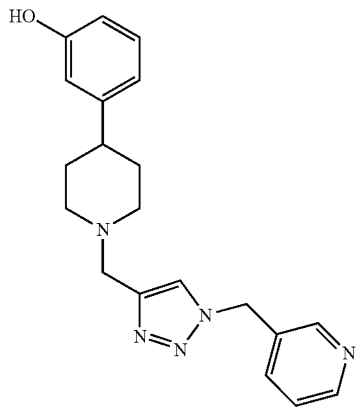 [SMILES: Oc1cccc(C2CCN(Cc3cn(Cc4cccnc4)nn3)CC2)c1] | 3-(1-((1-(pyridin-3-ylmethyl)-1H-1,2,3-triazol-4-yl)methyl)piperidin-4-yl)phenol | 3.95 | 350.1973 (M + H) |
| 146 | 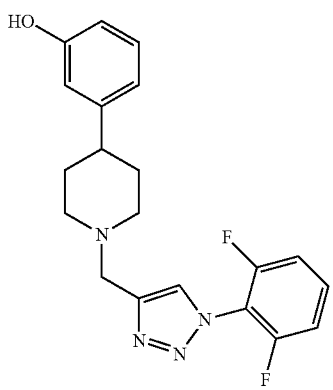 [SMILES: Oc1cccc(C2CCN(Cc3cn(-c4c(F)cccc4F)nn3)CC2)c1] | 3-(1-((1-(2,6-difluorophenyl)-1H-1,2,3-triazol-4-yl)methyl)piperidin-4-yl)phenol | 5.26 | 371.1675 (M + H) |
| 147 | 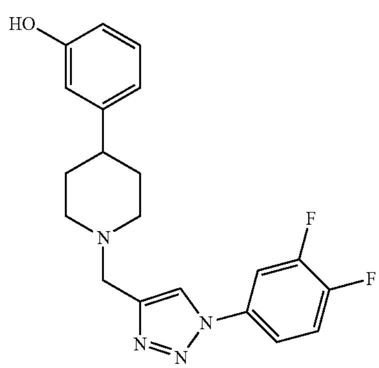 [SMILES: Oc1cccc(C2CCN(Cc3cn(-c4ccc(F)c(F)c4)nn3)CC2)c1] | 3-(1-((1-(3,4-difluorophenyl)-1H-1,2,3-triazol-4-yl)methyl)piperidin-4-yl)phenol | 5.55 | 371.1674 (M + H) |

| EX | Structure | Chemical name | Ret time (min) | HRMS |
|---|---|---|---|---|
| 148 | 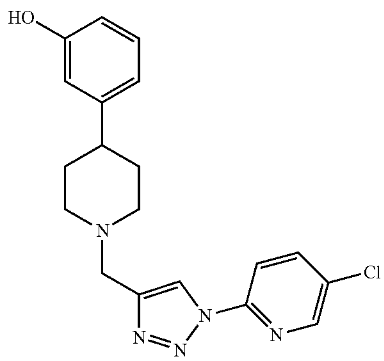 [SMILES: Oc1cccc(C2CCN(Cc3cn(-c4ccc(Cl)cn4)nn3)CC2)c1] | 3-(1-((1-(5-chloropyridin-2-yl)-1H-1,2,3-triazol-4-yl)methyl)piperidin-4-yl)phenol | 5.43 | 370.1430 (M + H) |
| 149 | 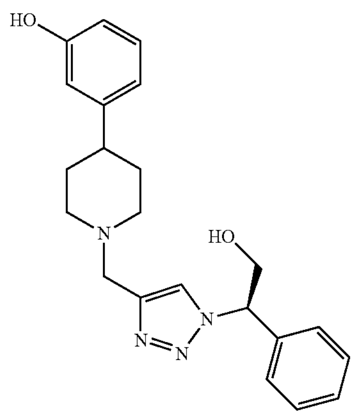 [SMILES: OC[C@@H](c1ccccc1)n1cc(CN2CCC(c3cccc(O)c3)CC2)nn1] | (R)-3-(1-((1-(2-hydroxy-1-phenylethyl)-1H-1,2,3-triazol-4-yl)methyl)piperidin-4-yl)phenol | 4.97 | |
| 150 | 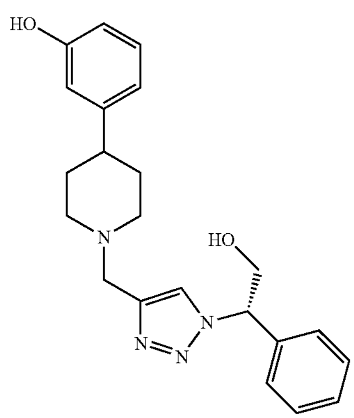 [SMILES: OC[C@H](c1ccccc1)n1cc(CN2CCC(c3cccc(O)c3)CC2)nn1] | (S)-3-(1-((1-(2-hydroxy-1-phenylethyl)-1H-1,2,3-triazol-4-yl)methyl)piperidin-4-yl)phenol | 4.97 | |

| EX | Structure | Chemical name | Ret time (min) | HRMS |
|---|---|---|---|---|
| 151 | 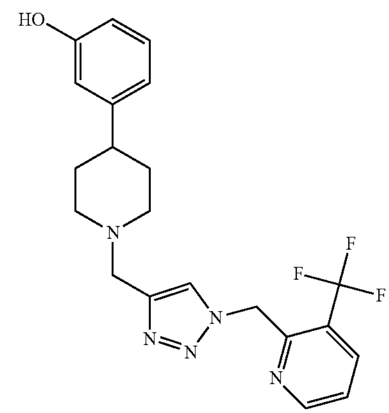 [SMILES: Oc1cccc(C2CCN(Cc3cn(Cc4ncccc4C(F)(F)F)nn3)CC2)c1] | 3-(1-((1-((3-(trifluoromethyl)pyridin-2-yl)methyl)-1H-1,2,3-triazol-4-yl)methyl)piperidin-4-yl)phenol | 5.26 | 418.1848 (M + H) |
| 152 | 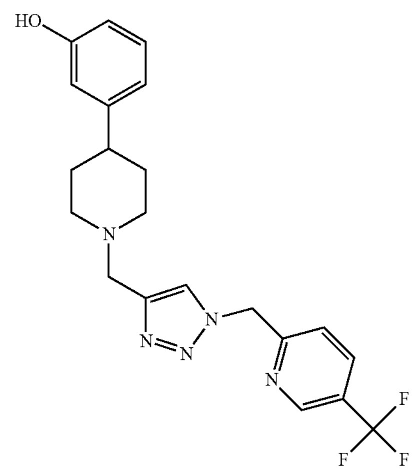 [SMILES: Oc1cccc(C2CCN(Cc3cn(Cc4ccc(C(F)(F)F)cn4)nn3)CC2)c1] | 3-(1-((1-((5-(trifluoromethyl)pyridin-2-yl)methyl)-1H-1,2,3-triazol-4-yl)methyl)piperidin-4-yl)phenol | 5.44 | 418.1845 (M + H) |
| 153 | 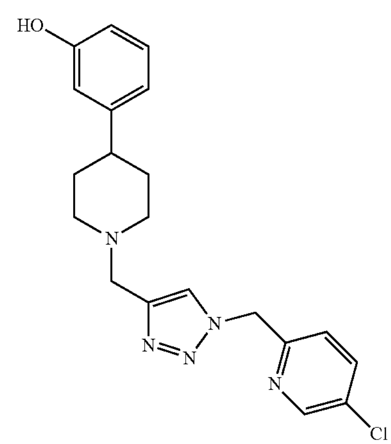 [SMILES: Oc1cccc(C2CCN(Cc3cn(Cc4ccc(Cl)cn4)nn3)CC2)c1] | 3-(1-((1-((5-chloropyridin-2-yl)methyl)-1H-1,2,3-triazol-4-yl)methyl)piperidin-4-yl)phenol | 5.09 | 384.1595 (M + H) |

-continued

| EX | Structure | Chemical name | Ret time (min) | HRMS |
|---|---|---|---|---|
| 154 | 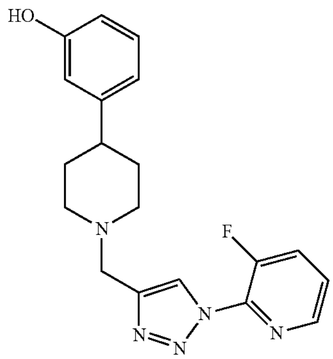 [SMILES: Oc1cccc(C2CCN(Cc3cn(-c4ncccc4F)nn3)CC2)c1] | 3-(1-((1-(3-fluoropyridin-2-yl)-1H-1,2,3-triazol-4-yl)methyl)piperidin-4-yl)phenol | 4.82 | 354.1732 (M + H) |
| 155 | 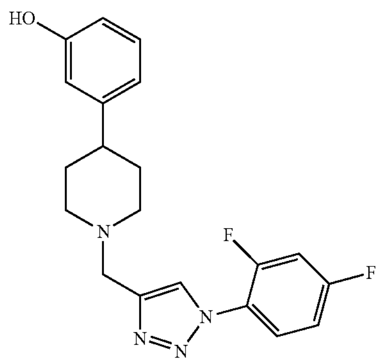 [SMILES: Oc1cccc(C2CCN(Cc3cn(-c4ccc(F)cc4F)nn3)CC2)c1] | 3-(1-((1-(2,4-difluorophenyl)-1H-1,2,3-triazol-4-yl)methyl)piperidin-4-yl)phenol | 5.41 | 371.1672 (M + H) |
| 156 | 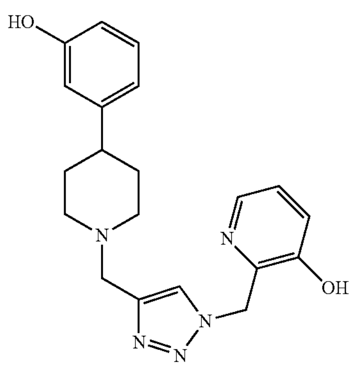 [SMILES: Oc1cccc(C2CCN(Cc3cn(Cc4ncccc4O)nn3)CC2)c1] | 2-((4-((4-(3-hydroxyphenyl)piperidin-1-yl)methyl)-1H-1,2,3-triazol-1-yl)methyl)pyridin-3-ol | 4.20 | 364.1796 (M − H) |
| 157 | 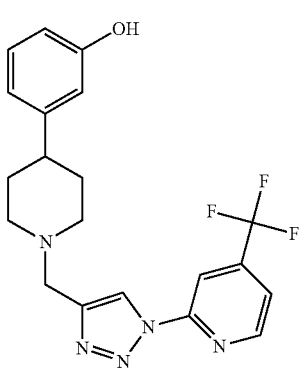 [SMILES: Oc1cccc(C2CCN(Cc3cn(-c4cc(C(F)(F)F)ccn4)nn3)CC2)c1] | 3-(1-((1-(4-(trifluoromethyl)pyridin-2-yl)-1H-1,2,3-triazol-4-yl)methyl)piperidin-4-yl)phenol | 5.73 | 404.1678 (M + H) |

| EX | Structure | Chemical name | Ret time (min) | HRMS |
|---|---|---|---|---|
| 158 | 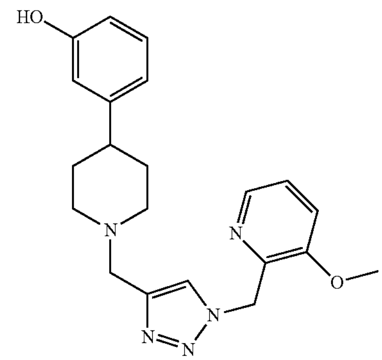 [SMILES: COc1cccnc1Cn1cc(CN2CCC(c3cccc(O)c3)CC2)nn1] | 3-(1-((1-((3-methoxypyridin-2-yl)methyl)-1H-1,2,3-triazol-4-yl)methyl)piperidin-4-yl)phenol | 4.69 | 378.1937 (M − H) |
| 159 | 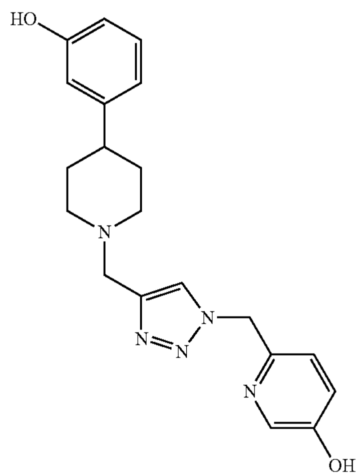 [SMILES: Oc1ccc(Cn2cc(CN3CCC(c4cccc(O)c4)CC3)nn2)nc1] | 6-((4-((4-(3-hydroxyphenyl)piperidin-1-yl)methyl)-1H-1,2,3-triazol-1-yl)methyl)pyridin-3-ol | 4.46 | 364.1774 (M − H) |
| 160 | 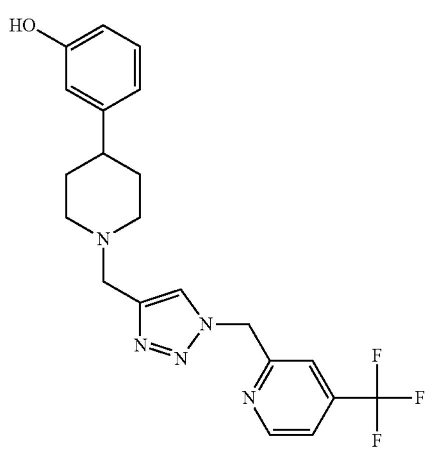 [SMILES: Oc1cccc(C2CCN(Cc3cn(Cc4cc(C(F)(F)F)ccn4)nn3)CC2)c1] | 3-(1-((1-((4-(trifluoromethyl)pyridin-2-yl)methyl)-1H-1,2,3-triazol-4-yl)methyl)piperidin-4-yl)phenol | 5.39 | 418.1860 (M + H) |

| EX | Structure | Chemical name | Ret time (min) | HRMS |
|---|---|---|---|---|
| 161 | 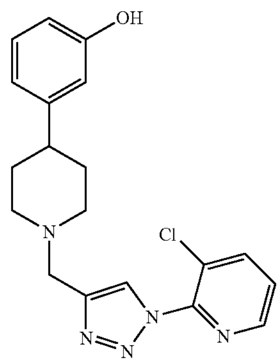 [SMILES: Oc1cccc(C2CCN(Cc3cn(-c4ncccc4Cl)nn3)CC2)c1] | 3-(1-((1-(3-chloropyridin-2-yl)-1H-1,2,3-triazol-4-yl)methyl)piperidin-4-yl)phenol | 4.85 | |
| 162 | 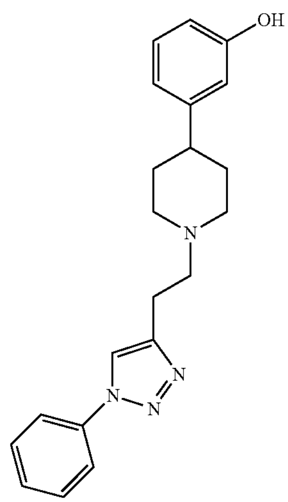 [SMILES: Oc1cccc(C2CCN(CCc3cn(-c4ccccc4)nn3)CC2)c1] | 3-(1-(2-(1-phenyl-1H-1,2,3-triazol-4-yl)ethyl)piperidin-4-yl)phenol | 5.36 | 349.2013 (M + H) |
| 163 | 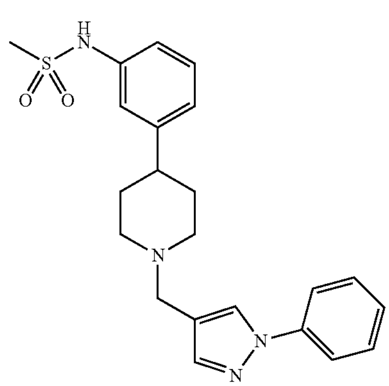 | N-(3-(1-((1-phenyl-1H-pyrazol-4-yl)methyl)piperidin-4-yl)phenyl)methane-sulfonamide | 5.45 | 411.1868 (M + H) |

| EX | Structure | Chemical name | Ret time (min) | HRMS |
|---|---|---|---|---|
| 164 | 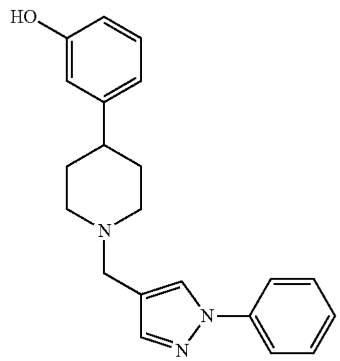 [SMILES: Oc1cccc(C2CCN(Cc3cnn(-c4ccccc4)c3)CC2)c1] | 3-(1-((1-phenyl-1H-pyrazol-4-yl)methyl)piperidin-4-yl)phenol | 5.40 | 332.1751 (M − H) |
| 165 | 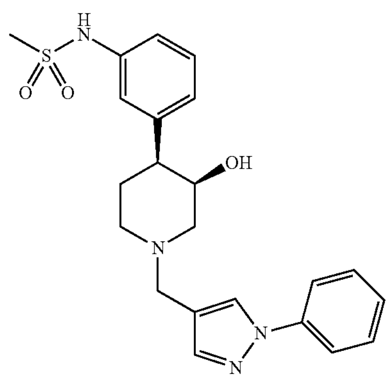 [SMILES: CS(=O)(=O)Nc1cccc([C@@H]2CCN(Cc3cnn(-c4ccccc4)c3)C[C@@H]2O)c1] | N-(3-((3R,4S)-3-hydroxy-1-((1-phenyl-1H-pyrazol-4-yl)methyl)piperidin-4-yl)phenyl)methane-sulfonamide | 5.28 | 427.1798 (M + H) |
| 166 | 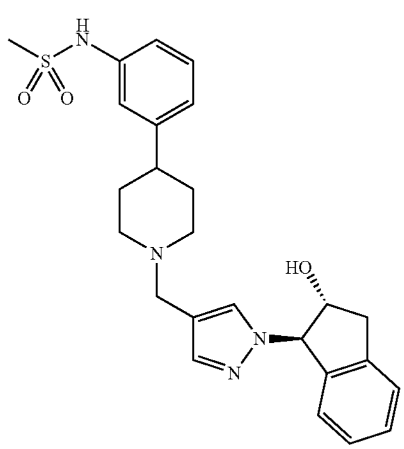 [SMILES: CS(=O)(=O)Nc1cccc(C2CCN(Cc3cnn([C@@H]4c5ccccc5C[C@H]4O)c3)CC2)c1] | N-(3-(1-((1-((1R,2R)-2-hydroxy-2,3-dihydro-1H-inden-1-yl)-1H-pyrazol-4-yl)methyl)piperidin-4-yl)phenyl)methane-sulfonamide | 5.17 | 465.1963 (M − H) |

| EX | Structure | Chemical name | Ret time (min) | HRMS |
|---|---|---|---|---|
| 167 | 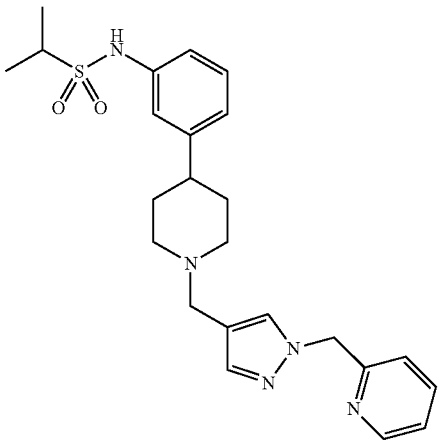 [SMILES: CC(C)S(=O)(=O)Nc1cccc(C2CCN(Cc3cnn(Cc4ccccn4)c3)CC2)c1] | N-(3-(1-((1-(pyridin-2-ylmethyl)-1H-pyrazol-4-yl)methyl)piperidin-4-yl)phenyl)propane-2-sulfonamide | 4.75 | 452.2120 (M − H) |
| 168 | 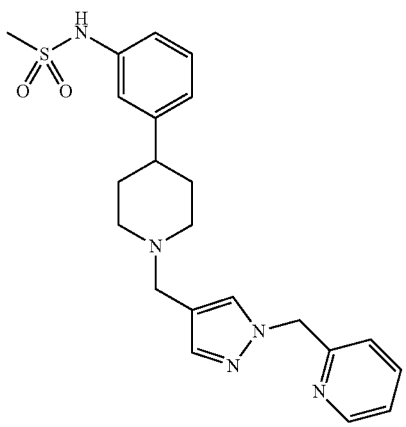 | N-(3-(1-((1-(pyridin-2-ylmethyl)-1H-pyrazol-4-yl)methyl)piperidin-4-yl)phenyl)methanesulfonamide | 4.27 | 425.1767 (M − H) |
| 169 | 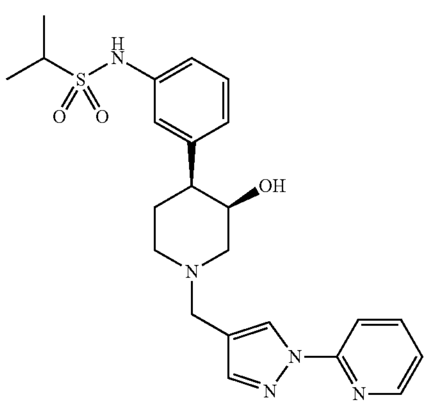 [SMILES: CC(C)S(=O)(=O)Nc1cccc([C@@H]2CCN(Cc3cnn(-c4ccccn4)c3)C[C@@H]2O)c1] | N-(3-((3R,4S)-3-hydroxy-1-((1-(pyridin-2-yl)-1H-pyrazol-4-yl)methyl)piperidin-4-yl)phenyl)propane-2-sulfonamide | 5.27 | 456.2072 (M + H) |

-continued

| EX | Structure | Chemical name | Ret time (min) | HRMS |
|---|---|---|---|---|
| 170 | 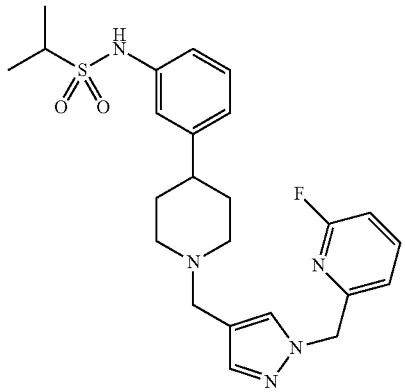 [SMILES: CC(C)S(=O)(=O)Nc1cccc(C2CCN(Cc3cnn(Cc4cccc(F)n4)c3)CC2)c1] | N-(3-(1-((1-((6-fluoropyridin-2-yl)methyl)-1H-pyrazol-4-yl)methyl)piperidin-4-yl)phenyl)propane-2-sulfonamide | 5.33 | 472.2179 (M + H) |
| 171 | 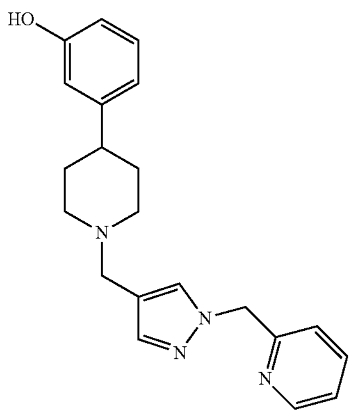 [SMILES: Oc1cccc(C2CCN(Cc3cnn(Cc4ccccn4)c3)CC2)c1] | 3-(1-((1-(pyridin-2-ylmethyl)-1H-pyrazol-4-yl)methyl)piperidin-4-yl)phenol | 4.27 | 349.2012 (M + H) |
| 172 | 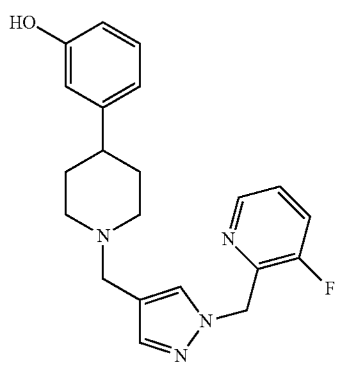 [SMILES: Oc1cccc(C2CCN(Cc3cnn(Cc4ncccc4F)c3)CC2)c1] | 3-(1-((1-((3-fluoropyridin-2-yl)methyl)-1H-pyrazol-4-yl)methyl)piperidin-4-yl)phenol | 4.80 | 367.1922 (M + H) |
| 173 | 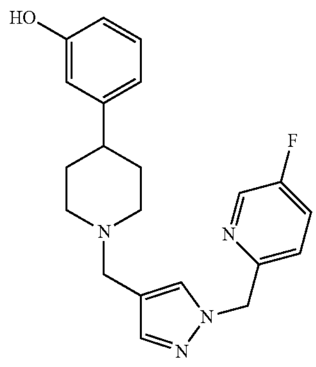 [SMILES: Oc1cccc(C2CCN(Cc3cnn(Cc4ccc(F)cn4)c3)CC2)c1] | 3-(1-((1-((5-fluoropyridin-2-yl)methyl)-1H-pyrazol-4-yl)methyl)piperidin-4-yl)phenol | 4.85 | |

-continued

| EX | Structure | Chemical name | Ret time (min) | HRMS |
|---|---|---|---|---|
| 174 | 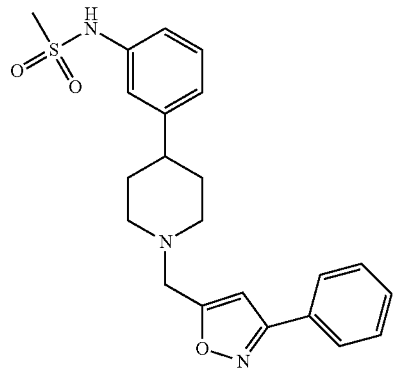 [SMILES: CS(=O)(=O)Nc1cccc(C2CCN(Cc3cc(-c4ccccc4)no3)CC2)c1] | N-(3-(1-((3-phenylisoxazol-5-yl)methyl)piperidin-4-yl)phenyl)methane-sulfonamide | 5.38 | 412.1714 |
| 175 | 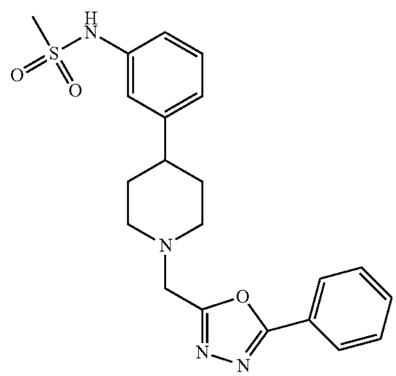 [SMILES: CS(=O)(=O)Nc1cccc(C2CCN(Cc3nnc(-c4ccccc4)o3)CC2)c1] | N-(3-(1-((5-phenyl-1,3,4-oxadiazol-2-yl)methyl)piperidin-4-yl)phenyl)methane-sulfonamide | 5.27 | 435.1487 (M + Na) |
| 176 | 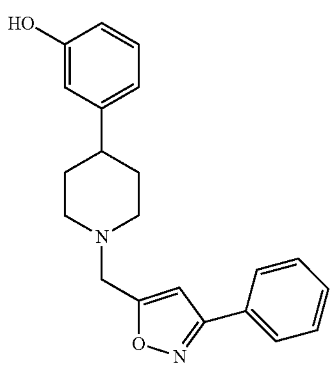 [SMILES: Oc1cccc(C2CCN(Cc3cc(-c4ccccc4)no3)CC2)c1] | 3-(1-((3-phenylisoxazol-5-yl)methyl)piperidin-4-yl)phenol | 5.59 | 335.1754 (M + H) |
| 177 | 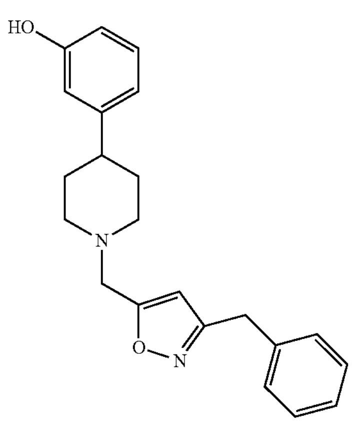 [SMILES: Oc1cccc(C2CCN(Cc3cc(Cc4ccccc4)no3)CC2)c1] | 3-(1-((3-benzylisoxazol-5-yl)methyl)piperidin-4-yl)phenol | 5.66 | 347.1761 (M − H) |

-continued

| EX | Structure | Chemical name | Ret time (min) | HRMS |
|---|---|---|---|---|
| 178 | 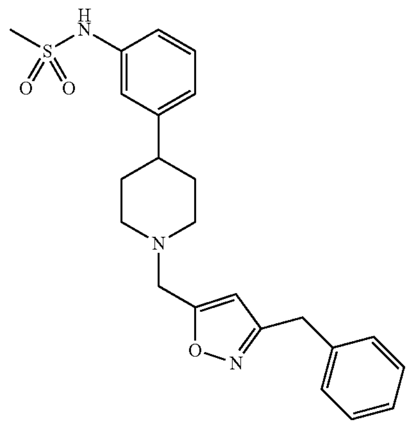 [SMILES: CS(=O)(=O)Nc1cccc(C2CCN(Cc3cc(Cc4ccccc4)no3)CC2)c1] | N-(3-(1-((3-benzylisoxazol-5-yl)methyl)piperidin-4-yl)phenyl)methane-sulfonamide | 5.65 | 424.1675 (M − H) |
| 179 | 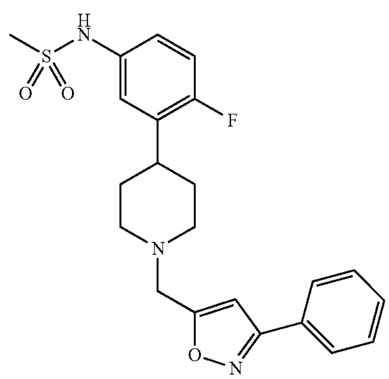 [SMILES: CS(=O)(=O)Nc1ccc(F)c(C2CCN(Cc3cc(-c4ccccc4)no3)CC2)c1] | N-(4-fluoro-3-(1-((3-phenylisoxazol-5-yl)methyl)piperidin-4-yl)phenyl)methane-sulfonamide | 5.81 | 428.1451 (M − H) |
| 180 | 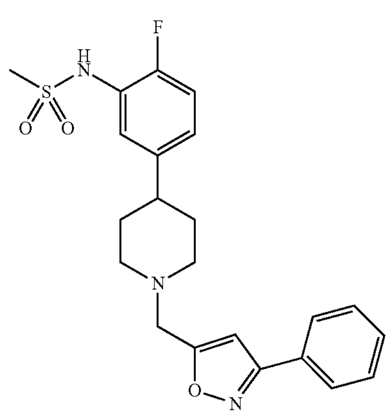 [SMILES: CS(=O)(=O)Nc1cc(C2CCN(Cc3cc(-c4ccccc4)no3)CC2)ccc1F] | N-(2-fluoro-5-(1-((3-phenylisoxazol-5-yl)methyl)piperidin-4-yl)phenyl)methane-sulfonamide | 5.66 | 428.1450 (M − H) |

-continued

| EX | Structure | Chemical name | Ret time (min) | HRMS |
|---|---|---|---|---|
| 181 | 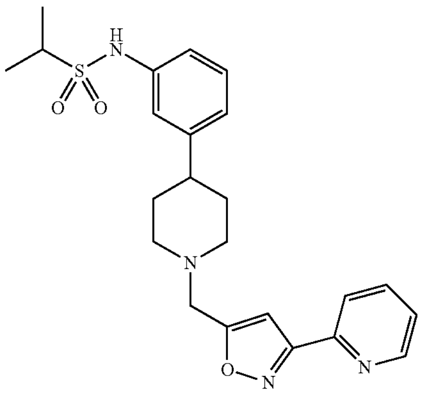 [SMILES: CC(C)S(=O)(=O)Nc1cccc(C2CCN(Cc3cc(-c4ccccn4)no3)CC2)c1] | N-(3-(1-((3-(pyridin-2-yl)isoxazol-5-yl)methyl)piperidin-4-yl)phenyl)propane-2-sulfonamide | 5.35 | 439.1817 (M − H) |
| 182 | 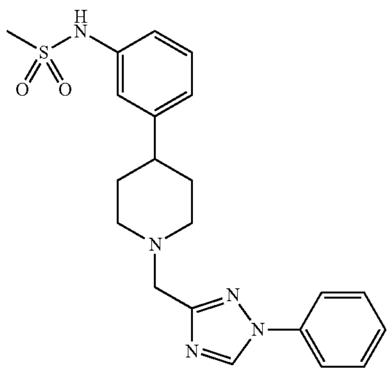 [SMILES: CS(=O)(=O)Nc1cccc(C2CCN(Cc3ncn(-c4ccccc4)n3)CC2)c1] | N-(3-(1-((1-phenyl-1H-1,2,4-triazol-3-yl)methyl)piperidin-4-yl)phenyl)methane-sulfonamide | 5.26 | 410.1652 (M − H) |
| 183 | 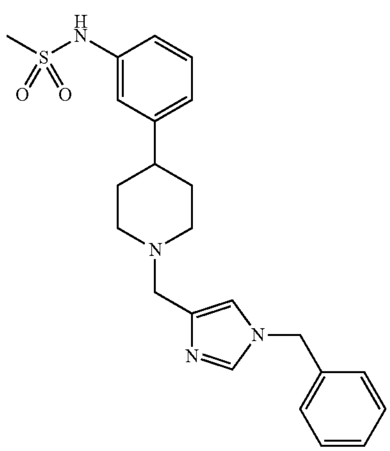 [SMILES: CS(=O)(=O)Nc1cccc(C2CCN(Cc3cn(Cc4ccccc4)cn3)CC2)c1] | N-(3-(1-((1-benzyl-1H-imidazol-4-yl)methyl)piperidin-4-yl)phenyl)methane-sulfonamide | 4.82 | 423.1837 (M − H) |
| 184 | 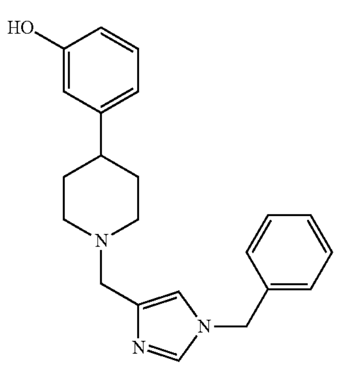 [SMILES: Oc1cccc(C2CCN(Cc3cn(Cc4ccccc4)cn3)CC2)c1] | 3-(1-((1-benzyl-1H-imidazol-4-yl)methyl)piperidin-4-yl)phenol | 4.73 | 346.1914 (M − H) |

-continued

| EX | Structure | Chemical name | Ret time (min) | HRMS |
|---|---|---|---|---|
| 185 | 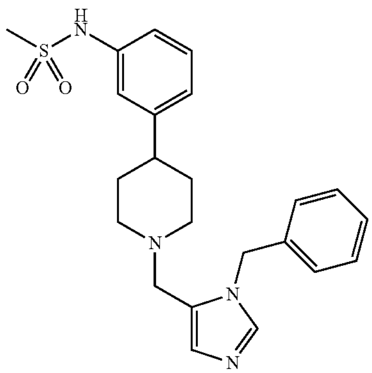 [SMILES: CS(=O)(=O)Nc1cccc(C2CCN(Cc3cncn3Cc3ccccc3)CC2)c1] | N-(3-(1-((1-benzyl-1H-imidazol-5-yl)methyl)piperidin-4-yl)phenyl)methane-sulfonamide | 4.67 | 423.1856 (M − H) |
| 186 | 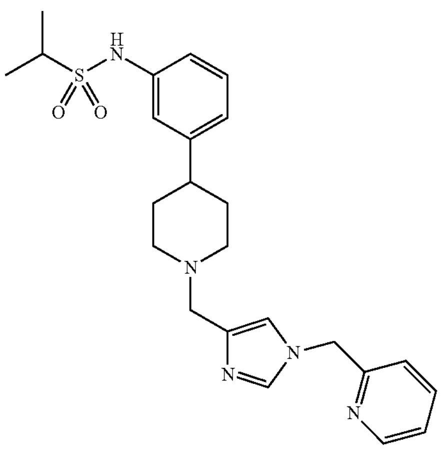 [SMILES: CC(C)S(=O)(=O)Nc1cccc(C2CCN(Cc3cn(Cc4ccccn4)cn3)CC2)c1] | N-(3-(1-((1-(pyridin-2-ylmethyl)-1H-imidazol-4-yl)methyl)piperidin-4-yl)phenyl)propane-2-sulfonamide | 4.60 | 454.2272 (M + H) |
| 187 | 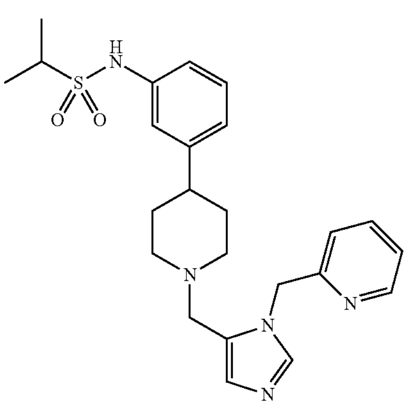 [SMILES: CC(C)S(=O)(=O)Nc1cccc(C2CCN(Cc3cncn3Cc3ccccn3)CC2)c1] | N-(3-(1-((1-(pyridin-2-ylmethyl)-1H-imidazol-5-yl)methyl)piperidin-4-yl)phenyl)propane-2-sulfonamide | 4.53 | 454.2272 (M + H) |

-continued
| EX | Structure | Chemical name | Ret time (min) | HRMS |
|---|---|---|---|---|
| 188 | 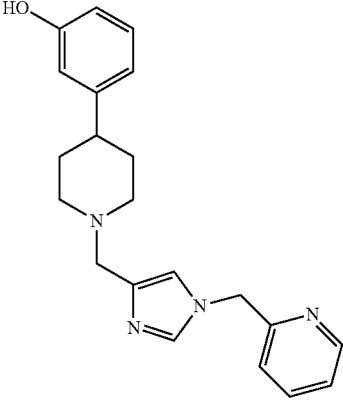 [SMILES: Oc1cccc(C2CCN(Cc3cn(Cc4ccccn4)cn3)CC2)c1] | 3-(1-((1-(pyridin-2-ylmethyl)-1H-imidazol-4-yl)methyl)piperidin-4-yl)phenol | 4.20 | 349.2012 (M + H) |
| 189 | 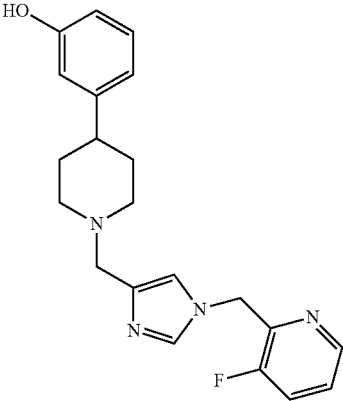 [SMILES: Oc1cccc(C2CCN(Cc3cn(Cc4ncccc4F)cn3)CC2)c1] | 3-(1-((1-((3-fluoropyridin-2-yl)methyl)-1H-imidazol-4-yl)methyl)piperidin-4-yl)phenol | 4.37 | 367.1937 (M + H) |
| 190 | 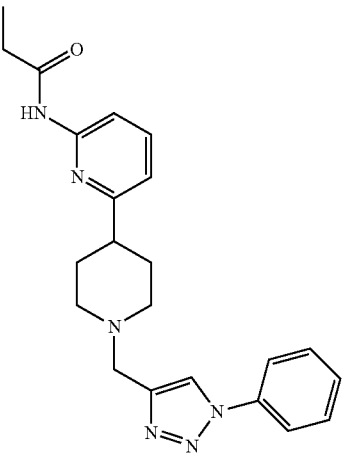 [SMILES: CCC(=O)Nc1cccc(C2CCN(Cc3cn(-c4ccccc4)nn3)CC2)n1] | N-(6-(1-((1-phenyl-1H-1,2,3-triazol-4-yl)methyl)piperidin-4-yl)pyridin-2-yl)propionamide | 5.12 | 391.2232 (M + H) |

-continued
| EX | Structure | Chemical name | Ret time (min) | HRMS |
|---|---|---|---|---|
| 191 | 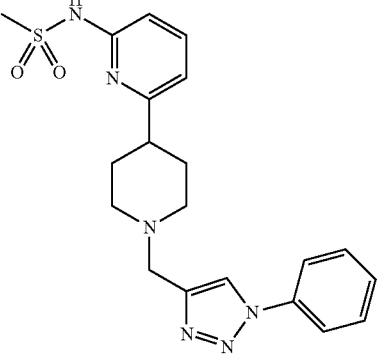 | N-(6-(1-((1-phenyl-1H-1,2,3-triazol-4-yl)methyl)piperidin-4-yl)pyridin-2-yl)methanesulfonamide | 5.08 | 413.1758 (M + H) |
| 192 | 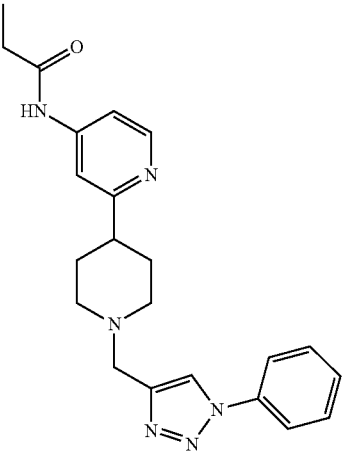 [SMILES: CCC(=O)Nc1ccnc(C2CCN(Cc3cn(-c4ccccc4)nn3)CC2)c1] | N-(2-(1-((1-phenyl-1H-1,2,3-triazol-4-yl)methyl)piperidin-4-yl)pyridin-4-yl)propionamide | 4.44 | 391.2250 (M + H) |
| 193 | 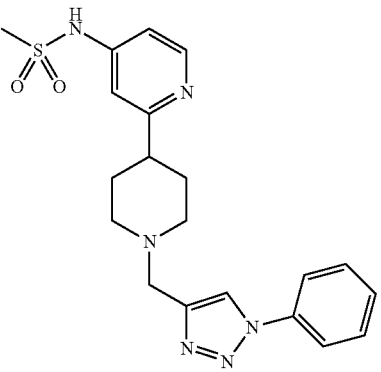 [SMILES: CS(=O)(=O)Nc1ccnc(C2CCN(Cc3cn(-c4ccccc4)nn3)CC2)c1] | N-(2-(1-((1-phenyl-1H-1,2,3-triazol-4-yl)methyl)piperidin-4-yl)pyridin-4-yl)methanesulfonamide | 4.37 | 411.1605 (M − H) |

-continued

| EX | Structure | Chemical name | Ret time (min) | HRMS |
|---|---|---|---|---|
| 194 | 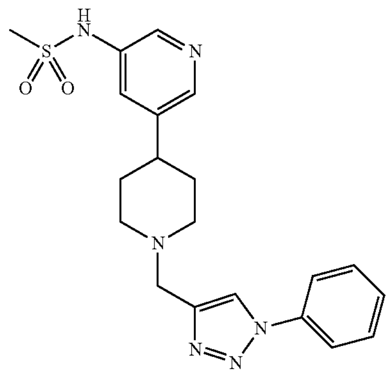 [SMILES: CS(=O)(=O)Nc1cncc(C2CCN(Cc3cn(-c4ccccc4)nn3)CC2)c1] | N-(5-(1-((1-phenyl-1H-1,2,3-triazol-4-yl)methyl)piperidin-4-yl)pyridin-3-yl)methanesulfonamide | 4.46 | 411.1593 (M − H) |
| 195 | 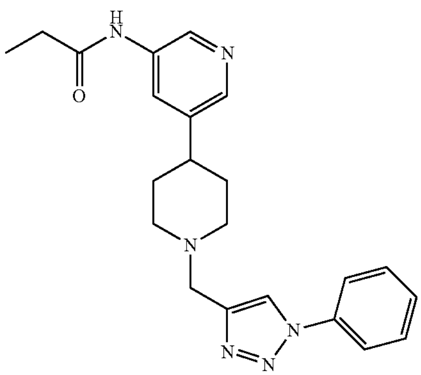 [SMILES: CCC(=O)Nc1cncc(C2CCN(Cc3cn(-c4ccccc4)nn3)CC2)c1] | N-(5-(1-((1-phenyl-1H-1,2,3-triazol-4-yl)methyl)piperidin-4-yl)pyridin-3-yl)propionamide | 4.43 | 389.2087 (M − H) |
| 196 | 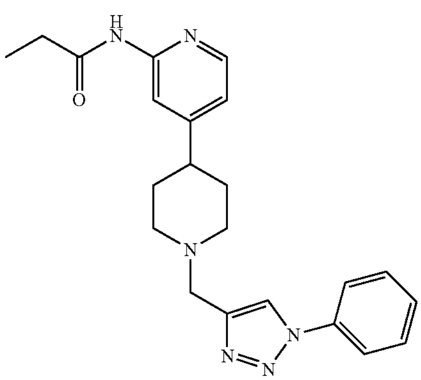 [SMILES: CCC(=O)Nc1cc(C2CCN(Cc3cn(-c4ccccc4)nn3)CC2)ccn1] | N-(4-(1-((1-phenyl-1H-1,2,3-triazol-4-yl)methyl)piperidin-4-yl)pyridin-2-yl)propionamide | 5.50 | 389.2071 (M − H) |
| 197 | 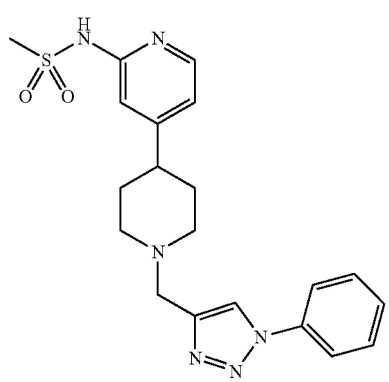 [SMILES: CS(=O)(=O)Nc1cc(C2CCN(Cc3cn(-c4ccccc4)nn3)CC2)ccn1] | N-(4-(1-((1-phenyl-1H-1,2,3-triazol-4-yl)methyl)piperidin-4-yl)pyridin-2-yl)methanesulfonamide | 4.65 | 413.1763 (M + H) |

-continued

| EX | Structure | Chemical name | Ret time (min) | HRMS |
|---|---|---|---|---|
| 198 | 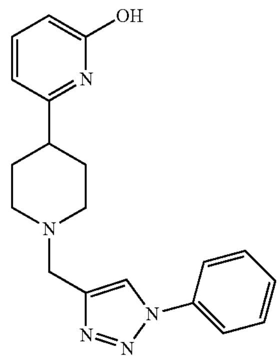 [SMILES: Oc1cccc(C2CCN(Cc3cn(-c4ccccc4)nn3)CC2)n1] | 6-(1-((1-phenyl-1H-1,2,3-triazol-4-yl)methyl)piperidin-4-yl)pyridin-2-ol | 4.49 | 334.1661 (M − H) |
| 199 | 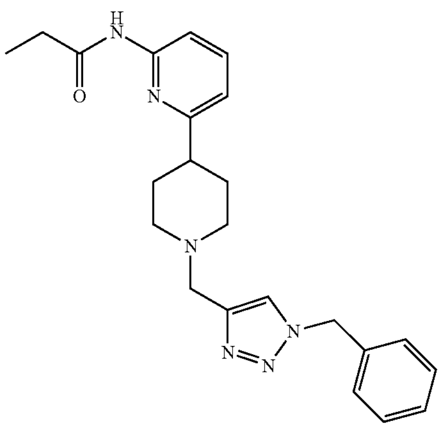 [SMILES: CCC(=O)Nc1cccc(C2CCN(Cc3cn(Cc4ccccc4)nn3)CC2)n1] | N-(6-(1-((1-benzyl-1H-1,2,3-triazol-4-yl)methyl)piperidin-4-yl)pyridin-2-yl)propionamide | 5.08 | 405.2403 (M + H) |
| 200 | 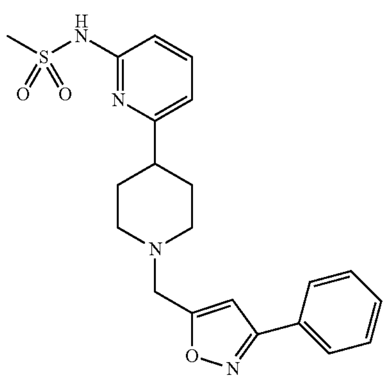 [SMILES: CS(=O)(=O)Nc1cccc(C2CCN(Cc3cc(-c4ccccc4)no3)CC2)n1] | N-(6-(1-((3-phenylisoxazol-5-yl)methyl)piperidin-4-yl)pyridin-2-yl)methanesulfonamide | 5.33 | 413.1628 (M + H) |
| 201 | 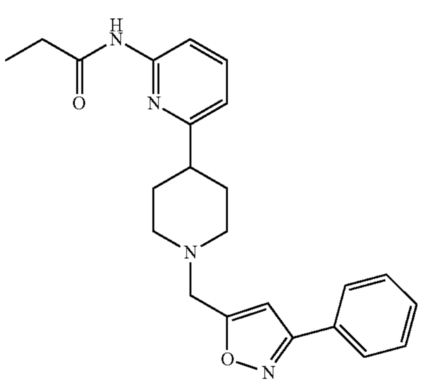 [SMILES: CCC(=O)Nc1cccc(C2CCN(Cc3cc(-c4ccccc4)no3)CC2)n1] | N-(6-(1-((3-phenylisoxazol-5-yl)methyl)piperidin-4-yl)pyridin-2-yl)propionamide | 5.45 | 391.2147 (M + H) |

| EX | Structure | Chemical name | Ret time (min) | HRMS |
|---|---|---|---|---|
| 202 | 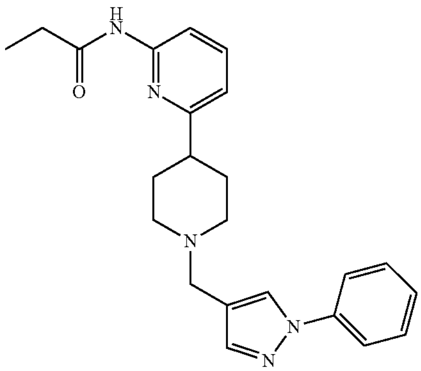 [SMILES: CCC(=O)Nc1cccc(C2CCN(Cc3cnn(-c4ccccc4)c3)CC2)n1] | N-(6-(1-((1-phenyl-1H-pyrazol-4-yl)methyl)piperidin-4-yl)pyridin-2-yl)propionamide | 5.21 | 390.2298 (M + H) |
| 203 | 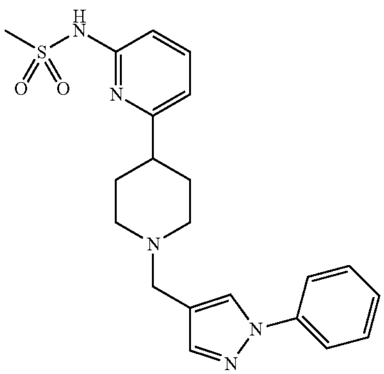 [SMILES: CS(=O)(=O)Nc1cccc(C2CCN(Cc3cnn(-c4ccccc4)c3)CC2)n1] | N-(6-(1-((1-phenyl-1H-pyrazol-4-yl)methyl)piperidin-4-yl)pyridin-2-yl)methanesulfonamide | 5.22 | 412.1818 (M + H) |
| 204 | 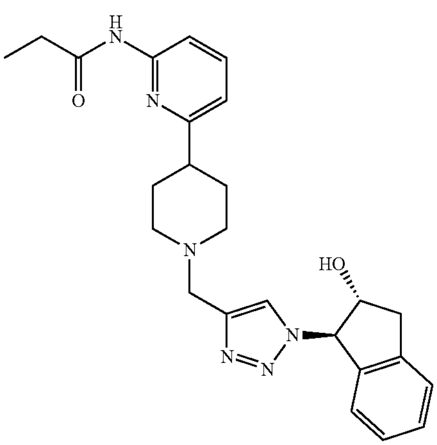 [SMILES: CCC(=O)Nc1cccc(C2CCN(Cc3cn([C@@H]4c5ccccc5C[C@H]4O)nn3)CC2)n1] | N-(6-(1-((1-(((1R,2R)-2-hydroxy-2,3-dihydro-1H-inden-1-yl)-1H-1,2,3-triazol-4-yl)methyl)piperidin-4-yl)pyridin-2- | 4.92 | 447.2507 (M + H) |
| 205 | 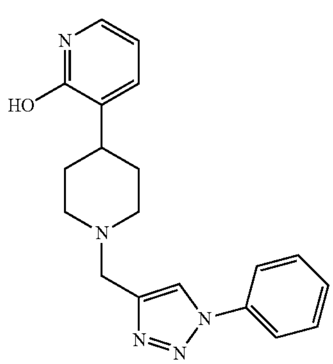 [SMILES: Oc1ncccc1C1CCN(Cc2cn(-c3ccccc3)nn2)CC1] | 3-(1-((1-phenyl-1H-1,2,3-triazol-4-yl)methyl)piperidin-4-yl)pyridin-2-ol | 4.60 | 334.1675 (M − H) |

| EX | Structure | Chemical name | Ret time (min) | HRMS |
|---|---|---|---|---|
| 206 | 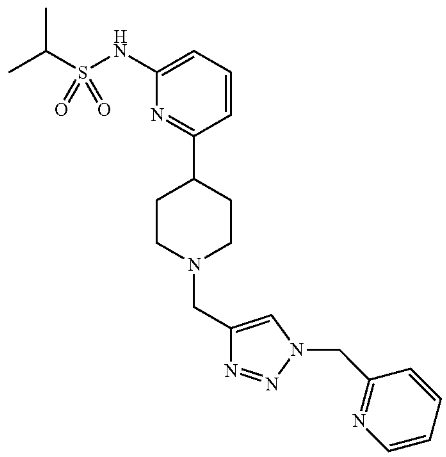 [SMILES: CC(C)S(=O)(=O)Nc1cccc(C2CCN(Cc3cn(Cc4ccccn4)nn3)CC2)n1] | N-(6-(1-((1-(pyridin-2-ylmethyl)-1H-1,2,3-triazol-4-yl)methyl)piperidin-4-yl)pyridin-2-yl)propane-2-sulfonamide | 4.63 | 456.2181 (M + H) |
| 207 | 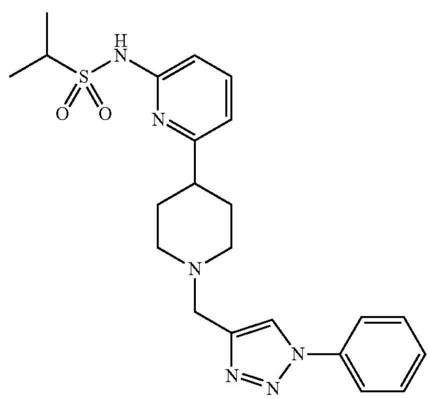 [SMILES: CC(C)S(=O)(=O)Nc1cccc(C2CCN(Cc3cn(-c4ccccc4)nn3)CC2)n1] | N-(6-(1-((1-phenyl-1H-1,2,3-triazol-4-yl)methyl)piperidin-4-yl)pyridin-2-yl)propane-2-sulfonamide | 5.40 | 441.2081 (M + H) |
| 208 | 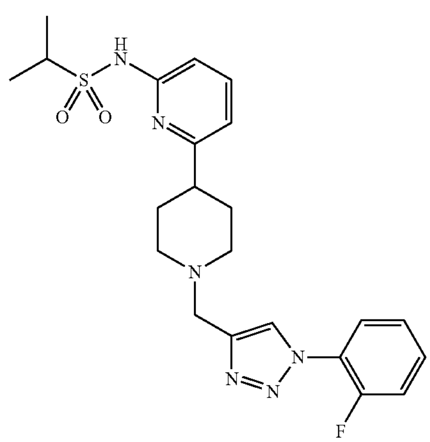 [SMILES: CC(C)S(=O)(=O)Nc1cccc(C2CCN(Cc3cn(-c4ccccc4F)nn3)CC2)n1] | N-(6-(1-((1-(2-fluorophenyl)-1H-1,2,3-triazol-4-yl)methyl)piperidin-4-yl)pyridin-2-yl)propane-2-sulfonamide | 5.42 | 457.1833 (M − H) |

-continued

| EX | Structure | Chemical name | Ret time (min) | HRMS |
|---|---|---|---|---|
| 209 | 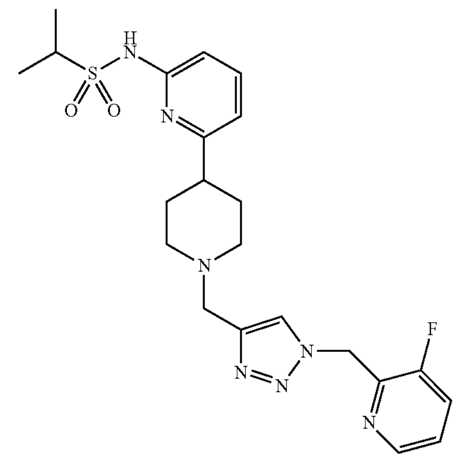 [SMILES: CC(C)S(=O)(=O)Nc1cccc(C2CCN(Cc3cn(Cc4ncccc4F)nn3)CC2)n1] | N-(6-(1-((1-((3-fluoropyridin-2-yl)methyl)-1H-1,2,3-triazol-4-yl)methyl)piperidin-4-yl)pyridin-2-yl)propane-2-sulfonamide | 4.93 | 472.1939 (M − H) |
| 210 | 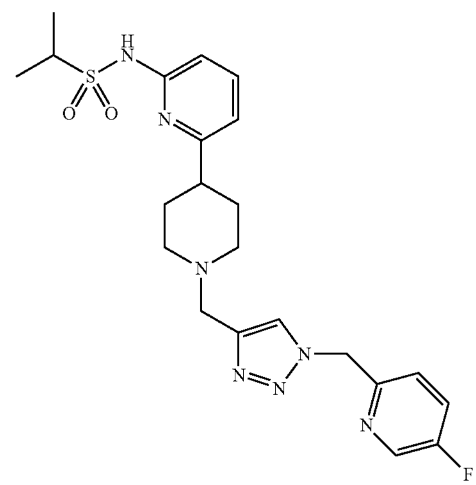 [SMILES: CC(C)S(=O)(=O)Nc1cccc(C2CCN(Cc3cn(Cc4ccc(F)cn4)nn3)CC2)n1] | N-(6-(1-((1-((5-fluoropyridin-2-yl)methyl)-1H-1,2,3-triazol-4-yl)methyl)piperidin-4-yl)pyridin-2-yl)propane-2-sulfonamide | 5.01 | 472.1930 (M − H) |
| 211 | 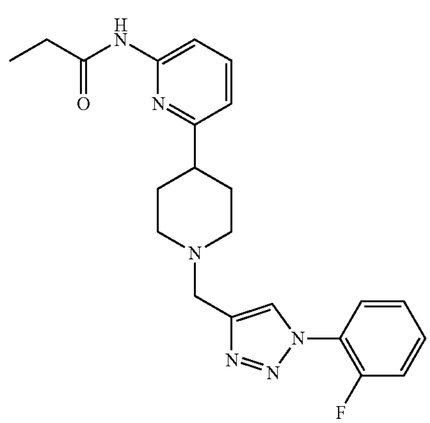 [SMILES: CCC(=O)Nc1cccc(C2CCN(Cc3cn(-c4ccccc4F)nn3)CC2)n1] | N-(6-(1-((1-(2-fluorophenyl)-1H-1,2,3-triazol-4-yl)methyl)piperidin-4-yl)pyridin-2-yl)propionamide | 5.08 | 409.2143 (M + H) |

-continued

| EX | Structure | Chemical name | Ret time (min) | HRMS |
|---|---|---|---|---|
| 212 | 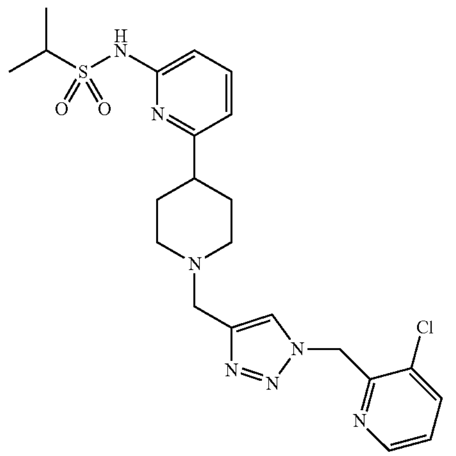 [SMILES: CC(C)S(=O)(=O)Nc1cccc(C2CCN(Cc3cn(Cc4ncccc4Cl)nn3)CC2)n1] | N-(6-(1-((1-((3-chloropyridin-2-yl)methyl)-1H-1,2,3-triazol-4-yl)methyl)piperidin-4-yl)pyridin-2-yl)propane-2-sulfonamide | 5.12 | 490.1786 (M + H) |
| 213 | 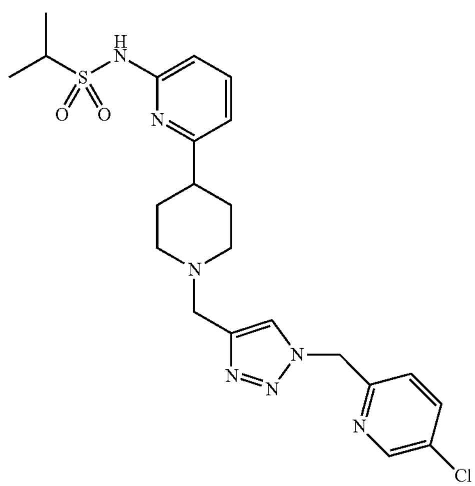 [SMILES: CC(C)S(=O)(=O)Nc1cccc(C2CCN(Cc3cn(Cc4ccc(Cl)cn4)nn3)CC2)n1] | N-(6-(1-((1-((5-chloropyridin-2-yl)methyl)-1H-1,2,3-triazol-4-yl)methyl)piperidin-4-yl)pyridin-2-yl)propane-2-sulfonamide | 5.23 | 490.1792 (M + H) |
| 214 | 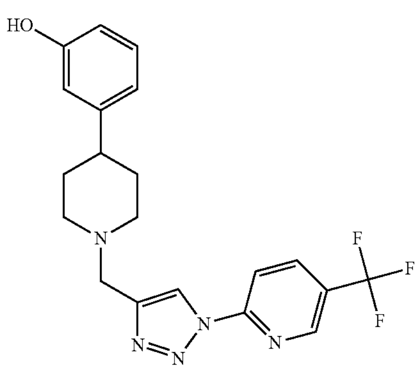 [SMILES: Oc1cccc(C2CCN(Cc3cn(-c4ccc(C(F)(F)F)cn4)nn3)CC2)c1] | 3-(1-((1-(5-(trifluoromethyl)pyridin-2-yl)-1H-1,2,3-triazol-4-yl)methyl)piperidin-4-yl)phenol | 5.74 | 402.1546 (M + H) |

| EX | Structure | Chemical name | Ret time (min) | HRMS |
|---|---|---|---|---|
| 215 | 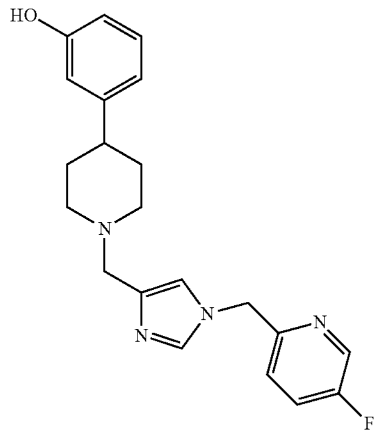 [SMILES: Oc1cccc(C2CCN(Cc3cn(Cc4ccc(F)cn4)cn3)CC2)c1] | 3-(1-((1-((5-fluoropyridin-2-yl)methyl)-1H-imidazol-4-yl)methyl)piperidin-4-yl)phenol | 4.43 | 365.1781 (M − H) |
| 216 | 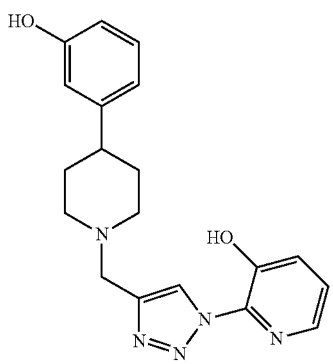 [SMILES: Oc1cccc(C2CCN(Cc3cn(-c4ncccc4O)nn3)CC2)c1] | 2-(4-((4-(3-hydroxyphenyl)piperidin-1-yl)methyl)-1H-1,2,3-triazol-1-yl)pyridin-3-ol | 4.65 | 350.1624 (M − H) |
| 217 | 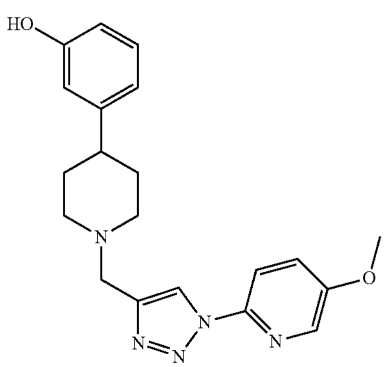 [SMILES: COc1ccc(-n2cc(CN3CCC(c4cccc(O)c4)CC3)nn2)nc1] | 3-(1-((1-(5-methoxypyridin-2-yl)-1H-1,2,3-triazol-4-yl)methyl)piperidin-4-yl)phenol | 5.15 | 364.1779 (M − H) |
| 218 | 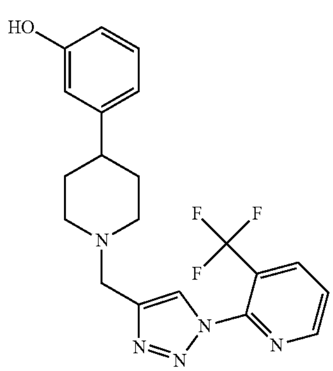 [SMILES: Oc1cccc(C2CCN(Cc3cn(-c4ncccc4C(F)(F)F)nn3)CC2)c1] | 3-(1-((1-(3-(trifluoromethyl)pyridin-2-yl)-1H-1,2,3-triazol-4-yl)methyl)piperidin-4-yl)phenol | 5.34 | 402.1536 (M − H) |

| EX | Structure | Chemical name | Ret time (min) | HRMS |
|---|---|---|---|---|
| 219 | 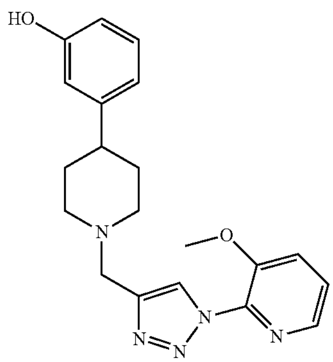 [SMILES: COc1cccnc1-n1cc(CN2CCC(c3cccc(O)c3)CC2)nn1] | 3-(1-((1-(3-methoxypyridin-2-yl)-1H-1,2,3-triazol-4-yl)methyl)piperidin-4-yl)phenol | 4.76 | 366.1936 (M + H) |
| 220 | 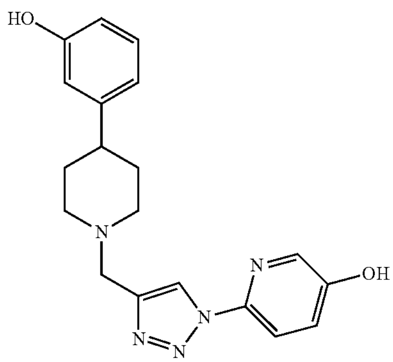 [SMILES: Oc1ccc(-n2cc(CN3CCC(c4cccc(O)c4)CC3)nn2)nc1] | 6-(4-((4-(3-hydroxyphenyl)piperidin-1-yl)methyl)-1H-1,2,3-triazol-1-yl)pyridin-3-ol | 4.76 | 350.1622 (M − H) |
| 221 | 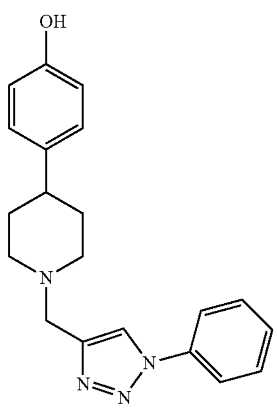 [SMILES: Oc1ccc(C2CCN(Cc3cn(-c4ccccc4)nn3)CC2)cc1] | 4-(1-((1-phenyl-1H-1,2,3-triazol-4-yl)methyl)piperidin-4-yl)phenol | 5.26 | 335.1856 (M + H) |
| 222 | 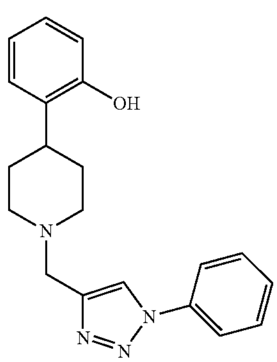 [SMILES: Oc1ccccc1C1CCN(Cc2cn(-c3ccccc3)nn2)CC1] | 2-(1-((1-phenyl-1H-1,2,3-triazol-4-yl)methyl)piperidin-4-yl)phenol | 5.52 | 333.1708 (M − H) |

-continued
| EX | Structure | Chemical name | Ret time (min) | HRMS |
|---|---|---|---|---|
| 223 | 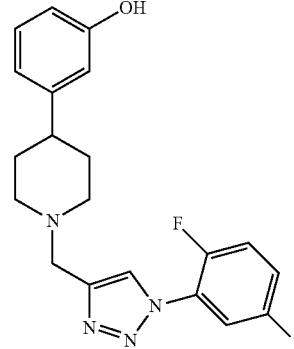 | 3-(1-((1-(2,5-difluorophenyl)-1H-1,2,3-triazol-4-yl)methyl)piperidin-4-yl)phenol | 5.45 | 371.1678 (M + H) |
| 224 | 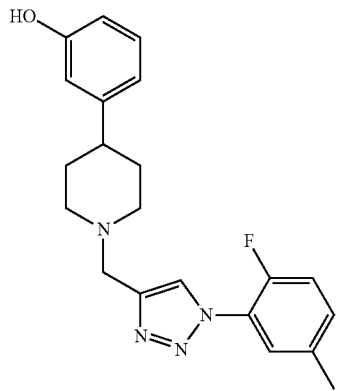 [SMILES: Cc1ccc(F)c(-n2cc(CN3CCC(c4cccc(O)c4)CC3)nn2)c1] | 3-(1-((1-(2-fluoro-5-methylphenyl)-1H-1,2,3-triazol-4-yl)methyl)piperidin-4-yl)phenol | 5.62 | 367.1932 (M + H) |
| 225 | 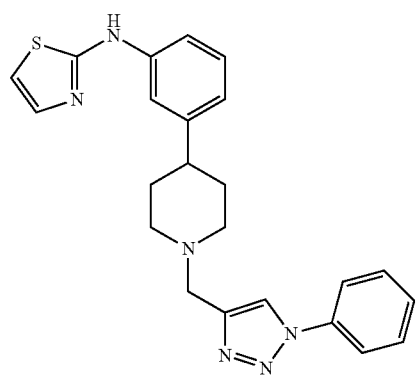 [SMILES: c1ccc(-n2cc(CN3CCC(c4cccc(Nc5nccs5)c4)CC3)nn2)cc1] | N-(3-(1-((1-phenyl-1H-1,2,3-triazol-4-yl)methyl)piperidin-4-yl)phenyl)thiazol-2-amine | 5.05 | 417.1850 (M + H) |
| 226 | 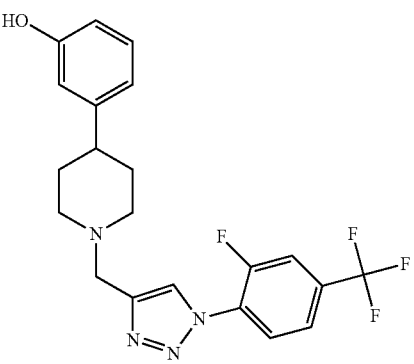 [SMILES: Oc1cccc(C2CCN(Cc3cn(-c4ccc(C(F)(F)F)cc4F)nn3)CC2)c1] | 3-(1-((1-(2-fluoro-4-(trifluoromethyl)phenyl)-1H-1,2,3-triazol-4-yl)methyl)piperidin-4-yl)phenol | 5.95 | 421.1646 (M + H) |

-continued

| EX | Structure | Chemical name | Ret time (min) | HRMS |
|---|---|---|---|---|
| 227 | 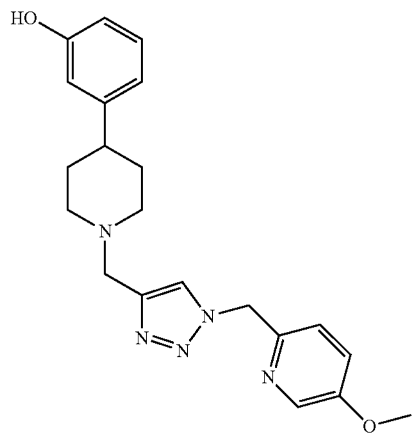 | 3-(1-((1-((5-methoxypyridin-2-yl)methyl)-1H-1,2,3-triazol-4-yl)methyl)piperidin-4-yl)phenol | 4.80 | 457.1839 (M + H) |
| 228 | 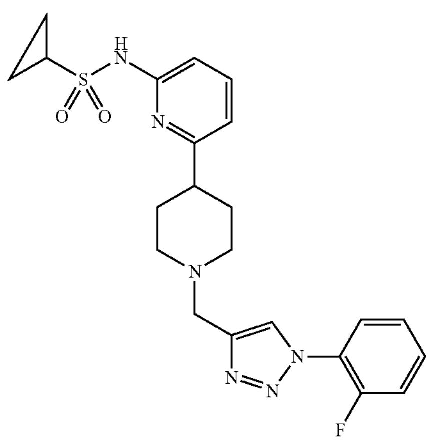 [SMILES: O=S(=O)(Nc1cccc(C2CCN(Cc3cn(-c4ccccc4F)nn3)CC2)n1)C1CC1] | N-(6-(1-((1-(2-fluorophenyl)-1H-1,2,3-triazol-4-yl)methyl)piperidin-4-yl)pyridin-2-yl)cyclopropanesulfonamid | 5.33 | 457.1839 (M + H) |
| 229 | 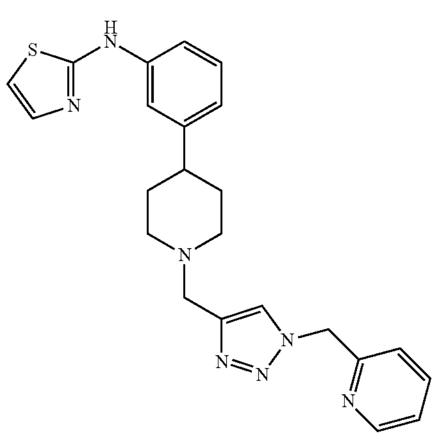 [SMILES: c1ccc(Cn2cc(CN3CCC(c4cccc(Nc5nccs5)c4)CC3)nn2)nc1] | N-(3-(1-((1-(pyridin-2-ylmethyl)-1H-1,2,3-triazol-4-yl)methyl)piperidin-4-yl)phenyl)thiazol-2-amine | 4.39 | 432.1967 (M + H) |

-continued

| EX | Structure | Chemical name | Ret time (min) | HRMS |
|---|---|---|---|---|
| 230 | 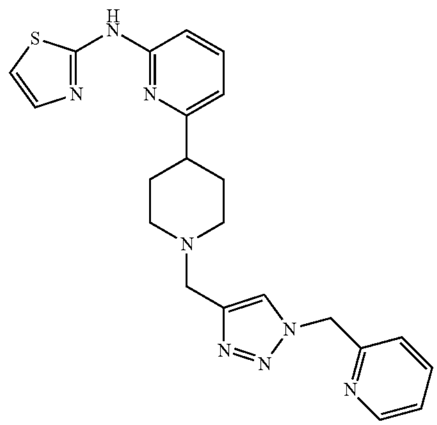 [SMILES: c1ccc(Cn2cc(CN3CCC(c4cccc(Nc5nccs5)n4)CC3)nn2)nc1] | N-(6-(1-((1-(pyridin-2-ylmethyl)-1H-1,2,3-triazol-4-yl)methyl)piperidin-4-yl)pyridin-2-yl)thiazol-2-amine | 4.27 | 433.1912 (M + H) |
| 231 | 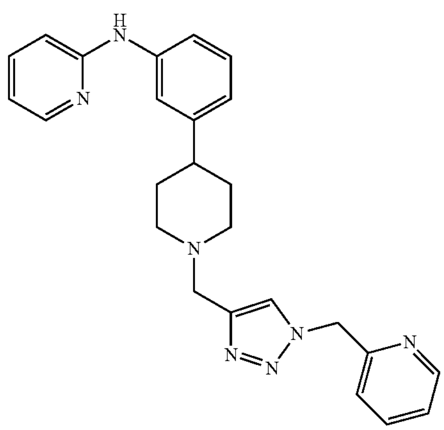 [SMILES: c1ccc(Cn2cc(CN3CCC(c4cccc(Nc5ccccn5)c4)CC3)nn2)nc1] | N-(3-(1-((1-(pyridin-2-ylmethyl)-1H-1,2,3-triazol-4-yl)methyl)piperidin-4-yl)phenyl)pyridin-2-amine | 4.15 | 426.2411 (M + H) |
| 232 | 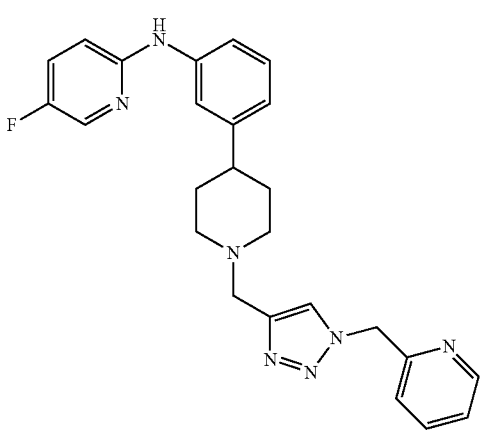 [SMILES: Fc1ccc(Nc2cccc(C3CCN(Cc4cn(Cc5ccccn5)nn4)CC3)c2)nc1] | 5-fluoro-N-(3-(1-((1-(pyridin-2-ylmethyl)-1H-1,2,3-triazol-4-yl)methyl)piperidin-4-yl)phenyl)pyridin-2-amine | 5.07 | 444.2299 (M + H) |

| EX | Structure | Chemical name | Ret time (min) | HRMS |
|---|---|---|---|---|
| 233 | 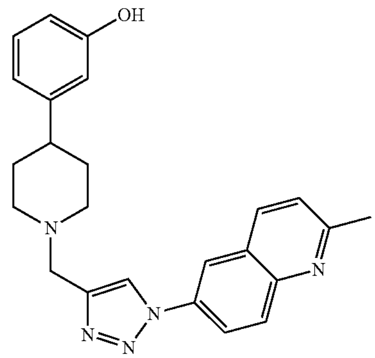 [SMILES: Cc1ccc2cc(-n3cc(CN4CCC(c5cccc(O)c5)CC4)nn3)ccc2n1] | 3-(1-((1-(2-methylquinolin-6-yl)-1H-1,2,3-triazol-4-yl)methyl)piperidin-4-yl)phenol | 4.36 | 400.2123 (M + H) |

Biological Activity
Pharmacological Study
Human $\sigma_1$ Receptor Radioligand Assay To investigate binding properties of $\sigma_1$ receptor ligands to human $\sigma_1$ receptor, transfected HEK-293 membranes and [$^3$H](+)-pentazocine (Perkin Elmer, NET-1056), as the radioligand, were used. The assay was carried out with 7 µg of membrane suspension, 5 nM of [$^3$H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human µ-Opioid Receptor Radioligand Assay To investigate binding properties of mu-opioid receptor ligands to human µ-opioid receptor, transfected CHO-K1 cell membranes and [$^3$H]-DAMGO (Perkin Elmer, ES-542-C), as the radioligand, were used. The assay was carried out with 20 µg of membrane suspension, 1 nM of [$^3$H]-DAMGO in either absence or presence of either buffer or 10 µM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the µ-opiod receptor it is a very preferred embodiment in which the compounds are selected which act as dual ligands of the $\sigma_1$ receptor and the µ-opiod receptor and especially compounds which have a binding expressed as $K_i$ which is preferably <1000 nM for both receptors, more preferably <500 nM, even more preferably <100 nM.

The following scale as been adopted for representing the binding to the $\sigma_1$ receptor and the µ-opiod receptor expressed as Ki:
+ Both $K_i$-µ and $K_i$-$\sigma_1$>=500 nM
++ One $K_i$<500 nM while the other Ki is >=500 nM
+++ Both $K_i$-µ and $K_i$-$\sigma_1$<500 nM
++++ Both $K_i$-µ and $K_i$-$\sigma_1$<100 nM All compounds prepared in the present application exhibit binding to the $\sigma_1$ receptor and the µ-opiod receptor, in particular the following binding results are shown:

| EX | µ and $\sigma_1$ dual binding |
|---|---|
| 1 | ++++ |
| 2 | ++++ |
| 3 | +++ |
| 4 | ++++ |
| 5 | ++ |
| 6 | +++ |
| 7 | +++ |
| 8 | ++++ |
| 9 | +++ |
| 10 | +++ |
| 11 | ++ |
| 12 | ++ |
| 13 | ++ |
| 14 | +++ |
| 15 | +++ |
| 16 | +++ |
| 17 | ++ |
| 18 | ++++ |
| 19 | ++++ |
| 20 | ++ |
| 21 | +++ |
| 22 | +++ |
| 23 | +++ |
| 24 | ++ |
| 25 | ++++ |
| 26 | ++ |
| 27 | ++++ |
| 28 | ++++ |
| 29 | +++ |
| 30 | +++ |
| 31 | ++ |
| 32 | ++ |
| 33 | ++ |
| 34 | +++ |
| 35 | ++++ |
| 36 | ++++ |
| 37 | +++ |
| 38 | ++ |

| EX | μ and σ₁ dual binding |
|---|---|
| 39 | +++ |
| 40 | ++++ |
| 41 | ++++ |
| 42 | +++ |
| 43 | ++++ |
| 44 | ++++ |
| 45 | ++ |
| 46 | ++++ |
| 47 | +++ |
| 48 | +++ |
| 49 | ++++ |
| 50 | ++++ |
| 51 | + |
| 52 | ++++ |
| 53 | ++++ |
| 54 | +++ |
| 55 | +++ |
| 56 | +++ |
| 57 | +++ |
| 58 | +++ |
| 59 | ++++ |
| 60 | ++++ |
| 61 | ++++ |
| 62 | ++++ |
| 63 | ++++ |
| 64 | ++++ |
| 65 | +++ |
| 66 | +++ |
| 67 | +++ |
| 68 | ++ |
| 69 | ++ |
| 70 | ++ |
| 71 | ++++ |
| 72 | ++++ |
| 73 | +++ |
| 74 | ++ |
| 75 | +++ |
| 76 | +++ |
| 77 | ++++ |
| 78 | +++ |
| 79 | +++ |
| 80 | ++ |
| 81 | ++ |
| 82 | ++++ |
| 83 | ++++ |
| 84 | ++++ |
| 85 | + |
| 86 | ++ |
| 87 | +++ |
| 88 | +++ |
| 89 | ++++ |
| 90 | ++ |
| 91 | ++ |
| 92 | +++ |
| 93 | +++ |
| 94 | ++++ |
| 95 | ++ |
| 96 | +++ |
| 97 | ++ |
| 98 | ++ |
| 99 | ++ |
| 100 | ++ |
| 101 | +++ |
| 102 | ++ |
| 103 | ++ |
| 104 | ++ |
| 105 | ++ |
| 106 | ++ |
| 107 | ++++ |
| 108 | +++ |
| 109 | ++ |
| 110 | ++ |
| 111 | + |
| 112 | ++ |
| 113 | ++++ |
| 114 | +++ |
| 115 | +++ |
| 116 | +++ |
| 117 | ++ |
| 118 | ++ |
| 119 | ++ |
| 120 | ++ |
| 121 | ++ |
| 122 | ++ |
| 123 | ++ |
| 124 | ++ |
| 125 | ++ |
| 126 | +++ |
| 127 | ++ |
| 128 | ++ |
| 129 | ++ |
| 130 | ++ |
| 131 | ++ |
| 132 | +++ |
| 133 | +++ |
| 134 | +++ |
| 135 | ++ |
| 136 | +++ |
| 137 | +++ |
| 138 | + |
| 139 | ++ |
| 140 | + |
| 141 | + |
| 142 | ++++ |
| 143 | ++++ |
| 144 | +++ |
| 145 | +++ |
| 146 | ++++ |
| 147 | ++++ |
| 148 | ++++ |
| 149 | +++ |
| 150 | +++ |
| 151 | +++ |
| 152 | ++++ |
| 153 | ++++ |
| 154 | +++ |
| 155 | ++++ |
| 156 | ++ |
| 157 | +++ |
| 158 | ++ |
| 159 | + |
| 160 | ++++ |
| 161 | +++ |
| 162 | ++++ |
| 163 | ++++ |
| 164 | ++++ |
| 165 | +++ |
| 166 | ++ |
| 167 | +++ |
| 168 | ++ |
| 169 | ++ |
| 170 | ++++ |
| 171 | +++ |
| 172 | +++ |
| 173 | +++ |
| 174 | ++++ |
| 175 | ++ |
| 176 | ++++ |
| 177 | ++++ |
| 178 | +++ |
| 179 | +++ |
| 180 | +++ |
| 181 | ++ |
| 182 | ++ |
| 183 | +++ |
| 184 | ++++ |
| 185 | ++ |
| 186 | ++ |
| 187 | ++ |
| 188 | ++ |
| 189 | ++ |
| 190 | +++ |

-continued

| EX | μ and σ₁ dual binding |
|---|---|
| 191 | ++ |
| 192 | ++ |
| 193 | + |
| 194 | + |
| 195 | + |
| 196 | + |
| 197 | + |
| 198 | + |
| 199 | ++ |
| 200 | +++ |
| 201 | +++ |
| 202 | ++++ |
| 203 | +++ |
| 204 | ++ |
| 205 | ++ |
| 206 | +++ |
| 207 | +++ |
| 208 | +++ |
| 209 | ++ |
| 210 | ++ |
| 211 | ++ |
| 212 | ++ |
| 213 | ++ |
| 214 | ++++ |
| 215 | +++ |
| 216 | ++ |
| 217 | +++ |
| 218 | +++ |
| 219 | ++ |
| 220 | ++ |
| 221 | +++ |
| 222 | +++ |
| 223 | ++++ |
| 224 | ++++ |
| 225 | ++++ |
| 226 | ++++ |
| 227 | +++ |
| 228 | +++ |
| 229 | +++ |
| 230 | ++ |
| 231 | ++ |
| 232 | +++ |
| 233 | +++ |

The invention claimed is:

1. A compound of general formula (I):

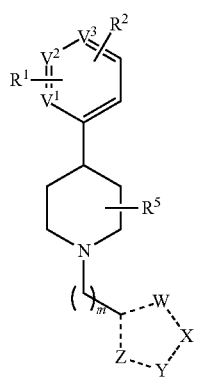

(I)

wherein
m is 1 or 2;
one of $V^1$, $V^2$ and $V^3$ is nitrogen or carbon while the other two are carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl or substituted or unsubstituted heterocyclyl;
$R^2$ is hydrogen, halogen, —$NR^6R^7$, —$SR^6$, —$OR^6$, substituted or unsubstituted alkyl, substituted of unsubstituted saturated cycloalkyl, substituted or unsubstituted alkenyl, substituted or unsubstituted alkynyl, substituted or unsubstituted aryl or substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

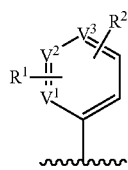

of the core structure of formula I, which may be condensed with a further unsubstituted or substituted ring system;
$R^5$ is hydrogen, halogen, hydroxy, substituted or unsubstituted O-alkyl, or substituted or unsubstituted alkyl;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or $R^5$, $R^7$ or $R^8$ together with their respective connecting carbon or nitrogen atom may form a cycloalkylic or heterocyclic 4 to 7-membered ring;
and wherein W, X, Y and Z are selected from carbon, nitrogen, or oxygen while W—X—Y—Z together with the bridging C-atom, that is connected to the core scaffold, form a 5-membered heterocyclic ring, which is either substituted on one of W, X, Y or Z by

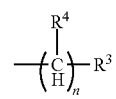

or in which this 5-membered heterocyclic ring—being otherwise unsubstituted—is fused at W and X to a further ring system;
wherein
n is 0 or 1;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl or substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl or substituted of unsubstituted heterocyclyl;
optionally as a stereoisomer, including enantiomers and diastereomers, a racemate or a mixture of at least two stereoisomers, including enantiomers and/or diastereomers, in any mixing ratio, or a salt thereof, or a solvate thereof;
with the following provisos:
with the proviso that if $V^1$, $V^2$ and $V^3$ are carbon and one of W, X, Y or Z is

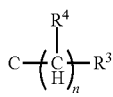

wherein n is 0, then $R^1$ may not be —NHC(O)-alkyl in the meta position;
with the proviso that if $V^1$ is nitrogen while $V^2$ and $V^3$ are carbon and either X or Y is

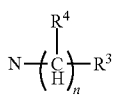

wherein n=0 and $R^3$ is alkyl, then neither $R^1$ nor $R^2$ may be —$NR^6R^7$ in the meta position and $R^2$ may not be —$CH_3$ in the meta position; and
with the proviso that if $V^1$ is nitrogen while $V^2$ and $V^3$ are carbon and either W or Z is

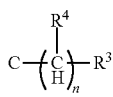

wherein n=0 and $R^3$ is alkyl, then $R^2$ may not be —$NR^6R^7$ in the meta position.

2. A compound of Formula II:

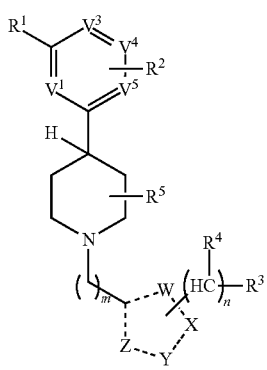

(II)

wherein
m is 1 or 2;
n is 0 or 1;
one of $V^1$, $V^3$, $V^4$ and $V^5$ is nitrogen or carbon while the other three are carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl or substituted or unsubstituted heterocyclyl;
$R^2$ is hydrogen, halogen, —$NR^6R^7$, —$SR^6$, —$OR^6$, substituted or unsubstituted alkyl, substituted of unsubstituted saturated cycloalkyl, substituted or unsubstituted alkenyl, substituted or unsubstituted alkynyl, substituted or unsubstituted aryl or substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

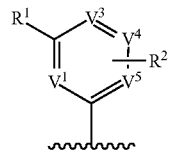

of the core structure of formula II, which may be condensed with a further unsubstituted or substituted ring system;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl or substituted or unsubstituted heterocyclyl;
$R^4$ is hydrogen, substituted or unsubstituted alkyl, substituted or unsubstituted cycloalkyl, substituted or unsubstituted alkenyl, substituted or unsubstituted alkynyl, substituted of unsubstituted aryl or substituted of unsubstituted heterocyclyl;
$R^5$ is hydrogen, halogen, hydroxy, substituted or unsubstituted O-alkyl, or substituted or unsubstituted alkyl;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom form a cycloalkylic or heterocyclic 4 to 7-membered ring;
and wherein W, X, Y and Z are selected from carbon, nitrogen, and oxygen while W—X—Y—Z together with the bridging C-atom, that is connected to the core scaffold, form a 5-membered heterocyclic ring,
or wherein

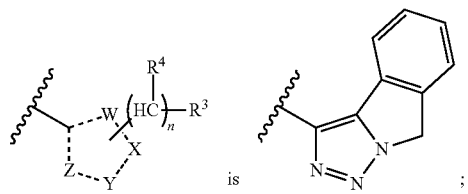

optionally as a stereoisomer, including enantiomers and diastereomers, a racemate or a mixture of at least two stereoisomers, including enantiomers and/or diastereomers, in any mixing ratio, or a salt thereof;
with the following provisos:
with the proviso that if $V^1$, $V^3$, $V^4$ and $V^6$ are carbon and one of W, X, Y or Z is

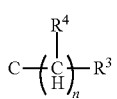

wherein n is 0, then $R^1$ may not be —NHC(O)-alkyl; with the proviso that if $V^1$ is nitrogen while $V^3$, $V^4$ and $V^6$ are carbon and either X or Y is

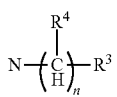

wherein n=0 and $R^3$ is alkyl, then $R^3$ may not be —$NR^6R^7$.

3. A compound of Formula III:

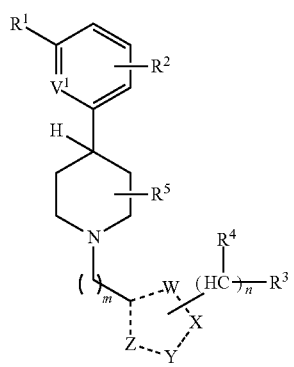

(III)

wherein
m is 1 or 2;
n is 0 or 1;
$V^1$ is nitrogen or carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl or substituted or unsubstituted heterocyclyl;
$R^2$ is hydrogen, halogen, —$NR^6R^7$, —$SR^6$, —$OR^6$, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

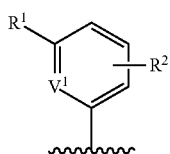

of the core structure of formula III, which may be condensed with a further unsubstituted or substituted ring system;

$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl or substituted or unsubstituted heterocyclyl;

$R^4$ is hydrogen, substituted or unsubstituted alkyl, substituted of unsubstituted cycloalkyl, substituted or unsubstituted alkenyl, substituted or unsubstituted alkynyl, substituted or unsubstituted aryl or substituted of unsubstituted heterocyclyl;

$R^5$ is hydrogen, halogen, hydroxy, substituted or unsubstituted O-alkyl, or substituted or unsubstituted alkyl;

$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom form a cycloalkylic or heterocyclic 4 to 7-membered ring;

and

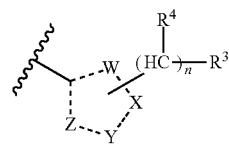

is:

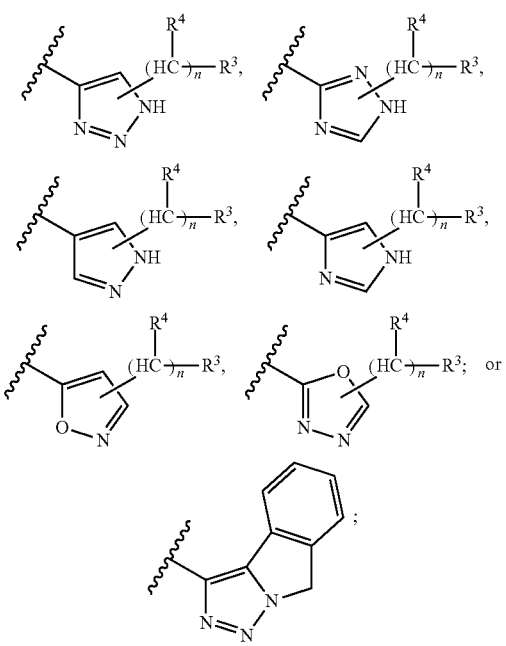

optionally as a stereoisomer, including enantiomers and diastereomers, a racemate or a mixture of at least two stereoisomers, including enantiomers and/or diastereomers, in any mixing ratio, or a salt thereof;

with the following provisos:
with the proviso that if V¹ is nitrogen and

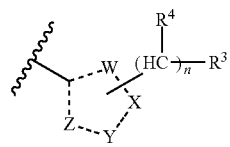

is,

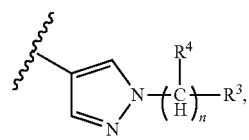

wherein n=0 and R³ is alkyl, then R¹ may not be —NR⁶R⁷;
with the proviso that if V¹ is carbon and

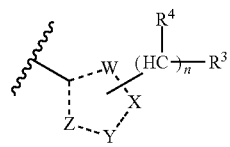

is

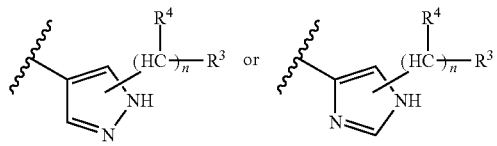

or wherein n is 0, then R¹ may not be —NHC(O)-alkyl in the meta position.

4. The compound according to claim 3, which is a compound of formula IV:

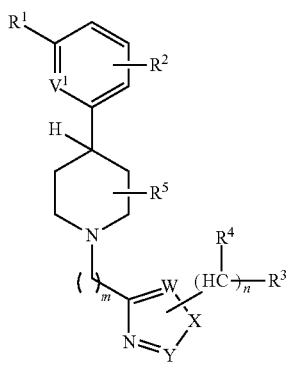

wherein
m is 1 or 2;
n is 0 or 1;
V¹ is carbon or nitrogen;

one of W, X and Y is carbon, while the other two are nitrogen;
R¹ is hydroxy, NR⁶R⁷, —NR⁶S(O)₂R⁷, —NR⁶COR⁷, —NR⁶CONR⁷R⁸, —SR, —S(O)₂R⁵, —S(O)₂NR⁶R⁷, —CONR⁶R⁷, substituted or unsubstituted aryl or substituted or unsubstituted heterocyclyl;
R² is hydrogen, halogen, —NR⁶R⁷, —SR⁶, —OR⁶, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl;
or
R¹ and R² are bonded to neighbouring atoms in the ring and together with these atoms form a saturated or unsaturated, substituted or unsubstituted ring, fused to the ring

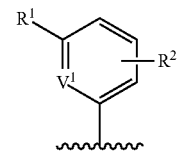

of the core structure of formula IV, which may be condensed with a further unsubstituted or substituted ring system;
R³ is substituted or unsubstituted alkyl, CONR⁶R⁷, substituted or unsubstituted cycloalkyl, substituted or unsubstituted alkenyl, substituted or unsubstituted alkynyl, substituted or unsubstituted aryl or substituted or unsubstituted heterocyclyl;
R⁴ is hydrogen, substituted or unsubstituted alkyl, substituted or unsubstituted cycloalkyl, substituted or unsubstituted alkenyl, substituted or unsubstituted alkynyl, substituted of unsubstituted aryl or substituted of unsubstituted heterocyclyl;
R⁵ is hydrogen, halogen, hydroxy, substituted or unsubstituted O-alkyl, or substituted or unsubstituted alkyl;
R⁶, R⁷ and R⁸ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or R⁶, R⁷ or R⁸ together with their respective connecting carbon or nitrogen atom form a cycloalkylic or heterocyclic 4 to 7-membered ring;
optionally as a stereoisomer, including enantiomers and diastereomers, a racemate or a mixture of at least two stereoisomers, including enantiomers and/or diastereomers, in any mixing ratio, or a salt thereof.

5. The compound according to claim 3, wherein

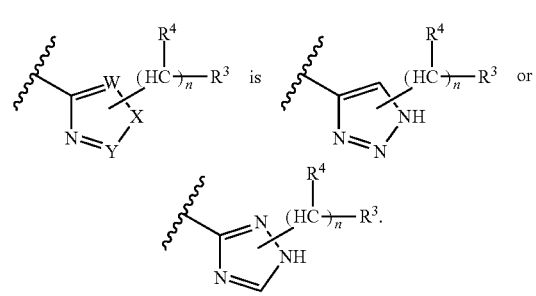

6. The compound according to claim 3, wherein

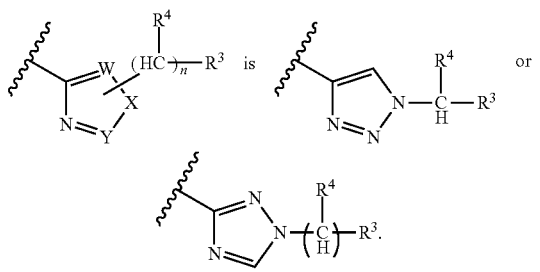 is

7. The compound according to claim 3, which is a compound of formula V:

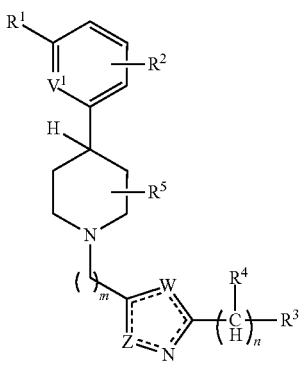

wherein
m is 1 or 2;
n is 0 or 1;
$V^1$ is CH or N;
W is CH or O and Z is N or O, with a maximum of one of them being O;
$R^1$ is hydroxy, $NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl or substituted or unsubstituted heterocyclyl;
$R^2$ is hydrogen, halogen, —$NR^6R^7$, —$SR^6$, —$OR^6$, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

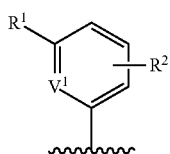

of the core structure of formula V, which may be condensed with a further unsubstituted or substituted ring system;

$R^3$ is substituted or unsubstituted cycloalkyl, substituted or unsubstituted aryl or substituted or unsubstituted heterocyclyl;
$R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl or substituted of unsubstituted heterocyclyl;
$R^5$ is hydrogen, halogen, hydroxy, substituted or unsubstituted O-alkyl, or substituted or unsubstituted alkyl;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom form a cycloalkylic or heterocyclic 4 to 7-membered ring;
optionally as a stereoisomer, including enantiomers and diastereomers, a racemate or a mixture of at least two of the stereoisomers, including enantiomers and/or diastereomers, in any mixing ratio, or a salt thereof.

8. The compound according claim 3, which is a compound of formula VI:

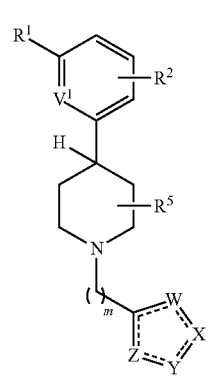

wherein
m is 1 or 2;
$V^1$ is nitrogen or carbon;
n is 0 or 1;
one of W and X is N or CH, while the other is

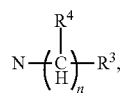

and
one of Y and Z is selected from N or CH, while the other is N, with only a maximum of 2 of W, X, Y or Z being N;
$R^1$ is hydroxy, $NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl, or substituted or unsubstituted heterocyclyl;
$R^2$ is hydrogen, halogen, —$NR^6R^7$, —$SR^6$, —$OR^6$, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

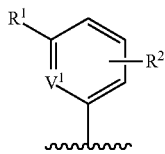

of the core structure of formula VI, which may be condensed with a further unsubstituted or substituted ring system;
$R^3$ is substituted or unsubstituted cycloalkyl, substituted or unsubstituted aryl or substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
$R^5$ is hydrogen, halogen, hydroxy, substituted or unsubstituted O-alkyl, or substituted or unsubstituted alkyl;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom form a cycloalkylic or heterocyclic 4 to 7-membered ring;
optionally as a stereoisomer, including enantiomers and diastereomers, a racemate a mixture of at least two stereoisomers, including enantiomers and/or diastereomers, in any mixing ratio, or a salt thereof.

9. The compound according to claim 3, wherein
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl or substituted or unsubstituted heterocyclyl, wherein
the aryl is selected from phenyl, naphthyl, or anthracene;
the heterocyclyl is a heterocyclic ring system of one or more saturated or unsaturated rings of which at least one ring contains one or more heteroatoms from the group consisting of nitrogen, oxygen and/or sulfur in the ring;
$R^2$ is hydrogen, halogen, —$NR^6R^7$, —$SR^6$, —$OR^6$, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl, wherein
the aryl is phenyl, naphthyl or anthracene;
the heterocyclyl is a heterocyclic ring system of one or more saturated or unsaturated rings of which at least one ring contains one or more heteroatoms selected from the group consisting of nitrogen, oxygen and sulfur the alkyl is $C_{1-8}$alkyl;
the alkenyl is $C_{2-10}$-alkenyl;
the alkynyl is $C_{2-10}$-alkynyl;
the cycloalkyl is $C_{3-8}$cycloalkyl;
the halogen is fluorine, chlorine, iodine or bromine;
or
$R^1$ and $R^2$ are bonded to neighbouring atoms in the ring and together with these atoms form a saturated or unsaturated, substituted or unsubstituted ring, fused to the ring

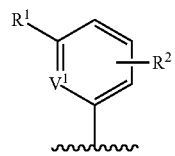

of the core structure of formula I, which may be condensed with a further unsubstituted or substituted ring system, wherein
the ring is either unsubstituted or substituted by one or more of halogen, —OH, —$NH_2$, —SH, =O, —$OC_{1-4}$alkyl being unsubstituted or substituted by one or more of OH or halogen, —CN, or $C_{1-4}$alkyl being unsubstituted or substituted by one or more of OH or halogen;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl, wherein
the aryl is phenyl, naphthyl or anthracene;
the heterocyclyl is a heterocyclic ring system of one or more saturated or unsaturated rings of which at least one ring contains one or more heteroatoms selected from the group consisting of nitrogen, oxygen and sulfur,
the alkyl is $C_{1-8}$alkyl;
the alkenyl is $C_{2-10}$-alkenyl;
the alkynyl is $C_{2-10}$-alkynyl;
the cycloalkyl is $C_{3-8}$cycloalkyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl, wherein
the aryl is phenyl, naphthyl or anthracene;
the heterocyclyl is a heterocyclic ring system of one or more saturated or unsaturated rings of which at least one ring contains one or more heteroatoms selected from the group consisting of nitrogen, oxygen and sulfur;
the alkyl is $C_{1-8}$alkyl;
the alkenyl is $C_{2-10}$-alkenyl;
the alkynyl is $C_{2-10}$-alkynyl;
the cycloalkyl is $C_{3-8}$cycloalkyl;
$R^5$ is hydrogen, halogen, hydroxy, substituted or unsubstituted O-alkyl, substituted or unsubstituted alkyl, wherein
the alkyl is $C_{1-8}$alkyl;
the O-alkyl is —O—$C_{1-6}$alkyl;
the halogen is fluorine, chlorine, iodine or bromine;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring, wherein the aryl is phenyl, naphthyl or anthracene;

the alkyl-aryl is $C_{1-4}$-alkyl-aryl;

the heterocyclyl is a heterocyclic ring system of one or more saturated or unsaturated rings of which at least one ring contains one or more heteroatoms selected from the group consisting of nitrogen, oxygen and sulfur, the alkyl is $C_{1-8}$alkyl;

the alkenyl is $C_{2-10}$-alkenyl;

the alkynyl is $C_{2-10}$-alkynyl;

the cycloalkyl is $C_{3-8}$cycloalkyl;

and when $R^6$, $R^7$ or $R^8$ together with their respective connecting carbon or nitrogen atom form a cycloalkylic or heterocyclic ring the ring is 5 or 6 membered.

10. The compound according to claim 9, wherein $R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, —$CONR^6R^7$, substituted or unsubstituted phenyl or substituted or unsubstituted imidazolyl;

$R^2$ is hydrogen, fluorine, $CH_3$ or $CF_3$;

or wherein the ring formed by $R^1$ and $R^2$ with the core structure is selected from benzoimidazole, indazole, indoline and benzothiazole, which ring may be unsubstituted or substituted by one or more substituents selected from the group consisting of halogen, —OH, —$NH_2$, —SH, =O, —$OC_{1-4}$alkyl unsubstituted or substituted by one or more of OH or halogen, —CN, or $C_{1-4}$alkyl unsubstituted or substituted by one or more of OH or halogen;

$R^3$ is substituted or unsubstituted propyl or butyl, diethylacetamide, substituted or unsubstituted cyclopentyl or cyclohexyl, substituted or unsubstituted phenyl, or substituted or unsubstituted pyridyl, imidazolyl, indenyl, 2,3-dihydroindenyl, benzofuryl, pyrimidinyl;

$R^4$ is hydrogen, $CH_3$ or $CH_2OH$;

$R^5$ is hydrogen or hydroxyl; and $R^6$, $R^7$, and $R^8$ are independently from each other selected from the group consisting of hydrogen, substituted or unsubstituted methyl, ethyl, propyl or butyl, substituted or unsubstituted phenyl, substituted or unsubstituted pyrrolidinyl, or substituted or unsubstituted benzyl, or $R^6$ and $R^7$ together with their connecting carbon atom form a cycloalkylic 5 or 6-membered ring.

11. The compound according to claim 3, which is a compound of formula VII:

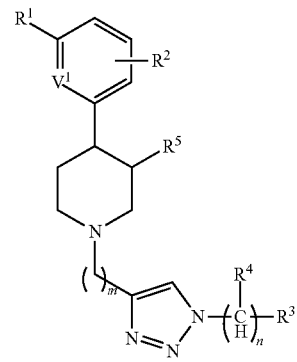

VII wherein
$V^1$ is CH or N;
m is 1 or 2;
n is 0 or 1;
$R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, —$CONR^6R^7$, substituted or unsubstituted aryl and substituted or unsubstituted heterocyclyl;
$R^2$ is hydrogen, halogen, or $C_{1-4}$alkyl;
or
$R^1$ and $R^2$ are bonded to neighbouring atoms in the ring and together with these atoms form a saturated or unsaturated, substituted or unsubstituted ring, fused to the—with $V^1$ being carbon—phenyl ring

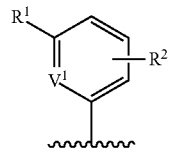

of the core structure of formula VII

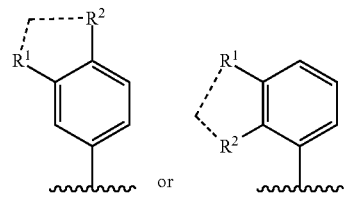

forming a double ring;
$R^3$ is substituted or unsubstituted alkyl, $CONR^6R^7$, substituted or unsubstituted cycloalkyl, substituted or unsubstituted aryl, or substituted or unsubstituted heterocyclyl;
$R^4$ is hydrogen or substituted or unsubstituted $C_{1-4}$alkyl;
$R^5$ is hydrogen, halogen, hydroxy, substituted or unsubstituted O-alkyl, or substituted or unsubstituted alkyl;
$R^6$, $R^7$ and $R^8$ are independently from each other selected from the group consisting of hydrogen, substituted or unsubstituted $C_{1-4}$alkyl, substituted or unsubstituted aryl, substituted or unsubstituted heterocyclyl, substituted or unsubstituted cycloalkyl, substituted or unsubstituted alkyl-aryl, or $R^6$ and $R^7$ together with their connecting carbon atom form a cycloalkylic 5 or 6-membered ring;

optionally as a stereoisomer, including enantiomers and diastereomers, a racemate or a mixture of at least two stereoisomers, including enantiomers and/or diastereomers, in any mixing ratio, or a salt thereof, or a solvate thereof.

12. The compound according to claim 11, wherein
$R^1$ is substituted or unsubstituted phenyl or substituted or unsubstituted imidazolyl;
$R^2$ is hydrogen, fluorine, $CH_3$ or $CF_3$;
or wherein the ring formed by $R^1$ and $R^2$ with the core structure is selected from benzoimidazole, indazole, indoline and benzothiazole, which ring may be unsubstituted or substituted by one or more substituents selected from the group consisting of halogen, —OH, —$NH_2$, —SH, =O, —$OC_{1-4}$alkyl unsubstituted or substituted by one or more of OH or halogen, —CN, or $C_{1-4}$alkyl unsubstituted or substituted by one or more of OH or halogen;
$R^3$ is substituted or unsubstituted methyl, propyl, isopropyl, isobutyl or butyl, $CONR^6R^7$, substituted or unsubstituted cyclopentyl or cyclohexyl, substituted or unsubstituted phenyl, or substituted or unsubstituted pyridyl, imidazolyl, indenyl, indolinyl, 2,3-dihydroindenyl, benzofuryl, pyrimidinyl, quinolinyl;
$R^4$ is hydrogen, $CH_3$ or $CH_2OH$;
$R^5$ is hydrogen or hydroxyl; and
$R^6$, $R^7$, and $R^8$ are independently from each other selected from the group consisting of hydrogen, substituted or unsubstituted methyl, ethyl, propyl isopropyl or butyl, substituted or unsubstituted phenyl, substituted or unsubstituted pyrrolidinyl, thiazolyl or pyridyl, substituted or unsubstituted cyclopropyl or substituted or unsubstituted benzyl, or $R^6$ and $R^7$ together with their connecting carbon atom form a cycloalkylic 5 or 6-membered ring.

13. A pharmaceutical composition which comprises a compound according to claim 1, or a pharmaceutically acceptable salt thereof, and a pharmaceutically acceptable carrier, adjuvant or vehicle.

14. A pharmaceutical composition which comprises a compound according to claim 2 or a pharmaceutically acceptable salt thereof, and a pharmaceutically acceptable carrier, adjuvant or vehicle.

15. A pharmaceutical composition which comprises a compound according to claim 3 or a pharmaceutically acceptable salt thereof, and a pharmaceutically acceptable carrier, adjuvant or vehicle.

16. A method of treating pain in a subject in need thereof, comprising administration of an effective amount of a compound according to claim 1.

17. The method of claim 16, wherein the pain is medium to severe pain, visceral pain, chronic pain, cancer pain, migraine, inflammatory pain, acute pain or neuropathic pain, allodynia or hyperalgesia.

18. A method of treating pain in a subject in need thereof, comprising administration of an effective amount of a compound according to claim 1 having a dual activity binding to the $\sigma_1$ receptor and the μ-opioid receptor.

19. A method of treating pain in a subject in need thereof, comprising administration of an effective amount of a compound according to claim 2.

20. The method according to claim 19, wherein the pain is medium to severe pain, visceral pain, chronic pain, cancer pain, migraine, inflammatory pain, acute pain or neuropathic pain, allodynia or hyperalgesia.

21. A method of treating pain in a subject in need thereof, comprising administration of an effective amount of a compound according to claim 3.

22. The method according to claim 21, wherein the pain is medium to severe pain, visceral pain, chronic pain, cancer pain, migraine, inflammatory pain, acute pain or neuropathic pain, allodynia or hyperalgesia.

23. A process for the production of a compound of formula I according to claim 1:

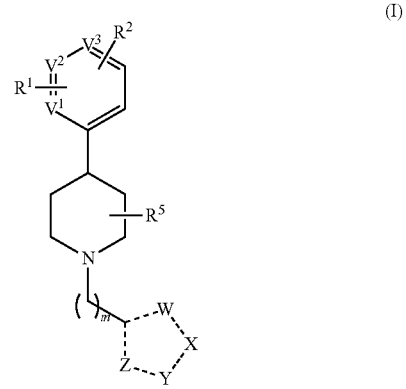

wherein $R^1$, $R^2$, $R^5$, $V^1$, $V^2$, $V^3$, W, X, Y, Z and m are as defined in claim 1 or a compound of formula Ia

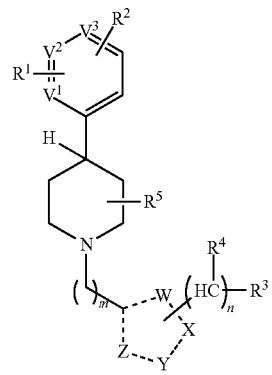

wherein $R^1$, $R^2$, $R^3$, $R^4$, $R^5$, $V^1$, $V^2$, $V^3$, W, X, Y, Z, n and m are as defined in claim 1,
wherein a compound of formula X or its suitable salt,

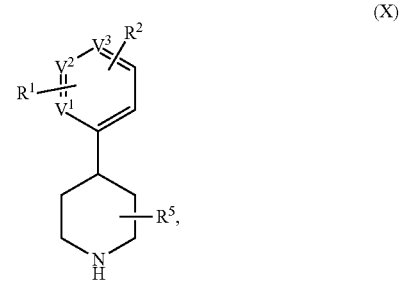

wherein $R^1$, $R^2$, $R^5$, $V^1$, $V^2$, and $V^3$ are as defined in claim 1, is reacted with a compound of formula XI (for a compound of formula I) or a compound of formula XIa (for a compound of formula Ia) under the conditions of Step 1

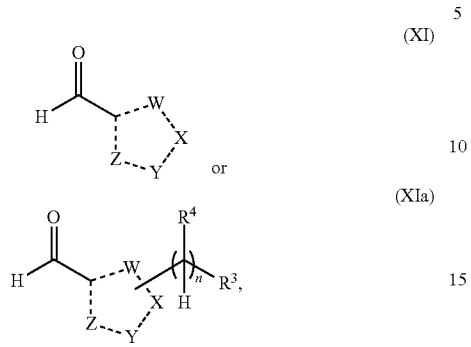

wherein $R^3$, $R^4$, W, X, Y, Z and n are as defined in claim 1, leading to a compound according to formula (I) or formula (Ia) respectively, wherein the reductive amination reaction of the compounds of formula (X) and (XI or XIa) of Step 1 is carried out with a reductive reagent in an aprotic solvent in the presence of an organic base thereby producing a compound of formula (I) as recited in claim 1.

24. A process for the production of a compound of formula VII according to claim 11:

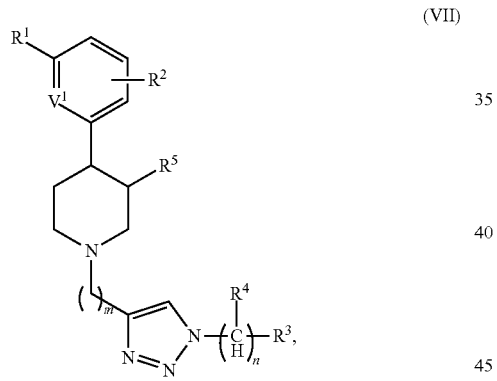

wherein $R^1$, $R^2$, $R^3$, $R^4$, $R^5$, n and m are as defined in claim 11, wherein a compound of formula XII or its suitable salt,

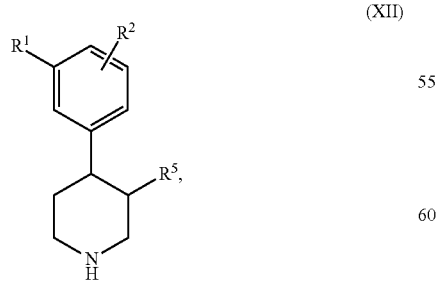

wherein $R^1$, $R^2$, and $R^5$ are as defined in claim 11, is reacted with a compound of formula XIV under the conditions of Step 2

wherein m is as defined in claim 11, leading to a compound according to formula XIII,

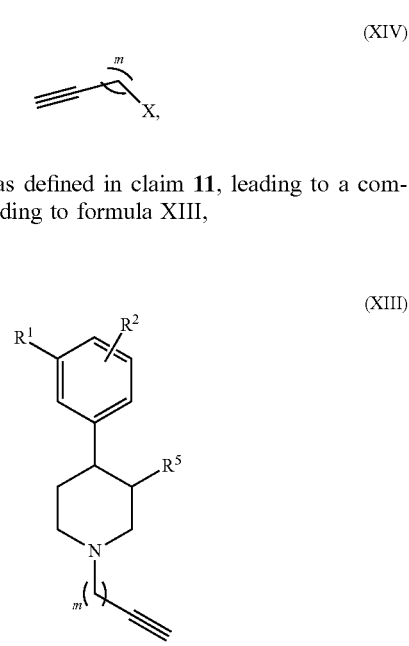

wherein $R^1$, $R^2$, $R^5$ and m are as defined in claim 11, followed by reacting the compound of formula XIII with a compound of formula XV under the conditions of Step 3

(XV)

$$\text{N}_3 \underset{H}{\overset{R^4}{-}} \!\!\!\big(\!\big)_n\! R^3$$

wherein $R^3$, $R^4$ and n are as defined in claim 11, under the conditions of Step 3, leading to a compound of formula (VII), wherein X is a leaving group, wherein the reaction of Step 2 of the compounds of formula (XII) with the compounds of formula (XIV) is carried out in the presence of a base in an aprotic solvent;

wherein the reaction of Step 3 of the compounds of formula (XIII) with the compounds of formula (XV) is carried out in the presence of a copper salt and sodium ascorbate in a mixture of protic organic solvent and water thereby producing a compound of formula VII as recited in claim 11.

* * * * *